United States Patent
Sun

(10) Patent No.: US 10,106,791 B2
(45) Date of Patent: Oct. 23, 2018

(54) SHORT HAIRPIN RNA COMPOSITIONS, METHODS OF MAKING AND APPLICATIONS THEREOF

(71) Applicant: CITY OF HOPE, Duarte, CA (US)

(72) Inventor: Guihua Sun, Arcadia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/998,166

(22) Filed: Dec. 23, 2015

(65) Prior Publication Data

US 2016/0251654 A1    Sep. 1, 2016

Related U.S. Application Data

(60) Provisional application No. 62/096,838, filed on Dec. 24, 2014.

(51) Int. Cl.
C12N 15/113    (2010.01)

(52) U.S. Cl.
CPC ........ *C12N 15/113* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS 8,273,871 B2 *  9/2012  Hannon ................ C12N 15/111
                                                   435/455

OTHER PUBLICATIONS

Ramirez, A., et al., "Human RNA 5'-Kinase (hClp1) can Function as a tRNA Splicing Enzyme In Vivo," RNA 14:1737-1745 (2008).
Reuter, J. S., et al., "RNAStructure: Software for RNA Secondary Structure Prediction and Analysis," BMC Bioinformatics 11:129 (2010).
Saxena, S., et al., "Small RNAs with Imperfect Match to Endogenous mRNA Repress Translation," J. Biol. Chem. 278(45):44312-44319 (2003).
Schirle, N. T., et al., "Structural Basis for MicroRNA Targeting," Science 346(6209):608-613 (2014).
Schwarz, D. S., et al., "Asymmetry in the Assembly of the RNAi Enzyme Complex," Cell 115:199-208 (2003).
Siolas, D., et al., "Synthetic shRNAs as Potent RNAi Triggers," Nat. Biotechnol. 23(2):227-231 (2005).
Sun, G., et al., "Molecular Properties, Functional Mechanisms, and Applications of Sliced siRNA," Mol. Ther. Nucleic Acids 4:e221 (2015).
Sun, G., et al., "Sequence Context Outside the Target Region Influences the Effectiveness of miR-223 Target Sites in the RhoB 3'UTR," Nucleic Acids Res. 38(1):239-252 (2010).
Sun, G., et al., "SNPs in Human miRNA Genes Affect Biogenesis and Function," RNA 15:1640-1651 (2009).
Sun, G., et al., "A Bias-Reducing Strategy in Profiling Small RNAs Using Solexa," RNA 17:2256-2262 (2011).
Sun, G., et al., "Problems Associated with Reporter Assays in RNAi Studies," RNA Biol. 6(4):406-411 (2009).
Sun, X., et al., "Asymmetric RNA Duplexes Mediate RNA Interference in Mammalian Cells," Nat. Biotechnol. 26(12):1379-1383 (2008).
Waterhouse, A. M., et al., "Jalview Version 2—A Multiple Sequence Alignment Editor and Analysis Workbench," Bioinformatics 25(9):1189-1191 (2009).
Wee, L. M., et al., "Argonaute Divides Its RNA Guide into Domains with Distinct Functions and RNA-Binding Properties," Cell 151(5)1055-1067 (2012).
Yang, J.S., et al., "Conserved Vertebrate mir-451 Provides a Platform for Dicer-Independent, Ago2-Mediated MicroRNA Biogenesis," PNAS 107(34):15163-15168 (2010).
Yang, J.S., et al., "Functional Parameters of Dicer-Independent MicroRNA Biogenesis," RNA 18:945-957 (2012).
Ye, X., et al., "Structure of C3PO and Mechanism of Human RISC Activation," Nat. Struct. Mol. Biol. 18(6):650-657 (2011).
Yoda, M., et al., "PARN Mediates 3'-End Trimming of Argonaute2-Cleaved Precursor MicroRNAs," Cell Rep. 5(3):715-726 (2013).
Zeng, Y., et al., "MicroRNAs and Small Interfering RNAs can Inhibit mRNA Expression by Similar Mechanisms," PNAS 100(17)9779-9784 (2003).
Zuker, M. "Mfold Web Server for Nucleic Acid Folding and Hybridization Prediction," Nucleic Acids Res. 31(13):3406-3415 (2003).
Aagaard, L., et al., "A Facile Lentiviral Vector System for Expression of Doxycycline-Inducible shRNAs: Knockdown of the Pre-miRNA Processing Enzyme Drosha," Mol. Ther. 15(5):938-945 (2007).
Bramsen, J. B., et al., "Improved Silencing Properties Using Small Internally Segmented Interfering RNAs," Nucleic Acids Research 35(17):5886-5897 (2007).
Brennecke, J., et al., "Principles of MicroRNA-Target Recognition," PLoS Biol. 3(3):e85 (2005).
Brummelkamp, T. R., et al., "A System for Stable Expression of Short Interfering RNAs in Mammalian Cells," Science 296:550-553 (2002).
Chang, C. II, et al., "Asymmetric Shorter-Duplex siRNA Structures Trigger Efficient Gene Silencing With Reduced Nonspecific Effects," Mol. Ther. 17(4):725-732 (2009).
Cheloufi, S., et al., "A Dicer-Independent miRNA Biogenesis Pathway that Requires Ago Catalysis," Nature 465 (7298):584-589 (2010).
Chi, S. W., et al., "An Alternative Mode of microRNA Target Recognition," Nat. Struct. Mol. Biol. 19(3):321-327 (2013).
Chu, C.Y., et al., "Potent RNAi by Short RNA Triggers," RNA 14:1714-1719 (2008).
Cifuentes, D., et al., "A Novel miRNA Processing Pathway Independent of Dicer Requires Argonaute2 Catalytic Activity," Science 328(5986):1694-1698 (2010).

(Continued)

*Primary Examiner* — J. E. Angell
(74) *Attorney, Agent, or Firm* — Perkins Coie LLP; Courtney Prochnow

(57) ABSTRACT

Provided herein are novel synthetic short hairpin RNA (shRNA) molecules and compositions and kits comprising such molecules, as well as methods of making and using these molecules, compositions, and kits.

20 Claims, 71 Drawing Sheets

Specification includes a Sequence Listing.

(56) References Cited

OTHER PUBLICATIONS

Dallas, A., et al., "Right- and Left-Loop Short shRNAs Have Distinct and Unusual Mechanisms of Gene Silencing," Nucleic Acids Res. 40(18):9255-9271 (2012).
Doench, J. G., et al., "siRNAs Can Function as miRNAs," Genes & Devel. 17:438-442 (2003).
Dueck, A., et al., "MicroRNAs Associated with the Different Human Argonaute Proteins," Nucleic Acids Res. 40(19):9850-9862 (2012).
Elbashir, S. M., et al., "Duplexes of 21-Nucleotide RNAs Mediate RNA Interference in Cultured Mammalian Cells," Nature 411:494-498 (2001).
Elkayam, E., et al., "The Structure of Human Argonaute-2 in Complex with miR-20a," Cell 150(1):100-110 (2012).
Faehnle, C. R., et al., "The Making of a Slicer: Activation of Human Argonaute-1," Cell Rep. 3(6):1901-1909 (2013).
Foulkes, W. D., et al., "Dicer1: Mutations, MicroRNAs and Mechanisms," Nat. Rev. Cancer 14:662-673 (2014).
Frank, F., et al., "Structural Basis for 5'-Nucleotide Base-Specific Recognition of Guide RNA by Human AGO2," Nature 465:818-822 (2010).
Ge, Q., et al., "Minimal-Length Short Hairpin RNAs: The Relationship of Structure and RNAi Activity," RNA 16:106-117 (2010).
Ge, Q., et al., "Effects of Chemical Modification on the Potency, Serum Stability, and Immunostimulatory Properties of Short shRNAs," RNA 16:118-130 (2010).
Grimm, D., et al., "Argonaute Proteins are Key Determinants of RNAi Efficacy, Toxicity, and Persistence in the Adult Mouse Liver," J. Clin. Invest. 120(9):3106-3119 (2010).
Grimson, A., et al., "MicroRNA Targeting Specificity in Mammals: Determinants Beyond Seed Pairing," Mol. Cell 27 (1):91-105 (2007).
Gu, S., et al., "The Loop Position of shRNAs and Pre-miRNAs is Critical for the Accuracy of Dicer Processing In Vivo," Cell 151(4):900-911 (2012).
Ha, M., et al., "Regulation of MicroRNA Biogenesis," Nat. Rev. Mol. Cell Biol. 15:509-524 (2014).
Hauptmann, J., et al., "Turning Catalytically Inactive Human Argonaute Proteins into Active Slicer Enzymes," Nat. Struct. Mol. Biol. 20(7):814-818 (2013).
Hauptmann, J., et al., "Generation of Catalytic Human Ago4 Identifies Structural Elements Important for RNA cleavage," RNA 20:1532-1538 (2014).
Heale, B. S. E, et al., "siRNA Target Site Secondary Structure Predictions Using Local Stable Substructures," Nucleic Acids Res. 33(3):e30 (2005).
Herrera-Carrillo, E., et al., "Probing the shRNA Characteristics That Hinder Dicer Recognition and Consequently Allow Ago-Mediated Processing and AgoshRNA Activity," RNA 20:1410-1418 (2014).
Hofacker, I. L., "Vienna RNA Secondary Structure Server," Nucleic Acids Res. 31(13):3429-3431 (2003).
Jackson, A. L., et al., "Expression of Profiling Reveals Off-Target Gene Regulation by RNAi," Nat. Biotechnol. 21(6):635-637 (2003).
Jackson, A. L., et al., "Widespreads siRNA "Off-Target" Transcript Silencing Mediated by Seed Region Sequence Complementarity," RNA 12:1179-1187 (2006).
Jackson, A. L., et al., "Recognizing and Avoiding siRNA Off-Target Effects for Target Identification and Therapeutic Application," Nat. Rev. Drug Discov. 9:57-67 (2010).
Jinek, M., et al., "A Three-Dimensional View of the Molecular Machinery of RNA Interference," Nature 457:405-412 (2009).
Khvorova, A., et al., "Functional siRNAs and miRNAs Exhibit Strand Bias," Cell 115:209-216 (2003).
Lewis, B. P., et al., "Prediction of Mammalian MicroRNA Targets," Cell 115:787-798 (2003).
Lewis, B. P. et al. "Conserved Seed Pairing, Often Flanked by Adenosines, Indicates that Thousands of Human Genes are MicroRNA Targets," Cell 120:15-20 (2005).
Li, M.J., et al. "Inhibition of HIV-1 Infection by Lentiviral Vectors Expressing Pol III-Promoted Anti-HIV RNAs," Mol. Ther. 8(2):196-206 (2003).
Li, M., et al., "Lentiviral Vector Delivery of siRNA and shRNA Encoding Genes Into Cultured and Primary Hematopoietic Cells," Methods Mol. Biol. 433(1):287-299 (2008).
Liu, Y. et al., "C3PO, An Endoribonuclease that Promotes RNAi by Facilitating RISC Activation," Science 325(5941):750-753 (2009).
Liu, Y. P., et al., "Dicer-Independent Processing of Short Hairpin RNAs," Nucleic Acids Res. 41(6):3723-3733 (2013).
Ma, H., et al., "Designing Ago2-Specific siRNA/shRNA to Avoid Competition with Endogenous miRNAs," Mol. Ther. Nucleic Acids 3:e176 (2014).
Ma, J.B., et al., "Structural Basis for 5'-End-Specific Recognition of Guide RNA by the A. Fulgidus Piwi Protein," Nature 434(7033):666-670 (2005).
Martinez, J., et al., "Single-Stranded Antisense siRNAs Guide Target RNA Cleavage in RNAi," Cell 110:563-574 (2002).
Matveeva, O. V., et al., "Optimization of Duplex Stability and Terminal Asymmetry for shRNA Design," PLoS One 5(4):e10180 (2010).
McIntyre, G. J., et al., "The Effects of Stem Length and Core Placement on shRNA Activity," BMC Mol. Biol. 12:34 (2011).
McManus, M. T., et al., "Gene Silencing Using Micro-RNA Designed Hairpins," RNA 8:842-850 (2002).
Parisien, M., et al., "The MC-Fold and MC-Sym Pipeline Infers RNA Structure from Sequence Data," Nature 452:51-55 (2008).
Park, J. H., et al., "Slicer-Independent Mechanism Drives Small-RNA Strand Separation During Human RISC Assembly," Nucleic Acids Res. 43(19):9418-9433 (2015).
Petri, S., et al., "Increased siRNA Duplex Stability Correlates with Reduced Off-Target and Elevated On-Target Effects," RNA 17:737-749 (2011).
Petri, S., et al., "siRNA Design Principles and Off-Target Effects," Methods Mol. Biol. 986:59-71 (2013).
Popenda, M., et al., "Automated 3D Structure Composition for Large RNAs," Nucleic Acids Res. 40(14):e112 (2012).

* cited by examiner p1-p22 = antisense strand    p23-p40 = sense strand hsa/mmu-pre-miR-451 hsa/dre-pre-miR-451

Fig. 5

| Base pair positions | | | Bases | | Base pair properties on pre-miR-451 | | | Base pair properties on sli-siRNA | |
|---|---|---|---|---|---|---|---|---|---|
| 5p | 3p | # bp | 5p | 3p | # stem | # seed | Possible bp | Preferred | Alternative |
| p1 | p40 | $1^{st}$ | A | C | n/a | n/a | mm | A/U:C mm | other mm |
| p2 | p39 | $2^{nd}$ | A | U | $1^{st}$ | $1^{st}$ | wc | wc | mm/wb |
| p3 | p38 | $3^{rd}$ | A | U | $2^{nd}$ | $2^{nd}$ | wc | wc | n/a |
| p4 | p37 | $4^{th}$ | C | G | $3^{rd}$ | $3^{rd}$ | wc | wc | n/a |
| p5 | p36 | $5^{th}$ | C | G | $4^{th}$ | $4^{th}$ | wc | wc | n/a |
| p6 | p35 | $6^{th}$ | G | C/G/U | $5^{th}$ | $5^{th}$ | wc/mm/wb | wc | wb/mm |
| p7 | p34 | $7^{th}$ | U | A | $6^{th}$ | $6^{th}$ | wc | wc | wb/mm |
| p8 | p33 | $8^{th}$ | U | A | $7^{th}$ | $7^{th}$ | wc | wc | n/a |
| p9 | p32 | $9^{th}$ | A | U | $8^{th}$ | n/a | wc | wc | n/a |
| p10 | p31 | $10^{th}$ | C | G | $9^{th}$ | n/a | wc | wc | n/a |
| p11 | p30 | $11^{th}$ | C | G | $10^{th}$ | n/a | wc | wc | n/a |
| p12 | p29 | $12^{th}$ | A | U | $11^{th}$ | n/a | wc | wc | n/a |
| p13 | p28 | $13^{th}$ | U | A | $12^{th}$ | n/a | wc | wc | n/a |
| p14 | p27 | $14^{th}$ | U | A | $13^{th}$ | n/a | wc | wc | n/a |
| p15 | p26 | $15^{th}$ | A | U | $14^{th}$ | n/a | wc | wc | n/a |
| p16 | p25 | $16^{th}$ | C/U* | G/A* | $15^{th}$ | n/a | wc | wc | n/a |
| p17 | p24 | $17^{th}$ | U | A | $16^{th}$ | n/a | wc | wc | n/a |
| p18 | p23 | $18^{th}$ | G | U/C* | $17^{th}$ | n/a | wb/wc* | wb/wc | mm |
| p19 | p22 | $19^{th}$ | A/U* | U/C* | n/a | n/a | wc/mm* | mm | wb |
| p20 | p21 | n/a | G/A* | U/A* | n/a | n/a | connected | connected | n/a |

Fig. 9

| | Top 10 isoforms read count | agshRNA-273 seq:<br>AGCGGCGAGAGCTGCAGCTGCTGCTGCAGCTCTCGCCGCC | % of isoforms reads count > 50 |
|---|---|---|---|
| 5p | 4718 | AGCGGCGAGAGCTGCAGCTGCTGCTGCAGC | 54.35 |
| | 1045 | CGGCGAGAGCTGCAG | 12.04 |
| | 669 | AGCGGCGAGAGCTGCAGCTGCTGCTGCAGT | 7.71 |
| | 389 | AGCGGCGAGAGCTGCAGCTGCTGCTGCAG | 4.48 |
| | 322 | AGCGGCGAGAGCTGCAGCTGC | 3.71 |
| | 222 | AGCGGCGAGAGCTGCAGCTGCTGCTGCAGA | 2.56 |
| | 181 | CGGCGAGAGCTGCAGC | 2.09 |
| | 133 | AGCGGCGAGAGCTGCAGCTGCTGCTGCAGCTTT | 1.53 |
| | 118 | AGCGGCGAGAGCTGCAGCTGCTGCTGCAGCA | 1.36 |
| | 104 | AGCGGCGAGAGCTGCAGCTGCTGCTGCAGCAT | 1.20 |
| 3p | 63 | CTGCTGCAGCTCTCGCCGCC | |
| | 33 | GCTGCTGCAGCTCTCGCCGCC | |
| | 30 | CTGCTGCAGCTCTCGCCGC | |
| | 29 | TGCTGCAGCTCTCGCCGCCTTT | |
| | 22 | GCTGCTGCAGCTCTCGCCGC | |
| | 17 | CTGCTGCAGCTCTCGCCGCT | |
| | 17 | CTGCTGCAGCTCTCGCCGTT | |
| | 15 | CTGCTGCAGCTCTCGCCGCCTTT | |
| | 14 | TGCTGCAGCTCTCGCCGCC | |
| | 13 | CTGCTGCAGCTCTCGCCGCCT | |

| | Top 10 isoforms read count | agshRNA-359 seq:<br>CTCCTCGCGGTCTTGCTGGCCACAGCAAGACCGCGAGGAC | % of isoforms reads count > 50 |
|---|---|---|---|
| 5p | 18715 | CTCCTCGCGGTCTTGCTGGCCACAGC | 57.93 |

Fig. 9 continued

| | | |
|---|---|---|
| | 3037 | CTCCTCGCGGTCTTGCTGGCCACAG | 9.40 |
| | 1814 | CTCCTCGCGGTCTTGCTGGCCACA | 5.61 |
| | 920 | CTCCTCGCGGTCTTGCTGGC | 2.85 |
| | 811 | CTCCTCGCGGTCTTGCTGGCCAC | 2.51 |
| | 793 | CTCCTCGCGGTCTTGCTGGCCACAGC | 2.45 |
| | 773 | CTCCTCGCGGTCTTGCTGGCCACAGCAAT | 2.39 |
| | 753 | CTCCTCGCGGTCTTGCTGGCCACAGCAAG | 2.33 |
| | 551 | CTCCTCGCGGTCTTGCTGGCCACAGT | 1.71 |
| | 323 | CTCCTCGCGGTCTTGCTGGCCACAGCA | 1.00 |
| | 26 | CTCCTCGCGGTCTTGCTGGCCACAGCAAGACCGCGAGGA | |
| | 8 | TCGCGGTCTTGCTGGCCACAGCAAGACCGCGAGG | |
| | 5 | CTCCTCGCGGTCTTGCTGGCCACAGCAAGACCGCGAGG | |
| | 4 | ACAGCAAGACCGCGAGGACTGT | |
| | 3 | CAGCAAGACCGCGAGGACTGT | |
| 3p | 3 | CCACAGCAAGAC | |
| | 2 | CAGCAAGACCGCGAGGACTTT | |
| | 2 | ACAGCAAGACCGCGAGGACTTT | |
| | 2 | CAGCAAGACCGCGAGGACTTTGA | |
| | 2 | ACAGCAAGACCGCGAGGACTTTAG | |

| Top 10 isoforms read count | agshRNA-484 seq:<br><br>TGCCAGATATCATGGTACTCGAGTACCATGATATCTGGCC | % of isoforms reads count > 50 |
|---|---|---|
| | 32607 | CTGCCAGATATCATGGTACTCGAGTACCATGA | 43.04 |
| | 11395 | CTGCCAGATATCATGGTACTCGAGTACCATG | 15.04 |
| | 8021 | TGCCAGATATCATGGTACTCGAGTACCATG | 10.59 |
| | 2378 | CTGCCAGATATCATGGTACTCGAGTACCATGAT | 3.14 |
| 5p | 2331 | CTGCCAGATATCATGGTACTCGAGTACCAT | 3.08 |
| | 2300 | GCCAGATATCATGGTACTCGAGTACCATGAT | 3.04 |
| | 2203 | TGCCAGATATCATGGTACTCGAGTACCATGT | 2.91 |
| | 2186 | CTGCCAGATATCATGGTACTCGAGTACCATGT | 2.89 |
| | 1960 | GCCAGATATCATGGTACTCGAGTACCAT | 2.59 |

Fig. 9 continued

|    | 1166  | CTGCCAGATATCATGGTACTCGAG             | 1.54 |
|----|-------|--------------------------------------|------|
|    | 21042 | TCGAGTACCATGATATCTG                  |      |
|    | 5032  | TCGAGTACCATGATATCTGT                 |      |
|    | 2196  | GCCAGATATCATGGTACTCGAGTACCATGAT       |      |
|    | 2031  | TCGAGTACCATGATATCTGA                 |      |
| 3p | 770   | GTACCATGATATCTGGCCC                  |      |
|    | 752   | TCGAGTACCATGATATCTGTT                |      |
|    | 567   | CGAGTACCATGATATCTG                   |      |
|    | 544   | GAGTACCATGATATCTG                    |      |
|    | 374   | CCAGATATCATGGTACTCGAGTACCATGAT        |      |
|    | 368   | TCGAGTACCATGATATCTGG                 |      |

| | Top 10 isoforms read count | agshRNA-541 seq:<br><br>CTTGGAGAGGTCCACCTCCTCGGAGGTGGACCTCTCCAAC | % of isoforms reads count > 50 |
|----|------|-------------------------------------------------|-------|
|    | 3022 | CTTGGAGAGGTCCACCTCCTCGGAGGTGGAT                 | 32.67 |
|    | 2686 | CTTGGAGAGGTCCACCTCCTCGGAGGTGGA                  | 29.04 |
|    | 1082 | CTTGGAGAGGTCCACCTCCTCGGAGGTGG                   | 11.70 |
|    | 715  | CTTGGAGAGGTCCACCTCCTCGGAGGTGGAA                 | 7.73  |
| 5p | 540  | CCTTGGAGAGGTCCACCTCCTCGGAGGTGGAC                | 5.84  |
|    | 232  | CTTGGAGAGGTCCACCTCCTCGGAGGTGGATT                | 2.51  |
|    | 207  | TTGGAGAGGTCCACCTCCTCGGAGGTGG                    | 2.24  |
|    | 191  | CCTTGGAGAGGTCCACCTCCTCGGAGGTGGACT               | 2.07  |
|    | 120  | CTTGGAGAGGTCCACCTCCTCGGAGGTGGAT                 | 1.30  |
|    | 103  | CCTTGGAGAGGTCCACCTCCTCGGAGGTGGAT                | 1.11  |
|    | 174  | TCGGAGGTGGACCTCTCCAAC                           |       |
|    | 130  | TGGACCTCTCCAAC                                  |       |
|    | 88   | GAGGTGGACCTCTCCATT                              |       |
| 3p | 70   | GGAGGTGGACCTCTCCATT                             |       |
|    | 53   | TCGGAGGTGGACCTCTCCATT                           |       |
|    | 49   | GGAGGTGGACCTCTCCACC                             |       |
|    | 44   | GAGGTGGACCTCTCCA                                |       |

Fig. 9 continued

| | 41 | CGGAGGTGGACCTCTCCATT | |
|---|---|---|---|
| | 40 | GAGGTGGACCTCTCCAC | |
| | 32 | TGGACCTCTCCA | |

| | Top 10 isoforms read count | agshRNA-829 seq:<br><br>TGCCTTCTTCTTGACACAAGGCTGTGTCAAGAAGAAGGCC | % of isoforms reads count > 50 |
|---|---|---|---|
| 5p | 1102 | TGCCTTCTTCTTGACACAAGGCTGTGT | 15.52 |
| | 652 | CTGCCTTCTTCTTGACACAAGGC | 9.18 |
| | 545 | GCCTTCTTCTTGACACAAGGCTGTGTCAAGAAGAAGGCC | 7.68 |
| | 422 | GCCTTCTTCTTGACACAAGGCTGTGTC | 5.94 |
| | 335 | GCCTTCTTCTTGACACAAGGCTGTGTCAAGAAGAAGGAT | 4.72 |
| | 334 | TGCCTTCTTCTTGACACAAGGCTG | 4.70 |
| | 284 | CTGCCTTCTTCTTGACACAAGGCTG | 4.00 |
| | 273 | TGCCTTCTTCTTGACACAAGGCTGTG | 3.85 |
| | 262 | GCCTTCTTCTTGACACAAGGCTGTG | 3.69 |
| | 205 | CTGCCTTCTTCTTGACACAAGGCT | 2.89 |
| 3p | 12286 | GCTGTGTCAAGAAGAAGGCCT | 22.29 |
| | 8970 | GCTGTGTCAAGAAGAAGGCCTT | 16.27 |
| | 6850 | GCTGTGTCAAGAAGAAGGCCTTT | 12.43 |
| | 2037 | GCTGTGTCAAGAAGAAGGCCA | 3.70 |
| | 2033 | GGCTGTGTCAAGAAGAAG | 3.69 |
| | 1836 | AGGCTGTGTCAAGAAGAAG | 3.33 |
| | 1612 | GCTGTGTCAAGAAGAAGGCCC | 2.92 |
| | 1340 | GCTGTGTCAAGAAGAAGGCCTTA | 2.43 |
| | 1291 | GCTGTGTCAAGAAGAAGGCCTA | 2.34 |
| | 1160 | GCTGTGTCAAGAAGAAGGCCTTTT | 2.10 |

Fig. 9 continued

| Top 10 isoforms read count | | agshRNA-1001 seq:<br><br>TCTGCTAATAAGTTCATTAGAAAATGAACTTATTAGCAGC | % of isoforms reads count > 50 |
|---|---|---|---|
| 5p | 8524 | CTCTGCTAATAAGTTCATTAGA | 32.43 |
| | 7430 | CTCTGCTAATAAGTTCATTAGAAAATGAACTT | 28.27 |
| | 2700 | TCTGCTAATAAGTTCATTAGA | 10.27 |
| | 1782 | CTCTGCTAATAAGTTCATTAGAAAATGAACTTATTAGCA | 6.78 |
| | 991 | CTCTGCTAATAAGTTCATTAGAAAATGA | 3.77 |
| | 843 | CTCTGCTAATAAGTTCATTAGAAAATGAACT | 3.21 |
| | 545 | TCTGCTAATAAGTTCATTAG | 2.07 |
| | 536 | CTCTGCTAATAAGTTCATTAGAA | 2.04 |
| | 463 | CTCTGCTAATAAGTTCATTAGAAA | 1.76 |
| | 433 | CTCTGCTAATAAGTTCATTAGAAAAT | 1.65 |
| 3p | 36 | TAGAAAATGAACTTATTAGCAGC | |
| | 26 | ATGAACTTATTAGCAGC | |
| | 19 | GAACTTATTAGCAGC | |
| | 18 | GAAAATGAACTTATTAGCAGC | |
| | 11 | AAAATGAACTTATTAGCAGC | |
| | 10 | TAGAAAATGAACTTATTAGCAGCT | |
| | 9 | AGAAAATGAACTTATTAGCAGC | |
| | 9 | GCTAATAAGTTCATTAGAAAATGAACTTATTAGCAGC | |
| | 8 | AAAATGAACTTATTAGCAGCT | |
| | 6 | TTAGAAAATGAACTTATTAGCAGC | |

| Top 10 isoforms read count | | agshRNA-1111 seq:<br><br>CTGTTCTATCCGAACAGCATTGGCTGTTCGGATAGAACAC | % of isoforms reads count > 50 |
|---|---|---|---|
| 5p | 1868 | CTGTTCTATCCGAACAGCATTGGCTGTTCGT | 24.67 |

Fig. 9 continued

|   | | | |
|---|---:|---|---:|
|   | 1272 | CTGTTCTATCCGAACAGCATTGGCTGTTCG | 16.80 |
|   | 684 | CCTGTTCTATCCGAACAGCATTGGCTGTTCGG | 9.03 |
|   | 610 | CTGTTCTATCCGAACAGCATTGGCTGTTCGTTT | 8.06 |
|   | 471 | CTGTTCTATCCGAACAGCATTGGCTGTTCGGATAGAACA | 6.22 |
|   | 331 | CTGTTCTATCCGAACAGCATTGGC | 4.37 |
|   | 327 | CTGTTCTATCCGAACAGCATTGGCTGTTCGTT | 4.32 |
|   | 229 | CTGTTCTATCCGAACAGCATTGGCTGTTCGTAT | 3.02 |
|   | 174 | TGTTCTATCCGAACAGCATTGGCTG | 2.30 |
|   | 169 | CTGTTCTATCCGAACAGCATTGGCTGTTCGA | 2.23 |
| 3p | 1137 | TTGGCTGTTCGGATAGAA | |
|   | 495 | TGGCTGTTCGGATAGAAC | |
|   | 472 | CTGTTCTATCCGAACAGCATTGGCTGTTCGGATAGAAC | |
|   | 337 | TTGGCTGTTCGGATAGAACA | |
|   | 303 | TTGGCTGTTCGGATAGAACACT | |
|   | 243 | TGGCTGTTCGGATAGAACA | |
|   | 213 | TTGGCTGTTCGGATAGA | |
|   | 206 | TGGCTGTTCGGATAGAACACT | |
|   | 148 | TTGGCTGTTCGGATAGAACT | |
|   | 122 | TTGGCTGTTCGGATAGAA | |

|   | Top 10 isoforms read count | agshRNA-1207 seq:<br><br>CAGCATAAGTCTGTCTGCCCACAGCAGACAGACTTATGCTC | % of isoforms reads count > 50 |
|---|---:|---|---:|
|   | 4105 | CAGCATAAGTCTGTCTGCCACAGC | 26.39 |
|   | 3665 | CAGCATAAGTCTGTCTGCCACAGCAGACAG | 23.56 |
|   | 1175 | CCAGCATAAGTCTGTCTGCCACAGC | 7.55 |
|   | 1124 | CAGCATAAGTCTGTCTGCCACAG | 7.23 |
| 5p | 915 | AGCATAAGTCTGTCTGCCACAGCAGACA | 5.88 |
|   | 868 | AGCATAAGTCTGTCTGCCACAGC | 5.58 |
|   | 585 | AGCATAAGTCTGTCTGCCACAGCAG | 3.76 |
|   | 470 | CAGCATAAGTCTGTCTGCCACAGCAGACAGT | 3.02 |
|   | 386 | CCAGCATAAGTCTGTCTGCCACAGCAGACAG | 2.48 |
|   | 312 | CAGCATAAGTCTGTCTGCCACAGCAGACA | 2.01 |
| 3p | 535 | GCAGACAGACTTATGCTC | |

Fig. 9 continued

| | | | |
|---|---|---|---|
| 192 | GCAGACAGACTTATGCTCC | |
| 108 | CAGACAGACTTATGCTC | |
| 79 | GCAGACAGACTTATGCTCA | |
| 66 | GCAGACAGACTTATGCTCT | |
| 56 | GCAGACAGACTTATGC | |
| 56 | ACAGCAGACAGACTT | |
| 26 | GCAGACAGACTTATGCT | |
| 20 | ACAGCAGACAGACTTATGCTCC | |
| 18 | CAGACAGACTTATGCTCA | |

Fig. 11
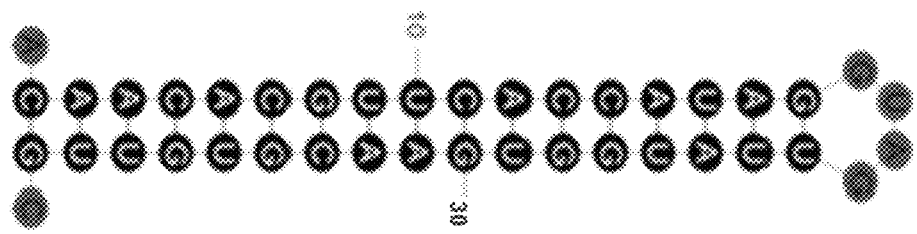
agsiRNA-887
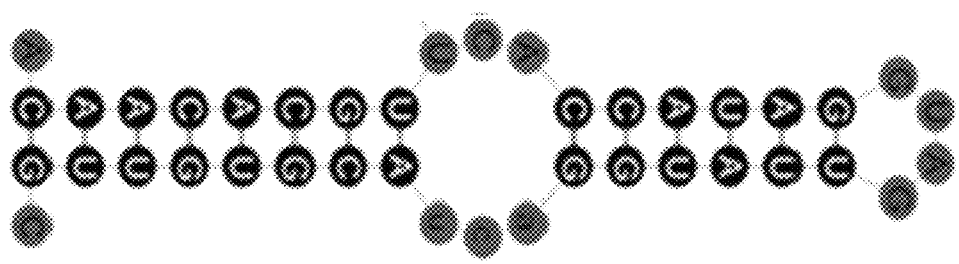
agsiRNA-887-mut
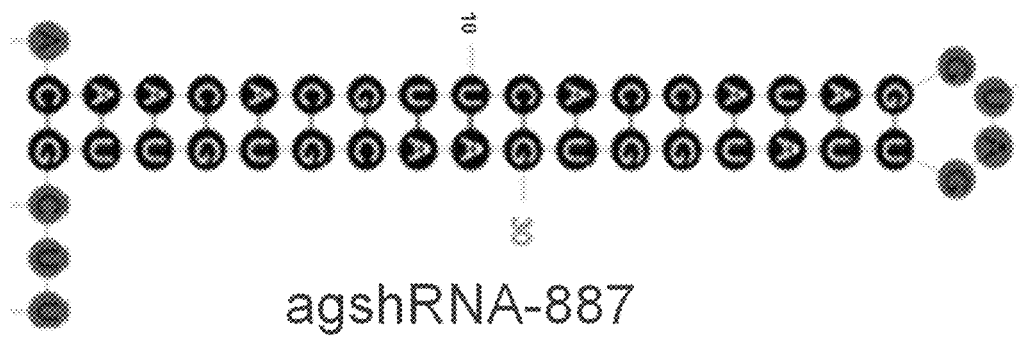
agshRNA-887

| shRNAs, siRNAs | | SEQ ID NOs |
|---|---|---|
| Name | Sequence | |
| agshRNA-scramble-control | GATCAGCGTTCTACACTCGACGTACTTGTCGAGTGTAGAACGCcTTTTTTCGA | SEQ ID NO: 1 |
| RRM2-agshRNA-279 | GATCCTTCAGCGGCGAGAGCTGCAGCTAGCTCTCGCCGCTGAACTTTTTTCGA | SEQ ID NO: 2 |
| RRM2-agshRNA-366 | GATCGAAGATCCTCCTCGCGGTCTTGGCCGCGAGGAGGATCTTATTTTTTCGA | SEQ ID NO: 3 |
| RRM2-agshRNA-488 | GATCATCTGCCAGATATCATGGTACTTCATGATATCTGGCAGACTTTTTTCGA | SEQ ID NO: 4 |
| RRM2-agshRNA-490 | GATCACATCTGCCAGATATCATGGTAGTGATATCTGGCAGATGCTTTTTTCGA | SEQ ID NO: 5 |
| RRM2-agshRNA-497 | GATCTTCTTATACATCTGCCAGATATATGGCAGATGTATAAGACTTTTTTCGA | SEQ ID NO: 6 |
| RRM2-agshRNA-534 | GATCGTCCACCTCCTCGGCGGTCCAAGCCGCCGAGGAGGTGGAATTTTTTCGA | SEQ ID NO: 7 |
| RRM2-agshRNA-632 | GATCACTATGCCATCGCTTGCTGCAAGGCAAGCGATGGCATAGCTTTTTTCGA | SEQ ID NO: 8 |
| RRM2-agshRNA-632-mmp7 | GATCACTATGCCATCGCTTGCTGCAAGGCAAGCGATGcCATAGCTTTTTTCGA | SEQ ID NO: 9 |
| RRM2-agshRNA-632-GU | GATCACTATGCCATCGCTTGCTGCAAGGCAAGCGATGGtATAGCTTTTTTCGA | SEQ ID NO: 10 |
| RRM2-agshRNA-634 | GATCTTACTATGCCATCGCTTGCTGCTAAGCGATGGCATAGTACTTTTTTCGA | SEQ ID NO: 11 |
| RRM2-agshRNA-883 | GATCCACGTTCACCATAGGTAGCCTCTTACCTATGGTGAACGTCTTTTTTCGA | SEQ ID NO: 12 |
| RRM2-agshRNA-887 | GATCACAACACGTTCACCATAGGTAGTTATGGTGAACGTGTTGCTTTTTTCGA | SEQ ID NO: 13 |
| RRM2-agshRNA-887-mut | GATCACAACACGTTCACCATAGGTAGTTATGGactACGTGTTGCTTTTTTCGA | SEQ ID NO: 14 |
| RRM2-agshRNA-887-mmp6 | GATCACAACACGTTCACCATAGGTAGTTATGGTGAACGaGTTGCTTTTTTCGA | SEQ ID NO: 15 |
| RRM2-agshRNA-887-mmp7 | GATCACAACACGTTCACCATAGGTAGTTATGGTGAACcTGTTGCTTTTTTCGA | SEQ ID NO: 16 |
| RRM2-agshRNA-887-mmp8 | GATCACAACACGTTCACCATAGGTAGTTATGGTGAgGTGTTGCTTTTTTCGA | SEQ ID NO: 17 |
| RRM2-agshRNA-887-mmp13 | GATCACAACACGTTCACCATAGGTAGTTATGcTGAACGTGTTGCTTTTTTCGA | SEQ ID NO: 18 |
| RRM2-agshRNA-887-mmp14 | GATCACAACACGTTCACCATAGGTAGTTATcGTGAACGTGTTGCTTTTTTCGA | SEQ ID NO: 19 |
| RRM2-agshRNA-887-mmp15 | GATCACAACACGTTCACCATAGGTAGTTAaGGTGAACGTGTTGCTTTTTTCGA | SEQ ID NO: 20 |
| RRM2-agshRNA-887-Bulge-p7 | GATCACAACACGTTCACCATAGGTAGTTATGGTGAAC-TGTTGCTTTTTTCGA | SEQ ID NO: 21 |
| RRM2-agshRNA-887-NL | GATCACAACACGTTCACCATAGGCCTATGGTGAACGTGTTGTTTTTTTCGA | SEQ ID NO: 22 |
| RRM2-agshRNA-887-S14 | GATCACAACACGTTCACCATAGGTGGTGAACGTGTTGCTTTTTTCGA | SEQ ID NO: 23 |
| RRM2-agshRNA-887-S15 | GATCACAACACGTTCACCATAGGTATGGTGAACGTGTTGCTTTTTTCGA | SEQ ID NO: 24 |
| RRM2-agshRNA-887-S16 | GATCACAACACGTTCACCATAGGTATATGGTGAACGTGTTGCTTTTTTCGA | SEQ ID NO: 25 |
| RRM2-agshRNA-887-S18 | GATCACAACACGTTCACCATAGGTAGTTCTATGGTGAACGTGTTGCTTTTTTCGA | SEQ ID NO: 26 |
| RRM2-agshRNA-887-S19 | GATCACAACACGTTCACCATAGGTAGTTACCTATGGTGAACGTGTTGCTTTTTTCGA | SEQ ID NO: 27 |
| RRM2-agshRNA-887-S20 | GATCACAACACGTTCACCATAGGTAGTTATACCTATGGTGAACGTGTTGCTTTTTTCGA | SEQ ID NO: 28 |
| agsiRNA-scramble-control | AGCGUUCUACACUCGACGUACUUGUCGAGUGUAGAACGCC | SEQ ID NO: 29 |
| RRM2-agsiRNA-887(wt,L40,S17) | ACAACACGUUCACCAUAGGUAGUUAUGGUGAACGUGUUGC | SEQ ID NO: 30 |

Fig. 28 continued

| | | |
|---|---|---|
| ⁵ⓅーRRM2-agsiRNA-887 | ⁵Ⓟ-ACAACACGUUCACCAUAGG*UA*GUUAUGGUGAACGUGUUGC | SEQ ID NO: 31 |
| RRM2-agsiRNA-887-mut | ACAACACGUUCACCAUAGG*UA*GUUAUGGacuACGUGUUGc | SEQ ID NO: 32 |
| RRM2-agsiRNA-887-p18GC | ACAACACGUUCACCAUAGG*UA*GcUAUGGUGAACGUGUUGC | SEQ ID NO: 33 |
| RRM2-agsiRNA-887-mmp2 | ACAACACGUUCACCAUAGG*UA*GUUAUGGUGAACGUGUUcC | SEQ ID NO: 34 |
| RRM2-agsiRNA-887-mmp2-3 | ACAACACGUUCACCAUAGG*UA*GUUAUGGUGAACGUGUccC | SEQ ID NO: 35 |
| RRM2-agsiRNA-887-mmp6 | ACAACACGUUCACCAUAGG*UA*GUUAUGGUGAACGaGUUGC | SEQ ID NO: 36 |
| RRM2-agsiRNA-887-mmp7 | ACAACACGUUCACCAUAGG*UA*GUUAUGGUGAACcUGUUGC | SEQ ID NO: 37 |
| RRM2-agsiRNA-887-mmp16 | ACAACACGUUCACCAUAGG*UA*GgUAUGGUGAACGUGUUGC | SEQ ID NO: 38 |
| RRM2-agsiRNA-887-mmp17-18 | ACAACACGUUCACCAUAGG*UA*GgaUGGUGAACGUGUUGC | SEQ ID NO: 39 |
| RRM2-agsiRNA-887-mmp16-17-18 | ACAACACGUUCACCAUAGG*UA*GgauUGGUGAACGUGUUGC | SEQ ID NO: 40 |
| RRM2-agsiRNA-887-3L12 | AACGUGUUGCUU | SEQ ID NO: 41 |
| RRM2-agsiRNA-5a887 | aACAACACGUUCACCAUAGG*UA*GUUAUGGUGAACGUGUUGC | SEQ ID NO: 42 |
| RRM2-agsiRNA-5aa887 | aaACAACACGUUCACCAUAGG*UA*GUUAUGGUGAACGUGUUGC | SEQ ID NO: 43 |
| RRM2-agsiRNA-5aaa887 | aaaACAACACGUUCACCAUAGG*UA*GUUAUGGUGAACGUGUUGC | SEQ ID NO: 44 |
| RRM2-agsiRNA-5aaaa887 | aaaaACAACACGUUCACCAUAGG*UA*GUUAUGGUGAACGUGUUGC | SEQ ID NO: 45 |
| RRM2-sshRNA887 | ACAACACGUUCACCAUAGG*uu*CCUAUGGUGAACGUGUUGU | SEQ ID NO: 46 |
| RRM2-agsiRNA-887-NL | ACAACACGUUCACCAUAGGCCUAUGGUGAACGUGUUGU | SEQ ID NO: 47 |
| RRM2-agsiRNA-887-Ux5 | ACAACACGUUCACCAUAGG*UA*GUUAUGGUGAACGUGUUGCUUUUU | SEQ ID NO: 48 |
| RRM2-agsiRNA-887-U | ACAACACGUUCACCAUAGG*UA*GUUAUGGUGAACGUGUUGCU | SEQ ID NO: 49 |
| RRM2-agsiRNA-887-UU | ACAACACGUUCACCAUAGG*UA*GUUAUGGUGAACGUGUUGCUU | SEQ ID NO: 50 |
| RRM2-agsiRNA-887-dTdT | ACAACACGUUCACCAUAGG*UA*GUUAUGGUGAACGUGUUGCdTdT | SEQ ID NO: 51 |
| RRM2-agsiRNA-887-ddC | ACAACACGUUCACCAUAGG*UA*GUUAUGGUGAACGUGUUGddC | SEQ ID NO: 52 |
| RRM2-agsiRNA-887-S11 | ACAACACGUUCACCAU*G*GAACGUGUUG | SEQ ID NO: 53 |
| RRM2-agsiRNA-887-S12 | ACAACACGUUCACCAU*AG*UGAACGUGUUG | SEQ ID NO: 54 |
| RRM2-agsiRNA-887-S13 | ACAACACGUUCACCAU*AGG*UGAACGUGUUG | SEQ ID NO: 55 |
| RRM2-agsiRNA-887-S14 | ACAACACGUUCACCAU*AGGU*GUGAACGUGUUGC | SEQ ID NO: 56 |
| RRM2-agsiRNA-887-S15 | ACAACACGUUCACCAU*AGGUA*UGGUGAACGUGUUGC | SEQ ID NO: 57 |
| RRM2-agsiRNA-887-S16 | ACAACACGUUCACCAU*AGGUAU*AUGGUGAACGUGUUGC | SEQ ID NO: 58 |
| RRM2-agsiRNA-887-L25 | ACAACACGUUCACCAUAGG*UA*GUUA | SEQ ID NO: 59 |
| RRM2-agsiRNA-887-L27 | ACAACACGUUCACCAUAGG*UA*GUUAUG | SEQ ID NO: 60 |
| RRM2-agsiRNA-887-L29 | ACAACACGUUCACCAUAGG*UA*GUUAUGGU | SEQ ID NO: 61 |
| RRM2-agsiRNA-887-L30 | ACAACACGUUCACCAUAGG*UA*GUUAUGGUG | SEQ ID NO: 62 |

Fig. 28 continued

| Name | Sequence | SEQ ID NO |
|---|---|---|
| RRM2-agsiRNA-887-L35 | ACAACACGUUCACCAUAGG*UA*GUUAUGGUGAACGU | SEQ ID NO: 63 |
| RRM2-agsiRNA-887-L37 | ACAACACGUUCACCAUAGG*UA*GUUAUGGUGAACGUGU | SEQ ID NO: 64 |
| RRM2-agsiRNA-887-L38 | ACAACACGUUCACCAUAGG*UA*GUUAUGGUGAACGUGUU | SEQ ID NO: 65 |
| RRM2-agsiRNA-887-L39 | ACAACACGUUCACCAUAGG*UA*GUUAUGGUGAACGUGUUG | SEQ ID NO: 66 |
| RRM2-agsiRNA-887-LP451 | ACAACACGUUCACCAUAG*aguu*UUAUGGUGAACGUGUUGC | SEQ ID NO: 67 |
| RRM2-agsiRNA-5U887 | uCAACACGUUCACCAUAGG*UA*GUUAUGGUGAACGUGUUGC | SEQ ID NO: 68 |
| RRM2-agsiRNA-5C887 | cCAACACGUUCACCAUAGG*UA*GUUAUGGUGAACGUGUUGC | SEQ ID NO: 69 |
| 5siRNA-887 | ACAACACGUUCACCAUAGGUA | SEQ ID NO: 70 |
| 3siRNA-887 | CCUAUGGUGAACGUGUUGUag | SEQ ID NO: 71 |
| 5rsiRNA-887 | ACAACACGUUCACCAUAGGUA | SEQ ID NO: 72 |
| 3rsiRNA-887 | ACUACCUAUGGUGAACGUGUU | SEQ ID NO: 73 |
| RRM2-agshRNA-1148 | ATGAGCTTCACAGGCAAGGCC*T*ATTGCCTGTGAAGCTCAC*TTTTT* | SEQ ID NO: 74 |
| RRM2-agshRNA-1148-mmp7 | ATGAGCTTCACAGGCAAG*g*CC*T*ATTGCCTGTGA*c*GCTCAC*TTTTT* | SEQ ID NO: 75 |
| RRM2-agshRNA-1148-GU | ATGAGCTTCACAGGCAAGGCC*T*ATTG*t*CTGTGAAG*t*CAC*TTTTT* | SEQ ID NO: 76 |
| RRM2-agshRNA-1148-mut | ATGAGCTTC*tgt*GGCAAGGCC*T*ATTGCC*aca*GAAGCTCAC*TTTTT* | SEQ ID NO: 77 |
| RRM2-agsiRNA-1148 | AUGAGCUUCACAGGCAAGGCC*U*AUUGCCUGUGAAGCUCAC | SEQ ID NO: 78 |
| RRM2-agsiRNA-1148-mmp7 | AUGAGCUUCACAGGCAAGGCC*U*AUUGCCUGUGAcGCUCAC | SEQ ID NO: 79 |
| RRM2-agsiRNA-1148-GU | AUGAGCUUCACAGGCAAGGCC*U*AUUGuCUGUGAAGuUCAC | SEQ ID NO: 80 |
| RRM2-agsiRNA-1148-mut | AUGAGCUUC*ugu*GGCAAGGCC*U*AUUGCC*aca*GAAGCUCAC | SEQ ID NO: 81 |
| RRM2-agsiRNA-1148-LP451 | AUGAGCUUCACAGGCAA*gaguuu*UUGCCUGUGAAGCUCAC | SEQ ID NO: 82 |
| RRM2-agsiRNA-1148-LP887 | AUGAGCUUCACAGGCAA*gguagc*UUGCCUGUGAAGCUCAC | SEQ ID NO: 83 |
| RRM2-agshRNA-1354 | AATTCTCTGTTGGACTTGA*CA*TTAAGTCCAACAGAGAATC*TTTTT* | SEQ ID NO: 84 |
| RRM2-agshRNA-1354-mmp7 | AATTCTCTGTTGGACTTGA*CA*TTAAGTCCAACAcAGAATC*TTTTT* | SEQ ID NO: 85 |
| RRM2-agshRNA-1354-GU | AATTCTCTGTTGGACTTGA*CA*TTAAGTCCAAtAGAGAATC*TTTTT* | SEQ ID NO: 86 |
| RRM2-agsiRNA-1354 | AAUUCUCUGUUGGACUUGA*CA*UUAAGUCCAACAGAGAAUC | SEQ ID NO: 87 |
| RRM2-agsiRNA-1354-mmp7 | AAUUCUCUGUUGGACUUGA*CA*UUAAGUCCAACAcAGAAUC | SEQ ID NO: 88 |
| RRM2-agsiRNA-1354-GU | AAUUCUCUGUUGGACUUGA*CA*UUAAGUCCAAuAGAGAAUC | SEQ ID NO: 89 |
| RRM2-agsiRNA-1354-LP451 | AAUUCUCUGUUGGACUU*caguuu*AAGUCCAACAGAGAAUC | SEQ ID NO: 90 |
| RRM2-agsiRNA-1354-LP887 | AAUUCUCUGUUGGACUU*gguagc*AAGUCCAACAGAGAAUC | SEQ ID NO: 91 |
| hmiR-451 | AAACCGUUACCAUUACUGAGUUUAGUAAUGGUAAUGGUUC | SEQ ID NO: 92 |
| mmiR-451 | AAACCGUUACCAUUACUGAGUUUAGUAAUGGUAAcGGUUC | SEQ ID NO: 93 |
| dmiR-451 | AAACCGUUACCAUUACUGAGUUUAGUAAUGGUAAgGGUUC | SEQ ID NO: 94 |

Fig. 28 continued

| | | |
|---|---|---|
| hmiR-451-LP887 | AAACCGUUACCAUUACUGguagUAGUAAUGGUAAuGGUUC | SEQ ID NO: 95 |
| 5siRNA-451 | AAACCGUUACCAUUACUGAgu | SEQ ID NO: 96 |
| 3siRNA-451 | UCAGUAAUGGUAACGGUUUcu | SEQ ID NO: 97 |
| RRM1-agshRNA-481mmp6 | AGCCAAAGTATCTAGTTCCACTGAACTAGATACTaTGGCc | SEQ ID NO: 98 |
| RRM1-agsiRNA-481mmp6 | AGCCAAAGUAUCUAGUUCCACUGAACUAGAUACUaUGGCc | SEQ ID NO: 99 |
| RRM1-agshRNA-869 | ATATCCAATGTTGACTTGGCCAtAAGTCAACATTGGATAc | SEQ ID NO: 100 |
| RRM1-agsiRNA-869 | AUAUCCAAUGUUGACUUGGCCAuAAGUCAACAUUGGAUAc | SEQ ID NO: 101 |
| RRM1-agshRNA-2290 | ATTGCATGCAATAATCTGCTATTAGATTATTGCATGCAAc | SEQ ID NO: 102 |
| RRM1-agsiRNA-2290 | AUUGCAUGCAAUAAUCUGCUAUUAGAUUAUUGCAUGCAAc | SEQ ID NO: 103 |
| RRM2B-agshRNA-445mmp6 | ATCCTTTGATAAGTCGACCTCTGTCGACTTATCtAAGGAc | SEQ ID NO: 104 |
| RRM2B-agsiRNA-445mmp6 | AUCCUUUGAUAAGUCGACCUCUGUCGACUUAUCuAAGGAc | SEQ ID NO: 105 |
| RRM2B-agshRNA-948 | AAGTATTGGAACATCAGGCAAGTCTGATGTTCCAATACTc | SEQ ID NO: 106 |
| RRM2B-agsiRNA-948 | AAGUAUUGGAACAUCAGGCAAGUCUGAUGUUCCAAUACUc | SEQ ID NO: 107 |
| RRM2B-agshRNA-1061 | AATTCATTCCAATGAGGCCAACGCCTCATTGGAATGAATc | SEQ ID NO: 108 |
| RRM2B-agsiRNA-1061 | AAUUCAUUCCAAUGAGGCCAACGCCUCAUUGGAAUGAAUc | SEQ ID NO: 109 |
| Northern blotting probes | | |
| Names of probes | Sequences | SEQ ID NOs: |
| U6 | TATGGAACGCTTCTCGAATT | SEQ ID NO: 110 |
| U2 | AGAACAGATACTACACTTGA | SEQ ID NO: 111 |
| sli-siRNA-887-5pp | CTACCTATGGTGAACGTGTTGT | SEQ ID NO: 112 |
| sli-siRNA-887-3pp | GCAACACGTTCACCATAA | SEQ ID NO: 113 |
| sli-siRNA-1148-5pp | AGGCCTTGCCTGTGAAGCTCAT | SEQ ID NO: 114 |
| sli-siRNA-1148-3pp | GTGAGCTTCACAGGCAAT | SEQ ID NO: 115 |
| miR-21p | TCAACATCAGTCTGATAAGCTA | SEQ ID NO: 116 |
| miR-31p | CAGCTATGCCAGCATCTTGCC | SEQ ID NO: 117 |
| miR-143p | GAGCTACAGTGCTTCATCTCA | SEQ ID NO: 118 |
| miR-ID primers | | |
| Names | Sequences | SEQ ID NOs: |
| miR-ID-RT21-5p | TCAGTCTGAT | SEQ ID NO: 119 |
| miR-ID-F21-5p | GACTGATGTTGATAGCTT | SEQ ID NO: 120 |
| miR-ID-R21-5p | CTATCAACATCAGTCTGA | SEQ ID NO: 121 |
| miR-ID-RT143-5P | ACAGTGCTTC | SEQ ID NO: 122 |
| miR-ID-F143-5P | GCACTGTAGCTCTGAGAT | SEQ ID NO: 123 |

Fig. 28 continued

| Names | Sequences | SEQ ID NOs |
|---|---|---|
| miR-ID-R143-5P | TCAGAGCTACAGTGCTTC | SEQ ID NO: 124 |
| miR-ID-RT31-5p | TGCCAGCATC | SEQ ID NO: 125 |
| miR-ID-F31-5p | GCTGGCATAGCTgaAGGC | SEQ ID NO: 126 |
| miR-ID-R31-5p | TtcAGCTATGCCAGCATC | SEQ ID NO: 127 |
| miR-ID-RT-U6RNA | ATGGAACGCTTCACGAATTTG | SEQ ID NO: 128 |
| miR-ID-f-U6RNA | CCATATTTTGTGCTCGCTTCGG | SEQ ID NO: 129 |
| miR-ID-r-U6RNA | GAAGCGAGCACAAAATATGGAA | SEQ ID NO: 130 |
| qPCR primers | | |
| Names | Sequences | SEQ ID NOs |
| IRF9-F | GACTTGGTCAGGTACTTTCAGG | SEQ ID NO: 131 |
| IRF9-R | TCTACACCAGGGACAGAATG | SEQ ID NO: 132 |
| IFITM1-F | CCAAAGCCAGAAGATGCAC | SEQ ID NO: 133 |
| IFITM1-R | GCTATGAAGCCCAGACAGC | SEQ ID NO: 134 |
| 5CDKL2 | GCCTCCTTGGGTTCGTCTATAA | SEQ ID NO: 135 |
| 3CDKL2 | CTCAGGGCCCGCTCATAGTA | SEQ ID NO: 136 |
| 5RRM2-841 | AAGAAGAAGGCAGACTGGGC | SEQ ID NO: 137 |
| 3RRM2-960 | TATCGACGCAAAAGAACCGG | SEQ ID NO: 138 |
| 5RRM2-1081 | CCATCGGAGGAGAGAGTAAG | SEQ ID NO: 139 |
| 3RRM2-1200 | GTATTGCTTCATTAGAGTGC | SEQ ID NO: 140 |
| 5RRM2-1281 | GGAGAATATTTCACTGGAAG | SEQ ID NO: 141 |
| 3RRM2-1400 | TAGAAGTCAGCATCCAAGGT | SEQ ID NO: 142 |
| U6 Promoters used to Express agshRNA | | |
| Names | Sequences | SEQ ID NOs |
| U6+MCS | GATCAGGATC CGTCGACGCG GCCGCACCGG TCCAAGGTCG GGCAGGAAGA GGGCCTATTT CCCATGATTC CTTCATATTT GCATATACGA TACAAGGCTG TTAGAGAGAT AATTAGAATT AATTTGACTG TAAACACAAA GATATTAGTA CAAAATACGT GACGTAGAAA GTAATAATTT CTTGGGTAGT TTGCAGTTTT AAAATTATGT TTTAAAATGG ACTATCATAT GCTTACCGTA ACTTGAAAGT ATTTCGATTT CTTGGCTTTA TATATCTTGT GGAAAGGACG AAAGATCTGG TACCGAATTC GATATCACTA GTGCGGCCGC TGCAGCTCGA GCTTAAGTCT AGAGGGCCCG TTTAAACCCG CTGATCAGCC TCGACTGTGC CTTCTAGTTG | SEQ ID NO: 143 |
| U6TO+MCS | GATCAGGATC CGTCGACGCG GCCGCACCGG TCCAAGGTCG GGCAGGAAGA GGGCCTATTT CCCATGATTC CTTCATATTT GCATATACGA TACAAGGCTG TTAGAGAGAT AATTAGAATT AATTTGACTG TAAACACAAA GATATTAGTA CAAAATACGT GACGTAGAAA GTAATAATTT CTTGGGTAGT TTGCAGTTTT AAAATTATGT TTTAAAATGG ACTATCATAT GCTTACCGTA ACTTGAAAGT ATTTCGATTT CTTGGCTTTA TATATCTCCC TATCAGTGAT AGAGATCTGG TACCGAATTC GATATCACTA GTGCGGCCGC TGCAGCTCGA GCTTAAGTCT AGAGGGCCCG TTTAAACCCG CTGATCAGCC TCGACTGTGC CTTCTAGTTG | SEQ ID NO: 144 |

Fig. 29A

U6+MCS Sequence (SEQ ID NO: 143)

```
           BamHI         NotI       AgeI
 751  GATCAGGATC  CGTCGACGCG  GCCGCACCGG  TCCAAGGTCG  GGCAGGAAGA

801  GGGCCTATTT  CCCATGATTC  CTTCATATTT  GCATATACGA  TACAAGGCTG

851  TTAGAGAGAT  AATTAGAATT  AATTTGACTG  TAAACACAAA  GATATTAGTA

901  CAAAATACGT  GACGTAGAAA  GTAATAATTT  CTTGGGTAGT  TTGCAGTTTT

951  AAAATTATGT  TTTAAAATGG  ACTATCATAT  GCTTACCGTA  ACTTGAAAGT
                                                          BglII KpnI
1001  ATTTCGATTT  CTTGGCTTTA  TATATCTTGT  GGAAAGGACG  AAAGATCTGG
           EcoRI    EcoRV SpeI    NotI          XhoI    AflII XbaI
1051  TACCGAATTC  GATATCACTA  GTGCGGCCGC  TGCAGCTCGA  GCTTAAGTCT

1101  AGAGGGCCCG  TTTAAACCCG  CTGATCAGCC  TCGACTGTGC  CTTCTAGTTG
```

Fig. 29B

U6TO+MCS Sequence (SEQ ID NO: 144)

```
           BamHI         NotI       AgeI
 751  GATCAGGATC  CGTCGACGCG  GCCGCACCGG  TCCAAGGTCG  GGCAGGAAGA

801  GGGCCTATTT  CCCATGATTC  CTTCATATTT  GCATATACGA  TACAAGGCTG

851  TTAGAGAGAT  AATTAGAATT  AATTTGACTG  TAAACACAAA  GATATTAGTA

901  CAAAATACGT  GACGTAGAAA  GTAATAATTT  CTTGGGTAGT  TTGCAGTTTT

951  AAAATTATGT  TTTAAAATGG  ACTATCATAT  GCTTACCGTA  ACTTGAAAGT
                                                          BglII KpnI
1001  ATTTCGATTT  CTTGGCTTTA  TATATCTCCC  TATCAGTGAT  AGAGATCTGG
           EcoRI    EcoRV SpeI    NotI          XhoI    AflII XbaI
1051  TACCGAATTC  GATATCACTA  GTGCGGCCGC  TGCAGCTCGA  GCTTAAGTCT

1101  AGAGGGCCCG  TTTAAACCCG  CTGATCAGCC  TCGACTGTGC  CTTCTAGTTG
```

Fig. 31

| Name | Sequence |
|---|---|
| sli-siRNA-887 | ACAACACGUUCACCAUAG*GUA*GUUAUGGUGAACGUGUUGc |
| 5di-siRNA-887 | ACAACACGUUCACCAUAGGua |
| 3di-siRNA-887 | CCUAUGGUGAACGUGUUGag |
| sli-siRNA-ARX1 | ACUGGCUGAUCUUGAGCG*UGU*CUGCUCAAGAUCAGCCAGc |
| 5di-siRNA-ARX1 | ACUGGCUGAUCUUGAGCGUgu |
| 3di-siRNA-ARX1 | ACGCUCAAGAUCAGCCAGUcg |
| sli-siRNA-451 (mmiR-451) | AAACCGUUACCAUUACUG*AGUU*UAGUAAUGGUAACGGUUc |
| 5di-siRNA-451 | AAACCGUUACCAUUACUGAgu |
| 3di-siRNA-451 | UCAGUAAUGGUAACGGUUUcu |

Fig. 32

| SEQ ID NO:112 | wt | CTACCTATGGTGAACGTGTTGT |
| SEQ ID NO:145 | U3A | CTACCTATGGTGAACGTGTaGT |
| SEQ ID NO:146 | U4A | CTACCTATGGTGAACGTGaTGT |
| SEQ ID NO:147 | G5C | CTACCTATGGTGAACGTcTTGT |
| SEQ ID NO:148 | U6G | CTACCTATGGTGAACGgGTTGT |
| SEQ ID NO:149 | G7C | CTACCTATGGTGAACcTGTTGT |
| SEQ ID NO:150 | C8G | CTACCTATGGTGAAgGTGTTGT |
| SEQ ID NO:151 | A9U | CTACCTATGGTGAtCGTGTTGT |
| SEQ ID NO:152 | A10G | CTACCTATGGTGgACGTGTTGT |
| SEQ ID NO:153 | G11C | CTACCTATGGTcAACGTGTTGT |
| SEQ ID NO:154 | U12G | CTACCTATGGgGAACGTGTTGT |
| SEQ ID NO:155 | G13C | CTACCTATGcTGAACGTGTTGT |
| SEQ ID NO:156 | G14C | CTACCTATcGTGAACGTGTTGT |
| SEQ ID NO:157 | U15A | CTACCTAaGGTGAACGTGTTGT |
| SEQ ID NO:158 | A16G | CTACCTgTGGTGAACGTGTTGT |
| SEQ ID NO:159 | U17A | CTACCaATGGTGAACGTGTTGT |
| SEQ ID NO:160 | C18G | CTACgTATGGTGAACGTGTTGT |
| SEQ ID NO:161 | U6G-U12G | CTACCTATGGgGAACGgGTTGT |
| | | |
| SEQ ID NO:112 | wt | CTACCTATGGTGAACGTGTTGT |
| SEQ ID NO:162 | U3C | CTACCTATGGTGAACGTGTcGT |
| SEQ ID NO:163 | U4C | CTACCTATGGTGAACGTGcTGT |
| SEQ ID NO:164 | G5A | CTACCTATGGTGAACGTaTTGT |
| SEQ ID NO:165 | U6C | CTACCTATGGTGAACGcGTTGT |
| SEQ ID NO:166 | G7A | CTACCTATGGTGAACaTGTTGT |
| SEQ ID NO:167 | C8A | CTACCTATGGTGAAaGTGTTGT |
| SEQ ID NO:168 | A9C | CTACCTATGGTGAcCGTGTTGT |
| SEQ ID NO:169 | A10C | CTACCTATGGTGcACGTGTTGT |
| SEQ ID NO:170 | G11A | CTACCTATGGTaAACGTGTTGT |
| SEQ ID NO:171 | U12C | CTACCTATGGcGAACGTGTTGT |
| SEQ ID NO:172 | G13A | CTACCTATGaTGAACGTGTTGT |
| SEQ ID NO:173 | G14A | CTACCTATaGTGAACGTGTTGT |
| SEQ ID NO:174 | U15C | CTACCTAcGGTGAACGTGTTGT |
| SEQ ID NO:175 | A16C | CTACCTcTGGTGAACGTGTTGT |
| SEQ ID NO:176 | U17C | CTACCcATGGTGAACGTGTTGT |
| SEQ ID NO:177 | C18A | CTACaTATGGTGAACGTGTTGT |
| SEQ ID NO:178 | U4C-U15C | CTACCTAcGGTGAACGTGcTGT |

Fig. 36

SEQ ID NO:179    WT,ACACGCTCAAGATCAGCCAGT

SEQ ID NO:180    T1G,ACACGCTCAAGATCAGCCAGg
SEQ ID NO:181    T1C,ACACGCTCAAGATCAGCCAGc
SEQ ID NO:182    G2A,ACACGCTCAAGATCAGCCAaT
SEQ ID NO:183    G2C,ACACGCTCAAGATCAGCCAcT
SEQ ID NO:184    A3T,ACACGCTCAAGATCAGCCtGT
SEQ ID NO:185    A3C,ACACGCTCAAGATCAGCCcGT
SEQ ID NO:186    C4G,ACACGCTCAAGATCAGCgAGT
SEQ ID NO:187    C4A,ACACGCTCAAGATCAGCaAGT
SEQ ID NO:188    C5G,ACACGCTCAAGATCAGgCAGT
SEQ ID NO:189    C5A,ACACGCTCAAGATCAGaCAGT
SEQ ID NO:190    G6C,ACACGCTCAAGATCAcCCAGT
SEQ ID NO:191    G6A,ACACGCTCAAGATCAaCCAGT
SEQ ID NO:192    A7T,ACACGCTCAAGATCtGCCAGT
SEQ ID NO:193    A7C,ACACGCTCAAGATCcGCCAGT
SEQ ID NO:194    C8G,ACACGCTCAAGATgAGCCAGT
SEQ ID NO:195    C8A,ACACGCTCAAGATaAGCCAGT
SEQ ID NO:196    T9A,ACACGCTCAAGAaCAGCCAGT
SEQ ID NO:197    T9C,ACACGCTCAAGAcCAGCCAGT

SEQ ID NO:198    A10T,ACACGCTCAAGtTCAGCCAGT
SEQ ID NO:199    A10C,ACACGCTCAAGcTCAGCCAGT
SEQ ID NO:200    G11C,ACACGCTCAAcATCAGCCAGT
SEQ ID NO:201    G11T,ACACGCTCAAtATCAGCCAGT
SEQ ID NO:202    A12T,ACACGCTCAtGATCAGCCAGT
SEQ ID NO:203    A12C,ACACGCTCAcGATCAGCCAGT
SEQ ID NO:204    A13T,ACACGCTCtAGATCAGCCAGT
SEQ ID NO:205    A13C,ACACGCTCcAGATCAGCCAGT
SEQ ID NO:206    C14G,ACACGCTgAAGATCAGCCAGT
SEQ ID NO:207    C14A,ACACGCTaAAGATCAGCCAGT
SEQ ID NO:208    T15A,ACACGCaCAAGATCAGCCAGT
SEQ ID NO:209    T15G,ACACGCgCAAGATCAGCCAGT
SEQ ID NO:210    C16G,ACACGgTCAAGATCAGCCAGT
SEQ ID NO:211    C16A,ACACGaTCAAGATCAGCCAGT
SEQ ID NO:212    G17C,ACACcTCAAGATCAGCCAGT
SEQ ID NO:213    G17A,ACACaTCAAGATCAGCCAGT
SEQ ID NO:214    C18G,ACAgCTCAAGATCAGCCAGT
SEQ ID NO:215    C18A,ACAaCTCAAGATCAGCCAGT
SEQ ID NO:216    A19T,ACtCGCTCAAGATCAGCCAGT
SEQ ID NO:217    A19C,ACcCGCTCAAGATCAGCCAGT

Fig. 38

| | | |
|---|---|---|
| SEQ ID NO:218 | WT | TAAACTCAGTAATGGTAACGGT |
| SEQ ID NO:219 | T3A, | TAAACTCAGTAATGGTAACGGa |
| SEQ ID NO:220 | T3C, | TAAACTCAGTAATGGTAACGGc |
| SEQ ID NO:221 | G4C, | TAAACTCAGTAATGGTAACGcT |
| SEQ ID NO:222 | G4A, | TAAACTCAGTAATGGTAACGaT |
| SEQ ID NO:223 | G5C, | TAAACTCAGTAATGGTAACcGT |
| SEQ ID NO:224 | G5A, | TAAACTCAGTAATGGTAACaGT |
| SEQ ID NO:225 | C6G, | TAAACTCAGTAATGGTAAgGGT |
| SEQ ID NO:226 | C6A, | TAAACTCAGTAATGGTAAaGGT |
| SEQ ID NO:227 | A7T, | TAAACTCAGTAATGGTAtCGGT |
| SEQ ID NO:228 | A7C, | TAAACTCAGTAATGGTAcCGGT |
| SEQ ID NO:229 | A8G, | TAAACTCAGTAATGGTgACGGT |
| SEQ ID NO:230 | A8C, | TAAACTCAGTAATGGTcACGGT |
| SEQ ID NO:231 | T9A, | TAAACTCAGTAATGGaAACGGT |
| SEQ ID NO:232 | T9C, | TAAACTCAGTAATGGcAACGGT |

| | | |
|---|---|---|
| SEQ ID NO:233 | G10A, | TAAACTCAGTAATGaTAACGGT |
| SEQ ID NO:234 | G10C, | TAAACTCAGTAATGcTAACGGT |
| SEQ ID NO:235 | G11A, | TAAACTCAGTAATaGTAACGGT |
| SEQ ID NO:236 | G11C, | TAAACTCAGTAATcGTAACGGT |
| SEQ ID NO:237 | T12A, | TAAACTCAGTAAaGGTAACGGT |
| SEQ ID NO:238 | T12C, | TAAACTCAGTAAcGGTAACGGT |
| SEQ ID NO:239 | A13T, | TAAACTCAGTAtTGGTAACGGT |
| SEQ ID NO:240 | A13C, | TAAACTCAGTAcTGGTAACGGT |
| SEQ ID NO:241 | A14T, | TAAACTCAGTtATGGTAACGGT |
| SEQ ID NO:242 | A14C, | TAAACTCAGTcATGGTAACGGT |
| SEQ ID NO:243 | T15A, | TAAACTCAGaAATGGTAACGGT |
| SEQ ID NO:244 | G16C, | TAAACTCAcTAATGGTAACGGT |
| SEQ ID NO:245 | G16A, | TAAACTCAaTAATGGTAACGGT |
| SEQ ID NO:246 | A17T, | TAAACTCtGTAATGGTAACGGT |
| SEQ ID NO:247 | A17C, | TAAACTCcGTAATGGTAACGGT |

| nts after 18th | Length | count | RPM | By % |
|---|---|---|---|---|
|  | L18 | 55 | 0.53 | 0.02 |
| A | L19 | 2996 | 37.80 | 1.23 |
| AG | L20 | 1979 | 22.20 | 0.72 |
| AGU | L21 | 7413 | 119.00 | 3.86 |
| AGUU | L22 | 24396 | 426.08 | 13.83 |
| AGUUU | L23 | 39075 | 505.34 | 16.40 |
| AGUUUA | L24 | 34073 | 406.00 | 13.18 |
| AGUUUAG | L25 | 66107 | 763.19 | 24.77 |
| AGUUUAGU | L26 | 66908 | 781.73 | 25.37 |
| AGUUUAGUA | L27 | 1815 | 19.10 | 0.62 |

Ago2

SEQUENCE LISTING

```
<160> NUMBER OF SEQ ID NOS: 247

<210> SEQ ID NO 1
<211> LENGTH: 53
<212> TYPE: DNA
<213> ORGANISM: Artificial Sequence
<220> FEATURE:
<223> OTHER INFORMATION: agshRNA-scramble-control

<400> SEQUENCE: 1
gatcagcgtt ctacactcga cgtacttgtc gagtgtagaa cgccttttt cga            53

<210> SEQ ID NO 2
<211> LENGTH: 53
<212> TYPE: DNA
<213> ORGANISM: Artificial Sequence
<220> FEATURE:
<223> OTHER INFORMATION: RRM2-agshRNA-279

<400> SEQUENCE: 2
gatccttcag cggcgagagc tgcagctagc tctcgccgct gaactttttt cga            53

<210> SEQ ID NO 3
<211> LENGTH: 53
<212> TYPE: DNA
<213> ORGANISM: Artificial Sequence
<220> FEATURE:
<223> OTHER INFORMATION: RRM2-agshRNA-366

<400> SEQUENCE: 3
gatcgaagat cctcctcgcg gtcttggccg cgaggaggat cttatttttt cga            53

<210> SEQ ID NO 4
<211> LENGTH: 53
<212> TYPE: DNA
<213> ORGANISM: Artificial Sequence
<220> FEATURE:
<223> OTHER INFORMATION: RRM2-agshRNA-488

<400> SEQUENCE: 4
gatcatctgc cagatatcat ggtacttcat gatatctggc agactttttt cga            53

<210> SEQ ID NO 5
<211> LENGTH: 53
<212> TYPE: DNA
<213> ORGANISM: Artificial Sequence
<220> FEATURE:
<223> OTHER INFORMATION: RRM2-agshRNA-490

<400> SEQUENCE: 5
```

-continued gatcacatct gccagatatc atggtagtga tatctggcag atgctttttt cga         53

<210> SEQ ID NO 6
<211> LENGTH: 53
<212> TYPE: DNA
<213> ORGANISM: Artificial Sequence
<220> FEATURE:
<223> OTHER INFORMATION: RRM2-agshRNA-497

<400> SEQUENCE: 6
gatcttctta tacatctgcc agatatatgg cagatgtata agactttttt cga         53

<210> SEQ ID NO 7
<211> LENGTH: 53
<212> TYPE: DNA
<213> ORGANISM: Artificial Sequence
<220> FEATURE:
<223> OTHER INFORMATION: RRM2-agshRNA-534

<400> SEQUENCE: 7
gatcgtccac ctcctcggcg gtccaagccg ccgaggaggt ggaattttttt cga        53

<210> SEQ ID NO 8
<211> LENGTH: 53
<212> TYPE: DNA
<213> ORGANISM: Artificial Sequence
<220> FEATURE:
<223> OTHER INFORMATION: RRM2-agshRNA-632

<400> SEQUENCE: 8
gatcactatg ccatcgcttg ctgcaaggca agcgatggca tagctttttt cga         53

<210> SEQ ID NO 9
<211> LENGTH: 53
<212> TYPE: DNA
<213> ORGANISM: Artificial Sequence
<220> FEATURE:
<223> OTHER INFORMATION: RRM2-agshRNA-632-mmp7

<400> SEQUENCE: 9
gatcactatg ccatcgcttg ctgcaaggca agcgatgcca tagctttttt cga         53

<210> SEQ ID NO 10
<211> LENGTH: 53
<212> TYPE: DNA
<213> ORGANISM: Artificial Sequence
<220> FEATURE:
<223> OTHER INFORMATION: RRM2-agshRNA-632-GU

<400> SEQUENCE: 10
gatcactatg ccatcgcttg ctgcaaggca agcgatggta tagctttttt cga         53

<210> SEQ ID NO 11
<211> LENGTH: 53
<212> TYPE: DNA
<213> ORGANISM: Artificial Sequence
<220> FEATURE:
<223> OTHER INFORMATION: RRM2-agshRNA-634

<400> SEQUENCE: 11
gatcttacta tgccatcgct tgctgctaag cgatggcata gtactttttt cga         53

<210> SEQ ID NO 12
<211> LENGTH: 53
<212> TYPE: DNA

<213> ORGANISM: Artificial Sequence
<220> FEATURE:
<223> OTHER INFORMATION: RRM2-agshRNA-883

<400> SEQUENCE: 12
gatccacgtt caccataggt agcctcttac ctatggtgaa cgtctttttt cga            53

<210> SEQ ID NO 13
<211> LENGTH: 53
<212> TYPE: DNA
<213> ORGANISM: Artificial Sequence
<220> FEATURE:
<223> OTHER INFORMATION: RRM2-agshRNA-887

<400> SEQUENCE: 13
gatcacaaca cgttcaccat aggtagttat ggtgaacgtg ttgctttttt cga            53

<210> SEQ ID NO 14
<211> LENGTH: 53
<212> TYPE: DNA
<213> ORGANISM: Artificial Sequence
<220> FEATURE:
<223> OTHER INFORMATION: RRM2-agshRNA-887-mut

<400> SEQUENCE: 14
gatcacaaca cgttcaccat aggtagttat ggactacgtg ttgctttttt cga            53

<210> SEQ ID NO 15
<211> LENGTH: 53
<212> TYPE: DNA
<213> ORGANISM: Artificial Sequence
<220> FEATURE:
<223> OTHER INFORMATION: RRM2-agshRNA-887-mmp6

<400> SEQUENCE: 15
gatcacaaca cgttcaccat aggtagttat ggtgaacgag ttgctttttt cga            53

<210> SEQ ID NO 16
<211> LENGTH: 53
<212> TYPE: DNA
<213> ORGANISM: Artificial Sequence
<220> FEATURE:
<223> OTHER INFORMATION: RRM2-agshRNA-887-mmp7

<400> SEQUENCE: 16
gatcacaaca cgttcaccat aggtagttat ggtgaacctg ttgctttttt cga            53

<210> SEQ ID NO 17
<211> LENGTH: 53
<212> TYPE: DNA
<213> ORGANISM: Artificial Sequence
<220> FEATURE:
<223> OTHER INFORMATION: RRM2-agshRNA-887-mmp8

<400> SEQUENCE: 17
gatcacaaca cgttcaccat aggtagttat ggtgaaggtg ttgctttttt cga            53

<210> SEQ ID NO 18
<211> LENGTH: 53
<212> TYPE: DNA
<213> ORGANISM: Artificial Sequence
<220> FEATURE:
<223> OTHER INFORMATION: RRM2-agshRNA-887-mmp13

<400> SEQUENCE: 18
gatcacaaca cgttcaccat aggtagttat gctgaacgtg ttgctttttt cga            53

<210> SEQ ID NO 19
<211> LENGTH: 53
<212> TYPE: DNA
<213> ORGANISM: Artificial Sequence
<220> FEATURE:
<223> OTHER INFORMATION: RRM2-agshRNA-887-mmp14

<400> SEQUENCE: 19
gatcacaaca cgttcaccat aggtagttat cgtgaacgtg ttgcttttttt cga      53

<210> SEQ ID NO 20
<211> LENGTH: 53
<212> TYPE: DNA
<213> ORGANISM: Artificial Sequence
<220> FEATURE:
<223> OTHER INFORMATION: RRM2-agshRNA-887-mmp15

<400> SEQUENCE: 20
gatcacaaca cgttcaccat aggtagttaa ggtgaacgtg ttgcttttttt cga      53

<210> SEQ ID NO 21
<211> LENGTH: 52
<212> TYPE: DNA
<213> ORGANISM: Artificial Sequence
<220> FEATURE:
<223> OTHER INFORMATION: RRM2-agshRNA-887-Bulge-p7

<400> SEQUENCE: 21
gatcacaaca cgttcaccat aggtagttat ggtgaactgt tgcttttttc ga        52

<210> SEQ ID NO 22
<211> LENGTH: 51
<212> TYPE: DNA
<213> ORGANISM: Artificial Sequence
<220> FEATURE:
<223> OTHER INFORMATION: RRM2-agshRNA-887-NL

<400> SEQUENCE: 22
gatcacaaca cgttcaccat aggcctatgg tgaacgtgtt gttttttttcg a        51

<210> SEQ ID NO 23
<211> LENGTH: 47
<212> TYPE: DNA
<213> ORGANISM: Artificial Sequence
<220> FEATURE:
<223> OTHER INFORMATION: RRM2-agshRNA-887-S14

<400> SEQUENCE: 23
gatcacaaca cgttcaccat aggtggtgaa cgtgttgctt ttttcga              47

<210> SEQ ID NO 24
<211> LENGTH: 49
<212> TYPE: DNA
<213> ORGANISM: Artificial Sequence
<220> FEATURE:
<223> OTHER INFORMATION: RRM2-agshRNA-887-S15

<400> SEQUENCE: 24
gatcacaaca cgttcaccat aggtatggtg aacgtgttgc tttttttcga           49

<210> SEQ ID NO 25
<211> LENGTH: 51
<212> TYPE: DNA
<213> ORGANISM: Artificial Sequence
<220> FEATURE:

```
<223> OTHER INFORMATION: RRM2-agshRNA-887-S16

<400> SEQUENCE: 25
gatcacaaca cgttcaccat aggtatatgg tgaacgtgtt gcttttttcg a         51

<210> SEQ ID NO 26
<211> LENGTH: 55
<212> TYPE: DNA
<213> ORGANISM: Artificial Sequence
<220> FEATURE:
<223> OTHER INFORMATION: RRM2-agshRNA-887-S18

<400> SEQUENCE: 26
gatcacaaca cgttcaccat aggtagttct atggtgaacg tgttgctttt ttcga     55

<210> SEQ ID NO 27
<211> LENGTH: 57
<212> TYPE: DNA
<213> ORGANISM: Artificial Sequence
<220> FEATURE:
<223> OTHER INFORMATION: RRM2-agshRNA-887-S19

<400> SEQUENCE: 27
gatcacaaca cgttcaccat aggtagttac ctatggtgaa cgtgttgctt ttttcga   57

<210> SEQ ID NO 28
<211> LENGTH: 59
<212> TYPE: DNA
<213> ORGANISM: Artificial Sequence
<220> FEATURE:
<223> OTHER INFORMATION: RRM2-agshRNA-887-S20

<400> SEQUENCE: 28
gatcacaaca cgttcaccat aggtagttat acctatggtg aacgtgttgc ttttttcga 59

<210> SEQ ID NO 29
<211> LENGTH: 40
<212> TYPE: RNA
<213> ORGANISM: Artificial Sequence
<220> FEATURE:
<223> OTHER INFORMATION: agsiRNA-scramble-control

<400> SEQUENCE: 29
agcguucuac acucgacgua cuugucgagu guagaacgcc                      40

<210> SEQ ID NO 30
<211> LENGTH: 40
<212> TYPE: RNA
<213> ORGANISM: Artificial Sequence
<220> FEATURE:
<223> OTHER INFORMATION: RRM2-agsiRNA-887(wt,L40,S17)

<400> SEQUENCE: 30
acaacacguu caccauaggu aguuauggug aacguguugc                      40

<210> SEQ ID NO 31
<211> LENGTH: 40
<212> TYPE: RNA
<213> ORGANISM: Artificial Sequence
<220> FEATURE:
<223> OTHER INFORMATION: 5P-RRM2-agsiRNA-887
<220> FEATURE:
<221> NAME/KEY: misc_feature
<222> LOCATION: (1)..(1)
<223> OTHER INFORMATION: adenine at position 1 is phosphorylated

<400> SEQUENCE: 31
```
acaacacguu caccauaggu aguuauggug aacguguugc    40

<210> SEQ ID NO 32
<211> LENGTH: 40
<212> TYPE: RNA
<213> ORGANISM: Artificial Sequence
<220> FEATURE:
<223> OTHER INFORMATION: RRM2-agsiRNA-887-mut

<400> SEQUENCE: 32
acaacacguu caccauaggu aguuauggac uacguguugc    40

<210> SEQ ID NO 33
<211> LENGTH: 40
<212> TYPE: RNA
<213> ORGANISM: Artificial Sequence
<220> FEATURE:
<223> OTHER INFORMATION: RRM2-agsiRNA-887-p18GC

<400> SEQUENCE: 33
acaacacguu caccauaggu agcuaugguy aacguguugc    40

<210> SEQ ID NO 34
<211> LENGTH: 40
<212> TYPE: RNA
<213> ORGANISM: Artificial Sequence
<220> FEATURE:
<223> OTHER INFORMATION: RRM2-agsiRNA-887-mmp2

<400> SEQUENCE: 34
acaacacguu caccauaggu aguuauggug aacguguucc    40

<210> SEQ ID NO 35
<211> LENGTH: 40
<212> TYPE: RNA
<213> ORGANISM: Artificial Sequence
<220> FEATURE:
<223> OTHER INFORMATION: RRM2-agsiRNA-887-mmp2-3

<400> SEQUENCE: 35
acaacacguu caccauaggu aguuauggug aacgugnccc    40

<210> SEQ ID NO 36
<211> LENGTH: 40
<212> TYPE: RNA
<213> ORGANISM: Artificial Sequence
<220> FEATURE:
<223> OTHER INFORMATION: RRM2-agsiRNA-887-mmp6

<400> SEQUENCE: 36
acaacacguu caccauaggu aguuauggug aacgaguugc    40

<210> SEQ ID NO 37
<211> LENGTH: 40
<212> TYPE: RNA
<213> ORGANISM: Artificial Sequence
<220> FEATURE:
<223> OTHER INFORMATION: RRM2-agsiRNA-887-mmp7

<400> SEQUENCE: 37
acaacacguu caccauaggu aguuauggug aaccuguugc    40

<210> SEQ ID NO 38
<211> LENGTH: 40
<212> TYPE: RNA

```
<213> ORGANISM: Artificial Sequence
<220> FEATURE:
<223> OTHER INFORMATION: RRM2-agsiRNA-887-mmp18

<400> SEQUENCE: 38
acaacacguu caccauaggu agguauggug aacguguugc                              40

<210> SEQ ID NO 39
<211> LENGTH: 40
<212> TYPE: RNA
<213> ORGANISM: Artificial Sequence
<220> FEATURE:
<223> OTHER INFORMATION: RRM2-agsiRNA-887-mmp17-18

<400> SEQUENCE: 39
acaacacguu caccauaggu aggaauggug aacguguugc                              40

<210> SEQ ID NO 40
<211> LENGTH: 40
<212> TYPE: RNA
<213> ORGANISM: Artificial Sequence
<220> FEATURE:
<223> OTHER INFORMATION: RRM2-agsiRNA-887-mmp16-17-18

<400> SEQUENCE: 40
acaacacguu caccauaggu aggauuggug aacguguugc                              40

<210> SEQ ID NO 41
<211> LENGTH: 12
<212> TYPE: RNA
<213> ORGANISM: Artificial Sequence
<220> FEATURE:
<223> OTHER INFORMATION: RRM2-agsiRNA-887-3L12

<400> SEQUENCE: 41
aacguguugc uu                                                            12

<210> SEQ ID NO 42
<211> LENGTH: 41
<212> TYPE: RNA
<213> ORGANISM: Artificial Sequence
<220> FEATURE:
<223> OTHER INFORMATION: RRM2-agsiRNA-5a887

<400> SEQUENCE: 42
aacaacacgu ucaccauagg uaguuauggu gaacguguug c                            41

<210> SEQ ID NO 43
<211> LENGTH: 42
<212> TYPE: RNA
<213> ORGANISM: Artificial Sequence
<220> FEATURE:
<223> OTHER INFORMATION: RRM2-agsiRNA-5aa887

<400> SEQUENCE: 43
aaacaacacg uucaccauag guaguuaugg ugaacguguu gc                           42

<210> SEQ ID NO 44
<211> LENGTH: 43
<212> TYPE: RNA
<213> ORGANISM: Artificial Sequence
<220> FEATURE:
<223> OTHER INFORMATION: RRM2-agsiRNA-5aaa887

<400> SEQUENCE: 44
aaaacaacac guucaccaua gguaguuaug ugaacgugu ugc                           43
```

<210> SEQ ID NO 45
<211> LENGTH: 44
<212> TYPE: RNA
<213> ORGANISM: Artificial Sequence
<220> FEATURE:
<223> OTHER INFORMATION: RRM2-agsiRNA-5aaaa887

<400> SEQUENCE: 45
aaaaacaaca cguucaccau agguaguuau ggugaacgug uugc                44

<210> SEQ ID NO 46
<211> LENGTH: 40
<212> TYPE: RNA
<213> ORGANISM: Artificial Sequence
<220> FEATURE:
<223> OTHER INFORMATION: RRM2-sshRNA887

<400> SEQUENCE: 46
acaacacguu caccauaggu uccuauggug aacguguugu                     40

<210> SEQ ID NO 47
<211> LENGTH: 38
<212> TYPE: RNA
<213> ORGANISM: Artificial Sequence
<220> FEATURE:
<223> OTHER INFORMATION: RRM2-agsiRNA-887-NL

<400> SEQUENCE: 47
acaacacguu caccauaggc cuauggugaa cguuugu                        38

<210> SEQ ID NO 48
<211> LENGTH: 45
<212> TYPE: RNA
<213> ORGANISM: Artificial Sequence
<220> FEATURE:
<223> OTHER INFORMATION: RRM2-agsiRNA-887-Ux5

<400> SEQUENCE: 48
acaacacguu caccauaggu aguuauggug aacguguugc uuuuu                45

<210> SEQ ID NO 49
<211> LENGTH: 41
<212> TYPE: RNA
<213> ORGANISM: Artificial Sequence
<220> FEATURE:
<223> OTHER INFORMATION: RRM2-agsiRNA-887-U

<400> SEQUENCE: 49
acaacacguu caccauaggu aguuauggug aacguguugc u                    41

<210> SEQ ID NO 50
<211> LENGTH: 42
<212> TYPE: RNA
<213> ORGANISM: Artificial Sequence
<220> FEATURE:
<223> OTHER INFORMATION: RRM2-agsiRNA-887-UU

<400> SEQUENCE: 50
acaacacguu caccauaggu aguuauggug aacguguugc uu                   42

<210> SEQ ID NO 51
<211> LENGTH: 44
<212> TYPE: RNA
<213> ORGANISM: Artificial Sequence
<220> FEATURE:

```
<223> OTHER INFORMATION: RRM2-agsiRNA-887-dTdT
<220> FEATURE:
<221> NAME/KEY: misc_feature
<222> LOCATION: (41)..(42)
<223> OTHER INFORMATION: deoxythymidine
<220> FEATURE:
<221> NAME/KEY: misc_feature
<222> LOCATION: (43)..(44)
<223> OTHER INFORMATION: deoxythymidine

<400> SEQUENCE: 51
acaacacguu caccauaggu aguuauggug aacguguugc dndn                44

<210> SEQ ID NO 52
<211> LENGTH: 42
<212> TYPE: RNA
<213> ORGANISM: Artificial Sequence
<220> FEATURE:
<223> OTHER INFORMATION: RRM2-agsiRNA-887-ddC
<220> FEATURE:
<221> NAME/KEY: misc_feature
<222> LOCATION: (41)..(42)
<223> OTHER INFORMATION: dideoxycytidine

<400> SEQUENCE: 52
acaacacguu caccauaggu aguuauggug aacguguugd dn                  42

<210> SEQ ID NO 53
<211> LENGTH: 27
<212> TYPE: RNA
<213> ORGANISM: Artificial Sequence
<220> FEATURE:
<223> OTHER INFORMATION: RRM2-agsiRNA-887-S11

<400> SEQUENCE: 53
acaacacguu caccauugaa cguguug                                   27

<210> SEQ ID NO 54
<211> LENGTH: 29
<212> TYPE: RNA
<213> ORGANISM: Artificial Sequence
<220> FEATURE:
<223> OTHER INFORMATION: RRM2-agsiRNA-887-S12

<400> SEQUENCE: 54
acaacacguu caccauagug aacguguug                                 29

<210> SEQ ID NO 55
<211> LENGTH: 31
<212> TYPE: RNA
<213> ORGANISM: Artificial Sequence
<220> FEATURE:
<223> OTHER INFORMATION: RRM2-agsiRNA-887-S13

<400> SEQUENCE: 55
acaacacguu caccauaggg ugaacguguu g                              31

<210> SEQ ID NO 56
<211> LENGTH: 34
<212> TYPE: RNA
<213> ORGANISM: Artificial Sequence
<220> FEATURE:
<223> OTHER INFORMATION: RRM2-agsiRNA-887-S14

<400> SEQUENCE: 56
acaacacguu caccauaggu ggugaacgug uugc                           34
```

```
<210> SEQ ID NO 57
<211> LENGTH: 36
<212> TYPE: RNA
<213> ORGANISM: Artificial Sequence
<220> FEATURE:
<223> OTHER INFORMATION: RRM2-agsiRNA-887-S15

<400> SEQUENCE: 57
acaacacguu caccauaggu auggugaacg uguugc                                    36

<210> SEQ ID NO 58
<211> LENGTH: 38
<212> TYPE: RNA
<213> ORGANISM: Artificial Sequence
<220> FEATURE:
<223> OTHER INFORMATION: RRM2-agsiRNA-887-S16

<400> SEQUENCE: 58
acaacacguu caccauaggu auauggugaa cguguugc                                  38

<210> SEQ ID NO 59
<211> LENGTH: 25
<212> TYPE: RNA
<213> ORGANISM: Artificial Sequence
<220> FEATURE:
<223> OTHER INFORMATION: RRM2-agsiRNA-887-L25

<400> SEQUENCE: 59
acaacacguu caccauaggu aguua                                                25

<210> SEQ ID NO 60
<211> LENGTH: 27
<212> TYPE: RNA
<213> ORGANISM: Artificial Sequence
<220> FEATURE:
<223> OTHER INFORMATION: RRM2-agsiRNA-887-L27

<400> SEQUENCE: 60
acaacacguu caccauaggu aguuaug                                              27

<210> SEQ ID NO 61
<211> LENGTH: 29
<212> TYPE: RNA
<213> ORGANISM: Artificial Sequence
<220> FEATURE:
<223> OTHER INFORMATION: RRM2-agsiRNA-887-L29

<400> SEQUENCE: 61
acaacacguu caccauaggu aguuauggu                                            29

<210> SEQ ID NO 62
<211> LENGTH: 30
<212> TYPE: RNA
<213> ORGANISM: Artificial Sequence
<220> FEATURE:
<223> OTHER INFORMATION: RRM2-agsiRNA-887-L30

<400> SEQUENCE: 62
acaacacguu caccauaggu aguuauggug                                           30

<210> SEQ ID NO 63
<211> LENGTH: 35
<212> TYPE: RNA
<213> ORGANISM: Artificial Sequence
<220> FEATURE:
<223> OTHER INFORMATION: RRM2-agsiRNA-887-L35
```

<400> SEQUENCE: 63
acaacacguu caccauaggu aguuauggug aacgu        35

<210> SEQ ID NO 64
<211> LENGTH: 37
<212> TYPE: RNA
<213> ORGANISM: Artificial Sequence
<220> FEATURE:
<223> OTHER INFORMATION: RRM2-agsiRNA-887-L37

<400> SEQUENCE: 64
acaacacguu caccauaggu aguuauggug aacgugu        37

<210> SEQ ID NO 65
<211> LENGTH: 38
<212> TYPE: RNA
<213> ORGANISM: Artificial Sequence
<220> FEATURE:
<223> OTHER INFORMATION: RRM2-agsiRNA-887-L38

<400> SEQUENCE: 65
acaacacguu caccauaggu aguuauggug aacguguu        38

<210> SEQ ID NO 66
<211> LENGTH: 39
<212> TYPE: RNA
<213> ORGANISM: Artificial Sequence
<220> FEATURE:
<223> OTHER INFORMATION: RRM2-agsiRNA-887-L39

<400> SEQUENCE: 66
acaacacguu caccauaggu aguuauggug aacguguug        39

<210> SEQ ID NO 67
<211> LENGTH: 40
<212> TYPE: RNA
<213> ORGANISM: Artificial Sequence
<220> FEATURE:
<223> OTHER INFORMATION: RRM2-agsiRNA-887-LP451

<400> SEQUENCE: 67
acaacacguu caccauagag uuuuauggug aacguguugc        40

<210> SEQ ID NO 68
<211> LENGTH: 40
<212> TYPE: RNA
<213> ORGANISM: Artificial Sequence
<220> FEATURE:
<223> OTHER INFORMATION: RRM2-agsiRNA-5U887

<400> SEQUENCE: 68
ucaacacguu caccauaggu aguuauggug aacguguugc        40

<210> SEQ ID NO 69
<211> LENGTH: 40
<212> TYPE: RNA
<213> ORGANISM: Artificial Sequence
<220> FEATURE:
<223> OTHER INFORMATION: RRM2-agsiRNA-5C887

<400> SEQUENCE: 69
ccaacacguu caccauaggu aguuauggug aacguguugc        40

<210> SEQ ID NO 70
<211> LENGTH: 21

```
<212> TYPE: RNA
<213> ORGANISM: Artificial Sequence
<220> FEATURE:
<223> OTHER INFORMATION: 5siRNA-887

<400> SEQUENCE: 70
acaacacguu caccauaggu a                                              21

<210> SEQ ID NO 71
<211> LENGTH: 21
<212> TYPE: RNA
<213> ORGANISM: Artificial Sequence
<220> FEATURE:
<223> OTHER INFORMATION: 3siRNA-887

<400> SEQUENCE: 71
ccuaugguga acguuugua g                                               21

<210> SEQ ID NO 72
<211> LENGTH: 21
<212> TYPE: RNA
<213> ORGANISM: Artificial Sequence
<220> FEATURE:
<223> OTHER INFORMATION: 5rsiRNA-887

<400> SEQUENCE: 72
acaacacguu caccauaggu a                                              21

<210> SEQ ID NO 73
<211> LENGTH: 21
<212> TYPE: RNA
<213> ORGANISM: Artificial Sequence
<220> FEATURE:
<223> OTHER INFORMATION: 3rsiRNA-887

<400> SEQUENCE: 73
acuaccuaug gugaacgugu u                                              21

<210> SEQ ID NO 74
<211> LENGTH: 53
<212> TYPE: DNA
<213> ORGANISM: Artificial Sequence
<220> FEATURE:
<223> OTHER INFORMATION: RRM2-agshRNA-1148

<400> SEQUENCE: 74
gatcatgagc ttcacaggca aggcctattg cctgtgaagc tcactttttt cga           53

<210> SEQ ID NO 75
<211> LENGTH: 53
<212> TYPE: DNA
<213> ORGANISM: Artificial Sequence
<220> FEATURE:
<223> OTHER INFORMATION: RRM2-agshRNA-1148-mmp7

<400> SEQUENCE: 75
gatcatgagc ttcacaggca aggcctattg cctgtgacgc tcactttttt cga           53

<210> SEQ ID NO 76
<211> LENGTH: 53
<212> TYPE: DNA
<213> ORGANISM: Artificial Sequence
<220> FEATURE:
<223> OTHER INFORMATION: RRM2-agshRNA-1148-GU

<400> SEQUENCE: 76
```
gatcatgagc ttcacaggca aggcctattg tctgtgaagt tcactttttt cga        53

<210> SEQ ID NO 77
<211> LENGTH: 53
<212> TYPE: DNA
<213> ORGANISM: Artificial Sequence
<220> FEATURE:
<223> OTHER INFORMATION: RRM2-agshRNA-1148-mut

<400> SEQUENCE: 77
gatcatgagc ttctgtggca aggcctattg ccacagaagc tcactttttt cga        53

<210> SEQ ID NO 78
<211> LENGTH: 40
<212> TYPE: RNA
<213> ORGANISM: Artificial Sequence
<220> FEATURE:
<223> OTHER INFORMATION: RRM2-agsiRNA-1148

<400> SEQUENCE: 78
augagcuuca caggcaaggc cuauugccug ugaagcucac                        40

<210> SEQ ID NO 79
<211> LENGTH: 40
<212> TYPE: RNA
<213> ORGANISM: Artificial Sequence
<220> FEATURE:
<223> OTHER INFORMATION: RRM2-agsiRNA-1148-mmp7

<400> SEQUENCE: 79
augagcuuca caggcaaggc cuauugccug ugacgcucac                        40

<210> SEQ ID NO 80
<211> LENGTH: 40
<212> TYPE: RNA
<213> ORGANISM: Artificial Sequence
<220> FEATURE:
<223> OTHER INFORMATION: RRM2-agsiRNA-1148-GU

<400> SEQUENCE: 80
augagcuuca caggcaaggc cuauugucug ugaaguucac                        40

<210> SEQ ID NO 81
<211> LENGTH: 40
<212> TYPE: RNA
<213> ORGANISM: Artificial Sequence
<220> FEATURE:
<223> OTHER INFORMATION: RRM2-agsiRNA-1148-mut

<400> SEQUENCE: 81
augagcuucu guggcaaggc cuauugccac agaagcucac                        40

<210> SEQ ID NO 82
<211> LENGTH: 40
<212> TYPE: RNA
<213> ORGANISM: Artificial Sequence
<220> FEATURE:
<223> OTHER INFORMATION: RRM2-agsiRNA-1148-LP451

<400> SEQUENCE: 82
augagcuuca caggcaagag uuuuugccug ugaagcucac                        40

<210> SEQ ID NO 83
<211> LENGTH: 40
<212> TYPE: RNA
<213> ORGANISM: Artificial Sequence
<220> FEATURE:
<223> OTHER INFORMATION: RRM2-agsiRNA-1148-LP887

<400> SEQUENCE: 83
augagcuuca caggcaaggu agcuugccug ugaagcucac                              40

<210> SEQ ID NO 84
<211> LENGTH: 53
<212> TYPE: DNA
<213> ORGANISM: Artificial Sequence
<220> FEATURE:
<223> OTHER INFORMATION: RRM2-agshRNA-1354

<400> SEQUENCE: 84
gatcaattct ctgttggact tgacattaag tccaacagag aatcttttt cga              53

<210> SEQ ID NO 85
<211> LENGTH: 53
<212> TYPE: DNA
<213> ORGANISM: Artificial Sequence
<220> FEATURE:
<223> OTHER INFORMATION: RRM2-agshRNA-1354-mmp7

<400> SEQUENCE: 85
gatcaattct ctgttggact tgacattaag tccaacacag aatcttttt cga              53

<210> SEQ ID NO 86
<211> LENGTH: 53
<212> TYPE: DNA
<213> ORGANISM: Artificial Sequence
<220> FEATURE:
<223> OTHER INFORMATION: RRM2-agshRNA-1354-GU

<400> SEQUENCE: 86
gatcaattct ctgttggact tgacattaag tccaatagag aatcttttt cga              53

<210> SEQ ID NO 87
<211> LENGTH: 40
<212> TYPE: RNA
<213> ORGANISM: Artificial Sequence
<220> FEATURE:
<223> OTHER INFORMATION: RRM2-agsiRNA-1354

<400> SEQUENCE: 87
aauucucugu uggacuugac auuaagucca acagagaauc                              40

<210> SEQ ID NO 88
<211> LENGTH: 40
<212> TYPE: RNA
<213> ORGANISM: Artificial Sequence
<220> FEATURE:
<223> OTHER INFORMATION: RRM2-agsiRNA-1354-mmp7

<400> SEQUENCE: 88
aauucucugu uggacuugac auuaagucca acacagaauc                              40

<210> SEQ ID NO 89
<211> LENGTH: 40
<212> TYPE: RNA
<213> ORGANISM: Artificial Sequence
<220> FEATURE:
<223> OTHER INFORMATION: RRM2-agsiRNA-1354-GU

<400> SEQUENCE: 89
aauucucugu uggacuugac auuaagucca auagagaauc                              40

<210> SEQ ID NO 90
<211> LENGTH: 40
<212> TYPE: RNA
<213> ORGANISM: Artificial Sequence
<220> FEATURE:
<223> OTHER INFORMATION: RRM2-agsiRNA-1354-LP451

<400> SEQUENCE: 90
aauucucugu uggacuugag uuuaagucca acagagaauc                    40

<210> SEQ ID NO 91
<211> LENGTH: 40
<212> TYPE: RNA
<213> ORGANISM: Artificial Sequence
<220> FEATURE:
<223> OTHER INFORMATION: RRM2-agsiRNA-1354-LP887

<400> SEQUENCE: 91
aauucucugu uggacuuggu agcaagucca acagagaauc                    40

<210> SEQ ID NO 92
<211> LENGTH: 40
<212> TYPE: RNA
<213> ORGANISM: Artificial Sequence
<220> FEATURE:
<223> OTHER INFORMATION: hmiR-451

<400> SEQUENCE: 92
aaaccguuac cauuacugag uuuaguaaug guaauggeuc                    40

<210> SEQ ID NO 93
<211> LENGTH: 40
<212> TYPE: RNA
<213> ORGANISM: Artificial Sequence
<220> FEATURE:
<223> OTHER INFORMATION: mmiR-451

<400> SEQUENCE: 93
aaaccguuac cauuacugag uuuaguaaug guaacgguuc                    40

<210> SEQ ID NO 94
<211> LENGTH: 40
<212> TYPE: RNA
<213> ORGANISM: Artificial Sequence
<220> FEATURE:
<223> OTHER INFORMATION: dmiR-451

<400> SEQUENCE: 94
aaaccguuac cauuacugag uuuaguaaug guaaggguuc                    40

<210> SEQ ID NO 95
<211> LENGTH: 40
<212> TYPE: RNA
<213> ORGANISM: Artificial Sequence
<220> FEATURE:
<223> OTHER INFORMATION: hmiR-451-LP887

<400> SEQUENCE: 95
aaaccguuac cauuacuggu aguaguaaug guaaugguuc                    40

<210> SEQ ID NO 96
<211> LENGTH: 21
<212> TYPE: RNA
<213> ORGANISM: Artificial Sequence
<220> FEATURE:
<223> OTHER INFORMATION: 5siRNA-451

<400> SEQUENCE: 96
aaaccguuac cauuacugag u    21

<210> SEQ ID NO 97
<211> LENGTH: 21
<212> TYPE: RNA
<213> ORGANISM: Artificial Sequence
<220> FEATURE:
<223> OTHER INFORMATION: 3siRNA-451

<400> SEQUENCE: 97
ucaguaaugg uaacgguuuc u    21

<210> SEQ ID NO 98
<211> LENGTH: 53
<212> TYPE: DNA
<213> ORGANISM: Artificial Sequence
<220> FEATURE:
<223> OTHER INFORMATION: RRM1-agshRNA-481mmp6

<400> SEQUENCE: 98
gatcagccaa agtatctagt tccactgaac tagatactat ggcctttttt cga    53

<210> SEQ ID NO 99
<211> LENGTH: 40
<212> TYPE: RNA
<213> ORGANISM: Artificial Sequence
<220> FEATURE:
<223> OTHER INFORMATION: RRM1-agsiRNA-481mmp6

<400> SEQUENCE: 99
agccaaagua ucuaguucca cugaacuaga uacuauggcc    40

<210> SEQ ID NO 100
<211> LENGTH: 53
<212> TYPE: DNA
<213> ORGANISM: Artificial Sequence
<220> FEATURE:
<223> OTHER INFORMATION: RRM1-agshRNA-669

<400> SEQUENCE: 100
gatcatatcc aatgttgact tggccataag tcaacattgg atactttttt cga    53

<210> SEQ ID NO 101
<211> LENGTH: 40
<212> TYPE: RNA
<213> ORGANISM: Artificial Sequence
<220> FEATURE:
<223> OTHER INFORMATION: RRM1-agsiRNA-669

<400> SEQUENCE: 101
auauccaaug uugacuuggc cauaagucaa cauuggauac    40

<210> SEQ ID NO 102
<211> LENGTH: 53
<212> TYPE: DNA
<213> ORGANISM: Artificial Sequence
<220> FEATURE:
<223> OTHER INFORMATION: RRM1-agshRNA-2290

<400> SEQUENCE: 102
gatcattgca tgcaataatc tgctattaga ttattgcatg caactttttt cga    53

<210> SEQ ID NO 103

```
<211> LENGTH: 40
<212> TYPE: RNA
<213> ORGANISM: Artificial Sequence
<220> FEATURE:
<223> OTHER INFORMATION: RRM1-agsiRNA-2290

<400> SEQUENCE: 103
auugcaugca auaaucugcu auuagauuau ugcaugcaac                            40

<210> SEQ ID NO 104
<211> LENGTH: 53
<212> TYPE: DNA
<213> ORGANISM: Artificial Sequence
<220> FEATURE:
<223> OTHER INFORMATION: RRM2B-agshRNA-445mmp6

<400> SEQUENCE: 104
gatcatcctt tgataagtcg acctctgtcg acttatctaa ggactttttt cga            53

<210> SEQ ID NO 105
<211> LENGTH: 40
<212> TYPE: RNA
<213> ORGANISM: Artificial Sequence
<220> FEATURE:
<223> OTHER INFORMATION: RRM2B-agsiRNA-445mmp6

<400> SEQUENCE: 105
auccuuugau aagucgaccu cugucgacuu aucuaaggac                            40

<210> SEQ ID NO 106
<211> LENGTH: 53
<212> TYPE: DNA
<213> ORGANISM: Artificial Sequence
<220> FEATURE:
<223> OTHER INFORMATION: RRM2B-agshRNA-948

<400> SEQUENCE: 106
gatcaagtat tggaacatca ggcaagtctg atgttccaat actctttttt cga            53

<210> SEQ ID NO 107
<211> LENGTH: 40
<212> TYPE: RNA
<213> ORGANISM: Artificial Sequence
<220> FEATURE:
<223> OTHER INFORMATION: RRM2B-agsiRNA-948

<400> SEQUENCE: 107
aaguauugga caucaggca agucugaugu uccaauacuc                             40

<210> SEQ ID NO 108
<211> LENGTH: 53
<212> TYPE: DNA
<213> ORGANISM: Artificial Sequence
<220> FEATURE:
<223> OTHER INFORMATION: RRM2B-agshRNA-1061

<400> SEQUENCE: 108
gatcaattca ttccaatgag gccaacgcct cattggaatg aatctttttt cga            53

<210> SEQ ID NO 109
<211> LENGTH: 40
<212> TYPE: RNA
<213> ORGANISM: Artificial Sequence
<220> FEATURE:
<223> OTHER INFORMATION: RRM2B-agsiRNA-1061

<400> SEQUENCE: 109
```
aauucauucc aaugaggcca acgccucauu ggaaugaauc        40

<210> SEQ ID NO 110
<211> LENGTH: 20
<212> TYPE: DNA
<213> ORGANISM: Artificial Sequence
<220> FEATURE:
<223> OTHER INFORMATION: U6 probe

<400> SEQUENCE: 110
tatggaacgc ttctcgaatt        20

<210> SEQ ID NO 111
<211> LENGTH: 20
<212> TYPE: DNA
<213> ORGANISM: Artificial Sequence
<220> FEATURE:
<223> OTHER INFORMATION: U2 probe

<400> SEQUENCE: 111
agaacagata ctacacttga        20

<210> SEQ ID NO 112
<211> LENGTH: 22
<212> TYPE: DNA
<213> ORGANISM: Artificial Sequence
<220> FEATURE:
<223> OTHER INFORMATION: sli-siRNA-887-5pp probe

<400> SEQUENCE: 112
ctacctatgg tgaacgtgtt gt        22

<210> SEQ ID NO 113
<211> LENGTH: 18
<212> TYPE: DNA
<213> ORGANISM: Artificial Sequence
<220> FEATURE:
<223> OTHER INFORMATION: sli-siRNA-887-3pp probe

<400> SEQUENCE: 113
gcaacacgtt caccataa        18

<210> SEQ ID NO 114
<211> LENGTH: 22
<212> TYPE: DNA
<213> ORGANISM: Artificial Sequence
<220> FEATURE:
<223> OTHER INFORMATION: sli-siRNA-1148-5pp probe

<400> SEQUENCE: 114
aggccttgcc tgtgaagctc at        22

<210> SEQ ID NO 115
<211> LENGTH: 18
<212> TYPE: DNA
<213> ORGANISM: Artificial Sequence
<220> FEATURE:
<223> OTHER INFORMATION: sli-siRNA-1148-3pp probe

<400> SEQUENCE: 115
gtgagcttca caggcaat        18

<210> SEQ ID NO 116
<211> LENGTH: 22
<212> TYPE: DNA

```
<213> ORGANISM: Artificial Sequence
<220> FEATURE:
<223> OTHER INFORMATION: miR-21p probe

<400> SEQUENCE: 116
tcaacatcag tctgataagc ta                                              22

<210> SEQ ID NO 117
<211> LENGTH: 21
<212> TYPE: DNA
<213> ORGANISM: Artificial Sequence
<220> FEATURE:
<223> OTHER INFORMATION: miR-31p probe

<400> SEQUENCE: 117
cagctatgcc agcatcttgc c                                               21

<210> SEQ ID NO 118
<211> LENGTH: 21
<212> TYPE: DNA
<213> ORGANISM: Artificial Sequence
<220> FEATURE:
<223> OTHER INFORMATION: miR-143p probe

<400> SEQUENCE: 118
gagctacagt gcttcatctc a                                               21

<210> SEQ ID NO 119
<211> LENGTH: 10
<212> TYPE: DNA
<213> ORGANISM: Artificial Sequence
<220> FEATURE:
<223> OTHER INFORMATION: miR-ID-RT21-5p primer

<400> SEQUENCE: 119
tcagtctgat                                                            10

<210> SEQ ID NO 120
<211> LENGTH: 18
<212> TYPE: DNA
<213> ORGANISM: Artificial Sequence
<220> FEATURE:
<223> OTHER INFORMATION: miR-ID-F21-5p primer

<400> SEQUENCE: 120
gactgatgtt gatagctt                                                   18

<210> SEQ ID NO 121
<211> LENGTH: 18
<212> TYPE: DNA
<213> ORGANISM: Artificial Sequence
<220> FEATURE:
<223> OTHER INFORMATION: miR-ID-R21-5p primer

<400> SEQUENCE: 121
ctatcaacat cagtctga                                                   18

<210> SEQ ID NO 122
<211> LENGTH: 10
<212> TYPE: DNA
<213> ORGANISM: Artificial Sequence
<220> FEATURE:
<223> OTHER INFORMATION: miR-ID-RT143-5P primer

<400> SEQUENCE: 122
acagtgcttc                                                            10
```

<210> SEQ ID NO 123
<211> LENGTH: 18
<212> TYPE: DNA
<213> ORGANISM: Artificial Sequence
<220> FEATURE:
<223> OTHER INFORMATION: miR-ID-F143-5P primer

<400> SEQUENCE: 123
gcactgtagc tctgagat                                                 18

<210> SEQ ID NO 124
<211> LENGTH: 18
<212> TYPE: DNA
<213> ORGANISM: Artificial Sequence
<220> FEATURE:
<223> OTHER INFORMATION: miR-ID-R143-5P primer

<400> SEQUENCE: 124
tcagagctac agtgcttc                                                 18

<210> SEQ ID NO 125
<211> LENGTH: 10
<212> TYPE: DNA
<213> ORGANISM: Artificial Sequence
<220> FEATURE:
<223> OTHER INFORMATION: miR-ID-RT31-5p primer

<400> SEQUENCE: 125
tgccagcatc                                                          10

<210> SEQ ID NO 126
<211> LENGTH: 18
<212> TYPE: DNA
<213> ORGANISM: Artificial Sequence
<220> FEATURE:
<223> OTHER INFORMATION: miR-ID-F31-5p primer

<400> SEQUENCE: 126
gctggcatag ctgaaggc                                                 18

<210> SEQ ID NO 127
<211> LENGTH: 18
<212> TYPE: DNA
<213> ORGANISM: Artificial Sequence
<220> FEATURE:
<223> OTHER INFORMATION: miR-ID-R31-5p primer

<400> SEQUENCE: 127
ttcagctatg ccagcatc                                                 18

<210> SEQ ID NO 128
<211> LENGTH: 21
<212> TYPE: DNA
<213> ORGANISM: Artificial Sequence
<220> FEATURE:
<223> OTHER INFORMATION: miR-ID-RT-U6RNA primer

<400> SEQUENCE: 128
atggaacgct tcacgaattt g                                             21

<210> SEQ ID NO 129
<211> LENGTH: 22
<212> TYPE: DNA
<213> ORGANISM: Artificial Sequence
<220> FEATURE:

<223> OTHER INFORMATION: miR-ID-f-U6RNA primer

<400> SEQUENCE: 129
ccatattttg tgctcgcttc gg                                    22

<210> SEQ ID NO 130
<211> LENGTH: 22
<212> TYPE: DNA
<213> ORGANISM: Artificial Sequence
<220> FEATURE:
<223> OTHER INFORMATION: miR-ID-r-U6RNA primer

<400> SEQUENCE: 130
gaagcgagca caaaatatgg aa                                    22

<210> SEQ ID NO 131
<211> LENGTH: 22
<212> TYPE: DNA
<213> ORGANISM: Artificial Sequence
<220> FEATURE:
<223> OTHER INFORMATION: IRF9-F primer

<400> SEQUENCE: 131
gacttggtca ggtactttca gg                                    22

<210> SEQ ID NO 132
<211> LENGTH: 20
<212> TYPE: DNA
<213> ORGANISM: Artificial Sequence
<220> FEATURE:
<223> OTHER INFORMATION: IRF9-R primer

<400> SEQUENCE: 132
tctacaccag ggacagaatg                                       20

<210> SEQ ID NO 133
<211> LENGTH: 19
<212> TYPE: DNA
<213> ORGANISM: Artificial Sequence
<220> FEATURE:
<223> OTHER INFORMATION: IFITM1-F primer

<400> SEQUENCE: 133
ccaaagccag aagatgcac                                        19

<210> SEQ ID NO 134
<211> LENGTH: 19
<212> TYPE: DNA
<213> ORGANISM: Artificial Sequence
<220> FEATURE:
<223> OTHER INFORMATION: IFITM1-R primer

<400> SEQUENCE: 134
gctatgaagc ccagacagc                                        19

<210> SEQ ID NO 135
<211> LENGTH: 22
<212> TYPE: DNA
<213> ORGANISM: Artificial Sequence
<220> FEATURE:
<223> OTHER INFORMATION: 5CDKL2 primer

<400> SEQUENCE: 135
gcctccttgg gttcgtctat aa                                    22

```
<210> SEQ ID NO 136
<211> LENGTH: 20
<212> TYPE: DNA
<213> ORGANISM: Artificial Sequence
<220> FEATURE:
<223> OTHER INFORMATION: 3CDKL2 primer

<400> SEQUENCE: 136
ctcagggccc gctcatagta                                              20

<210> SEQ ID NO 137
<211> LENGTH: 20
<212> TYPE: DNA
<213> ORGANISM: Artificial Sequence
<220> FEATURE:
<223> OTHER INFORMATION: 5RRM2-841 primer

<400> SEQUENCE: 137
aagaagaagg cagactgggc                                              20

<210> SEQ ID NO 138
<211> LENGTH: 20
<212> TYPE: DNA
<213> ORGANISM: Artificial Sequence
<220> FEATURE:
<223> OTHER INFORMATION: 3RRM2-960 primer

<400> SEQUENCE: 138
tatcgacgca aagaaccgg                                               20

<210> SEQ ID NO 139
<211> LENGTH: 20
<212> TYPE: DNA
<213> ORGANISM: Artificial Sequence
<220> FEATURE:
<223> OTHER INFORMATION: 5RRM2-1081 primer

<400> SEQUENCE: 139
ccatcggagg agagagtaag                                              20

<210> SEQ ID NO 140
<211> LENGTH: 20
<212> TYPE: DNA
<213> ORGANISM: Artificial Sequence
<220> FEATURE:
<223> OTHER INFORMATION: 3RRM2-1200 primer

<400> SEQUENCE: 140
gtattgcttc attagagtgc                                              20

<210> SEQ ID NO 141
<211> LENGTH: 20
<212> TYPE: DNA
<213> ORGANISM: Artificial Sequence
<220> FEATURE:
<223> OTHER INFORMATION: 5RRM2-1281 primer

<400> SEQUENCE: 141
ggagaatatt tcactggaag                                              20

<210> SEQ ID NO 142
<211> LENGTH: 20
<212> TYPE: DNA
<213> ORGANISM: Artificial Sequence
<220> FEATURE:
<223> OTHER INFORMATION: 3RRM2-1400 primer
```

<400> SEQUENCE: 142
tagaagtcag catccaaggt                                            20

<210> SEQ ID NO 143
<211> LENGTH: 400
<212> TYPE: DNA
<213> ORGANISM: Artificial Sequence
<220> FEATURE:
<223> OTHER INFORMATION: U6+MCS

<400> SEQUENCE: 143
gatcaggatc cgtcgacgcg gccgcaccgg tccaaggtcg ggcaggaaga gggcctattt    60
cccatgattc cttcatattt gcatatacga tacaaggctg ttagagagat aattagaatt   120
aatttgactg taaacacaaa gatattagta caaaatacgt gacgtagaaa gtaataattt   180
cttgggtagt ttgcagtttt aaaattatgt tttaaaatgg actatcatat gcttaccgta   240
acttgaaagt atttcgattt cttggcttta tatcttgt ggaaaggacg aaagatctgg    300
taccgaattc gatatcacta gtgcggccgc tgcagctcga gcttaagtct agagggcccg   360
tttaaacccg ctgatcagcc tcgactgtgc cttctagttg                         400

<210> SEQ ID NO 144
<211> LENGTH: 400
<212> TYPE: DNA
<213> ORGANISM: Artificial Sequence
<220> FEATURE:
<223> OTHER INFORMATION: U6TO+MCS

<400> SEQUENCE: 144
gatcaggatc cgtcgacgcg gccgcaccgg tccaaggtcg ggcaggaaga gggcctattt    60
cccatgattc cttcatattt gcatatacga tacaaggctg ttagagagat aattagaatt   120
aatttgactg taaacacaaa gatattagta caaaatacgt gacgtagaaa gtaataattt   180
cttgggtagt ttgcagtttt aaaattatgt tttaaaatgg actatcatat gcttaccgta   240
acttgaaagt atttcgattt cttggcttta tatctccc tatcagtgat agagatctgg    300
taccgaattc gatatcacta gtgcggccgc tgcagctcga gcttaagtct agagggcccg   360
tttaaacccg ctgatcagcc tcgactgtgc cttctagttg                         400

<210> SEQ ID NO 145
<211> LENGTH: 22
<212> TYPE: DNA
<213> ORGANISM: Artificial Sequence
<220> FEATURE:
<223> OTHER INFORMATION: sli-siRNA-887 U3A

<400> SEQUENCE: 145
ctacctatgg tgaacgtgta gt                                          22

<210> SEQ ID NO 146
<211> LENGTH: 22
<212> TYPE: DNA
<213> ORGANISM: Artificial Sequence
<220> FEATURE:
<223> OTHER INFORMATION: sli-siRNA-887 U4A

<400> SEQUENCE: 146
ctacctatgg tgaacgtgat gt                                          22

<210> SEQ ID NO 147
<211> LENGTH: 22

```
<212> TYPE: DNA
<213> ORGANISM: Artificial Sequence
<220> FEATURE:
<223> OTHER INFORMATION: sli-siRNA-887 G5C

<400> SEQUENCE: 147
ctacctatgg tgaacgtctt gt                                              22

<210> SEQ ID NO 148
<211> LENGTH: 22
<212> TYPE: DNA
<213> ORGANISM: Artificial Sequence
<220> FEATURE:
<223> OTHER INFORMATION: sli-siRNA-887 U6G

<400> SEQUENCE: 148
ctacctatgg tgaacgggtt gt                                              22

<210> SEQ ID NO 149
<211> LENGTH: 22
<212> TYPE: DNA
<213> ORGANISM: Artificial Sequence
<220> FEATURE:
<223> OTHER INFORMATION: sli-siRNA-887 G7C

<400> SEQUENCE: 149
ctacctatgg tgaacctgtt gt                                              22

<210> SEQ ID NO 150
<211> LENGTH: 22
<212> TYPE: DNA
<213> ORGANISM: Artificial Sequence
<220> FEATURE:
<223> OTHER INFORMATION: sli-siRNA-887 C8G

<400> SEQUENCE: 150
ctacctatgg tgaaggtgtt gt                                              22

<210> SEQ ID NO 151
<211> LENGTH: 22
<212> TYPE: DNA
<213> ORGANISM: Artificial Sequence
<220> FEATURE:
<223> OTHER INFORMATION: sli-siRNA-887 A9U

<400> SEQUENCE: 151
ctacctatgg tgatcgtgtt gt                                              22

<210> SEQ ID NO 152
<211> LENGTH: 22
<212> TYPE: DNA
<213> ORGANISM: Artificial Sequence
<220> FEATURE:
<223> OTHER INFORMATION: sli-siRNA-887 A10G

<400> SEQUENCE: 152
ctacctatgg tggacgtgtt gt                                              22

<210> SEQ ID NO 153
<211> LENGTH: 22
<212> TYPE: DNA
<213> ORGANISM: Artificial Sequence
<220> FEATURE:
<223> OTHER INFORMATION: sli-siRNA-887 G11C

<400> SEQUENCE: 153
```

```
ctacctatgg tcaacgtgtt gt                                              22

<210> SEQ ID NO 154
<211> LENGTH: 22
<212> TYPE: DNA
<213> ORGANISM: Artificial Sequence
<220> FEATURE:
<223> OTHER INFORMATION: sli-siRNA-887 U12G

<400> SEQUENCE: 154
ctacctatgg ggaacgtgtt gt                                              22

<210> SEQ ID NO 155
<211> LENGTH: 22
<212> TYPE: DNA
<213> ORGANISM: Artificial Sequence
<220> FEATURE:
<223> OTHER INFORMATION: sli-siRNA-887 G13C

<400> SEQUENCE: 155
ctacctatgc tgaacgtgtt gt                                              22

<210> SEQ ID NO 156
<211> LENGTH: 22
<212> TYPE: DNA
<213> ORGANISM: Artificial Sequence
<220> FEATURE:
<223> OTHER INFORMATION: sli-siRNA-887 G14C

<400> SEQUENCE: 156
ctacctatcg tgaacgtgtt gt                                              22

<210> SEQ ID NO 157
<211> LENGTH: 22
<212> TYPE: DNA
<213> ORGANISM: Artificial Sequence
<220> FEATURE:
<223> OTHER INFORMATION: sli-siRNA-887 U15A

<400> SEQUENCE: 157
ctacctaagg tgaacgtgtt gt                                              22

<210> SEQ ID NO 158
<211> LENGTH: 22
<212> TYPE: DNA
<213> ORGANISM: Artificial Sequence
<220> FEATURE:
<223> OTHER INFORMATION: sli-siRNA-887 A16G

<400> SEQUENCE: 158
ctacctgtgg tgaacgtgtt gt                                              22

<210> SEQ ID NO 159
<211> LENGTH: 22
<212> TYPE: DNA
<213> ORGANISM: Artificial Sequence
<220> FEATURE:
<223> OTHER INFORMATION: sli-siRNA-887 U17A

<400> SEQUENCE: 159
ctaccaatgg tgaacgtgtt gt                                              22

<210> SEQ ID NO 160
<211> LENGTH: 22
<212> TYPE: DNA
<213> ORGANISM: Artificial Sequence
```

-continued

```
<220> FEATURE:
<223> OTHER INFORMATION: sli-siRNA-887 C18G

<400> SEQUENCE: 160
ctacgtatgg tgaacgtgtt gt                                              22

<210> SEQ ID NO 161
<211> LENGTH: 22
<212> TYPE: DNA
<213> ORGANISM: Artificial Sequence
<220> FEATURE:
<223> OTHER INFORMATION: sli-siRNA-887 U6G-U12G

<400> SEQUENCE: 161
ctacctatgg ggaacgggtt gt                                              22

<210> SEQ ID NO 162
<211> LENGTH: 22
<212> TYPE: DNA
<213> ORGANISM: Artificial Sequence
<220> FEATURE:
<223> OTHER INFORMATION: sli-siRNA-887 U3C

<400> SEQUENCE: 162
ctacctatgg tgaacgtgtc gt                                              22

<210> SEQ ID NO 163
<211> LENGTH: 22
<212> TYPE: DNA
<213> ORGANISM: Artificial Sequence
<220> FEATURE:
<223> OTHER INFORMATION: sli-siRNA-887 U4C

<400> SEQUENCE: 163
ctacctatgg tgaacgtgct gt                                              22

<210> SEQ ID NO 164
<211> LENGTH: 22
<212> TYPE: DNA
<213> ORGANISM: Artificial Sequence
<220> FEATURE:
<223> OTHER INFORMATION: sli-siRNA-887 G5A

<400> SEQUENCE: 164
ctacctatgg tgaacgtatt gt                                              22

<210> SEQ ID NO 165
<211> LENGTH: 22
<212> TYPE: DNA
<213> ORGANISM: Artificial Sequence
<220> FEATURE:
<223> OTHER INFORMATION: sli-siRNA-887 U6C

<400> SEQUENCE: 165
ctacctatgg tgaacgcgtt gt                                              22

<210> SEQ ID NO 166
<211> LENGTH: 22
<212> TYPE: DNA
<213> ORGANISM: Artificial Sequence
<220> FEATURE:
<223> OTHER INFORMATION: sli-siRNA-887 G7A

<400> SEQUENCE: 166
ctacctatgg tgaacatgtt gt                                              22
```

<210> SEQ ID NO 167
<211> LENGTH: 22
<212> TYPE: DNA
<213> ORGANISM: Artificial Sequence
<220> FEATURE:
<223> OTHER INFORMATION: sli-siRNA-887 C8A

<400> SEQUENCE: 167
ctacctatgg tgaaagtgtt gt                                              22

<210> SEQ ID NO 168
<211> LENGTH: 22
<212> TYPE: DNA
<213> ORGANISM: Artificial Sequence
<220> FEATURE:
<223> OTHER INFORMATION: sli-siRNA-887 A9C

<400> SEQUENCE: 168
ctacctatgg tgaccgtgtt gt                                              22

<210> SEQ ID NO 169
<211> LENGTH: 22
<212> TYPE: DNA
<213> ORGANISM: Artificial Sequence
<220> FEATURE:
<223> OTHER INFORMATION: sli-siRNA-887 A10C

<400> SEQUENCE: 169
ctacctatgg tgcacgtgtt gt                                              22

<210> SEQ ID NO 170
<211> LENGTH: 22
<212> TYPE: DNA
<213> ORGANISM: Artificial Sequence
<220> FEATURE:
<223> OTHER INFORMATION: sli-siRNA-887 G11A

<400> SEQUENCE: 170
ctacctatgg taaacgtgtt gt                                              22

<210> SEQ ID NO 171
<211> LENGTH: 22
<212> TYPE: DNA
<213> ORGANISM: Artificial Sequence
<220> FEATURE:
<223> OTHER INFORMATION: sli-siRNA-887 U12C

<400> SEQUENCE: 171
ctacctatgg cgaacgtgtt gt                                              22

<210> SEQ ID NO 172
<211> LENGTH: 22
<212> TYPE: DNA
<213> ORGANISM: Artificial Sequence
<220> FEATURE:
<223> OTHER INFORMATION: sli-siRNA-887 G13A

<400> SEQUENCE: 172
ctacctatga tgaacgtgtt gt                                              22

<210> SEQ ID NO 173
<211> LENGTH: 22
<212> TYPE: DNA
<213> ORGANISM: Artificial Sequence
<220> FEATURE:
<223> OTHER INFORMATION: sli-siRNA-887 G14A

```
<400> SEQUENCE: 173
ctacctatag tgaacgtgtt gt                                              22

<210> SEQ ID NO 174
<211> LENGTH: 22
<212> TYPE: DNA
<213> ORGANISM: Artificial Sequence
<220> FEATURE:
<223> OTHER INFORMATION: sli-siRNA-887 U15C

<400> SEQUENCE: 174
ctacctacgg tgaacgtgtt gt                                              22

<210> SEQ ID NO 175
<211> LENGTH: 22
<212> TYPE: DNA
<213> ORGANISM: Artificial Sequence
<220> FEATURE:
<223> OTHER INFORMATION: sli-siRNA-887 A16C

<400> SEQUENCE: 175
ctacctctgg tgaacgtgtt gt                                              22

<210> SEQ ID NO 176
<211> LENGTH: 22
<212> TYPE: DNA
<213> ORGANISM: Artificial Sequence
<220> FEATURE:
<223> OTHER INFORMATION: sli-siRNA-887 U17C

<400> SEQUENCE: 176
ctacccatgg tgaacgtgtt gt                                              22

<210> SEQ ID NO 177
<211> LENGTH: 22
<212> TYPE: DNA
<213> ORGANISM: Artificial Sequence
<220> FEATURE:
<223> OTHER INFORMATION: sli-siRNA-887 C18A

<400> SEQUENCE: 177
ctacatatgg tgaacgtgtt gt                                              22

<210> SEQ ID NO 178
<211> LENGTH: 22
<212> TYPE: DNA
<213> ORGANISM: Artificial Sequence
<220> FEATURE:
<223> OTHER INFORMATION: sli-siRNA-887 U4C-U15C

<400> SEQUENCE: 178
ctacctacgg tgaacgtgct gt                                              22

<210> SEQ ID NO 179
<211> LENGTH: 21
<212> TYPE: DNA
<213> ORGANISM: Artificial Sequence
<220> FEATURE:
<223> OTHER INFORMATION: sli-siRNA-ARXI WT

<400> SEQUENCE: 179
acacgctcaa gatcagccag t                                               21

<210> SEQ ID NO 180
```

```
<211> LENGTH: 21
<212> TYPE: DNA
<213> ORGANISM: Artificial Sequence
<220> FEATURE:
<223> OTHER INFORMATION: sli-siRNA-ARXI T1G

<400> SEQUENCE: 180
acacgctcaa gatcagccag g                                              21

<210> SEQ ID NO 181
<211> LENGTH: 21
<212> TYPE: DNA
<213> ORGANISM: Artificial Sequence
<220> FEATURE:
<223> OTHER INFORMATION: sli-siRNA-ARXI T1C

<400> SEQUENCE: 181
acacgctcaa gatcagccag c                                              21

<210> SEQ ID NO 182
<211> LENGTH: 21
<212> TYPE: DNA
<213> ORGANISM: Artificial Sequence
<220> FEATURE:
<223> OTHER INFORMATION: sli-siRNA-ARXI G2A

<400> SEQUENCE: 182
acacgctcaa gatcagccaa t                                              21

<210> SEQ ID NO 183
<211> LENGTH: 21
<212> TYPE: DNA
<213> ORGANISM: Artificial Sequence
<220> FEATURE:
<223> OTHER INFORMATION: sli-siRNA-ARXI G2C

<400> SEQUENCE: 183
acacgctcaa gatcagccac t                                              21

<210> SEQ ID NO 184
<211> LENGTH: 21
<212> TYPE: DNA
<213> ORGANISM: Artificial Sequence
<220> FEATURE:
<223> OTHER INFORMATION: sli-siRNA-ARXI A3T

<400> SEQUENCE: 184
acacgctcaa gatcagcctg t                                              21

<210> SEQ ID NO 185
<211> LENGTH: 21
<212> TYPE: DNA
<213> ORGANISM: Artificial Sequence
<220> FEATURE:
<223> OTHER INFORMATION: sli-siRNA-ARXI A3C

<400> SEQUENCE: 185
acacgctcaa gatcagcccg t                                              21

<210> SEQ ID NO 186
<211> LENGTH: 21
<212> TYPE: DNA
<213> ORGANISM: Artificial Sequence
<220> FEATURE:
<223> OTHER INFORMATION: sli-siRNA-ARXI C4G

<400> SEQUENCE: 186
```

-continued acacgctcaa gatcagcgag t                                    21

<210> SEQ ID NO 187
<211> LENGTH: 21
<212> TYPE: DNA
<213> ORGANISM: Artificial Sequence
<220> FEATURE:
<223> OTHER INFORMATION: sli-siRNA-ARXI C4A

<400> SEQUENCE: 187
acacgctcaa gatcagcaag t                                    21

<210> SEQ ID NO 188
<211> LENGTH: 21
<212> TYPE: DNA
<213> ORGANISM: Artificial Sequence
<220> FEATURE:
<223> OTHER INFORMATION: sli-siRNA-ARXI C5G

<400> SEQUENCE: 188
acacgctcaa gatcaggcag t                                    21

<210> SEQ ID NO 189
<211> LENGTH: 21
<212> TYPE: DNA
<213> ORGANISM: Artificial Sequence
<220> FEATURE:
<223> OTHER INFORMATION: sli-siRNA-ARXI C5A

<400> SEQUENCE: 189
acacgctcaa gatcagacag t                                    21

<210> SEQ ID NO 190
<211> LENGTH: 21
<212> TYPE: DNA
<213> ORGANISM: Artificial Sequence
<220> FEATURE:
<223> OTHER INFORMATION: sli-siRNA-ARXI G6C

<400> SEQUENCE: 190
acacgctcaa gatcacccag t                                    21

<210> SEQ ID NO 191
<211> LENGTH: 21
<212> TYPE: DNA
<213> ORGANISM: Artificial Sequence
<220> FEATURE:
<223> OTHER INFORMATION: sli-siRNA-ARXI G6A

<400> SEQUENCE: 191
acacgctcaa gatcaaccag t                                    21

<210> SEQ ID NO 192
<211> LENGTH: 21
<212> TYPE: DNA
<213> ORGANISM: Artificial Sequence
<220> FEATURE:
<223> OTHER INFORMATION: sli-siRNA-ARXI A7T

<400> SEQUENCE: 192
acacgctcaa gatctgccag t                                    21

<210> SEQ ID NO 193
<211> LENGTH: 21
<212> TYPE: DNA

```
<213> ORGANISM: Artificial Sequence
<220> FEATURE:
<223> OTHER INFORMATION: sli-siRNA-ARXI A7C

<400> SEQUENCE: 193
acacgctcaa gatccgccag t                                              21

<210> SEQ ID NO 194
<211> LENGTH: 21
<212> TYPE: DNA
<213> ORGANISM: Artificial Sequence
<220> FEATURE:
<223> OTHER INFORMATION: sli-siRNA-ARXI C8G

<400> SEQUENCE: 194
acacgctcaa gatgagccag t                                              21

<210> SEQ ID NO 195
<211> LENGTH: 21
<212> TYPE: DNA
<213> ORGANISM: Artificial Sequence
<220> FEATURE:
<223> OTHER INFORMATION: sli-siRNA-ARXI C8A

<400> SEQUENCE: 195
acacgctcaa gataagccag t                                              21

<210> SEQ ID NO 196
<211> LENGTH: 21
<212> TYPE: DNA
<213> ORGANISM: Artificial Sequence
<220> FEATURE:
<223> OTHER INFORMATION: sli-siRNA-ARXI TPA

<400> SEQUENCE: 196
acacgctcaa gaacagccag t                                              21

<210> SEQ ID NO 197
<211> LENGTH: 21
<212> TYPE: DNA
<213> ORGANISM: Artificial Sequence
<220> FEATURE:
<223> OTHER INFORMATION: sli-siRNA-ARXI T9C

<400> SEQUENCE: 197
acacgctcaa gaccagccag t                                              21

<210> SEQ ID NO 198
<211> LENGTH: 21
<212> TYPE: DNA
<213> ORGANISM: Artificial Sequence
<220> FEATURE:
<223> OTHER INFORMATION: sli-siRNA-ARXI A10T

<400> SEQUENCE: 198
acacgctcaa gttcagccag t                                              21

<210> SEQ ID NO 199
<211> LENGTH: 21
<212> TYPE: DNA
<213> ORGANISM: Artificial Sequence
<220> FEATURE:
<223> OTHER INFORMATION: sli-siRNA-ARXI A10C

<400> SEQUENCE: 199
acacgctcaa gctcagccag t                                              21
```

<210> SEQ ID NO 200
<211> LENGTH: 21
<212> TYPE: DNA
<213> ORGANISM: Artificial Sequence
<220> FEATURE:
<223> OTHER INFORMATION: sli-siRNA-ARXI G11C

<400> SEQUENCE: 200
acacgctcaa catcagccag t                                              21

<210> SEQ ID NO 201
<211> LENGTH: 21
<212> TYPE: DNA
<213> ORGANISM: Artificial Sequence
<220> FEATURE:
<223> OTHER INFORMATION: sli-siRNA-ARXI G11T

<400> SEQUENCE: 201
acacgctcaa tatcagccag t                                              21

<210> SEQ ID NO 202
<211> LENGTH: 21
<212> TYPE: DNA
<213> ORGANISM: Artificial Sequence
<220> FEATURE:
<223> OTHER INFORMATION: sli-siRNA-ARXI A12T

<400> SEQUENCE: 202
acacgctcat gatcagccag t                                              21

<210> SEQ ID NO 203
<211> LENGTH: 21
<212> TYPE: DNA
<213> ORGANISM: Artificial Sequence
<220> FEATURE:
<223> OTHER INFORMATION: sli-siRNA-ARXI A12C

<400> SEQUENCE: 203
acacgctcac gatcagccag t                                              21

<210> SEQ ID NO 204
<211> LENGTH: 21
<212> TYPE: DNA
<213> ORGANISM: Artificial Sequence
<220> FEATURE:
<223> OTHER INFORMATION: sli-siRNA-ARXI A13T

<400> SEQUENCE: 204
acacgctcta gatcagccag t                                              21

<210> SEQ ID NO 205
<211> LENGTH: 21
<212> TYPE: DNA
<213> ORGANISM: Artificial Sequence
<220> FEATURE:
<223> OTHER INFORMATION: sli-siRNA-ARXI A13C

<400> SEQUENCE: 205
acacgctcca gatcagccag t                                              21

<210> SEQ ID NO 206
<211> LENGTH: 21
<212> TYPE: DNA
<213> ORGANISM: Artificial Sequence
<220> FEATURE:

<223> OTHER INFORMATION: sli-siRNA-ARXI C14G

<400> SEQUENCE: 206
acacgctgaa gatcagccag t    21

<210> SEQ ID NO 207
<211> LENGTH: 21
<212> TYPE: DNA
<213> ORGANISM: Artificial Sequence
<220> FEATURE:
<223> OTHER INFORMATION: sli-siRNA-ARXI C14A

<400> SEQUENCE: 207
acacgctaaa gatcagccag t    21

<210> SEQ ID NO 208
<211> LENGTH: 21
<212> TYPE: DNA
<213> ORGANISM: Artificial Sequence
<220> FEATURE:
<223> OTHER INFORMATION: sli-siRNA-ARXI T15A

<400> SEQUENCE: 208
acacgcacaa gatcagccag t    21

<210> SEQ ID NO 209
<211> LENGTH: 21
<212> TYPE: DNA
<213> ORGANISM: Artificial Sequence
<220> FEATURE:
<223> OTHER INFORMATION: sli-siRNA-ARXI T15G

<400> SEQUENCE: 209
acacgcgcaa gatcagccag t    21

<210> SEQ ID NO 210
<211> LENGTH: 21
<212> TYPE: DNA
<213> ORGANISM: Artificial Sequence
<220> FEATURE:
<223> OTHER INFORMATION: sli-siRNA-ARXI C16G

<400> SEQUENCE: 210
acacggtcaa gatcagccag t    21

<210> SEQ ID NO 211
<211> LENGTH: 21
<212> TYPE: DNA
<213> ORGANISM: Artificial Sequence
<220> FEATURE:
<223> OTHER INFORMATION: sli-siRNA-ARXI C16A

<400> SEQUENCE: 211
acacgatcaa gatcagccag t    21

<210> SEQ ID NO 212
<211> LENGTH: 21
<212> TYPE: DNA
<213> ORGANISM: Artificial Sequence
<220> FEATURE:
<223> OTHER INFORMATION: sli-siRNA-ARXI G17C

<400> SEQUENCE: 212
acaccctcaa gatcagccag t    21

<210> SEQ ID NO 213
<211> LENGTH: 21
<212> TYPE: DNA
<213> ORGANISM: Artificial Sequence
<220> FEATURE:
<223> OTHER INFORMATION: sli-siRNA-ARXI G17A

<400> SEQUENCE: 213
acacactcaa gatcagccag t                                              21

<210> SEQ ID NO 214
<211> LENGTH: 21
<212> TYPE: DNA
<213> ORGANISM: Artificial Sequence
<220> FEATURE:
<223> OTHER INFORMATION: sli-siRNA-ARXI C18G

<400> SEQUENCE: 214
acaggctcaa gatcagccag t                                              21

<210> SEQ ID NO 215
<211> LENGTH: 21
<212> TYPE: DNA
<213> ORGANISM: Artificial Sequence
<220> FEATURE:
<223> OTHER INFORMATION: sli-siRNA-ARXI C18A

<400> SEQUENCE: 215
acaagctcaa gatcagccag t                                              21

<210> SEQ ID NO 216
<211> LENGTH: 21
<212> TYPE: DNA
<213> ORGANISM: Artificial Sequence
<220> FEATURE:
<223> OTHER INFORMATION: sli-siRNA-ARXI A19T

<400> SEQUENCE: 216
actcgctcaa gatcagccag t                                              21

<210> SEQ ID NO 217
<211> LENGTH: 21
<212> TYPE: DNA
<213> ORGANISM: Artificial Sequence
<220> FEATURE:
<223> OTHER INFORMATION: sli-siRNA-ARXI A19C

<400> SEQUENCE: 217
acccgctcaa gatcagccag t                                              21

<210> SEQ ID NO 218
<211> LENGTH: 22
<212> TYPE: DNA
<213> ORGANISM: Artificial Sequence
<220> FEATURE:
<223> OTHER INFORMATION: sli-siRNA-451 WT

<400> SEQUENCE: 218
taaactcagt aatggtaacg gt                                             22

<210> SEQ ID NO 219
<211> LENGTH: 22
<212> TYPE: DNA
<213> ORGANISM: Artificial Sequence
<220> FEATURE:
<223> OTHER INFORMATION: sli-siRNA-451 T3A

<400> SEQUENCE: 219 taaaactcagt aatggtaacg ga                                           22

<210> SEQ ID NO 220
<211> LENGTH: 22
<212> TYPE: DNA
<213> ORGANISM: Artificial Sequence
<220> FEATURE:
<223> OTHER INFORMATION: sli-siRNA-451 T3C

<400> SEQUENCE: 220 taaaactcagt aatggtaacg gc                                           22

<210> SEQ ID NO 221
<211> LENGTH: 22
<212> TYPE: DNA
<213> ORGANISM: Artificial Sequence
<220> FEATURE:
<223> OTHER INFORMATION: sli-siRNA-451 G4C

<400> SEQUENCE: 221 taaaactcagt aatggtaacg ct                                           22

<210> SEQ ID NO 222
<211> LENGTH: 22
<212> TYPE: DNA
<213> ORGANISM: Artificial Sequence
<220> FEATURE:
<223> OTHER INFORMATION: sli-siRNA-451 G4A

<400> SEQUENCE: 222 taaaactcagt aatggtaacg at                                           22

<210> SEQ ID NO 223
<211> LENGTH: 22
<212> TYPE: DNA
<213> ORGANISM: Artificial Sequence
<220> FEATURE:
<223> OTHER INFORMATION: sli-siRNA-451 G5C

<400> SEQUENCE: 223 taaaactcagt aatggtaacc gt                                           22

<210> SEQ ID NO 224
<211> LENGTH: 22
<212> TYPE: DNA
<213> ORGANISM: Artificial Sequence
<220> FEATURE:
<223> OTHER INFORMATION: sli-siRNA-451 G5A

<400> SEQUENCE: 224 taaaactcagt aatggtaaca gt                                           22

<210> SEQ ID NO 225
<211> LENGTH: 22
<212> TYPE: DNA
<213> ORGANISM: Artificial Sequence
<220> FEATURE:
<223> OTHER INFORMATION: sli-siRNA-451 C6G

<400> SEQUENCE: 225 taaaactcagt aatggtaagg gt                                           22

<210> SEQ ID NO 226
<211> LENGTH: 22

```
<212> TYPE: DNA
<213> ORGANISM: Artificial Sequence
<220> FEATURE:
<223> OTHER INFORMATION: C6A

<400> SEQUENCE: 226
taaactcagt aatggtaaag gt                                              22

<210> SEQ ID NO 227
<211> LENGTH: 22
<212> TYPE: DNA
<213> ORGANISM: Artificial Sequence
<220> FEATURE:
<223> OTHER INFORMATION: sli-siRNA-451 A7T

<400> SEQUENCE: 227
taaactcagt aatggtatcg gt                                              22

<210> SEQ ID NO 228
<211> LENGTH: 22
<212> TYPE: DNA
<213> ORGANISM: Artificial Sequence
<220> FEATURE:
<223> OTHER INFORMATION: sli-siRNA-451 A7C

<400> SEQUENCE: 228
taaactcagt aatggtaccg gt                                              22

<210> SEQ ID NO 229
<211> LENGTH: 22
<212> TYPE: DNA
<213> ORGANISM: Artificial Sequence
<220> FEATURE:
<223> OTHER INFORMATION: sli-siRNA-451 A8G

<400> SEQUENCE: 229
taaactcagt aatggtgacg gt                                              22

<210> SEQ ID NO 230
<211> LENGTH: 22
<212> TYPE: DNA
<213> ORGANISM: Artificial Sequence
<220> FEATURE:
<223> OTHER INFORMATION: sli-siRNA-451 A8C

<400> SEQUENCE: 230
taaactcagt aatggtcacg gt                                              22

<210> SEQ ID NO 231
<211> LENGTH: 22
<212> TYPE: DNA
<213> ORGANISM: Artificial Sequence
<220> FEATURE:
<223> OTHER INFORMATION: sli-siRNA-451 T9A

<400> SEQUENCE: 231
taaactcagt aatggaaacg gt                                              22

<210> SEQ ID NO 232
<211> LENGTH: 22
<212> TYPE: DNA
<213> ORGANISM: Artificial Sequence
<220> FEATURE:
<223> OTHER INFORMATION: sli-siRNA-451 T9C

<400> SEQUENCE: 232
```
taaactcagt aatggcaacg gt                                                    22

<210> SEQ ID NO 233
<211> LENGTH: 22
<212> TYPE: DNA
<213> ORGANISM: Artificial Sequence
<220> FEATURE:
<223> OTHER INFORMATION: sli-siRNA-451 G10A

<400> SEQUENCE: 233
taaactcagt aatgataacg gt                                                    22

<210> SEQ ID NO 234
<211> LENGTH: 22
<212> TYPE: DNA
<213> ORGANISM: Artificial Sequence
<220> FEATURE:
<223> OTHER INFORMATION: sli-siRNA-451 G10C

<400> SEQUENCE: 234
taaactcagt aatgctaacg gt                                                    22

<210> SEQ ID NO 235
<211> LENGTH: 22
<212> TYPE: DNA
<213> ORGANISM: Artificial Sequence
<220> FEATURE:
<223> OTHER INFORMATION: sli-siRNA-451 G11A

<400> SEQUENCE: 235
taaactcagt aatagtaacg gt                                                    22

<210> SEQ ID NO 236
<211> LENGTH: 22
<212> TYPE: DNA
<213> ORGANISM: Artificial Sequence
<220> FEATURE:
<223> OTHER INFORMATION: sli-siRNA-451 G11C

<400> SEQUENCE: 236
taaactcagt aatcgtaacg gt                                                    22

<210> SEQ ID NO 237
<211> LENGTH: 22
<212> TYPE: DNA
<213> ORGANISM: Artificial Sequence
<220> FEATURE:
<223> OTHER INFORMATION: sli-siRNA-451 T12A

<400> SEQUENCE: 237
taaactcagt aaaggtaacg gt                                                    22

<210> SEQ ID NO 238
<211> LENGTH: 22
<212> TYPE: DNA
<213> ORGANISM: Artificial Sequence
<220> FEATURE:
<223> OTHER INFORMATION: sli-siRNA-451 T12C

<400> SEQUENCE: 238
taaactcagt aacggtaacg gt                                                    22

<210> SEQ ID NO 239
<211> LENGTH: 22
<212> TYPE: DNA
<213> ORGANISM: Artificial Sequence

```
<220> FEATURE:
<223> OTHER INFORMATION: sli-siRNA-451 A13T

<400> SEQUENCE: 239
taaactcagt attggtaacg gt                                              22

<210> SEQ ID NO 240
<211> LENGTH: 22
<212> TYPE: DNA
<213> ORGANISM: Artificial Sequence
<220> FEATURE:
<223> OTHER INFORMATION: sli-siRNA-451 A13C

<400> SEQUENCE: 240
taaactcagt actggtaacg gt                                              22

<210> SEQ ID NO 241
<211> LENGTH: 22
<212> TYPE: DNA
<213> ORGANISM: Artificial Sequence
<220> FEATURE:
<223> OTHER INFORMATION: sli-siRNA-451 A14T

<400> SEQUENCE: 241
taaactcagt tatggtaacg gt                                              22

<210> SEQ ID NO 242
<211> LENGTH: 22
<212> TYPE: DNA
<213> ORGANISM: Artificial Sequence
<220> FEATURE:
<223> OTHER INFORMATION: sli-siRNA-451 A14C

<400> SEQUENCE: 242
taaactcagt catggtaacg gt                                              22

<210> SEQ ID NO 243
<211> LENGTH: 22
<212> TYPE: DNA
<213> ORGANISM: Artificial Sequence
<220> FEATURE:
<223> OTHER INFORMATION: sli-siRNA-451 T15A

<400> SEQUENCE: 243
taaactcaga aatggtaacg gt                                              22

<210> SEQ ID NO 244
<211> LENGTH: 22
<212> TYPE: DNA
<213> ORGANISM: Artificial Sequence
<220> FEATURE:
<223> OTHER INFORMATION: sli-siRNA-451 G16C

<400> SEQUENCE: 244
taaactcact aatggtaacg gt                                              22

<210> SEQ ID NO 245
<211> LENGTH: 22
<212> TYPE: DNA
<213> ORGANISM: Artificial Sequence
<220> FEATURE:
<223> OTHER INFORMATION: sli-siRNA-451 G16A

<400> SEQUENCE: 245
taaactcaat aatggtaacg gt                                              22
```

```
<210> SEQ ID NO 246
<211> LENGTH: 22
<212> TYPE: DNA
<213> ORGANISM: Artificial Sequence
<220> FEATURE:
<223> OTHER INFORMATION: sli-siRNA-451 A17T

<400> SEQUENCE: 246
taaactctgt aatggtaacg gt                                          22

<210> SEQ ID NO 247
<211> LENGTH: 22
<212> TYPE: DNA
<213> ORGANISM: Artificial Sequence
<220> FEATURE:
<223> OTHER INFORMATION: sli-siRNA-451 A17C

<400> SEQUENCE: 247
taaactccgt aatggtaacg gt                                          22
```

SHORT HAIRPIN RNA COMPOSITIONS, METHODS OF MAKING AND APPLICATIONS THEREOF

PRIORITY CLAIM

This application claims priority of U.S. Provisional Application No. 62/096,838 filed Dec. 24, 2014, the subject matter of which is hereby incorporated by reference as if fully set forth herein.

BACKGROUND

Gene-silencing by siRNAs is a powerful technology for manipulating gene expression and a potential therapeutic strategy for treating human diseases. Canonical siRNAs are ~21-nucleotide (nt) small RNAs that mimic products of Dicer processed double strand RNAs and can be incorporated into the RNA-induced-silencing-complex (RISC) to trigger the degradation of mRNA targets that contain highly complementary sequences (Elbashir 2001). Canonical siRNAs are designed to resemble the biogenesis intermediates of microRNAs (miRNA), a family of endogenous small RNAs that can repress the translation of target mRNAs that contain fully or partially complementary sequences. Therefore, siRNA and miRNA share the same functional machineries in the cell (Doench 2003; Zeng 2003).

The majority of miRNAs use Dicer to process the precursor-miRNAs (pre-miRNAs) to create 21 to 23-nt duplex RNAs that consist of one strand from the 5' arm (5p) and one strand from the 3' arm (3p). The 3' end of each strand has an overhang of two nt. This duplex RNA is also referred to as miRNA/miRNA*(the dominant strand/the less abundant strand). Accordingly, siRNAs are designed as duplexes of antisense strand/sense strand (guide strand/passenger strand) RNAs that are 21-nt long, and have a 19 base pair dsRNA stem and an overhang of two nt at the 3' end of each strand (siRNA, FIG. 1A). In contrast, similar duplexes that have overhangs of two nt at the 5' end (hereafter referred to as reverse siRNA or rsiRNA, FIG. 1B) are thought to be mostly inactive (Elbashir 2001). DNA vector systems can also be used to express siRNAs as short hairpin RNAs (shRNAs, exp-shRNA), which can be used to express corresponding siRNAs in stable cell lines (McManus 2002; Brummelkamp 2002).

Several recent publications have revealed critical roles for loops, length of stems, and base pairing in the stem in exp-shRNA processing and silencing potency (Gu 2012; Herrera-Carrillo 2014; McIntyre 2011). In vitro T7 transcribed or chemically synthesized shRNAs (syn-shRNAs) were also shown to be potent RNAi triggers (Siolas 2005). The functional structure of syn-shRNAs was further characterized and the short stem version was named as short shRNAs (sshRNA), which are Dicer-independent (Ge 2012; Dallas 2012). Despite its extensive application as an effective gene manipulation reagent in research, the bright future of RNAi therapeutics is shadowed by growing evidence that many siRNAs have toxic side effects due to off-target activities of both the sense and anti-sense strands. These off-target effects will also produce biased research data (Jackson 2003). Therefore, siRNA molecules that have a potent on-target effect and lack off-target activities are highly desirable for both clinical and research applications. Despite extensive bodies of work accomplished in the past decade for this purpose, it remains a challenge to find an optimized siRNA for a specific target. Thus, there is a need for detailed parameters that can be used to effectively create optimal shRNAs that can be further processed into potent siRNAs.

SUMMARY

One aspect provided herein relates to a synthetic short hairpin RNA (shRNA) molecule designed to silence the expression of a target gene comprising a 5' arm and a 3' arm comprising a stem region comprising 16, 17 or 18 base pairs, the base pairs comprising nucleotides from the 5' arm paired with nucleotides from the 3' arm, and one or more unpaired nucleotides at the 5' terminal end of the 5' arm and one or more unpaired nucleotides at the 3' terminal end of the 3' arm; and a loop region comprising 4 nucleotides that connects the 5' arm to the 3' arm, wherein the shRNA molecule is processed by Argonaute 2 (Ago2) in a Dicer-independent manner. In certain embodiments, the stem region of the shRNA molecule may be 17 base pairs and the shRNA molecule consists of 40 nucleotides, wherein the first nucleotide positioned at the 5' terminal end of the 5' arm is designated as p1 and the last nucleotide positioned at the 3' terminal end of the 3' arm is designated as p40. In certain embodiments, an Ago2 nick site may be located near the middle of the 3' arm. In certain embodiments, the Ago nick site may be located between nucleotides p30 and p31. In certain embodiments, an antisense region may comprise the 5' arm and the loop region (i.e., nucleotides p1-p22) and a sense region may comprise the 3' arm (i.e., nucleotides p23-p40). In certain embodiments, when the shRNA is 40 nts, the antisense region may comprise a seed region comprising nucleotides p2-p8, a central region comprising nucleotides p9-p12, a 3' supplementary region comprising nucleotides p13-p17 and a tail region comprising nucleotides p18-p22. In certain embodiments, the seed region is fully complementary to a portion of a target RNA sequence of the target gene and the 3' supplementary region is generally complementary to a portion of the target RNA sequence of the target gene. In certain embodiments, the target RNA sequence comprises a messenger RNA sequence of the target gene. In certain embodiments, the nucleotide sequence of the tail region may be fully complementary to a portion of the target nucleotide sequence. In certain embodiments, the base pairs of the stem region may comprise nucleotides p2-p18 from the 5' arm base paired with nucleotides p39-p23 from the 3' arm, respectively (i.e., p2:p39, p3:p38, p4:p37, p5:p36, p6:p35, p7:p34, p8:p33, p9:p32, p10:p31, p11:p30, p12:p29, p13:p28, p14:p27, p15:p26, p16:p25, p17:p24, and p18:p23). In certain embodiments, the base pairs formed between nucleotides p2-p17 and nucleotides p39-p24, respectively, may form fully complementary base pairs. In certain embodiments, the base pair formed between nucleotides p18 and p23 may form through a guanine (G):uracil (U) (i.e., G:U) or U:G wobble base pair. In certain embodiments, the unpaired nucleotide at the 3' terminal end of the 3' arm may be a cytosine (C). In certain embodiments, the one or more unpaired nucleotide at the 5' terminal end of the 5' arm is not phosphorylated. In certain embodiments, the one or more unpaired nucleotide at the 5' terminal end of the 5' arm may be an adenine (A) or a U. In certain embodiments, when the shRNA molecule is a synthetic shRNA molecule, the one or more unpaired nucleotide at the 5' terminal end of the 5' arm may be two A's. In certain embodiments, when the shRNA molecule is a synthetic shRNA molecule, the one or more unpaired base at the 3' terminal end of the 3' arm may be two deoxythymidine nucleotides (i.e., dTdT) and a C, wherein the C may be positioned 5' relative to the dTdTs. In certain embodiments, when the shRNA molecule is a synthetic shRNA molecule, the one or more unpaired base at the 3' terminal end of the 3' arm may be one dideoxycytidine nucleotide (i.e, ddC). In certain embodiments, the shRNA molecule may be expressed by a vector (i.e., vector expressed shRNA). In certain embodiments, when the shRNA molecule is a vector expressed shRNA, the one or more unpaired nucleotides at the 5' terminal end of the 5' arm may be one A.

Another aspect provided herein relates to a vector comprising a nucleotide sequence encoding any one or more of the vector expressed shRNA molecules as described herein. In certain embodiments, the vector may be a conditional expression vector comprising a U6 promoter to drive expression of the one or more shRNA molecules. In certain embodiments, the vector may be an inducible expression promoter comprising a doxycycline [dox]-inducible U6 (U6TO) promoter to drive expression of the one or more shRNA molecules.

Another aspect provided herein relates to a cell comprising any one or more of the vectors comprising a nucleotide sequence encoding any one or more of the vector expressed shRNA molecules as described herein. In certain embodiments, the cell may be a mammalian cell. In certain embodiments, the cell may be infected with a virus comprising the vector as described herein. In certain embodiments, the virus may be a lentivirus.

Another aspect provided herein relates to a method of designing a synthetic shRNA molecule comprising designing any of the synthetic shRNA molecules as described herein. In certain embodiments, antisense strand selection software may be used to design the shRNA molecule.

Another aspect provided herein relates to a method of silencing expression of a target nucleotide sequence comprising obtaining a sample comprising the target nucleotide sequence, and providing any of the synthetic shRNA molecules described herein and/or vectors comprising a nucleotide sequence encoding any one or more of the vector expressed shRNA molecules as described herein to the sample. In certain embodiments, production of unwanted sense strand is reduced.

Another aspect provided herein relates to a method of treating a subject having a disease or condition comprising administering a therapeutically effective amount of one or more of any of the synthetic shRNA molecules described herein to the subject.

Another aspect provided herein relates to a method of treating a subject having a disease or condition comprising administering a vector comprising a nucleotide sequence encoding one or more of the vector expressed shRNA molecules as described herein to the subject. In certain embodiments, a therapeutically effective amount of the one or more vector expressed shRNA molecules may be expressed by the vector.

Also provided herein are compositions, formulations and kits comprising the synthetic shRNA molecules, vector expressed shRNA molecules, or vectors comprising nucleotides sequences encoding one or more vector expressed shRNA molecules as described herein.

BRIEF DESCRIPTION OF THE DRAWINGS

FIG. 1A shows a schematic of the secondary structures of siRNA with a 3' end overhang of two nts. Nucleotides 1-21 of the 5' arm of the siRNA molecule make up the antisense strand and nucleotides 1-21 of the 3' arm of the siRNA molecule make up the sense strand. FIG. 1B shows reverse siRNA (i.e., rsiRNA) with a 5' end overhang of two nucleotides (nts). Nucleotides 1-21 of the 5' arm of the rsiRNA molecule make up the antisense strand and nucleotides 1-21 of the 3' arm of the rsiRNA molecule make up the sense strand. FIG. 1C shows the canonical structure of the synthetic version of sli-siRNA (i.e., agsiRNA) and the expressed version of sli-siRNA (i.e., agshRNA). The thick vertical lines represent base pairing. Nucleotides 1-18 of the 5' arm and nucleotides 19-22 of the loop make up the antisense strand. Nucleotides 23-40 of the 3' arm make up the sense strand.

FIG. 2A shows the secondary structure of pre-mi-451. The sequence of the 5' arm (5p) including the stem loop is the mature miR-451. The short fragment generated by Ago2 from 3p is shown in dark grey on the bottom left (i.e., sequence 3'-CUCUUGGUAAUG-5'), and the light grey bases on the bottom right from the 3p (i.e., sequence 3'-GUAAUGAU-5') were trimmed during miR-451 maturation. FIGS. 2B and 2C show tertiary and surface representations, respectively, of the predicted structures of hsa-pre-miR-451 without the last 3' UC bases.

FIG. 4A shows an alignment of 18 species of pre-miR-451 from miRBase 19. FIGS. 4B and 4C show predicted tertiary structures of hmiR-451 aligned with mmiR-451, and hmiR-451 aligned with dmiR-451, respectively.

FIG. 5 shows a table of the properties of pre-miR-451 versus siRNA molecules. Abbreviations are as follows: "wc"=Watson-Crick base pairs; "wb"=wobble base pairs; "mm"=mismatch base pairs. The asterisk ("*") indicates bases that are only present in pma-pre-miR-451.

FIG. 8A shows Western blots of R2 targeted by agshRNAs. Vector indicates the U6-agshRNA. Actin was used as the loading control. FIG. 8B shows Western blots comparing the activity of the canonical form of agshRNA with the G:U form and mismatched forms (mmp7). Vector indicates the U6m-agshRNA. Actin was used as the loading control. FIG. 8C shows a reporter assay of agshRNA designed to target R2. The R2 coding sequence (NCBI reference sequence: NM_001165931.1) and reverse sequence were cloned into the 3'UTR of Rluc gene in psiCheck2.2 to make reporters for R2-CDS and R2-CDS-reverse. These constructs measured the 5p and 3p activity of agshRNAs designed to target R2. Rluc/Fluc ratios are plotted. Error bars represent the standard deviation. FIG. 8D shows reporter assays to measure the 5p and 3p activity of the wt, mmp7, and GU forms. Rluc/Fluc ratios are plotted. Error bars represent the standard deviation.

FIG. 9 shows a table listing the length distributions of the 5p and 3p arms from various agshRNAs after processing by Ago2. The full sequence for each agshRNA construct is provided and the sequence of the loop region is bolded and underlined.

FIG. 10A shows the secondary structure predicted by the RNA structure of the single molecular folding form (SMFF) of hmiR-451. FIG. 10B shows the secondary structures predicted by RNA structure of the cross molecular hybridization form (CMHF) of hmiR-451 and its potential products when processed by Dicer. Anti-sense strands are designated as A21 and A19 and sense strands are designated 21C and 19C. FIG. 10C shows a schematic of the processing of agsiRNA CMHF (A-S17-L4-C) into A21, A19, 21C, and 19C by Dicer.

FIG. 11 shows the structures predicted by mFold for agsiRNA-887, agsiRNA-887-mut, and agshRNA-887.

FIG. 13A shows the secondary structure of agsiRNA-887 (the L40, S17, or wild-type forms) and some of the variants used in this study. Mismatches were introduced at p18:23 to make the mmp18 form, at p18:23 and p17:24 to make the mmp17-18 form, at p18:23, p17:24, and p16:25 to make the mmp16-17-18 form, at p6:35 to make the mmp6 form, at p7:34 to make the mmp7 form, at p2:39 to make the mmp2 form, at p2:p39 and p3:p38 to make the mmp2-3 form. FIG. 13B shows the secondary structure of agshRNA-887-GUp8 (with the p33 C replaced by a U) and the bulge-p7 (which has the G at p34 removed). The first 19 nt of agsiRNA-887 were directly connected to its complementary sequence to make the non-loop version (NL). UU was used to connect the first 19 nt of agsiRNA-887 to its complementary sequence, to make the short shRNA version (ssh). FIG. 13C shows the secondary structure of the stem variants of sli-siRNA-887. Longer stem variants (agshRNA-887 only) were created by adding nt to the end of the L22 form, using antisense sequences to RRM2 mRNA, and using the last 4 nt to make the loop. S17, wt; S18, perfect base pair at p19 was added to the stem. S19: perfect base pair at p19 and p20 were added to the stem. S20: perfect base pair at p19, p20, and p21 were added to the stem. The short stem variants S16, S15, S14, S13, S12, and S11 (for both agsiRNA and agshRNA), were created by removing nt from the end of the L22 form, one nt at a time, and using the last 4 nt of the trimmed sequence to make the loop (The end Cs of the S11, S12, and S13 forms were removed unintentionally). FIG. 13D shows the secondary structures of length variants of agsiRNA-887. Variants were created by trimming nt from the 3' end of L40 (wt) to make the L39 to L25 forms.

FIG. 14A shows the results for agshRNA-887. FIG. 14B shows the results for agsiRNA-887. The abbreviations are as follows: w=wild-type; m=mutant; c=control sli-siRNA with a scrambled sequence. Both U2 and U6 snoRNAs were used as RNA loading controls.

FIG. 18A shows dose-dependent reporter assays of agsiRNA-887 (agsi887) and agsiRNA-887 that had a monophosphate at the 5' end (P-agsi887). Rluc/Fluc ratios are shown. Error bars represent the standard deviation. FIG. 18B shows reporter assays of agsiRNAs in which anchor bases were replaced. The anchor nt A in agsiRNA-887 was replaced with a U or a C. Rluc/Fluc ratios are shown. Error bars represent the standard deviation. FIG. 18C shows reporter assays for 5' end prefixing variants of agsiRNA-887 in HCT-116 cells. Rluc/Fluc ratios are shown. Error bars represent the standard deviation. FIG. 18D shows a comparison of the agsiRNA-887 3' overhang: wt versus UU and dTdT forms in HCT-116 cells. Rluc/Fluc ratios are plotted. Error bars represent the standard deviation. FIG. 18E shows a comparison of the agsiRNA-887 3' overhang: wt versus U and ddC forms in HCT-116 cells. Rluc/Fluc ratios are plotted. Error bars represent the standard deviation. FIG. 18F shows a comparison of agsiRNA-887-wt versus the -mmp2, -mmp2-3, -mmp,6 and -mmp7 forms in HCT-116 cells. Rluc/Fluc ratios are plotted. Error bars represent the standard deviation. FIG. 18G shows reporter assays of loop variants of agsiRNA-887 in HCT-116 cells. 'p18GU' is wt. Rluc/Fluc ratios are shown. Error bars represent the standard deviation.

FIG. 19A shows a Northern blot to detect the processed products from agsiRNA-887 that have extra bases on the 5' or 3' end in transfected HEK-293 cells. Ctrl, scrambled agsiRNA. U2 and U6 snoRNAs were used as RNA loading controls. FIG. 19B shows a Northern blot to detect the processed products of base and loop modified agsiRNA-887 in transfected HEK-293 cells. U2 snoRNA was used as the RNA loading control. FIG. 19C shows a Northern blot to detect the processed products of agshRNA-887 variants expressed by the U6m promoter in transfected HEK-293 cells. U6 snoRNA was used as the RNA loading control. FIG. 19D shows a Northern blot to detect the processed products of stem variants of agshRNA-887 in transfected HEK-293 cells. Ctrl, scrambled agshRNA; S17, the wt agshRNA-887; mut, agshRNA-887 non-cleavable mutant; U1, S17 driven by a modified U1 promoter; H1, S17 driven by a modified H1 promoter. All other agshRNAs were transcribed from U6m. U2 and U6 snoRNAs were used as RNA loading controls. FIG. 19E shows a Northern blot to detect the processed products of stem variants of agsiRNA-887 in transfected HEK-293 cells. Ctrl, agsiRNA with a scrambled RNA sequence; S17, the wt agsiRNA-887; rsi, rsiRNA-887; si, siRNA-887. U2 and U6 snoRNAs were used as RNA loading controls. FIG. 19F shows results from reporter assays of HCT-116 cells transfected with the agsiRNA-887 stem variants. Rluc/Fluc ratios are shown. Error bars represent the standard deviation. FIG. 19G shows a Northern blot to detect the processed products of agsiRNA-887 that have length variations in transfected HEK-293 cells. Ctrl, agsiRNA with a scrambled sequence; mut, agsiRNA-887-mut. The weak band in L38 was unintentionally caused by using only 1/10 of the molar concentration used for the others for transfection. U2 and U6 snoRNAs were used as RNA loading controls. FIG. 19H shows reporter assays of HCT-116 cells transfected with agsiRNA-887 that have length variations. Rluc/Fluc ratios are shown. Error bars represent the standard deviation.

FIGS. 20A, 20B and 20C show cleavage of fully complementary targets and the repression of partially complementary targets by agsiRNA-451 or sRNA-451. FIG. 20A shows a time course analyses of target knockdown when the target sequence is a perfect complement. Three miRNA-451 variants (hmiR-451, mmiR-451, dmiR-451) and sRNA-451 (si-451) were compared. Reporters and siRNAs (80 pM) were co-transfected into HCT-116 cells. Rluc/Fluc ratios are shown. Error bars represent standard deviation. Data for 12 hour, 24 hour, 36 hour, and 48 hour time points are represented by the bars in order from left to right, respectively. FIG. 20B shows results from reporter assays showing repression of partially complementary targets by hmiR-451 and sRNA-451 (80 pM). Rluc/Fluc ratios are bar plotted and grouped by RNAi molecules. Error bars represent standard deviation. FIG. 20C shows the sequences of four types of repression reporters. Each vector carried four copies of the same target sequence in tandem: 1) miR-451 seed sequence (SeedX4); 2) Seed plus sequence that base paired with the 3'supp region (Seed-3SuppX4); 3) Seed that had the middle base mutated plus 3Supp (mSeed-3SuppX4); and 4) Seed plus 3Supp that had the middle base mutated (Seed-m3SuppX4). Data for mSeed-3Suppx4, SeedX4, Seed-3SuppX4, and Seed-m3SuppX4 targets are represented by the bars in order from left to right, respectively.

FIG. 21A shows results from a reporter assay in which the bases from p18 to p23 (tail-bases) of agsiRNA-887 were replaced with the tail bases of hmiR-451 (GAGUUU: LP451). Rluc/Fluc ratios are plotted. Error bars represent the standard deviation. FIG. 21B shows results from a reporter assay in which the tail-bases of hmiR-451 were replaced with the tail bases of agsiRNA-887 (GGAUGU: LP887). Rluc/Fluc ratios are plotted. Error bars represent the standard deviation. FIG. 21C shows results from a reporter assay in which the tail-bases of agsiRNA-1148 were replaced with LP451 or LP887. Rluc/Fluc ratios are plotted. Error bars represent the standard deviation. FIG. 21D shows results from a reporter assay in which the tail-bases of agsiRNA-1354 were replaced with LP451 or LP887. Rluc/Fluc ratios are plotted. Error bars represent the standard deviation.

FIG. 24A shows predicted secondary structures of the agsiRNAs that target R1. FIG. 24B shows a Western blot analysis of RRM1 from HEK-293 cells transfected with sli-siRNAs targeting R1. The control (Ctrl) for agsiRNA was agsiRNA containing a scrambled sequence. The Ctrl for agshRNA was the U6-agshRNA containing a scrambled sequence. Actin was used as the loading control. Two of the three sli-siRNAs designed to target R1 (R1-445 and -2290) reduced R1 protein levels. FIG. 24C shows predicted secondary structures of agsiRNAs that target R2B. FIG. 24D shows Western blot analysis of R2B from HEK-293 cells transfected with sli-siRNAs targeting R2B. The Ctrl for agsiRNA was the agsiRNA containing a scrambled sequence. The Ctrl for agshRNA is the U6-agshRNA containing a scrambled sequence. Actin was used as the loading control. One of the three sli-siRNAs designed to target R2B (R2B-948) reduced R2B protein levels.

FIG. 25A shows a Northern blot analysis of products processed from agshRNA-1148. Blots were prepared from total RNA extracted from HEK-293 cells transiently transfected with U6-agshRNA-1148, -mmp7, -GU, U1-agshRNA-1148, and H1-agshRNA-1148. U2 and U6 snoRNA were used as loading controls. When under the control of the U1 and H1 promoters, agshRNA-1148 expression levels were so low that the processed product was barely detectable (U1) or undetectable (H1). FIG. 25B shows qPCR of miR-21 (very high expression), miR-31 (high expression), and miR-143 (low expression) in HCT-116 cells lines that constitutively expressed agshRNA-1148. Data were normalized to U6 snoRNA and calculated by the ΔΔCt method. Data for the miR-21, miR-31 and miR-143 constructs are represented by the bar graphs in order from left to right, respectively. FIG. 25C shows real time cell growth as measured by the RT-CES system. HCT-116 cells transduced by lentiviral vector (vector), agshRNA with a scrambled sequence (ctrl), mutated agshRNA-1148 (mut, Ago2 cleavable, bases from p10-11-12 were exchanged with bases from p31-30-29; the processed product can repress RRM2 mRNA), wt, mmp7, and the GU forms were plated and measured every 30 min for two days. Cell indexes, which correspond to the number of cells in the chambers, were plotted against time. FIG. 25D shows the invasion of HCT-116 cell lines constitutively expressing agshRNA-1148 and several variants of agshRNA-1148, as described in (C). Cell invasion assays were performed once for 24 h and twice for 48 h. Infiltrated cells were stained with Diff-Quik and counted. Three regions of each assay well were randomly chosen, and cells within these regions were counted. The 48 h data are an average of two independent experiments. FIG. 25E shows images from a wound healing assay of stable HCT-116 cell lines constitutively expressing agshRNA-1148 and variants described in (C). Cells plated in 24-well plates were scratched and floating cells were washed away. Images shown were taken immediately after making the scratch (upper panels) and after 48 h (lower panels).

FIG. 26A shows a Western blot analysis of R2 in HCT-116 cell lines constitutively expressing agshRNA-1148 and its variants. Actin was used as loading control. FIG. 26B shows qPCR results of R2 mRNAs in HCT-116 cell lines constitutively expressing agshRNA-1148 and its variants. Data was normalized to GAPDH, and then to the vector. Error bars represent standard deviation. FIG. 26C shows Northern blots of the processed products in HCT-116 cell lines constitutively expressing agshRNA-1148 or variants. U2 and U6 snoRNAs were used as RNA loading controls. FIG. 26D shows Northern blots of processed products in HCT-116 cell lines that were induced by Dox to express agshRNA-1148 and corresponding western blots of the R2 protein levels. U6 snoRNA was used as the RNA loading control, and GAPDH was used as the cell extract loading control.

FIG. 27A shows results wherein reporter constructs containing agshRNA-887 expressed by the U6, U1 or H1 promoters were transfected into HCT-116 cells and assayed. Rluc/Fluc ratios are plotted. Error bars represent the standard deviation. FIG. 27B shows results wherein reporter constructs containing agshRNA-1148 expressed by the U6, U1 or H1 promoter were transfected into HCT-116 cells and assayed. Rluc/Fluc ratios are plotted. Error bars represent the standard deviation. FIG. 27C shows results wherein reporter constructs containing agshRNA-1354 expressed by the U6, U1 or H1 promoter were transfected into HCT-116 cells and assayed. Rluc/Fluc ratios are plotted. Error bars represent the standard deviation.

FIG. 28 shows a table of the sequences of shRNAs, siRNAs, PCR primers and probes used for Northern blot analysis, and U6+multiple cloning sites (MCS) and U6TO+MCS. For the shRNAs and the siRNAs, nucleotides that form the antisense strands are underlined, nucleotides that form the loops are italicized and nucleotides that form the sense strands are bolded. For the U6TO+MCS, the nucleotides of the tet binding element are underlined and bolded. The corresponding SEQ ID NOs (i.e., SEQ ID NOs: 1-144) are listed for all of the sequences.

FIGS. 29A and 29B show the U6 promoters that were used to express agshRNA. FIG. 29A shows the sequence for U6+MCS (SEQ ID NO: 143). FIG. 29B shows the sequence for U6TO+MCS (SEQ ID NO: 144). For the U6TO+MCS sequence, the nucleotides of the tet binding element are underlined and bolded. The promoter and MCS were cloned into pcDNA3.1-Neo. The pcDNA3.1-Neo vector was modified as follows: 1) the CMV promoter was removed, 2) the Bgl II site was mutated to a BamH I site, and 3) either U6 or U6TO with MCSs was cloned into Bam HI and Xba sites.

FIG. 30A shows di-siRNA targeting. Nucleotides 1-21 of the 5' arm make up the antisense strand and nucleotides 1-21 of the 3' arm make up the sense strand. FIG. 30B shows sli-siRNA targeting. Nucleotides 1-22 make up the antisense strand, nucleotides 23-30 are uridylated and trimmed bases and nucleotides 31-40 make up the sense strand. FIG. 30C shows siRNA targeting. Nucleotides 1-21 of the 5' arm make up the antisense strand and the nucleotides of the 3' arm make up the target RNA.

FIG. 31 is a table showing the sequences of sli-siRNAs and di-siRNAs used for the experiments performed in Example 2. Nucleotides that form anti-sense strands are underlined, nucleotides that form loops for sli-siRNAs are italicized, nucleotides that form sense strands are bolded.

FIG. 32 shows highly complementary reporters designed for sli-siRNA-887. Mismatched reporters designed. Each position has two reporters with different single base mutations. U6G-U12G and U4C-U15C are reporters that carry two mutations.

FIG. 36 shows highly complementary reporters designed for sli-siRNA-ARX1. Mismatched reporters designed. Each position has two reporters with different single base mutations.

FIG. 38 shows highly complementary reporters designed for sli-siRNA-451. Mismatched reporters designed. Each position has two reporters with different single base mutations.

FIG. 41A is a table showing the top ten iso-miRs of mmu-miR-451. Raw reads for mmu-miR-451a (accession #MI000173) were originally from miRBase 19. Reads at the 5'end are AAA- and AA-forms were combined for further classification (the combined reads are 244,817 from total 272,429 isomiRs) according to bases at the 3' end that matched the mmu-pre-miR-451 sequence. FIG. 41B is a pie graph showing the top ten isomiRs of mmu-miR-451 in miRBase were plotted by length.

FIG. 42A shows a schematic representation of proposed function model of sli-smRNA versus di-smRNA. FIG. 42B shows a schematic representation of Ago2 molecule.

DETAILED DESCRIPTION

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

Provided herein are novel short hairpin RNA (shRNA) molecules and compositions and kits comprising such molecules, as well as methods of making and using these molecules, compositions, and kits.

As provided below in Example 1, the general molecular properties of shRNAs that are processed into potent siRNAs by Ago2 were characterized using pre-miR-451 as a model molecule. As shown in Example 1 below, the Ago2-sliced siRNAs (sli-siRNAs) have the same silencing potency as the classical Dicer-diced siRNAs (di-siRNAs), but with dramatically reduced unwanted sense strand activities. Additionally, as shown below, the popular U6 shRNA expression promoter that was modified (U6m), but not the H1 or U1 promoter, expressed sli-siRNAs in mammalian cells both constitutively and conditionally. Through lengthy analysis of the substrate properties of sli-siRNAs, the canonical structure of sli-siRNAs that will produce potent sli-siRNAs was defined and is provided herein.

siRNA molecules that have a potent on-target effect and lack off-target activities are highly desirable for both clinical and research applications. Although extensive research has been focused on this purpose, it is still a challenge to find an siRNA that is optimized for a specific target. Many design rules, including sequence selection, base modifications, target site accessibility, and the end thermodynamics stability of di-siRNAs have to be applied during design in order to find an ideal siRNA (Jackson 2010; Petri 2013).

Figure 1A:
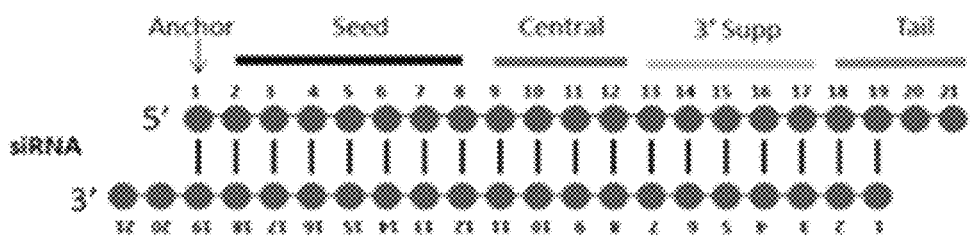
FIGS. 1A, 1B and 1C show Ago-2 sliced siRNA (i.e., sli-siRNA) molecules.
Figure 1B:
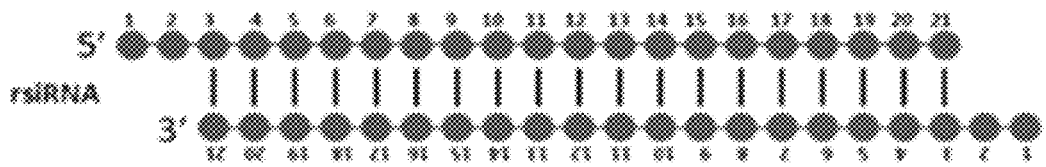
Figure 1C:
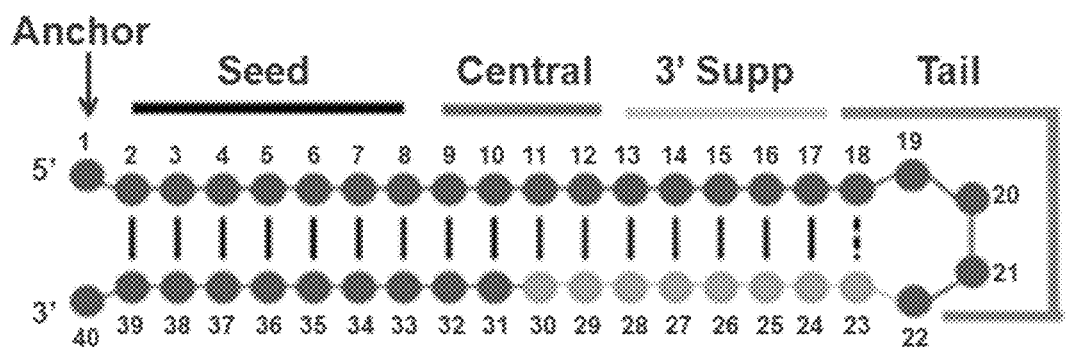
Figure 2A:
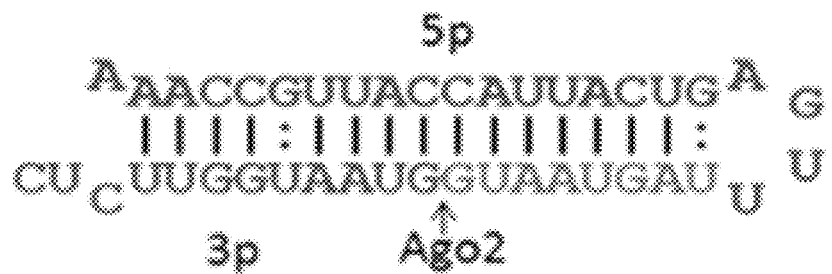
FIGS. 2A, 2B and 2C show the structure of human pre-miR-451.
Figure 2B:
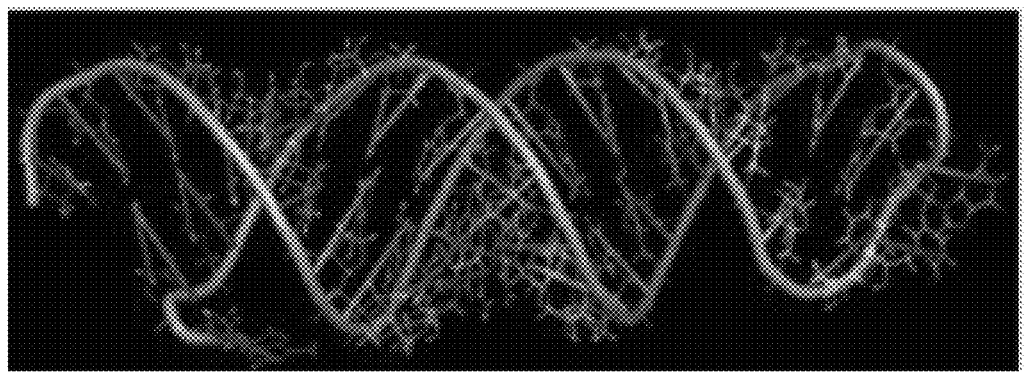
Figure 2C:
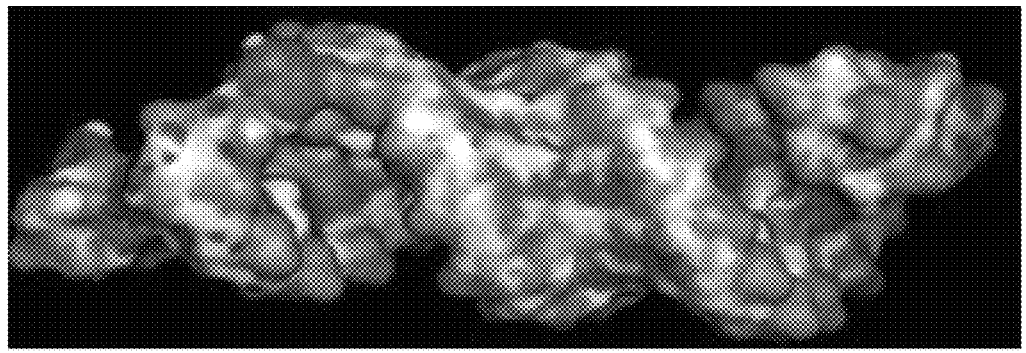
Figure 3:
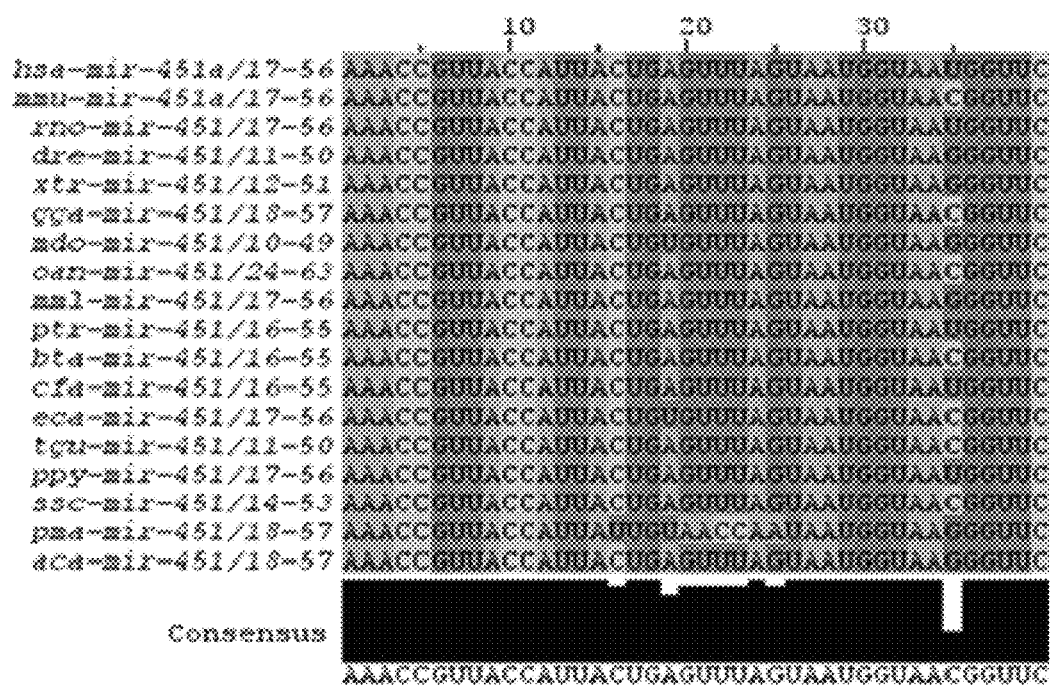
FIG. 3 shows an alignment of pre-miR-451 from 18 species found in miRBase 19.

Interestingly, miR-451 uses an elegant slicing biogenesis mechanism that involves Ago2, but not necessarily Dicer (Cheloufi 2010; Cifuentes 2010; Yang 2010). This mechanism can be used to design shRNAs that can be loaded onto Ago2 to be processed only by Ago2 into functional siRNAs without sense strand activity (FIG. 1C). Ago2 acts by first nicking the shRNA substrates in the middle of the 3p to produce a long fragment (bases 1 to 30, 30 nt long; hereafter referred to as L30) and a short fragment (bases 31 to 42, 12 nt long; hereafter referred to as 3L12). The 3' end of L30 is then trimmed by other enzymes to produce a functional siRNA that is capable of gene silencing (FIG. 2A-C) (Cheloufi 2010; Cifuentes 2010; Yang 2010). Although pre-miR-451 and mimic sequences can be loaded into RISCs formed by all Agos, they are exclusively processed by Ago2 (Dueck 2012; Yang 2012). This mechanism could also explain the mystery behind the potency of syn-shRNAs related to the length of its stems and the choice of strand used to implement anti-sense strand (Dallas 2012). This mechanism was applied to design shRNAs with short stems which were characterized as Dicer-independent and Ago2-prone processing agoshRNA (Liu 2013).

Despite published results of detailed parameters regarding miR-451 biogenesis and the fact that pre-miR-451 mimic sequences have reduced sense strand activities and may avoid the competition with endogenous miRNAs for processing machinery (Dueck 2012; Yang 2012; Liu 2013; Ma 2014), the application of sli-siRNAs is still very limited compared to traditional siRNAs. One reason is the lack of general rules to design sli-siRNAs. In addition, there are no versatile vectors that are specifically constructed to express sli-siRNAs. Furthermore, the effects of sli-siRNAs on their targets, endogenous miRNA pathways in cells, and other response of the host immune system to their presence, must be addressed in order for them to have a broad usage and serve as clinical therapeutic molecules. Detailed rules and parameters that are based on experimental data are still lacking in order to effectively create optimal shRNAs using a variety of shRNA expression promoters.

As set forth herein, the experiments in Example 1 below were used to define parameters and rules that can be used to engineer optimal synthetic shRNA molecules that can be preferentially processed by Ago2 into potent siRNAs. In addition, stable and inducible U6 driven expression systems were developed to express optimal vector expressed shRNAs. The potential effect of these shRNAs on endogenous miRNA pathways, in addition to understanding host immunoresponses to their presence, was also experimentally addressed as provided in Example 1.

As used herein, a synthetic version of a shRNA that is preferentially processed by Ago2, i.e., sli-siRNA, may be referred to as "agsiRNA" or "synthetic shRNA." As used herein, an expressed version of sli-siRNA (i.e., an sli-siRNA expressed from a vector) may be referred to as "agshRNA" or "vector expressed shRNA." The synthetic shRNA molecule and the vector expressed shRNA molecule may comprise the canonical structure provided in FIG. 1C. In certain embodiments, the shRNAs described herein may be designed to silence the expression of a target gene. In certain embodiments, silencing the expression of a target gene may include repression and/or cleavage of a target gene.

Although the agsiRNA and agshRNA model molecules are similar to the previously reported model molecules, sshRNA and agoshRNA, in that they all use Ago2 for processing and function, the major difference between these new types of small RNAs and the previously reported molecules lies in how the loop is designed: sli-siRNAs use 4 nt of the antisense as loop; sshRNA used UU to link a 19 nt antisense strand with a 19 nt sense strand; and agoshRNA used 5-7 nt universal loops (Ge 2010; Liu 2013). Although sli-siRNAs generally have similar silencing potency to di-siRNAs, sli-siRNAs have dramatically reduced sense strand activities, thus much less off-target effect. Thus, the parameters provided herein may be used to design exemplary synthetic shRNAs and vector expressed shRNAs that are potent RNAi triggers with reduced off-target effects.

One aspect provided herein relates to a synthetic short hairpin (shRNA) molecule comprising, consisting of, or consisting essentially of:
  (a) a 5' arm and a 3' arm comprising:
    (i) a stem region comprising 16, 17, or 18 base pairs, the base pairs comprising nucleotides from the 5' arm paired with nucleotides from the 3' arm, and
    (ii) one or more unpaired nucleotides at the 5' terminal end of the 5' arm and one or more unpaired nucleotides at the 3' terminal end of the 3' arm; and
  (b) a loop region comprising 4 nucleotides that connects the 5' arm to the 3' arm,
  wherein the synthetic shRNA molecule is processed by Argonaute 2 (Ago2) in a Dicer-independent manner.

In certain embodiments, the synthetic shRNA molecule may be a chemically synthesized shRNA and may comprise the canonical structure shown in FIG. 1C. The experimental parameters characterized in Examples 1 and 2 and provided below may be used to design synthetic shRNA molecules that will be preferentially processed by Ago2 into potent siRNAs used to silence the expression of target genes. The exemplary parameters for designing synthetic shRNAs are as follows and as detailed below in Examples 1 and 2:

As used herein, the "stem region" of the synthetic shRNA molecule refers to the portion of the synthetic shRNA in which bases from the 5' arm form base pairs with nucleotides from the 3' arm. In certain embodiments, the stem region may comprise, consist of, or consist essentially of 16, 17, or 18 base pairs. In certain preferred embodiments, the stem region is 17 base pairs in length. In certain embodiments, the base pairs are formed through pairing of nucleotides from the 5' arm with nucleotides from the 3' arm of the synthetic shRNA molecule. For example, in certain embodiments, when the stem region is 17 base pairs in length, the 17 base pairs may be comprised of 17 nucleotides from the 5' arm paired with 17 nucleotides of the 3' arm as shown, for example, in FIG. 1C.

As used herein, the term "complementary" can be used to describe bases that are "fully" complementary or "generally" complementary to each other. "Fully" complementary refers to base pairs that are comprised of the standard arrangement of bases in relation to their opposite pairing, such as C pairing with G and U pairing with A. These fully complementary base pairs may also be referred to as "Watson-Crick base pairs" (i.e., C:G and/or U:A base pairs). "Generally" complementary refers to nucleotides that form Watson-Crick base pairs in addition to nucleotides that may form mismatch pairs, wobble base pairs, and/or no base pairs (i.e., unpaired). As used herein, "mismatch base pair" refers to a base pair that is mismatched because the pattern of hydrogen donors and acceptors from the pair of nucleotides do not correspond (e.g., A:C, G:A, A:A, U:U, C:C, G:G). As used herein "wobble base pair" refers to pairs G:U or U:G. In certain embodiments, the base pairs of the stem region of the synthetic shRNA molecule may be formed by nucleotides that pair through one or more Watson-Crick base pairs, one or more mismatch base pairs, one or more unpaired bases, and/or one or more wobble base pairs.

In certain embodiments, the synthetic shRNA comprises one or more unpaired nucleotides at the 5' terminal end of the 5' arm and one or more unpaired nucleotides at the 3' terminal end of the 3' arm. As the 5' and 3' terminal nucleotides do not form a base pair, a small fork is formed by the nucleotide mismatch. As discussed below, Ago2 has a much higher binding affinity for substrates that have an A or U at the 5' terminal end as opposed to a C or G. In certain embodiments, the synthetic shRNA molecules herein may comprise one unpaired nucleotide at the 5' terminal end of the 5' arm that is selected from an A or a U. In certain embodiments, the one or more unpaired nucleotides at the 5' terminal end of the 5' arm may be two As. In certain embodiments, the one or more unpaired nucleotides at the 5' terminal end of the 5' arm may be one U and one A, wherein the A is positioned 5' relative to the U.

In certain embodiments, the synthetic shRNA molecules herein may comprise one or more unpaired nucleotides at the 5' terminal end of the 5 arm. In certain embodiments, the synthetic shRNA molecule may comprise one unpaired nucleotide at the 5' terminal end of the 5' arm that is non-phosphorylated. Phosphorylation of the 5' end may increase the potency of Dicer sliced siRNAs and is required for siRNA loading (Schwarz 2003). However, as shown below, no difference was observed in potency of synthetic shRNA molecules synthesized with or without phosphorylation of the 5' terminal end. In certain embodiments, the synthetic shRNA molecule may comprise one unpaired nucleotide at the 5' terminal end of the 5' arm that is phosphorylated.

In certain embodiments, the synthetic shRNA may comprise one or more unpaired nucleotides at the 3' terminal end of the 3' arm. In certain embodiments, the one or more unpaired nucleotides at the 3' terminal end of the 3' arm may be selected from the group consisting of a deoxythymidine nucleotide (dT), a dideoxycytidine (ddC) nucleotide, and a C. In certain preferred embodiments, the one or more unpaired nucleotides at the 3' terminal end of the 3' arm is one C. In certain embodiments, the one or more unpaired nucleotides at the 3' terminal end of the 3' arm are two deoxythymidine nucleotides (i.e., dTdT) and one C, wherein the C is positioned 5' relative to the two dTdTs. In certain embodiments, the one or more unpaired nucleotides at the 3' terminal end of the 3' arm is one unpaired dideoxycytidine nucleotide (i.e, ddC). As discussed below, the ddC modification can prevent degradation from the 3' end, which would be beneficial to the design of synthetic shRNAs to increase its stability.

As used herein, the "loop region" refers to the portion of the synthetic shRNA that connects the 5' arm to the 3' arm. In certain embodiments, the loop region of the synthetic shRNA comprises, consists of, or consists essentially of 3, 4, 5, or 6 nucleotides. In certain preferred embodiments, the loop region of the synthetic shRNA consists of or consists essentially of 4 nucleotides. As shown below in Example 1, the loop sequence and length of the synthetic shRNA may influence the silencing potential of the mature siRNA generated from the synthetic shRNA. In certain preferred embodiments, the loop region of the synthetic shRNA is 4 nucleotides long and connects the 5' arm to the 3' arm.

In certain embodiments, the synthetic shRNA molecule may comprise, consist of or consist essentially of 36, 37, 38, 39, 40, 41, 42, 43, 44, or 45 nucleotides (nts). In certain of these embodiments, the synthetic shRNA molecule may consist of or consist essentially of 40 nts. When the synthetic shRNA molecule is 40 nts, the first nucleotide positioned at the 5' terminal end of the 5' arm is designated as position (p) p1 and the last nucleotide positioned at the 3' terminal end of the 3' arm is designated as p40 (see e.g., FIG. 1C).

In certain embodiments, an antisense region of the synthetic shRNA may comprise, consist of, or consist essentially of the 5' arm and the loop region of the synthetic shRNA molecule and a sense region may comprise, consist of, or consist essentially of the 3' arm of the synthetic shRNA molecule. In certain embodiments, the antisense region is the guide strand and the sense region is the passenger strand. The antisense region of the synthetic shRNA molecule may comprise a seed region, a central region, a 3' supplementary region and a tail region (see e.g., FIG. 1C). In certain embodiments, when the synthetic shRNA is 40 nts, the antisense region may comprise a nucleotide sequence of a seed region comprising nucleotides p2-p8, a nucleotide sequence of a central region comprising nucleotides p9-p12, a nucleotide sequence of a 3' supplementary region comprising nucleotides p13-p17 and a nucleotide sequence of a tail region comprising nucleotides p18-p22 (see e.g., FIG. 1C). In certain embodiments, the sense region may be fully complementary or generally complementary to a portion of the antisense region. In certain embodiments, the antisense region may comprise a nucleotide sequence that is fully or generally complementary to a target nucleotide sequence. In certain embodiments, the target nucleotide sequence may comprise a portion of a nucleotide sequence of a target gene. In certain embodiments, the target gene may be any gene that is being targeted for gene silencing through RNA interference by the mature siRNA that results from Ago2 and other enzyme processing of the synthetic shRNA. In certain embodiments, the target nucleotide sequence may be a sequence of a portion of messenger RNA (mRNA).

As shown in Example 2 below, sli-siRNAs have a much higher tolerance for mismatch targets when the mismatch is located in the 3' supplementary region versus the seed region. In certain embodiments, the nucleotide sequence of the seed region may be fully complementary to a portion of the target nucleotide sequence. In certain embodiments, the nucleotide sequence of the seed region may be fully complementary to a portion of the target sequence, and the nucleotide sequence of the 3' supplementary region may be generally complementary to a portion of the target sequence. In these embodiments, the nucleotide sequence of the portion of the target sequence may form one, two, three, four, or five, mismatched base pairs with the 3' supplementary region. In certain embodiments, the nucleotide sequence of the seed region may be generally complementary to a portion of the target nucleotide sequence. In certain preferred embodiments, the nucleotide sequence of the central region may be fully complementary to a portion of the target nucleotide sequence. In certain embodiments, the nucleotide sequence of the central region may be generally complementary to a portion of the target nucleotide sequence. In certain preferred embodiments, the nucleotide sequence of the 3' supplementary region may be fully or generally complementary to a portion of the target nucleotide sequence. In certain preferred embodiments, the nucleotide sequence of the tail region may be fully complementary to a portion of the target nucleotide sequence. In certain embodiments, the nucleotide sequence of the tail region may be generally complementary to a portion of the target nucleotide sequence.

In certain embodiments, when the synthetic shRNA molecule comprises 40 nts (i.e., p1-p40) and the stem region comprises 17 base pairs, the base pairs of the stem region comprise nucleotides p2-p18 of the 5' arm base paired with nucleotides p39-p23 of the 3' arm, respectively (i.e., p2:p39, p3:p38, p4:p37, p5:p36, p6:p35, p7:p34, p8:p33, p9:p32, p10:p31, p11:p30, p12:p29, p13:p28, p14:p27, p15:p26, p16:p25, p17:p24, and p18:p23) as illustrated in FIG. 1C. In certain preferred embodiments, the base pairs formed between nucleotides p2-p18 and nucleotides p39-p23, respectively, may be fully complementary forming all Watson-Crick base pairs. In other preferred embodiments, the base pairs formed between nucleotides p2-p18 and nucleotides p39-p23 may be generally complementary, wherein the base pairs formed between nucleotides p2-p17 and nucleotides p39-p24 are Watson-Crick base pairs and the base pair formed between p18 and p23 is a wobble base pair. In certain embodiments, the base pairs formed between nucleotides p2-p18 and nucleotides p39-p23 may be generally complementary, wherein the base pairs p3:p38, p4:p39, p5:p36, p8:p33, p9:p32, p10:p31, p11:p30, p12:p29, p13:p28, p14:p27, p15:p26, p16:p25, p27:p24 are Watson Crick base pairs and the base pairs p2:p39, p6:p35, p7:p34, and p18:p23 may be selected from the group consisting of a Watson-Crick base pair, a mismatch base pair, a wobble base pair, and an unpaired base pair.

In certain embodiments, the synthetic shRNA molecule has the ability to bypass the Dicer processing step and be specifically processed by Ago2. The specific production of the synthetic shRNA molecules herein by Ago2 may limit their incorporation into other non-slicing Argonaute family members (Ago1, Ago3, and Ago4 for mammals) formed RISCs; therefore, it is possible that the synthetic shRNAs provided herein may also reduce RNAi off-target effects caused by siRNAs loading into other Argonautes (Petri 2011). Ago2 acts by first nicking the synthetic shRNA substrates in the middle of the 3p to produce a long fragment and a short fragment. In certain embodiments, the Ago2 nick site may be located near the middle of the 3' arm of the synthetic shRNA. In certain embodiments, when the synthetic shRNA molecule is 40 nts, the Ago nick site may be located between nucleotides p30 and p31.

In certain preferred embodiments, a synthetic shRNA may comprise:

(a) a 5' arm and a 3' arm comprising:

(i) a stem region that is 17 base pairs, the base pairs comprising nucleotides from the 5' arm paired with nucleotides from the 3' arm, wherein the base pairs formed between nucleotides p2-p18 from the 5' arm and nucleotides p39-p23 from the 3' arm may be generally complementary, the base pairs formed between nucleotides p2-p17 and nucleotides p39-p24 are Watson-Crick base pairs and the base pair formed between p18 and p23 is a wobble base pair, and (ii) one unpaired nucleotide at the 5' terminal end of the 5' arm that is not phosphorylated and is selected from the group consisting of an A and a U, and one unpaired nucleotide at the 3' terminal end of the 3' arm that is selected from the group consisting of a C or a dideoxycytidine nucleotide (ddC); and (b) a loop region comprising 4 nucleotides that connects the 5' arm to the 3' arm, wherein the shRNA molecule is processed by Argonaute 2 (Ago2) in a Dicer-independent manner.

Another aspect provided herein relates to a vector expressed short hairpin (shRNA) molecule comprising, consisting of or consisting essentially of:

(a) a 5' arm and a 3' arm comprising:

(i) a stem region comprising 16, 17, or 18 base pairs, the base pairs comprising nucleotides from the 5' arm paired with nucleotides from the 3' arm, and (ii) one or more unpaired nucleotides at the 5' terminal end of the 5' arm and one or more unpaired nucleotides at the 3' terminal end of the 3' arm; and (b) a loop region comprising 4 nucleotides that connects the 5' arm to the 3' arm, wherein the vector expressed shRNA molecule is processed by Argonaute 2 (Ago2) in a Dicer-independent manner.

In certain embodiments, the vector expressed shRNA molecule may be a shRNA that is expressed using a DNA vector system that encodes the vector expressed shRNA molecule. Similar to the synthetic shRNA molecules described above, the vector expressed shRNA molecules described herein may be potent RNAi triggers and can be used to silence the expression of target genes. Additionally, in certain embodiments, the vector expressed shRNA molecules may comprise the canonical structure illustrated in FIG. 1C. In certain embodiments, synthetic shRNA molecules may be any of the shRNA molecules as disclosed herein. The experimental parameters characterized in Examples 1 and 2 and provided herein may be used to design vector expressed shRNA molecules that will be preferentially processed by Ago2 into potent siRNAs. The exemplary parameters for designing vector expressed shRNAs are as follows:

As used herein, the "stem region" of the vector expressed shRNA molecule refers to the portion of the synthetic shRNA in which bases from the 5' arm form base pairs with nucleotides from the 3' arm. In certain embodiments, the stem region may comprise, consist of, or consist essentially of 16, 17, or 18 base pairs. In preferred embodiments, the stem region is 17 base pairs in length. In certain embodiments, the base pairs are formed through pairing of nucleotides from the 5' arm with nucleotides from the 3' arm of the vector expressed shRNA molecule. For example, in certain embodiments, when the stem region is 17 base pairs in length, the 17 base pairs may be comprised of 17 nucleotides from the 5' arm paired with 17 nucleotides of the 3' arm.

As used herein, the term "complementary" can be used to describe bases that are "fully" complementary or "generally" complementary to each other as described above. In certain embodiments, the base pairs of the stem region of the vector expressed shRNA molecule may be formed by nucleotides that pair through one or more Watson-Crick base pairs, one or more mismatch base pairs, one or more unpaired bases, and/or one or more wobble base pairs.

In certain embodiments, the vector expressed shRNA comprises one or more unpaired nucleotides at the 5' terminal end of the 5' arm and one or more unpaired nucleotides at the 3' terminal end of the 3' arm. As the 5' and 3' terminal nucleotides do not form a base pair, a small fork is formed by the nucleotide mismatch. In certain preferred embodiments, the vector expressed shRNA molecules herein may comprise one unpaired nucleotide at the 5' terminal end of the 5' arm that is an A.

As used herein, the "loop region" refers to the portion of the loop region of the vector expressed shRNA comprising, consisting of, or consisting essentially of 3, 4, 5, or 6 nucleotides. As shown below in Example 1, the loop sequence and length of the vector expressed shRNA may influence the silencing potential of the mature siRNA generated from the vector expressed shRNA. In preferred embodiments, the loop region of the vector expressed shRNA is 4 nucleotides long and connects the 5' arm to the 3' arm.

In certain embodiments, the vector expressed shRNA molecule may comprise, consist of or consist essentially of 36, 37, 38, 39, 40, 41, 42, 43, 44, or 45 nucleotides. In certain of these embodiments, the synthetic shRNA molecule may consist of or consist essentially of 40 nts. When the preferred vector expressed shRNA molecule is 40 nts, the first nucleotide positioned at the 5' terminal end of the 5' arm is designated as position p1 and the last nucleotide positioned at the 3' terminal end of the 3' arm is designated as p40 (see e.g., FIG. 1C).

In certain embodiments, an antisense region of the vector expressed shRNA may comprise, consist of, or consist essentially of the 5' arm and the loop region of the vector expressed shRNA molecule and a sense region may comprise, consist of, or consist essentially of the 3' arm of the vector expressed shRNA molecule. In certain embodiments, the antisense region is the guide strand and the sense region is the passenger strand. The antisense region of the vector expressed shRNA molecule may comprise a nucleotide sequence of a seed region, a nucleotide sequence of a central region, a nucleotide sequence of a 3' supplementary region and a nucleotide sequence of a tail region (see e.g., FIG. 1C). In certain embodiments, when the vector expressed shRNA is 40 nts, the antisense region may comprise a nucleotide sequence of a seed region comprising nucleotides p2-p8, a nucleotide sequence of a central region comprising nucleotides p9-p12, a nucleotide sequence of a 3' supplementary region comprising nucleotides p13-p17 and a nucleotide sequence of a tail region comprising nucleotides p18-p22 (see e.g., FIG. 1C). In certain embodiments, the sense region may be fully complementary or generally complementary to a portion of the antisense region. In certain embodiments, the antisense region may comprise a nucleotide sequence that is fully or generally complementary to a target nucleotide sequence. In certain embodiments, the target nucleotide sequence may comprise a portion of a nucleotide sequence of a target gene. In certain embodiments, the target gene may be any gene that is being targeted for gene silencing through RNA interference by the mature siRNA that results from Ago2 and other enzyme processing of the vector expressed shRNA. In certain embodiments, the target nucleotide sequence may be a sequence of a portion of messenger RNA (mRNA). For example, in certain embodiments, the target nucleotide sequence may be a target RNA sequence comprising a message RNA sequence of the target gene.

In certain embodiments, the nucleotide sequence of the seed region may be fully complementary to a portion of the target nucleotide sequence. In certain embodiments, the nucleotide sequence of the seed region may be fully complementary to a portion of the target sequence, and the nucleotide sequence of the 3' supplementary region may be generally complementary to a portion of the target sequence. In these embodiments, the nucleotide sequence of the portion of the target sequence may form one, two, three, four, or five, mismatched base pairs with the 3' supplementary region. In certain preferred embodiments, the nucleotide sequence of the seed region may be fully complementary to a portion of the target nucleotide sequence. In certain embodiments, the nucleotide sequence of the seed region may be generally complementary to a portion of the target nucleotide sequence. In certain preferred embodiments, the nucleotide sequence of the central region may be fully complementary to a portion of the target nucleotide sequence. In certain embodiments, the nucleotide sequence of the central region may be generally complementary to a portion of the target nucleotide sequence. In certain preferred embodiments, the nucleotide sequence of the 3' supplementary region may be fully or generally complementary to a portion of the target nucleotide sequence. In certain preferred embodiments, the nucleotide sequence of the tail region may be fully complementary to a portion of the target nucleotide sequence. In certain embodiments, the nucleotide sequence of the tail region may be generally complementary to a portion of the target nucleotide sequence.

In certain embodiments, when the vector expressed shRNA molecule comprises 40 nts (i.e., p1-p40) and the stem region comprises 17 base pairs, the base pairs of the stem region may comprise nucleotides p2-p18 of the 5' arm base paired with nucleotides p39-p23 of the 3' arm, respectively (i.e., p2:p39, p3:p38, p4:p37, p5:p36, p6:p35, p7:p34, p8:p33, p9:p32, p10:p31, p11:p30, p12:p29, p13:p28, p14: p27, p15:p26, p16:p25, p17:p24, and p18:p23) as illustrated in FIG. 1C. In certain preferred embodiments, the base pairs formed between nucleotides p2-p18 and nucleotides p39-p23, respectively, may be fully complementary forming all Watson-Crick base pairs. In other preferred embodiments, the base pairs formed between nucleotides p2-p18 and nucleotides p39-p23 may be generally complementary, wherein the base pairs formed between nucleotides p2-p17 and nucleotides p39-p24 are Watson-Crick base pairs and the base pair formed between p18 and p23 is a wobble base pair. In certain embodiments, the base pairs formed between nucleotides p2-p18 and nucleotides p39-p23 may be generally complementary, wherein the base pairs p3:p38, p4:p39, p5:p36, p8:p33, p9:p32, p10:p31, p11:p30, p12:p29, p13: p28, p14:p27, p15:p26, p16:p25, p27:p24 are Watson Crick base pairs and the base pairs p2:p39, p6:p35, p7:p34, and p18:p23 may be selected from the group consisting of a Watson-Crick base pair, a mismatch base pair, a wobble base pair, and an unpaired base pair.

In certain embodiments, the vector expressed shRNA molecule has the ability to bypass the Dicer processing step and be specifically processed by Ago2 as described herein. In certain embodiments, the Ago2 nick site may be located near the middle of the 3' arm of the vector expressed shRNA. In certain embodiments, when the vector expressed shRNA molecule is 40 nts, the Ago nick site may be located between nucleotides p30 and p31.

In certain embodiments, the vector expressed shRNA may be expressed by a vector as described herein.

In certain preferred embodiments, a vector expressed shRNA may comprise:

(a) a 5' arm and a 3' arm comprising:

(i) a stem region that is 17 base pairs, the base pairs comprising nucleotides from the 5' arm paired with nucleotides from the 3' arm, wherein the base pairs formed between nucleotides p2-p18 from the 5' arm and nucleotides p39-p23 from the 3' arm may be generally complementary, the base pairs formed between nucleotides p2-p17 and nucleotides p39-p24 are Watson-Crick base pairs and the base pair formed between p18 and p23 is a wobble base pair, and (ii) one unpaired nucleotide at the 5' terminal end of the 5' arm that is an A and one unpaired nucleotide at the 3' terminal end of the 3' arm that is a C; and (b) a loop region comprising 4 nucleotides that connects the 5' arm to the 3' arm, wherein the synthetic shRNA molecule is processed by Ago2 in a Dicer-independent manner.

Another aspect provided herein relates to a vector comprising a nucleotide sequence encoding one or more vector expressed shRNA molecules comprising, consisting of or consisting essentially of:

(a) a 5' arm and a 3' arm comprising:

(i) a stem region comprising 16, 17, or 18 base pairs, the base pairs comprising nucleotides from the 5' arm paired with nucleotides from the 3' arm, and (ii) one or more unpaired nucleotides at the 5' terminal end of the 5' arm and one or more unpaired nucleotides at the 3' terminal end of the 3' arm; and (b) a loop region comprising 4 nucleotides that connects the 5' arm to the 3' arm, wherein the vector expressed shRNA molecule is processed by Argonaute 2 (Ago2) in a Dicer-independent manner.

In certain embodiments, the vector may encode any one or more of the vector expressed shRNA molecules as described herein and provided in Examples 1 and 2 below. In certain embodiments, the vector may encode one, two, three, four, five, six, seven, eight, nine, or ten vector expressed shRNA. In certain embodiments, the vector comprises a DNA nucleotide sequence encoding the one or more vector expressed shRNA. In certain embodiments, the vector may encode any one or more of a vector expressed shRNA molecule designed using the parameters for designing vector expressed shRNA molecules that are provided herein.

As shown in Example 1, the U6 expression promoter was modified to express synthetic shRNAs in mammalian cells both constitutively and conditionally and certain synthetic shRNAs were shown to be correctly processed to repress the expression of their target genes. The design of the constitutive and inducible vectors described in Example 1 was based on a previously reported synthetic shRNA expression vector that contains the U6 promoter as described in Aagaard 2007, the subject matter of which is hereby incorporated by reference as if fully set forth herein. In certain embodiments, the vector may be a conditional expression vector comprising a U6 promoter to drive expression of the vector expressed shRNA molecule. In certain embodiments, the vector may be an inducible expression vector that may be designed by mutating a portion of the U6 promoter sequence into a TetR binding sequence (i.e., U6TO) as described in Aagaard 2007. In certain embodiments, the vector may be an inducible expression vector comprising a doxycycline [dox]-inducible U6 (U6TO) promoter to drive expression of the vector expressed shRNA molecule. In certain embodiments, the U6 sequence may be modified and may be used to express the synthetic shRNA. For example, in certain embodiments, the modified U6 promoter sequence may comprise the U6+MCS sequence (i.e., SEQ ID NO: 143) or the U6TO+MCS sequence (SEQ ID NO: 144).

In certain embodiments, the vector that is used to express the vector expressed shRNA may be any vector known to one of ordinary skill in the art that can be used to express synthetic shRNAs. For example, the vector may be a retroviral vector. In certain embodiments, the vector may be a lentivirus vector. In certain embodiments, the lentivirus vector may comprise an expression cassette comprising a U6 promoter (e.g., a modified U6 promoter) and a nucleotide sequence encoding a vector expressed shRNA. In certain embodiments, the vector may be an adenovirus. In certain embodiments, the vector may be an adeno-associated virus.

Another aspect provided herein relates to a cell comprising a vector comprising a nucleotide sequence encoding one or more vector expressed shRNA molecules comprising, consisting of or consisting essentially of:
(a) a 5' arm and a 3' arm comprising:
(i) a stem region comprising 16, 17, or 18 base pairs, the base pairs comprising nucleotides from the 5' arm paired with nucleotides from the 3' arm, and
(ii) one or more unpaired nucleotides at the 5' terminal end of the 5' arm and one or more unpaired nucleotides at the 3' terminal end of the 3' arm; and
(b) a loop region comprising 4 nucleotides that connects the 5' arm to the 3' arm,
wherein the vector expressed shRNA molecule is processed by Argonaute 2 (Ago2) in a Dicer-independent manner.

In certain embodiments, the vector and the one more vector expressed shRNA molecules are the same as described herein. In certain embodiments, the cell may comprise one or more vectors.

In certain embodiments, the cell may be a bacteria cell. In certain embodiments, the cell may be a mammalian cell, such as a human cell.

In certain embodiments, the cell may be infected with a virus comprising a vector as described herein. For example, in certain embodiments, the cell may be infected with a lentivirus comprising a vector as described herein.

Another aspect provided herein relates to a method of designing a synthetic shRNA molecule or a vector expressed shRNA molecule comprising designing the synthetic shRNA molecule or the vector expressed shRNA molecule as described herein.

In certain embodiments, the synthetic shRNA molecule or vector expressed shRNA molecule may be designed using the parameters as provided herein. In certain embodiments, the method may further comprise chemically synthesizing the synthetic shRNA molecule.

In certain embodiments, the method of designing a synthetic shRNA molecule and/or a vector expressed shRNA molecule provides for the synthesis and/or expression of synthetic shRNA molecules that produce less unwanted passenger strands, which results in the reduction of off-target effects and lower toxicity to the cell. The molecular structure of the synthetic and vector expressed shRNA affords that these siRNAs will be less toxic than their previous generations since their short lengths will limit their ability to stimulate innate immune responses. Additionally, these optimally designed synthetic shRNA molecules retain their potent inhibiting activity while reducing the production of unwanted passenger strands which causes off-target effects. Further, due to their short length, these synthetic and vector expressed shRNA molecules are less toxic to the cell because they have limited ability to stimulate the innate immune response. Moreover, they are cheap and easy to produce due to their small size.

In certain embodiments, the methods provided herein can be used to design synthetic shRNA molecules or vector expressed shRNAs using antisense strand selection software.

Another aspect provided herein relates to a method of silencing expression of a target nucleotide sequence comprising:
obtaining a sample comprising the target nucleotide sequence, and
providing any one or more of the synthetic shRNA molecules described herein to the sample.

Another aspect provided herein relates to a method of silencing expression of a target nucleotide sequence comprising:
obtaining a sample comprising the target nucleotide sequence, and
providing a vector encoding any one or more of the vector expressed shRNA molecules described herein to the sample.

In certain embodiments, the synthetic shRNA molecules and/or vector expressed shRNA molecules are the same as described herein.

In certain embodiments, the method of silencing expression of a target nucleotide sequence using the synthetic shRNA molecules described herein results in a reduced production of unwanted sense strand and off-target effects. The synthetic shRNA molecules and/or vector expressed shRNA molecules may be used to target molecules that are part of a cellular regulation pathway in order to determine the effect that suppression of the target molecule in relation to other molecules has on the pathway. In this sense, the synthetic shRNA molecules and/or vector expressed shRNA molecules may be used in research methods for determining the mechanism of action in signaling pathways for drug discovery or for the discovery of other research tools used for in vivo or in vitro assays. In other embodiments, the synthetic shRNA molecules and/or vector expressed shRNA molecules may be designed to suppress expression of a target gene or variant thereof which is associated with cancer or resistance to chemotherapy (or other cancer treatment). In certain embodiments, the vectors encoding the vector expressed shRNA as used herein may permit transgenic expression of many kinds of individual short sequences that bind to Ago2 that can be used to study their biological functions. The exemplary vector expressed shRNA system has the ability to also allow researchers to express short sequences in Dicer knockout mouse or cell lines and can provide a tool for performing genetic rescues experiments for some of the small noncoding RNAs.

Another aspect provided herein relates to a method of treating a subject having a disease or condition comprising administering a therapeutically effective amount of one or more of any of the synthetic shRNA molecules described herein to the subject.

Another aspect provided herein relates to a method of treating a subject having a disease or condition comprising administering a vector comprising a nucleotide sequence encoding one or more vector expressed shRNA molecules to the subject. In certain embodiments, a therapeutically effective amount of one or more of any of the vector expressed shRNA molecules may be expressed by the vector.

In certain embodiments, the disease or condition may be any disease or condition that can be manipulated by knockdown (e.g., silencing) of a particular gene. In certain embodiments, the disease or condition may be cancer. In certain embodiments, the disease or condition may be human immunodeficiency virus (HIV). In certain embodiments, the disease or condition may be hepatitis C virus (HCV).

In some embodiments, the synthetic shRNA molecules, vector expressed shRNA molecules, and/or vectors comprising a nucleotide sequence encoding one or more vector expressed shRNA molecules (i.e., vectors encoding shRNA) may be used as a therapeutic agent alone, conjugated to one or more additional delivery, diagnostic or therapeutic agents.

The terms "treat," "treating," or "treatment" as used herein with regards to a disease or condition refers to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, or some combination thereof.

According to some embodiments, the synthetic shRNA molecules, vector expressed shRNA molecules and/or vectors encoding synthetic shRNA may be part of a pharmaceutical composition. Such a pharmaceutical composition may include one or more of the synthetic shRNA molecules, vector expressed shRNA molecules and/or vector encoding synthetic shRNA and a pharmaceutically acceptable carrier. A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid, solid, or semi-solid filler, solvent, surfactant, diluent, excipient, adjuvant, binder, buffer, dissolution aid, solvent, encapsulating material, sequestering agent, dispersing agent, preservative, lubricant, disintegrant, thickener, emulsifier, antimicrobial agent, antioxidant, stabilizing agent, coloring agent, or some combination thereof.

Each component of the carrier is "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) natural polymers such as gelatin, collagen, fibrin, fibrinogen, laminin, decorin, hyaluronan, alginate and chitosan; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as trimethylene carbonate, ethyl oleate and ethyl laurate; (13) agar; (14) buffering agents, such as magnesium hydroxide and aluminum hydroxide; (15) alginic acid (or alginate); (16) pyrogen-free water; (17) isotonic saline; (18) Ringer's solution; (19) alcohol, such as ethyl alcohol and propane alcohol; (20) phosphate buffer solutions; (21) thermoplastics, such as polylactic acid, polyglycolic acid, (22) polyesters, such as polycaprolactone; (23) self-assembling peptides; and (24) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of synthetic shRNA molecules, vector expressed shRNA molecules and/or vectors encoding synthetic shRNA in the formulations provided herein can vary widely, and will be selected primarily based on fluid volumes, viscosities, organ size, body weight and the like in accordance with the particular mode of administration selected and the biological system's needs.

Synthetic shRNA molecules, vector expressed shRNA molecules, vectors encoding synthetic shRNA, and/or pharmaceutical compositions thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration. In one embodiment, the synthetic shRNA molecule, vector expressed shRNA molecule, vector encoding synthetic shRNA, and/or pharmaceutical composition thereof is administered parenterally. A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

In some embodiments, the synthetic shRNA molecules, vector expressing synthetic shRNA molecules, and/or vectors encoding synthetic shRNA may be administered with a pharmaceutically effective carrier that allows the synthetic shRNA molecules and/or vectors to be delivered locally or systemically to one or more target cells (i.e., virally infected cells or cancer cells) or target organs by one or more suitable delivery methods known in the art including, but not limited to, viral delivery, liposomal delivery, nanoparticle delivery, targeted delivery (e.g., using an antibody, aptamer or other targeting molecule to facilitate delivery), direct administration into target organs, systemic injection of synthetic shRNA molecules and/or vectors, and eukaryotic transcription plasmid delivery to produce vector expressed shRNA inside of the target cells.

Synthetic shRNA molecules, vector expressing synthetic shRNA molecules, vectors encoding synthetic shRNA, and/or pharmaceutical compositions thereof can be given to a subject in the form of formulations or preparations suitable for each administration route. The formulations useful in the methods of the invention include one or more synthetic shRNA molecules, vector expressing synthetic shRNA molecules, vectors encoding synthetic shRNA, and/or one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a synthetic shRNA molecule and/or vector which can be combined with a carrier material to produce a pharmaceutically effective dose will generally be that amount of a synthetic shRNA molecule and/or vector which produces a therapeutic effect.

In one embodiment of the invention, a synthetic shRNA molecule, vector expressed shRNA molecule, and/or vector encoding synthetic shRNA may be delivered to a disease or infection site in a therapeutically effective dose. A "therapeutically effective amount" or a "therapeutically effective dose" is an amount of a synthetic shRNA molecule, vector expressed shRNA molecule, and/or vector encoding synthetic shRNA that produces a desired therapeutic effect in a subject, such as preventing or treating a target condition or alleviating symptoms associated with the condition. The most effective results in terms of efficacy of treatment in a given subject will vary depending upon a variety of factors, including but not limited to the characteristics of the synthetic shRNA molecule, the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

Another aspect provided herein relates to a kit comprising one or more of the synthetic shRNA molecules and/or one or more of the vector expressed shRNA molecules described herein or compositions or formulations thereof. Other kits may comprise one or more vectors comprising a nucleotide sequence encoding the one or more vector expressed shRNA molecules as described herein. In certain embodiments, the one or more synthetic shRNA molecules and/or one or more vector expressed shRNA molecules in the kits may be used for silencing expression of a target nucleotide sequence. In certain embodiments, the kit may be used as a research tool to investigate the effect of silencing the expression of the target nucleotide sequence by the one or more synthetic shRNA molecules and/or one or more vector expressed shRNA molecules.

The term "about" as used herein means within 5% or 10% of a stated value or a range of values.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Molecular Properties, Functional Mechanisms, and Applications of Ago2-sliced siRNAs The general sequence parameters that can be used to design sli-siRNAs that are preferentially processed by Ago2 into potent siRNAs were experimentally characterized and defined as provided in this Example. A detailed characterization of the substrate properties of sli-siRNAs was performed, and a canonical structure of a synthetic shRNA called "agsiRNA" and the expressed version of sli-siRNA (i.e., vector expressed shRNA) called "agshRNA" was defined (see FIG. 1C). Vectors with the constitutive or inducible U6 promoter that can express sli-siRNAs in mammalian cells were built where the sli-siRNAs can be correctly processed to repress target genes. Additionally, as provided below, as a proof of principle for potential applications of sli-siRNAs in vivo, the expression of one Ago2 shRNA-1148 in HCT-116 colon cancer cells knocked down RRM2 expression and reduced the proliferation and invasiveness of the cells. As such, the structural parameters for designing and expressing sli-siRNAs that are as potent as di-siRNAs are provided below can be used to effectively create optimal sli-siRNAs that can be processed into potent siRNAs.

Results

Define canonical sli-siRNA. To characterize the structural properties of pre-miR-451 that are required for processing into the mature miR-451 by Ago2, all documented pre-miR-451 sequences from 18 species in miRBase 19 were aligned and it was discovered that pre-miR-451 sequences were highly conserved in 17 of the 18 species. Among all species, the 35th base (p35) was almost equally a C, U, or G, so it could form a perfect GC pair, or GU wobble, or mismatch with the G at p6, respectively, indicating that flexibility for this base pairing may have been maintained during evolution by an unknown selection mechanism (FIGS. 3, 4A, 4B, 4C, and 5). It was observed that pre-miR-451 was 42 nt long, and could be expressed by a RNA pol III promoter if the last two pre-miRNA nt were replaced with an UU. Therefore, pre-miR-451 that lacks the last two nt is 40 nt long; the anchor base A (p1) is mismatched with the end base C (p40) and forms a small fork; nt p2 to p18 and p23 to p39 form a 17-nt stem (S17), and nt p19 to p22 form a small loop of four nt (L4). Furthermore, the Mid domain of Ago2 has a much higher binding affinity for substrates that have an A or U at the 5' end, as opposed to a C or G (Frank 2010; Elkayam 2012). Therefore, the 5' nt should be an A or U. It was next reasoned that the CUC 3' overhang of pre-miR-451 are products of Drosha/DGCR8 complex and may not be essential for Ago2 processing and subsequent silencing function because it will be degraded as part of 3L12, but that the C at p40 may be used for end base modifications to prevent the RNA from degrading from the 3' end. Accordingly, the canonical agsiRNA structure was defined as the 40 nt structure A/U-S17-L4-C (L40, FIG. 1C, 3L12 becomes 3L10 from p31 to p40).

Figure 6:
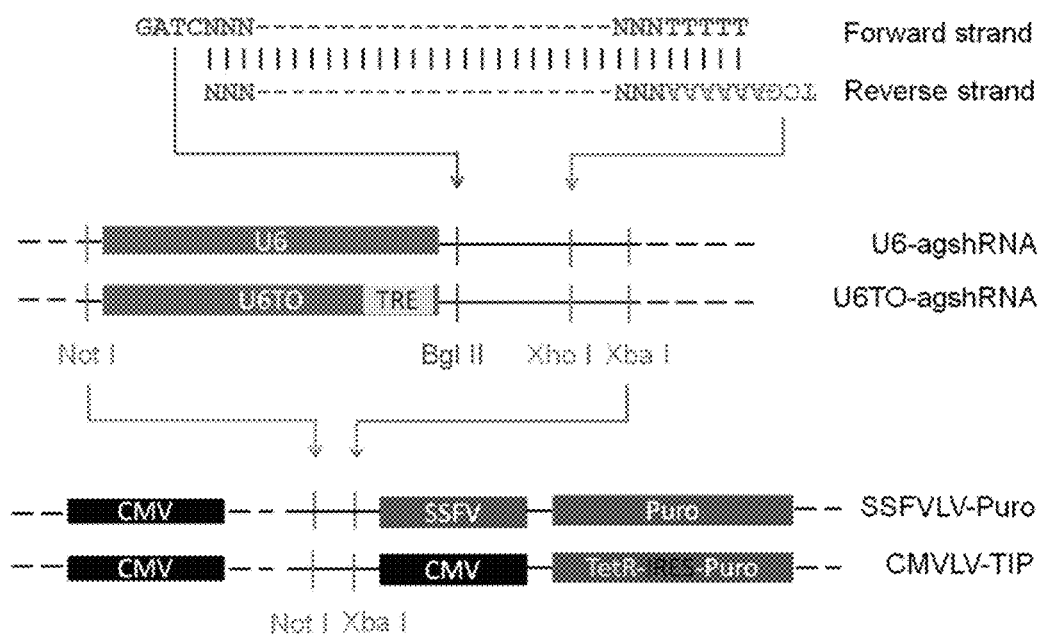
FIG. 6 shows schematic representations of agshRNA expression constructs. Two oligonucleotides were ordered for each agshRNA. The forward strand oligonucleotide had the 5' overhang GATC, followed by the agsiRNA sequence, then five Ts at the 3' end. The reverse strand oligonucleotide had the 5' overhang TCGA, followed by five 'A's, then the agsiRNA complementary sequence. The GATC and TCGA overhangs are complementary to the ends of U6-agshRNA and U6TO-agshRNA after digestion by Bgl II and Xho I, respectively. The Not I to Xba I fragment from U6-agshRNA was subcloned into the Not I and Xba I sites of the lentiviral vector SSFVLV-Puro to produce SSFVLV-U6-agshRNA-Puro, which can generate stable cell lines that constitutively express agshRNA. The Not I to Xba I fragment from a Doxycycline [Dox]-inducible U6m (U6TO)-agshRNA was subcloned into the Not I and Xba I sites of the lentiviral vector CMVLV-TIP (TetR-IRES-Puro) to produce CMVLV-U6TO-agshRNA-TIP, which can generate stable cell lines that can be induced to express agshRNA.
Figure 7:
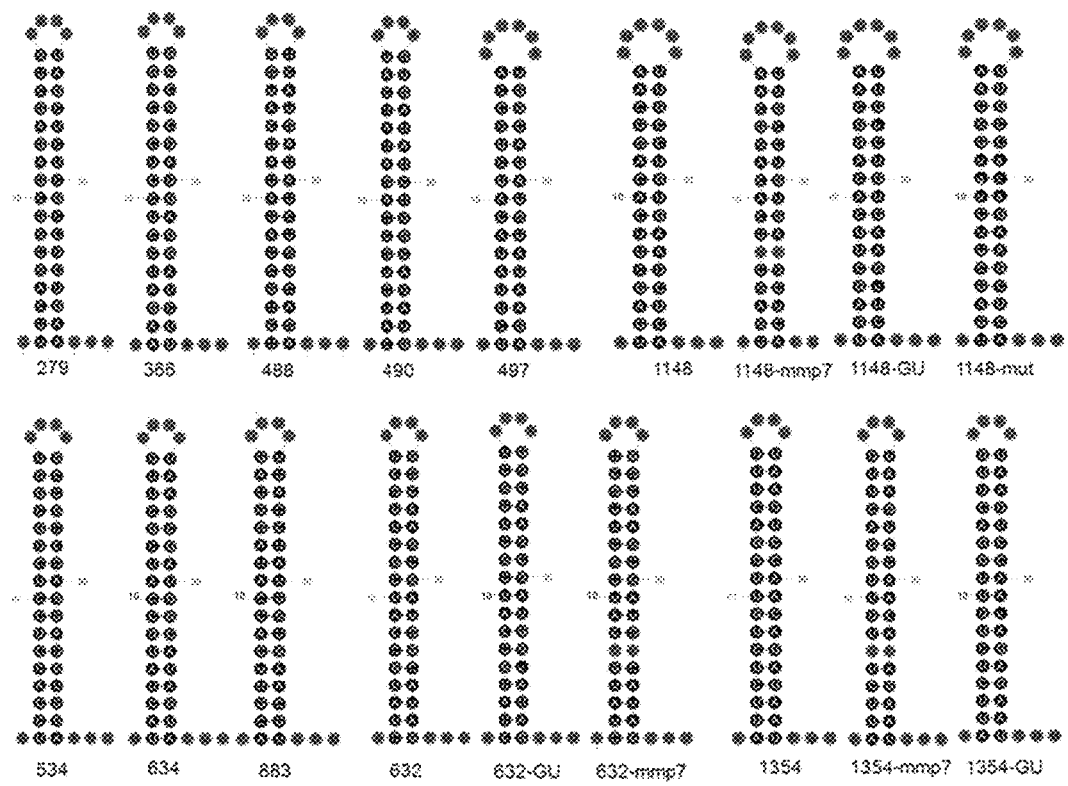
FIG. 7 shows the secondary structures predicted by mFold for the agshRNAs designed to target R2.

To convert agsiRNA to agshRNA, the choice of promoters and their transcription start sites will be critical for their function since agshRNA will default 5p as the antisense strand. Several agshRNAs were designed that would target the M2 subunit of ribonucleotide reductase RRM2 gene (R2). The antisense strands were defined as 22 nt long (L22: the first 18 nt plus 4 nt in the loop) and hairpins were expressed by the U6m promoter (FIG. 6). At least half of the agshRNAs efficiently reduced R2 protein levels and knocked down expression of a Renilla luciferase reporter gene that had the human R2 cDNA sequences inserted into its 3' UTR (FIGS. 7, 8A, 8B 8C and 8D). Thus, the U6m agshRNA expression vector can express this type of shRNA. To address the concern about how U6m will start its transcripts if the first nt of L22 is not a G, products from eight R2 agshRNAs were sequenced using small RNA deep sequencing (Sun 2011). In most cases, U6m mainly used bases A and C to initiate agshRNA transcripts, but the transcription will be initiated at the upstream C of U6m or the second base in agshRNA if the first base of the agshRNA sequence was a T. In addition, Ago2 processed these agshRNAs into L30, but there are many uridylated and trimmed intermediate products were also derived from L30. The length distributions of these L30-derived intermediates resembled that for isomiR-451 forms that are documented in miRBase, suggesting that agshRNA transcripts expressed from the U6m promoter are processed by Ago2, similar to the way miR-451 is processed (FIG. 9). Accordingly, the canonical agshRNA structure was defined as the 40 nt structure, A-S17-L4-C.

Figure 10A:
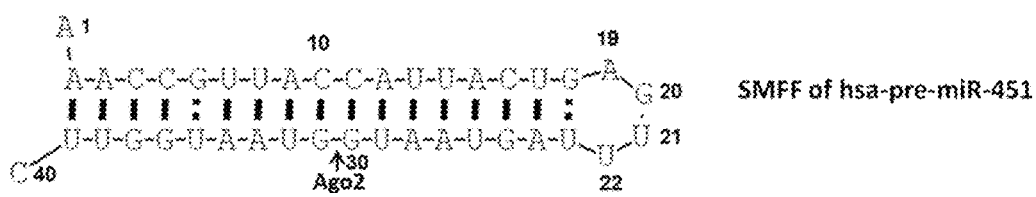
FIGS. 10A, 10B and 10C show the single molecular folding form and cross molecular hybridization form of agsiRNA.
Figure 10B:
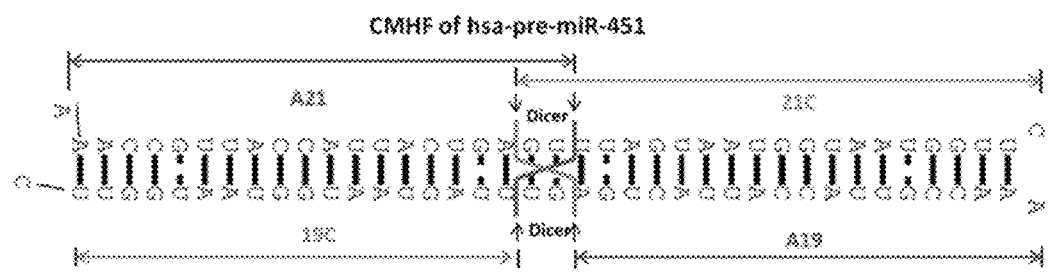
Figure 10C:
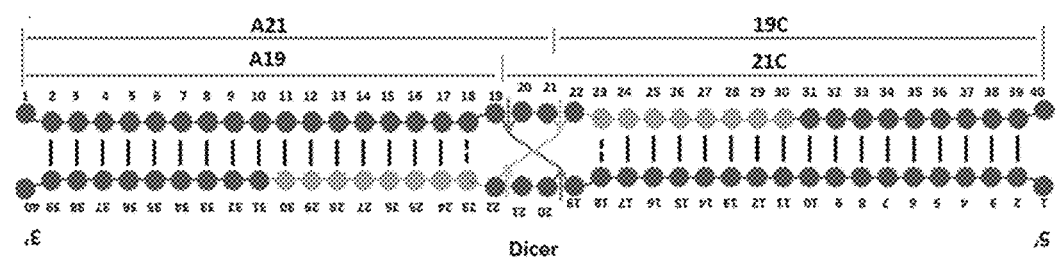

The secondary structures of agshRNA and agsiRNA likely differ in how they form. Presumably, agshRNA is folded in vivo and the single molecule folded form (SMFF, agsiRNA in FIG. 1C, FIG. 10A) is then exported to the cytoplasm. AgsiRNAs are artificially folded in vitro by denaturing and annealing. Thus, some agsiRNAs will be in the SMFF, while some will be in dimer form. Since the agsiRNAs in the dimer form is not necessary to be identical, these forms were named cross molecule hybridization form (CMHF). Once the agsiRNAs are transfected into the cytoplasm, Dicer should be able to process the CMHF of agsiRNA into four products (A21, A19, 21C, and 19C in FIGS. 10B and 10C), which will be similar to the products generated by RNases that nick the SMFF of agsiRNA between p19 and p20 or p21 and p22. Based on this hypothesis, the L40 form of pre-miR-451 may be less likely to be processed by Dicer than the 42 nt pre-miR-451 form.

Figure 8A:
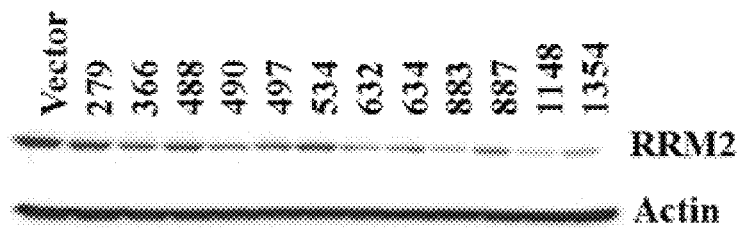
FIGS. 8A, 8B, 8C and 8D show data for agshRNAs that target R2.
Figure 8B:
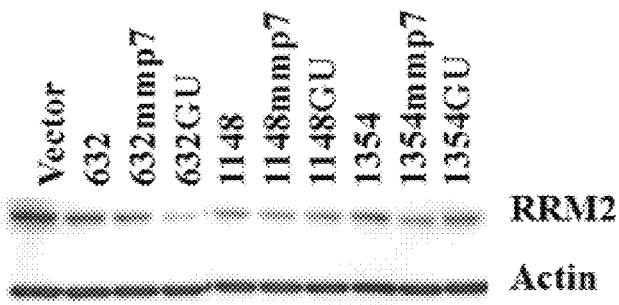
Figure 8C:
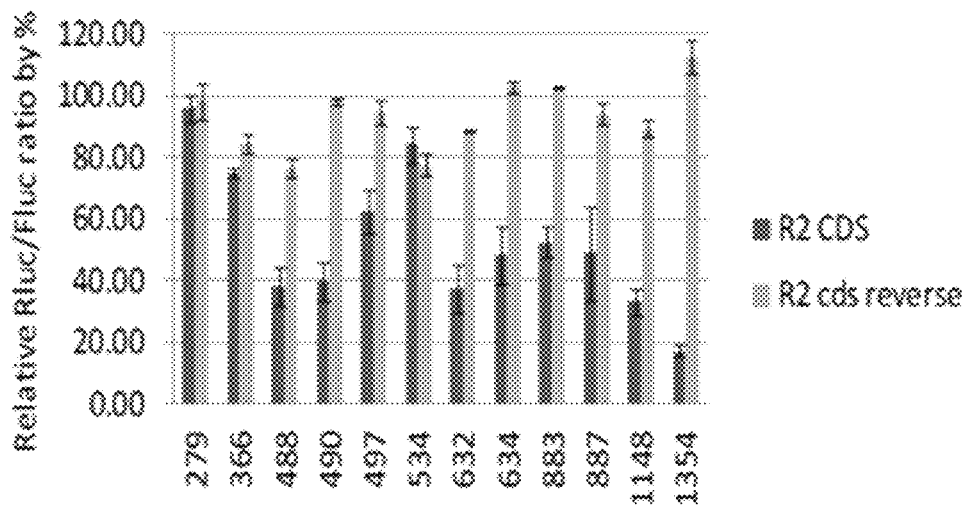
Figure 8D:
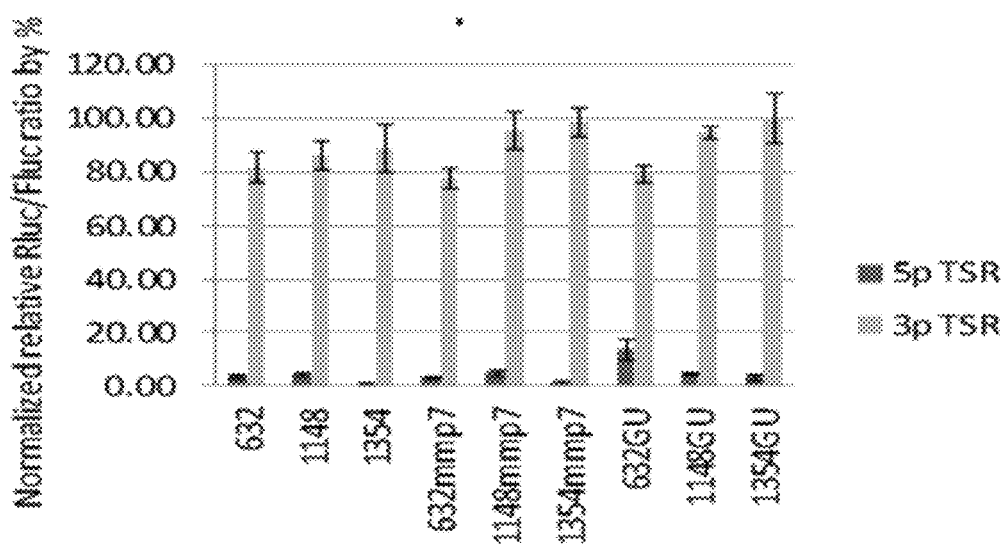
Figure 12:
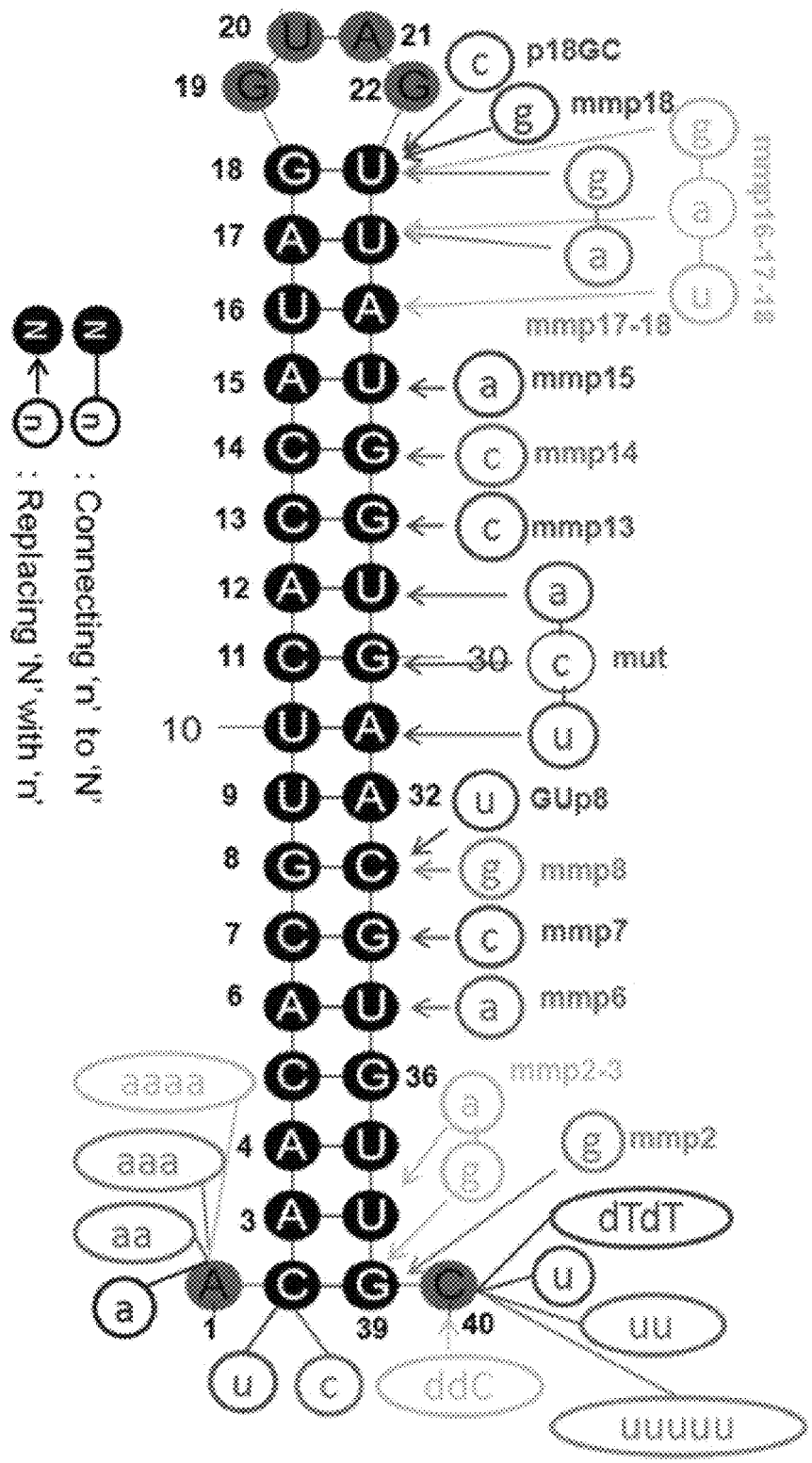
FIG. 12 shows sli-siRNA-887 and variants. Variants of agsiRNA-887 used in Example 1 were made by replacing nt(s) in the backbone or adding extra nt(s) to the 5' end or 3' end of the molecule. Based on the wt agsiRNA-887 backbone, modifications were made as following: replacing of the anchor 'A' (p1) with uracil ("U") or a cytosine ("C") to make U/C-S17-L4 forms; prefixing the anchor 'A' (p1) with an adenine ("A" or "a"), 'aa', 'aaaa', or 'aaaaa' to make 5' overhang variants a/aa/aaa/aaaa-A-S17-L4; mismatch base pairing at p6:35, p7:34, p8:33, p13:28, p14:27, and p15:26 to make the mmp6, mmp7, mmp8, mmp13, mmp14, and mmp15 forms, respectively; replacing the 'C' at p33 with an 'U' to make the GUp8 form; replacing the p31, p30 and p29 bases with the p10, p11 and p12 bases to make the mutant (mut) form; Replacing the 'C' at p40 with a dideoxycytidine ("ddC") to make the 'ddC' form; adding one 'U', two CU's, five 'U's, or two deoxythymidines ("dTs") to the 'C' at p40, respectively, to make the U, 2U, 5U, and dTdT forms; replacing 'G' at p39 with 'C' to make mmp2 form; replacing 'G' at p39 with 'C' and 'U' at p38 with 'A' to make mmp2-3 form; replacing 'U' at p23 with 'C' to make p18GC; replacing the 'U' at p23 with a guanine ("G") to make mmp18; replacing the 'U' at p23 with a 'G' and the 'U' at p24 with an 'A' to make mmp17-18; replacing the 'U' at p23 with a 'C', an 'U' at p24 with an 'A', and the 'A' at p25 with an 'U' to make mmp16-17-18
Figure 13A:
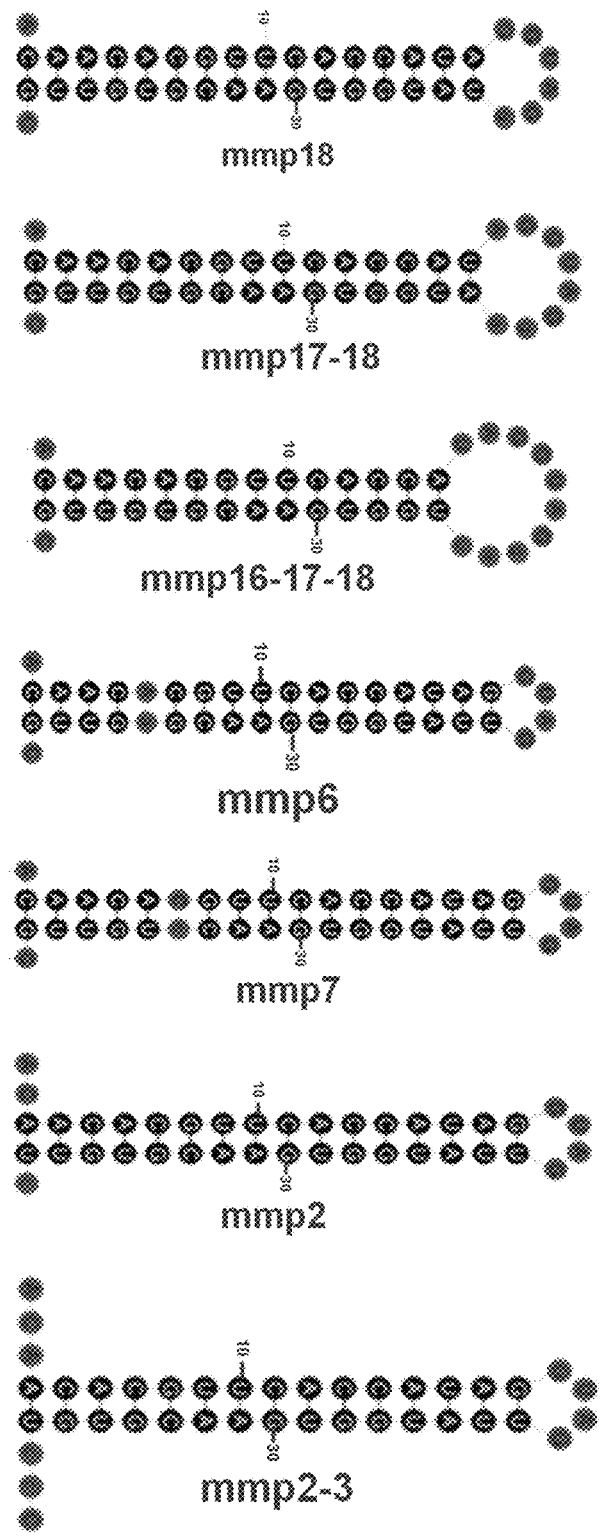
FIGS. 13A, 13B, 13C and 13D show the predicted secondary structures of sli-siRNA-887 variants used in this study.
Figure 13B:
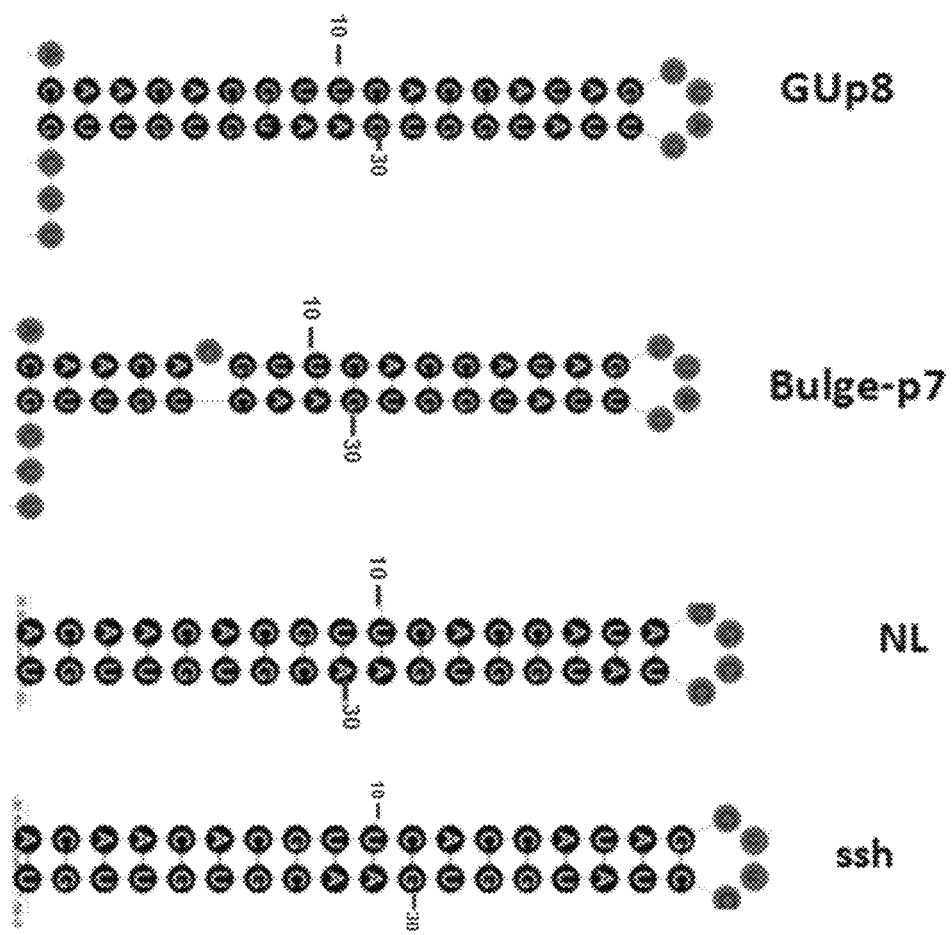
Figure 13C:
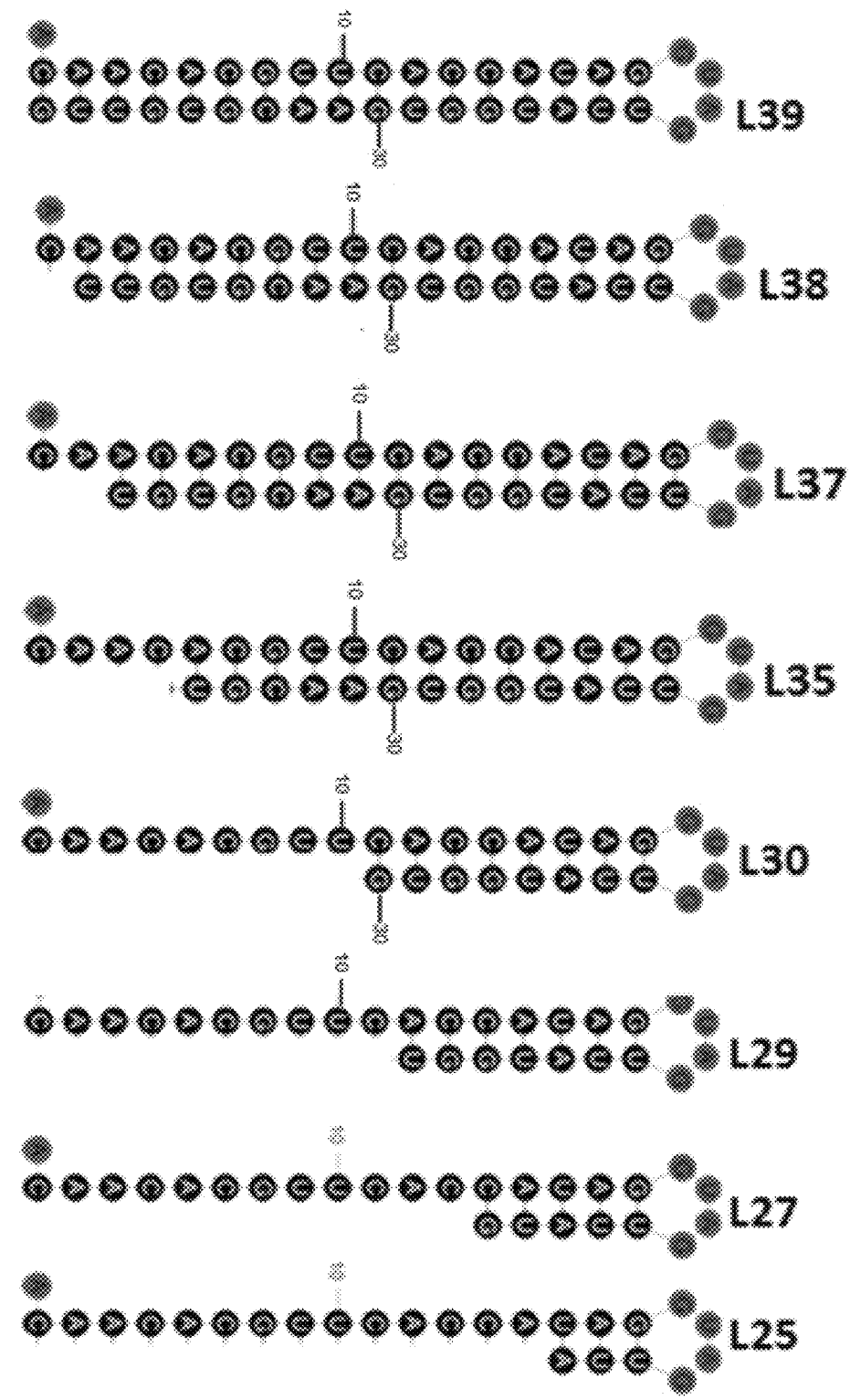
Figure 13D:
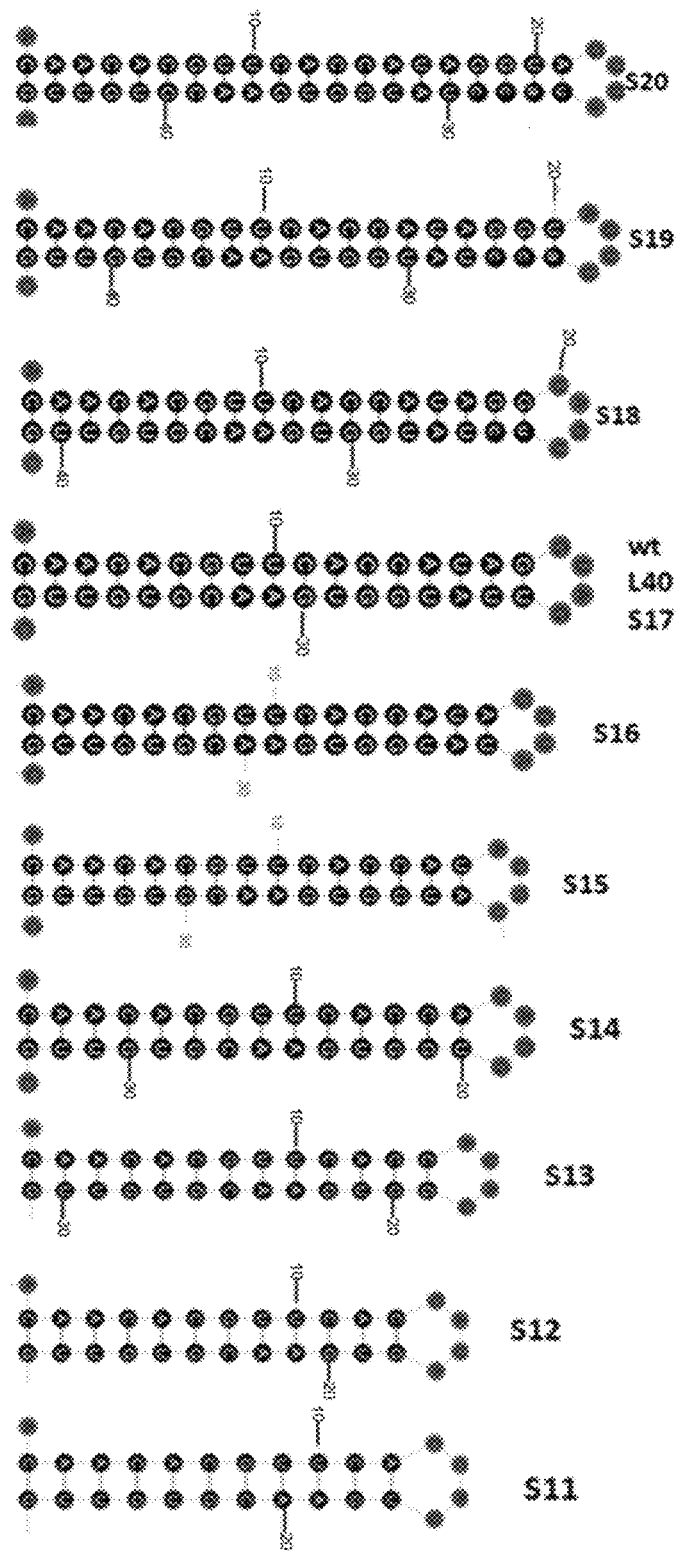

AgshRNA-887, -1148, and -1354 was further characterized and their synthetic forms, agsiRNA-887, -1148, and -1354, all of which target R2 (FIGS. 7, 8A, 8B 8C, 8D and 11) were also characterized. Sli-siRNA-887 was used for most of the studies because, among all of the R2 agshRNAs that were constructed, agshRNA-887 exhibited moderate knockdown of R2 (FIGS. 8A and 8B). It was reasoned that it would be easier to observe changes in the potency of this sli-siRNA in response to modifying its structure and base composition. The secondary structures of the agshRNA-887 forms used in the experiments are shown in FIG. 12, and individual structures are listed in FIGS. 13A, 13B, 13C and 13D.

Figure 14A:
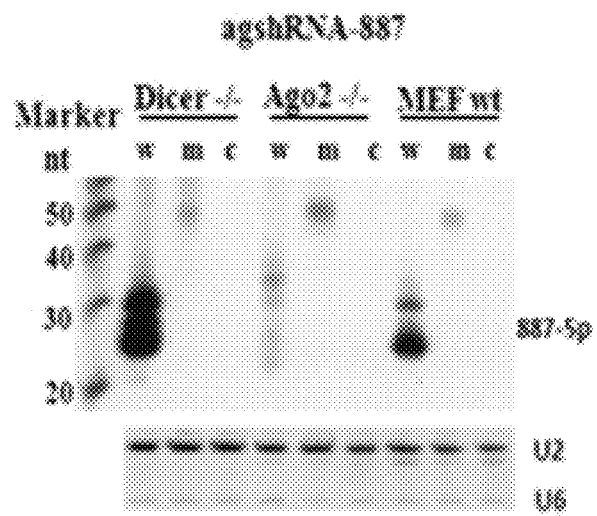
FIGS. 14A and 14B show results from northern blot analyses of agshRNA-887 and agsiRNA-887 in Dicer$^{-/-}$, Ago2$^{-/-}$, and wild-type MEFs.
Figure 14B:
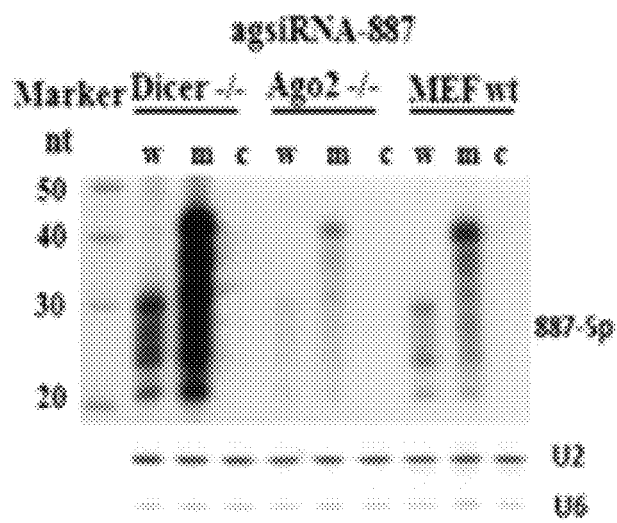
Figure 15:
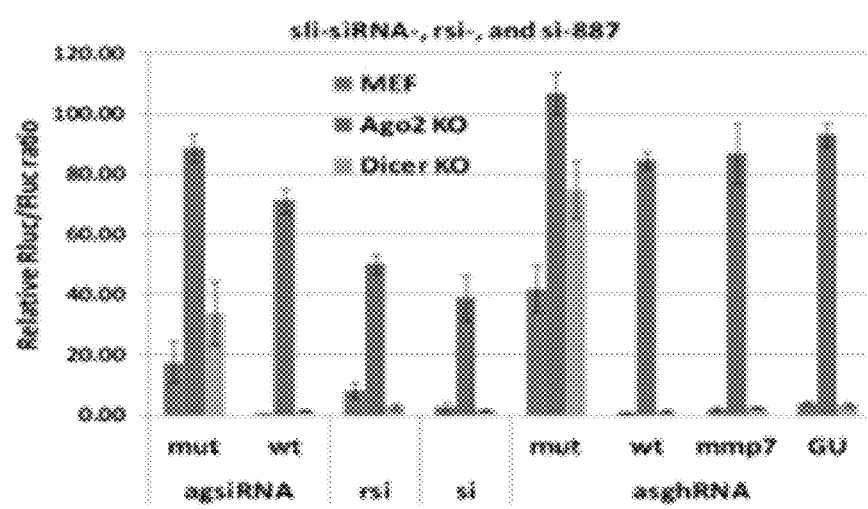
FIG. 15 shows a bar graph of results from reporter assays of sli-siRNA-887, rsiRNA-887, and siRNA-887 in Dicer$^{-/-}$, Ago2$^{-/-}$, and wild-type MEFs. Results from MEFs are represented by the bar on the left, results from Ago2$^{-/-}$ (i.e., Ago2KO) are represented by the middle bar, and results from Dicer$^{-/-}$ (i.e., DicerKO) are represented by the bar on the right. Abbreviations are as follows: mmp7: mismatch for base #7 with #34; wt, GU: mutated base #33 from C to U.

Sli-siRNAs are Ago2-specific and Dicer-independent. The processing of sli-siRNA-887 and its mutant that had mismatches at central bases (FIG. 11, FIGS. 14A and 14B) was tested in Dicer-knockout and Ago2-knockout mouse embryonic fibroblasts (MEFs). Northern blot analysis and reporter assays showed that both agshRNA-887 and agsiRNA-887 were Ago2-dependent and Dicer-independent, and that Ago2 could not process the mutant form of sli-siRNA-887 (FIG. 11; FIGS. 14A and 14B; FIG. 15). Northern blot analysis also indicated that the CMHF of sli-siRNA probably exists only at very low levels, because the predicted Dicer processed forms (A19) were not detected (FIGS. 14A and 14B). Reporter assays showed that depleting Ago2 reduced the silencing efficacy of agsiRNA significantly more than that of siRNA or rsiRNA, suggesting that agsiRNA mainly functioned through Ago2 RISCs, whereas siRNA or rsiRNA could be loaded into other Ago RISCs to repress their targets (FIG. 15).

Figure 16:
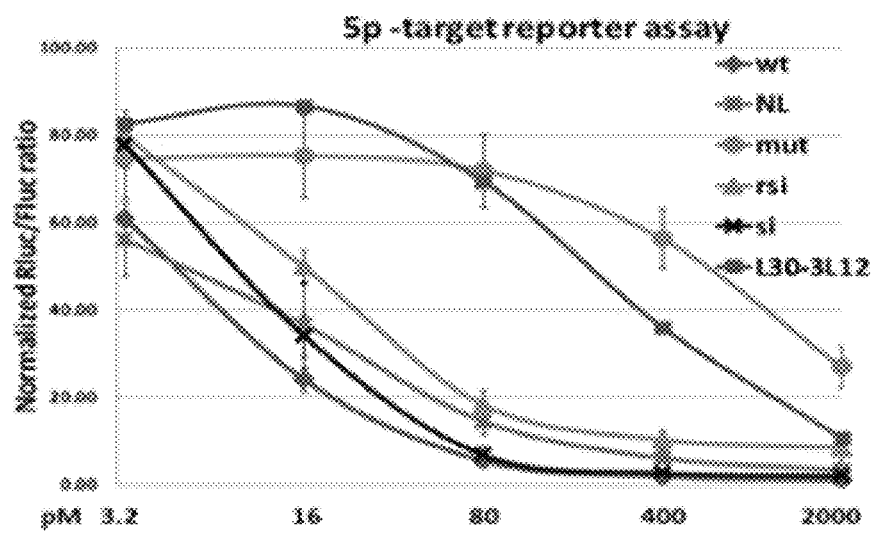
FIG. 16 shows results from antisense strand (5p) reporter assays in HCT-116 cells. Abbreviations are as follows: rsi=rsiRNA-887; si=siRNA-887; L30-3L12 is agsiRNA-887 that was reconstituted by annealing 3L12 with L30. Rluc/Fluc ratios are plotted. Error bars represent the standard deviation.
Figure 17:
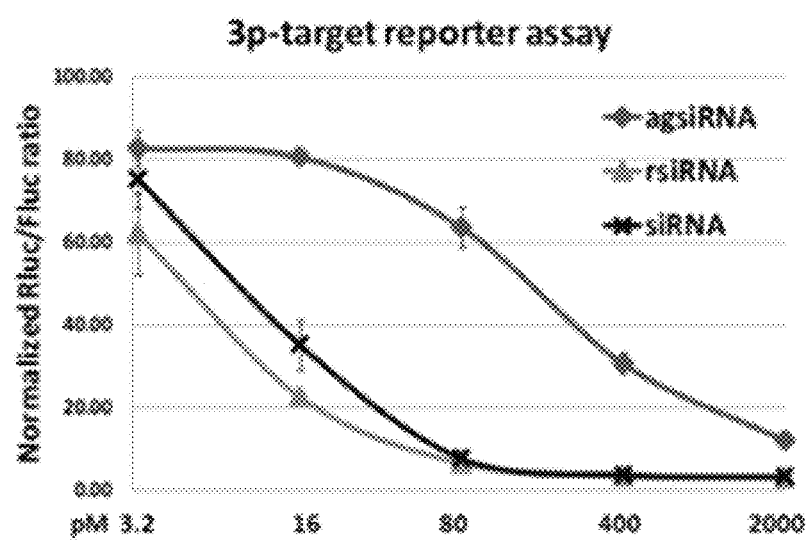
FIG. 17 shows results from sense strand (3p) reporter assays of agsiRNA-887 (wt), rsiRNA-887 (rsi), and siRNA-887 (si) in HCT-116 cells. Rluc/Fluc ratios are plotted. Error bars represent the standard deviation.

The potency of various concentrations of agsiRNA-887, rsiRNA-887, and siRNA-887 was also compared. An antisense reporter assay showed that agsiRNA-887 and siRNA-887 had similar potency, which was higher than that of rsiRNA-887 across all concentrations tested. Sense strand reporter assays showed that both siRNA-887 and rsiRNA-887 maintained strong sense strand activity (almost as potent as the antisense strand), but agsiRNA-887 had almost three orders of magnitude less sense strand activity (FIG. 16, FIG. 17). These data suggest that the antisense and sense strands of certain di-siRNAs can be nearly equally loaded into mature RISCs, but RISCs mainly selected the antisense strand for sli-siRNAs.

Figure 18A:
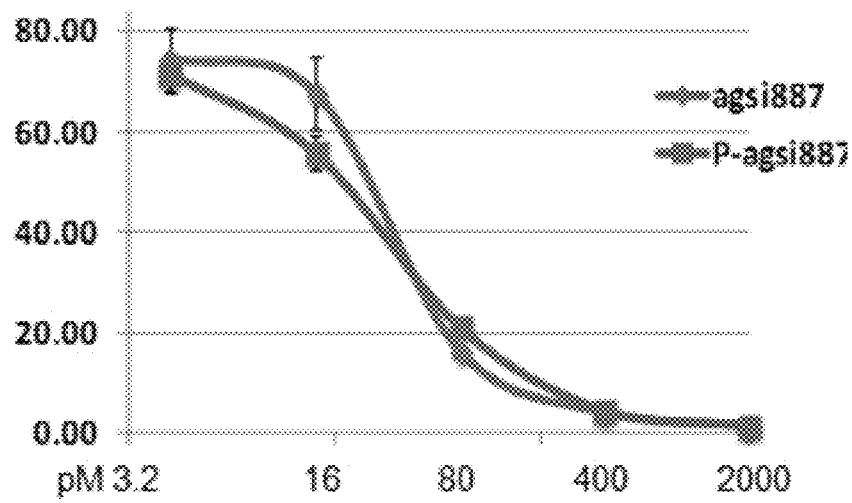
FIGS. 18A, 18B, 18C, 18D, 18E, 18F and 18G show results from reporter assays of agsiRNA-887 variants.
Figure 18B:
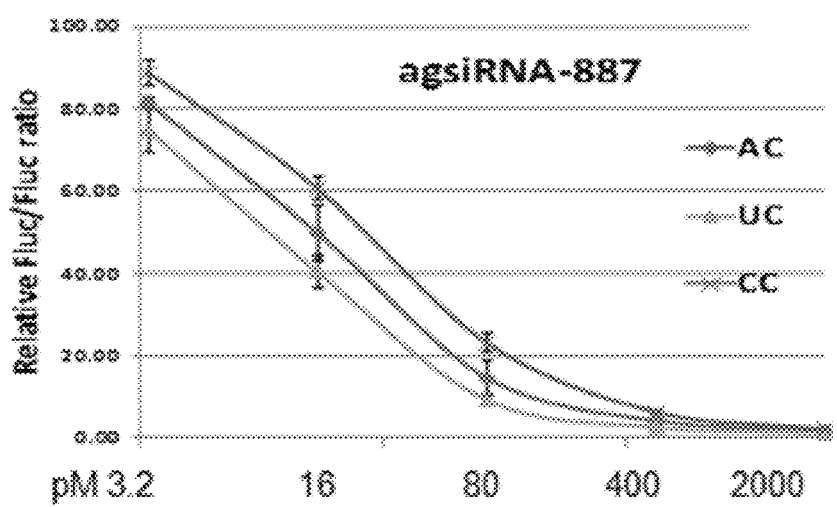
Figure 18C:
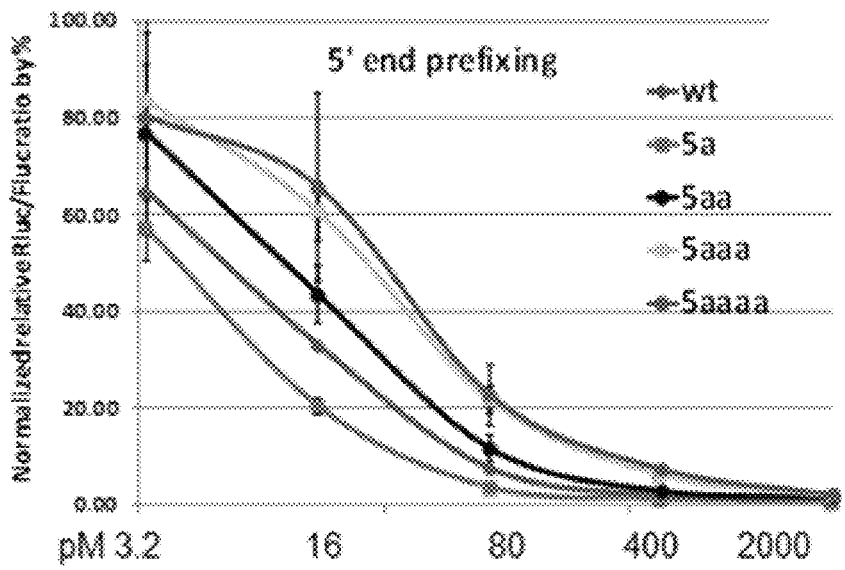
Figure 19A:
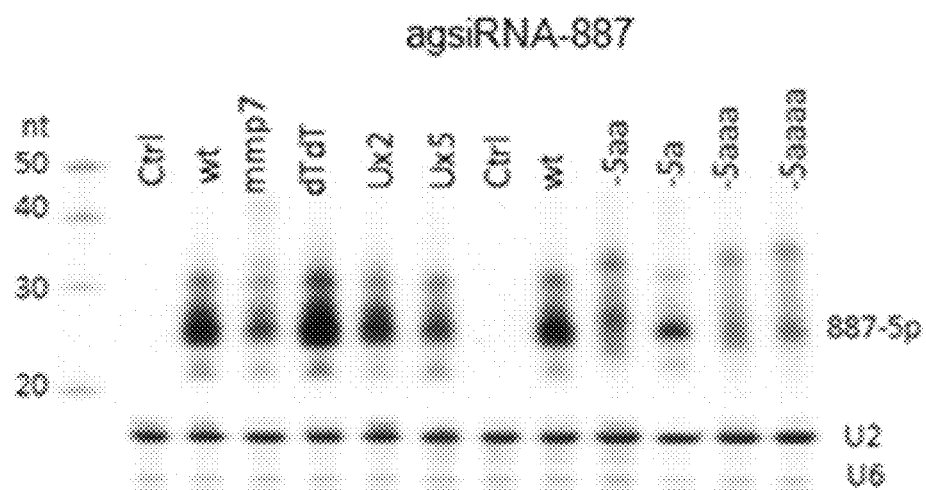
FIGS. 19A, 19B, 19C, 19D, 19E, 19F, 19G and 19H show the characterization of sli-siRNA-887.

5' end modification. Phosphorylation of the 5' end (5'p) increases the potency of di-siRNAs (Martinez 2002), and is required for siRNA loading (Schwarz 2003). It has also been proposed that 5'p will hold Ago2 in a special conformation (Ma 2005). However, an obvious difference was not observed in the potency of agsiRNA-887 synthesized with or without the 5'p (FIG. 18A). This result agrees with the first bases replacement test in pre-miR-451 (Yang 2012). It is possible that similar to di-siRNA, agsiRNA is phosphorylated in vivo by hClp1 (Ramirez 2008). Accordingly, all agsiRNAs and siRNAs used in the following experiments were synthetic oligonucleotides without 5'p. 5' end base replacements showed the U-S17-L4-C form performed similarly to the canonical form, but not the C-S17-L4-C form, indicating that an U-S17-L4-C form can be easily expressed as an agshRNA that begins with an A (FIG. 18B). It was also observed that extra bases added to the 5' end affected sli-siRNA potency. The addition of one A, which made the 5' overhang of the agsiRNA two nt long, slightly increased its potency, but the addition of two to four As reduced the potency (FIG. 18C). Northern blot analysis showed that the amount of mature agsiRNA-887 was reduced when extra bases were added to the 5' end, implying they are not Ago2 favorite substrates and it may be difficult to anchor these molecules to the Mid domain of Ago2, or to fit them into the Ago2 substrate groove to trigger Ago2 slicer activity. The lengths of the long fragments and mature products were also increased, suggesting that the Ago2 slicing sites on 3p were not shifted by adding extra bases to the 5' end and supporting a model that Ago2 slicing sites are defined by the stem region of agsiRNA (FIG. 19A).

Figure 18D:
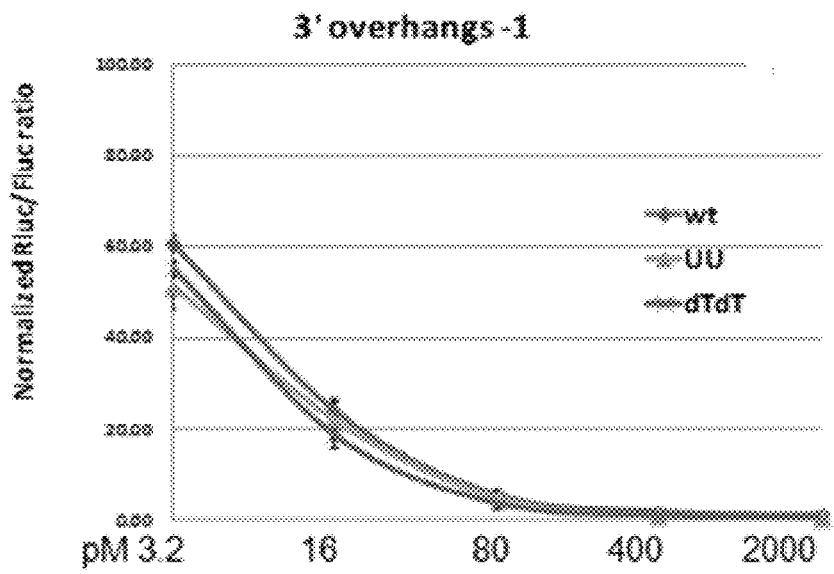
Figure 18E:
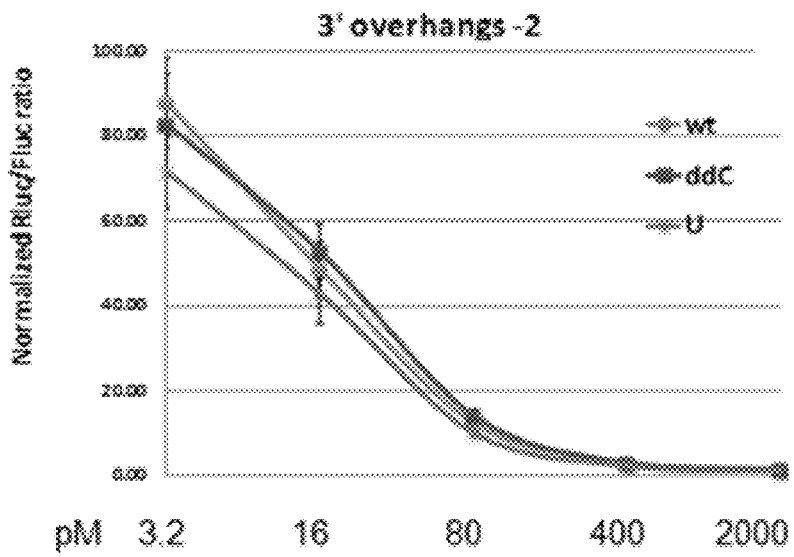

3' end overhangs. The original pre-miR-451 has a 3' overhang of CUC that arises from Drosha processing. When the agsiRNAs were designed, it was assumed that the last two bases would not be required for agsiRNA-mediated gene silencing. Firstly, because they would be degraded as part of the 3L12 after Ago2 nicks the substrate, and secondly, because experiments with the R2 agshRNAs showed that the UC bases could be replaced by UU. However, these bases could maintain the structure of the substrate to allow efficient Ago2 binding and processing, or protect pre-m iR-451 from being degraded from the 3' end. To test the function of different overhangs at the 3' end of agsiRNA, these bases were replaced with modified bases that were resistant to RNases to prevent agsiRNA degradation from the 3' end. 3' end variants of agsiRNA-887 were created by attaching U, UU, or UUUUU, or deoxy T deoxy T (dTdT) to the last C, or by converting the last C to a dideoxy C (ddC). Northern blot analysis showed that the UUUUU form produced fewer mature products, indicating increased degradation of this agsiRNA. Both the U and UU mutants produced slightly less product than the canonical form, and the dTdT and ddC forms produced mature products in similar amount to wild-type ("wt" in FIGS. 19A and 19B). Reporter assays showed that the modified 3' end bases, which were removed together with the short fragments, had little effect on the silencing potency of the mature agsiRNAs (FIGS. 18D and 18E). Because the ddC modification can prevent degradation from the 3' end, it would be a good addition to the design of agsiRNAs to increase their stability in vivo.

Figure 4A:
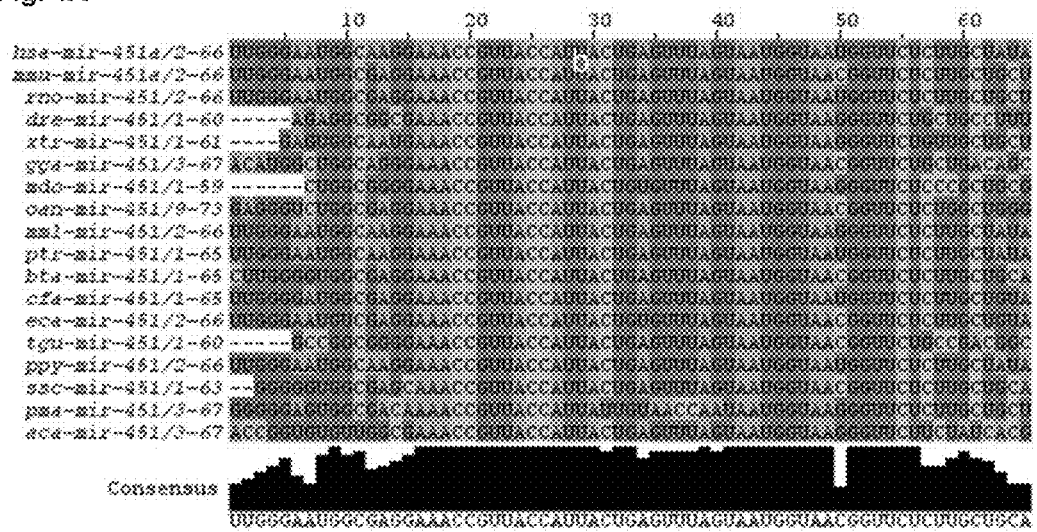
FIGS. 4A, 4B and 4C show the characterization of pre-miR-451.
Figure 4B:
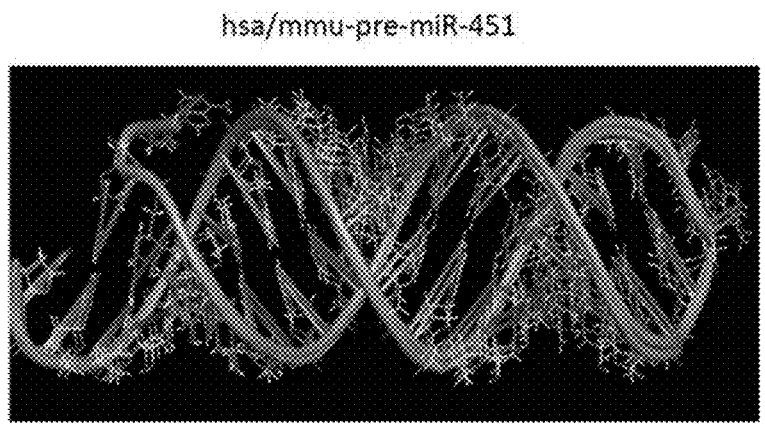
Figure 4C:
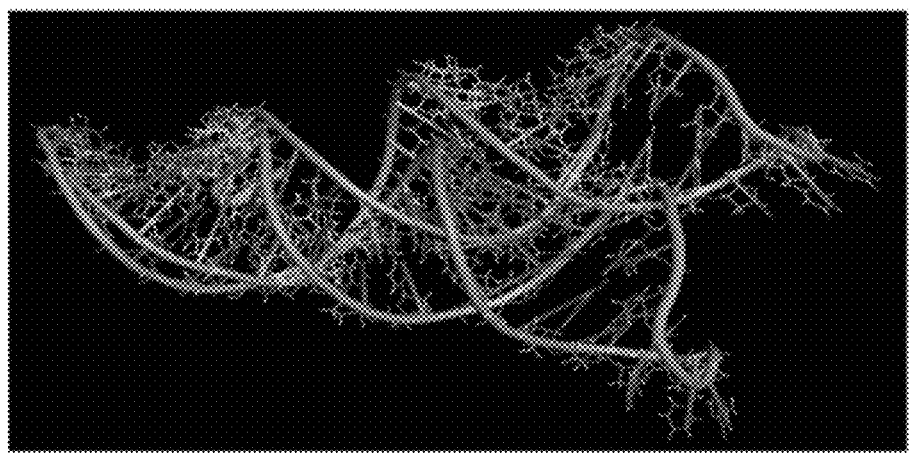
Figure 18F:
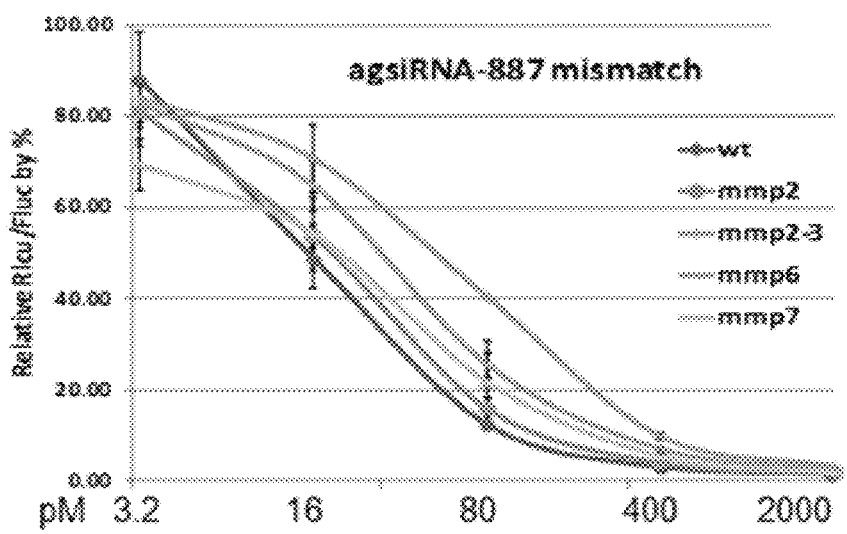
Figure 18G:
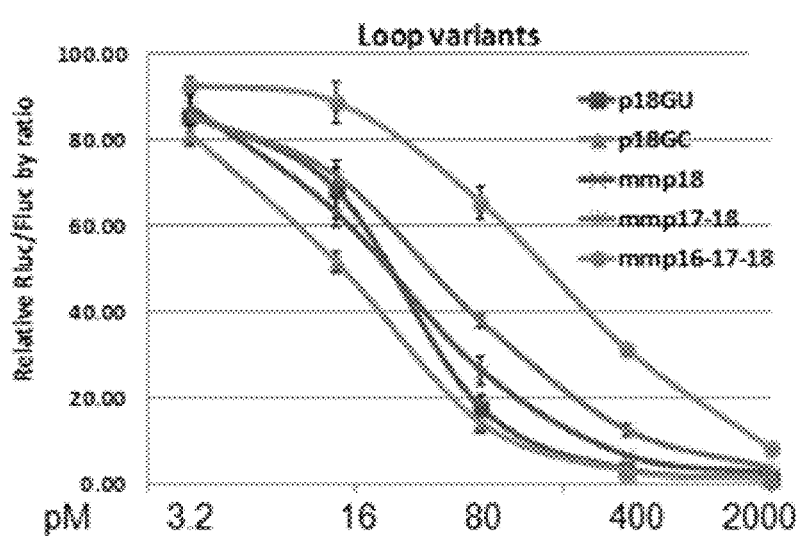
Figure 19B:
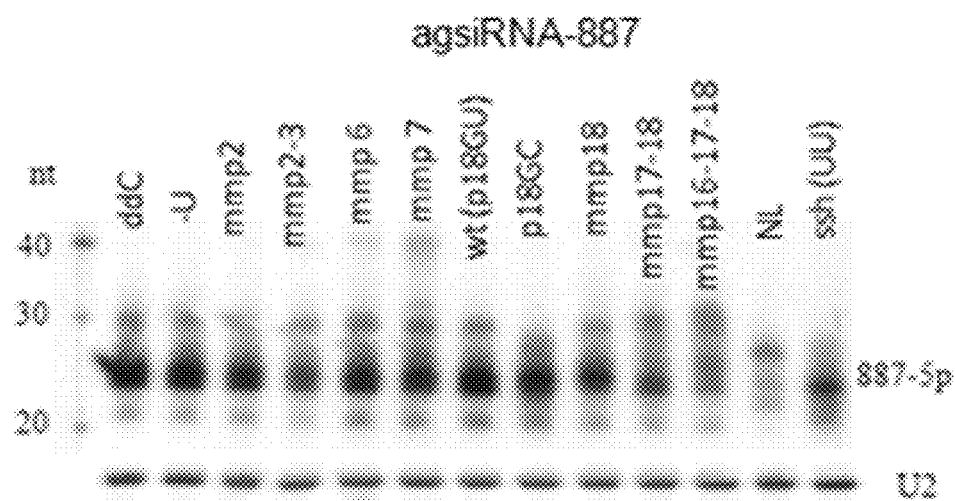
Figure 19C:
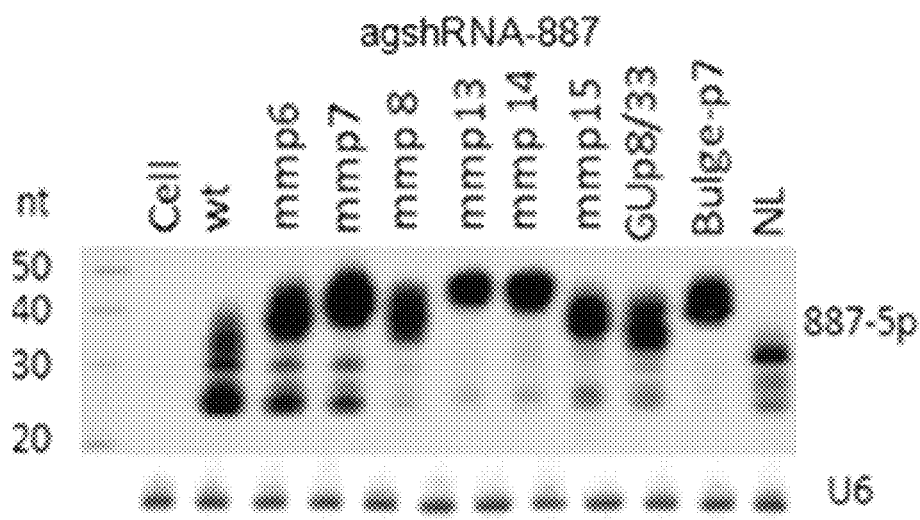
Figure 20A:
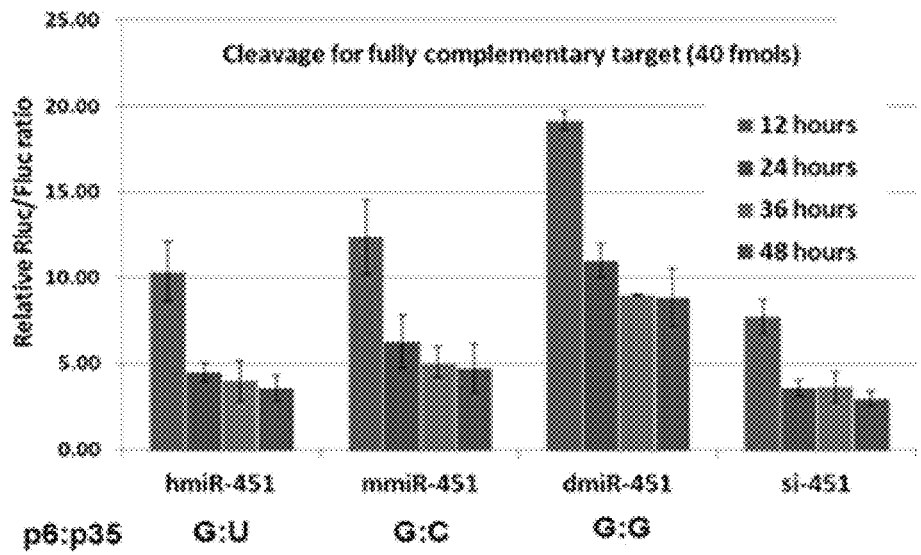
Figure 20B:
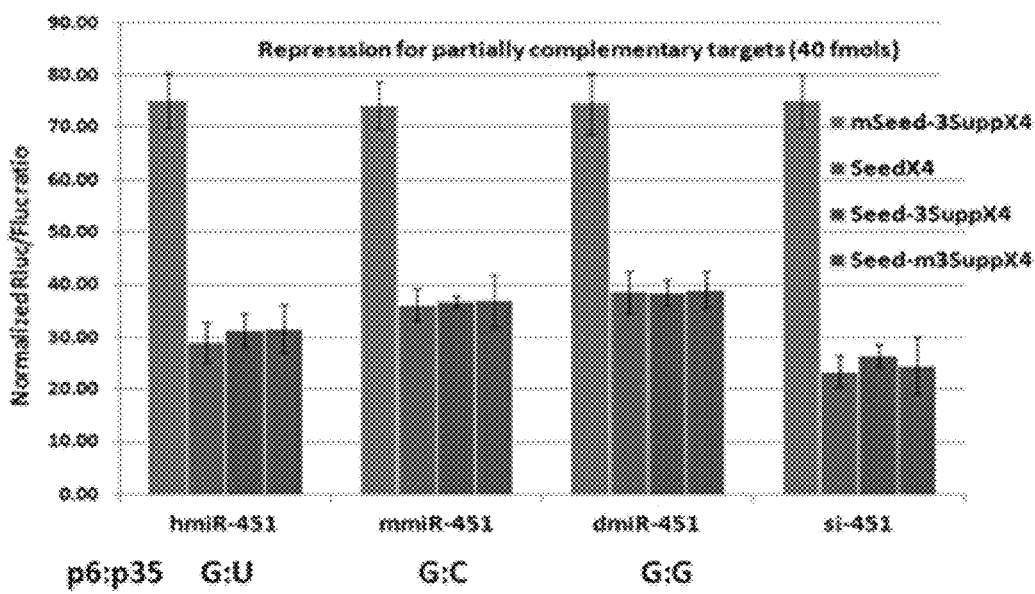

Base pairs in the stem Region. The stem region can be divided into the seed, central, and 3' supplementary (3' supp) regions (FIGS. 1A, 1B and 1C). Because the central bases are critical for the slicing reaction, only mismatches, GU wobbles, and bulges were introduced into the seed and 3' supp regions to determine their effects on sli-siRNA processing and silencing potency. In contrast to the reported miR-451 processing data that G:G mismatch for p6:35 enhances miR-451 function (Yang 2012), the Northern blot analysis showed that agsiRNA-887 with mmp6 (base #6 mismatched with #35) and mmp7 modifications produced fewer mature products than wild-type agsiRNA-887, and the effects on agshRNA were even stronger (FIGS. 19B and 19C). AgshRNA-887-mmp8, -mmp13, -mmp14, -mmp15, -GU-p8, and -bulge-p8 were also processed poorly; the amounts of mature products were dramatically reduced (FIG. 19C). While agshRNA-887-mmp13, 14, and 15 data agreed with the published miR-451 mutation data, agshRNA-887-mmp8, -GU-p8, and buldge-p7 showed a much stronger effect on the silencing potency and processing efficiency of sli-siRNA-887 than miR-451 mutations at these positions (Yang 2012). These data indicate that base pair modifications in the stem region affect agshRNA more severely than agsiRNA and also suggest that the seed region has more flexibility for mismatches and wobble base pairs, but bulges are not favored. It is possible that a mismatch (flexible for nt at any position) or a wobble base pair (context dependent, only for 'G' or 'U') in the seed bases could help release the 3L10 from the L30, and facilitate the binding of products trimmed from L30 to their targets (Yang 2012). Despite having the similar knockdown potency at higher concentrations, there was a several fold drop in the activity of the mmp6 and mmp7 mutants at lower concentrations compared to wild-type (FIG. 18G). The published result that mismatch of p6:35 (G:G) enhances miR-451 potency was also revisited (Yang 2012). The reporter assays using three natural existing miR-451 forms, the human (hmiR-451, G:U wobble pair for p6:p35), mouse (mmiR-451, G:C pair for p6:p35), and zebra fish miR-451 (dmiR-451, G:G mismatch pair for p6:p35), revealed that hmiR-451 was the most potent and dmiR-451 was the least potent in both target cleavage and repression (FIG. 4A; FIGS. 20A and 20B). It was also observed that the three forms of pre-miR-451 exist almost equally in nature. There are six G:G, six G:C, and five G:U paired pre-miR-451s in 18 species that were documented in miRBase 19 (FIG. 4A). Therefore, both our sli-siRNA-887 and pre-miR-45 results argue against the conclusion that the flexible base pairing of p6 with p35 in pre-miR-451s enhanced their potency. But, they support the hypothesis that the flexible base pairing of p6 with p35 in pre-miR-451s may arise from natural selection in balancing short fragment release and mature 5p binding to targets (Yang 2012). The p6 G of miR-451 may act as a 'pivot' residue for target recognition like the p6 C of miR-124 (Chi 2012).

Figure 19D:
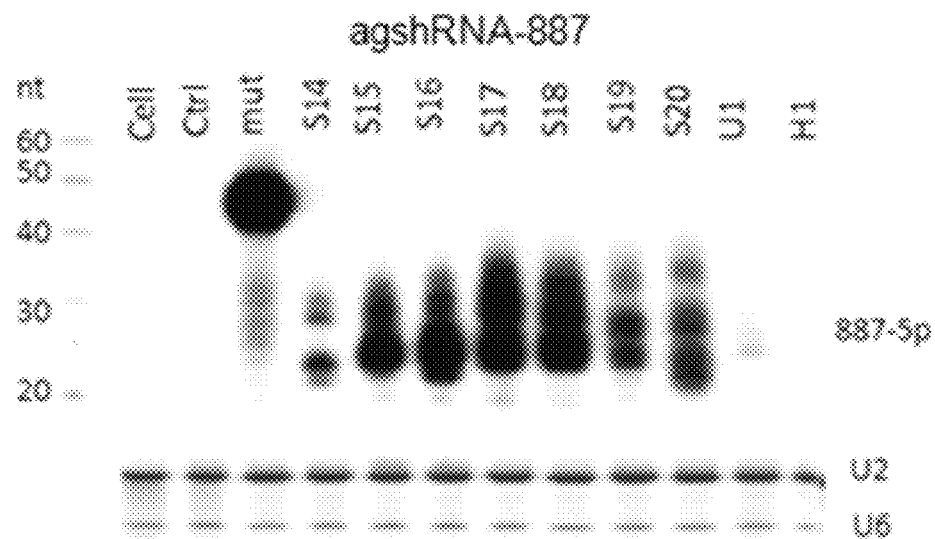
Figure 19E:
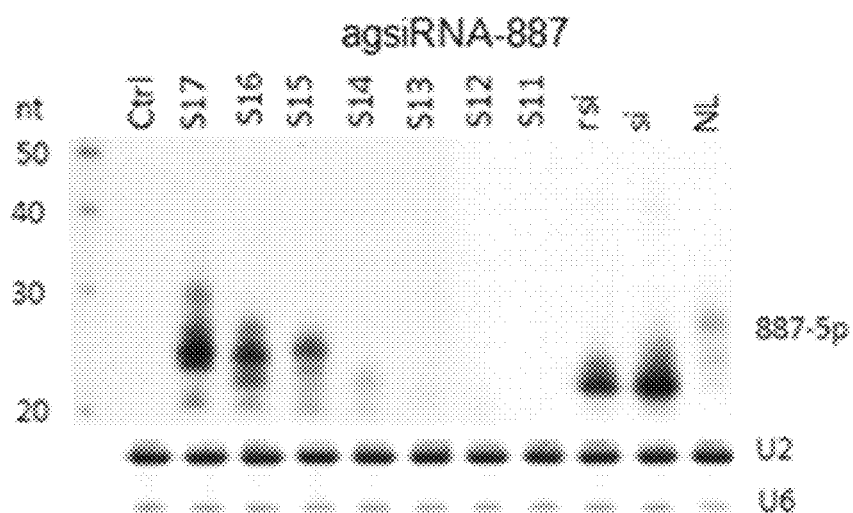
Figure 19F:
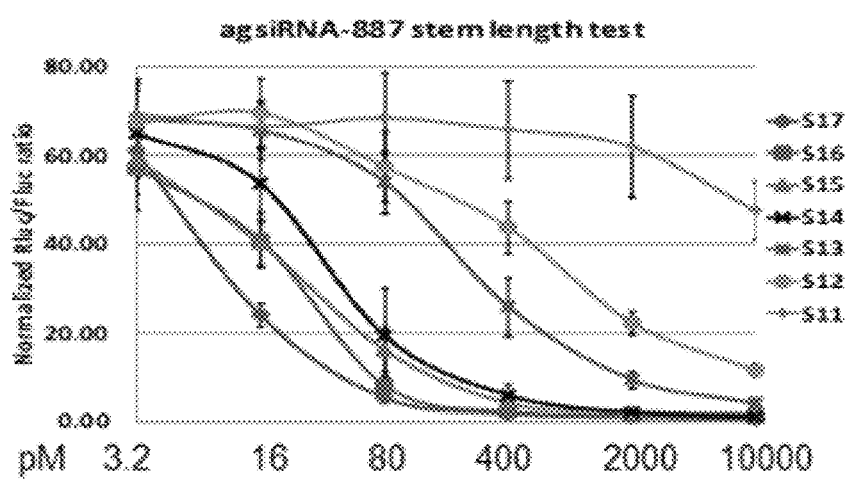

Optimal stem length. When one more mismatch by was added to the 5'/3' ends of the sli-siRNA hairpin (mmp2, 16 nt stem), the structure behaved like the canonical form. But, if two more bps (mmp2-3, 15 nt stem) were opened, the production and function of the mature form were negatively affected (FIGS. 18F and 19B). When the stem was opened from the loop region, which increased the loop size to 6 nt (mmp18, 16 nt stem), 8 nt (mmp17-18, 15 nt stem), or 10 nt (mmp16-17-18, 14 nt stem), only the mmp18 behaved like the canonical form (FIG. 19B; FIG. 18F). Next, an extra nt at the end of the agshRNA-887 stem (p18) was removed or added, but only the S18 (18 nt stem) was processed like the S17. Both the S19 and S20 forms were processed into less mature products, and the processing generated multiple products or intermediates (FIG. 19D). This agrees with the published results that Dicer and Ago2 will compete for processing shRNAs with stems of this range (Gu 2012; Liu 2013). For the short stem variants, only S16 was processed like the canonical S17; the rest produced less mature product for both agshRNA and agsiRNA, and these data correlated well with the reporter assay results (FIGS. 19D-19F). Northern blot data for both agshRNA-887 and agsiRNA-887 showed that the most noticeable processing defect that mature products were mostly lost when the stem was shortened from 15 to 14 bases (FIGS. 19D and 19E). Therefore, it is likely that Ago2 cannot efficiently process substrates with stems shorter than 15 bases. Similar results were reported in sshRNA study and agsiRNA study (Ge 2010; Ma 2014). This result supports the conclusion that the optimal length of the stem or dsRNA needed to fit into the Ago2 groove and trigger the Ago2 slicer activity is ~16 bases and agrees well with the length of the dsRNA region in the molecules of several potent siRNA variants reported (Sun 2008; Chang 2009; Chu 2008).

The small loop makes a difference. To test whether the four nt loop is required for silencing, the 5' and 3' ends were paired, p19 was paired with p22, and p20-p21 was replaced with UU to convert the agsiRNA-887 into sshRNA-887 (Ge 2010). Next, a no-loop version (NL) of both agshRNA-887 and agsiRNA-887 was made by directly connecting the first 19 nt of sli-siRNA-887 with its complementary strand. The major mature products from sshRNA-887 were less and shorter than agsiRNA-887 and there were many products longer or shorter than the major band on the blot (FIG. 19B). If RRM2 agshRNA-1111 is considered as a special case of sshRNA because its p20-21 bases are UU, the deep sequencing data showed this agshRNA produced almost equal amount of 5p and 3p products with a clear cleavage by unknown RNases between the UU (FIG. 9), and both 5p and 3p reads from this agshRNA actually are low compared to other 7 agshRNAs being sequenced. The processing of NL was affected, and the silencing activity of the NL form was several folds lower than that of the wild-type (FIG. 16). There were much less mature products for both the agsiRNA and agshRNA versions of NL (FIGS. 19B, 19C, and 19E).

Figure 21A:
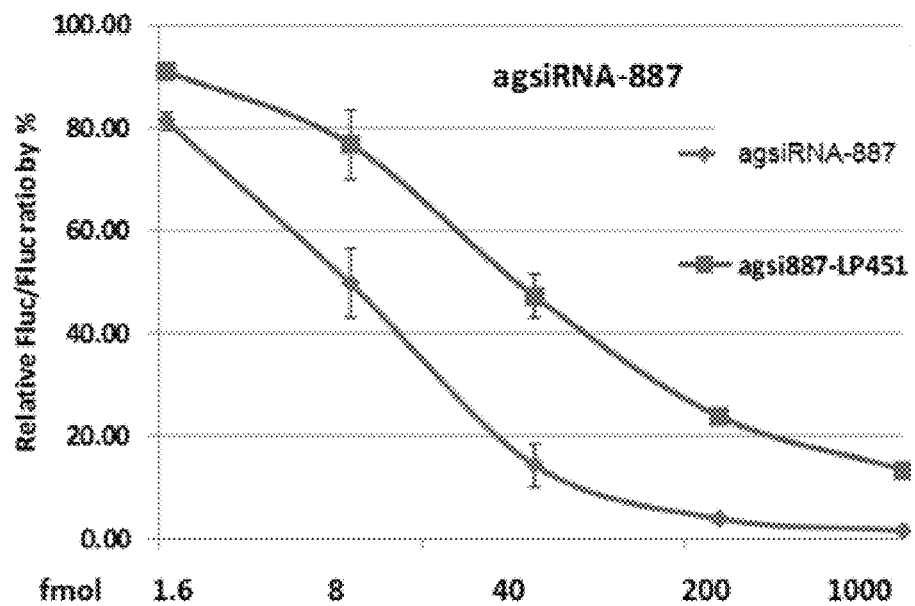
FIGS. 21A, 21B, 21C and 21D show results from reporter assays of tail-base replacements in HCT-116 cells.
Figure 21B:
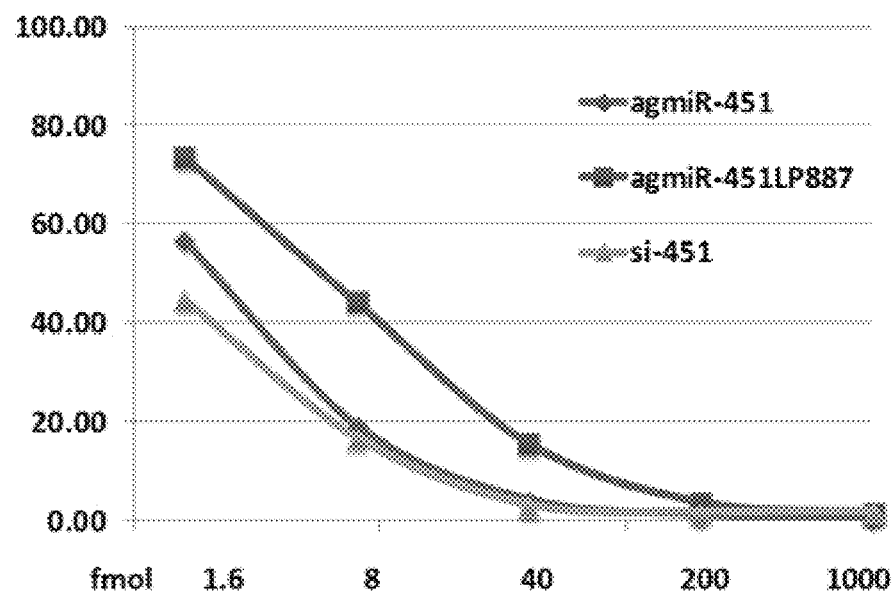
Figure 21C:
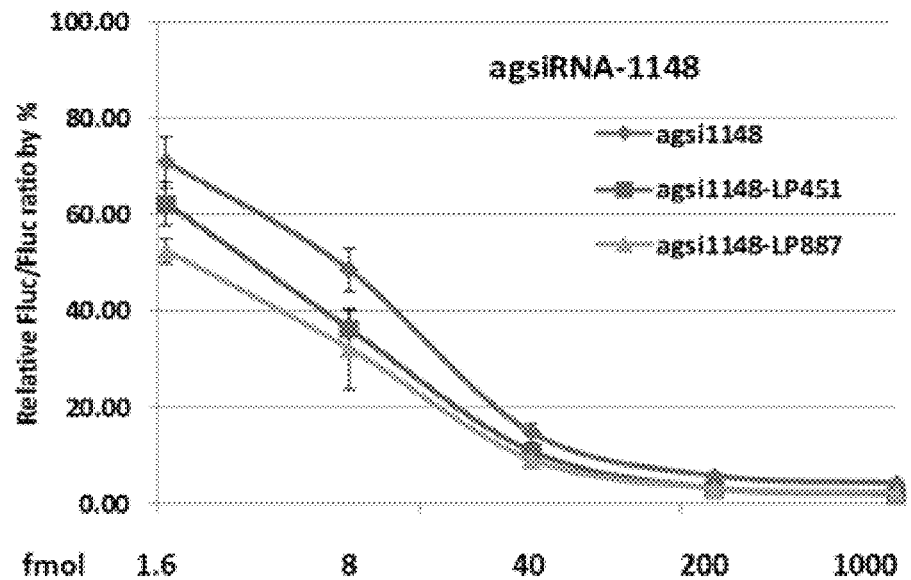
Figure 21D:
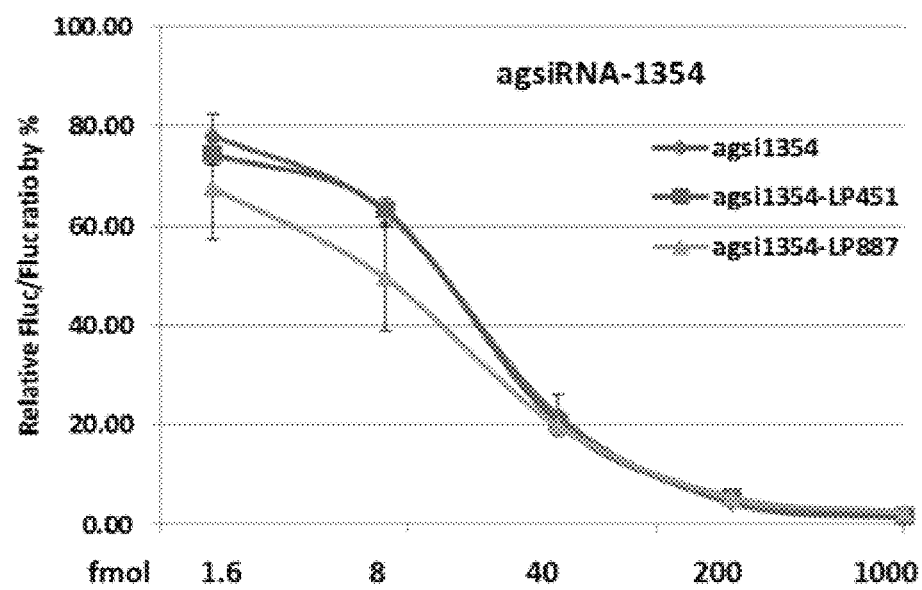

Whether the sequence context of the loop affected its potency was tested by changing the bases from p18 to p23 (tail bases) in agsiRNA. The effects on gene silencing were also tested. The tail bases of agsiRNA-887, -1148, and -1354 were replaced with the tail bases from miR-451 (GAGUUU: LP451), which caused a five-fold reduction in potency for agsiRNA-887, whereas the potency of agsiRNA-1148 increased, and the potency of agsiRNA-1354 showed no difference (FIGS. 21A, 21C, and 21D). The tail bases of agsiRNA-1148, agsiRNA-1354, and hmiR-451 were then replaced with the tail bases of agsiRNA-887 (GGAUGU: LP887). This change led to a slight increase in potency of agsiRNA-1148, whereas the potency of agsiRNA-1354 was not changed, and the potency of hmiR-451 was reduced about five-fold (FIGS. 21B, 21C and 21D). These data indicate the loop sequence (p18 to p23) may influence the silencing potency of sli-siRNA (FIGS. 21A, 21B, 21C and 21D). Therefore, the native sequence of the target should be used for the loop.

Figure 19G:
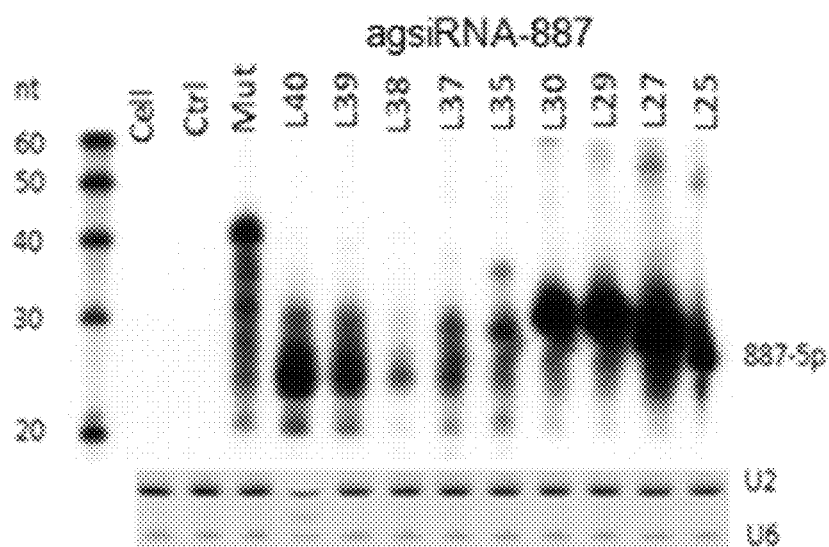
Figure 19H:
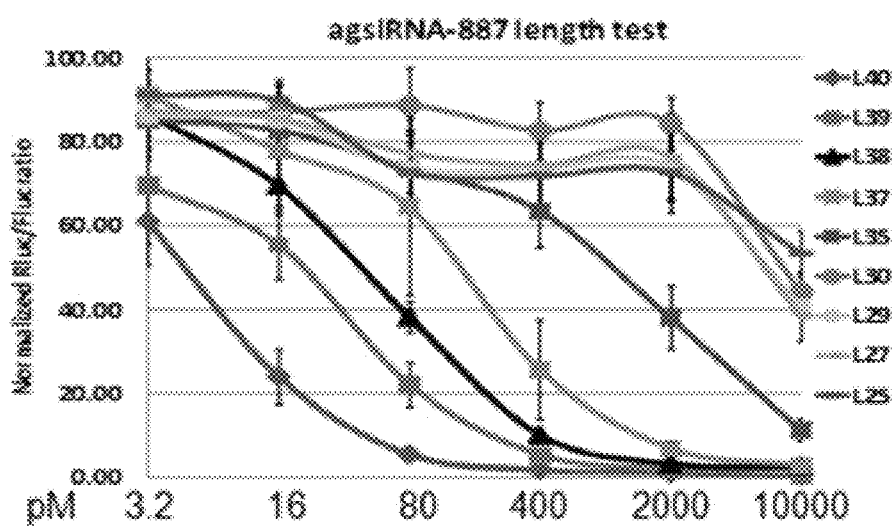

Activity of the L30. It has been shown the L30 of miR-451 is inactive (Yang 2012). To test the activity of L30 of agsiRNA-887, nts were removed from the 3' end to generate L39 (39 nt, wt is L40), L38, L37, L35, L30, L29, L27, and L25 forms of agsiRNA-887. Both L39 and L38 behaved like L40. However, the amount of mature processed products from L37 and L35 was dramatically reduced, as was their gene silencing activity in reporter assays (FIGS. 19G and 19H). No mature products were observed that were processed from L30 or the other shorter forms; instead, unprocessed CMHFs of these molecules were detected on Northern blots (FIG. 19G). More importantly, when L30 annealed with 3L12, it mimicked the intermediate products that were sliced from an agsiRNA by Ago2, and showed a ~2-fold increase in activity over L30, which was hundreds of fold lower than the activity of L40 (FIG. 16). These data indicate that, unlike di-siRNA, which can use a segmented passenger strand (Bramsen 2007), sli-siRNA need the intact hairpin to be potent (Yang 2012).

Target cleavage and repression by sli-siRNAs and di-siRNAs. Next, silencing potency was compared, including both target cleavage and repression activities, by the two types of RNAi triggers using reporter assays.

Figure 22:
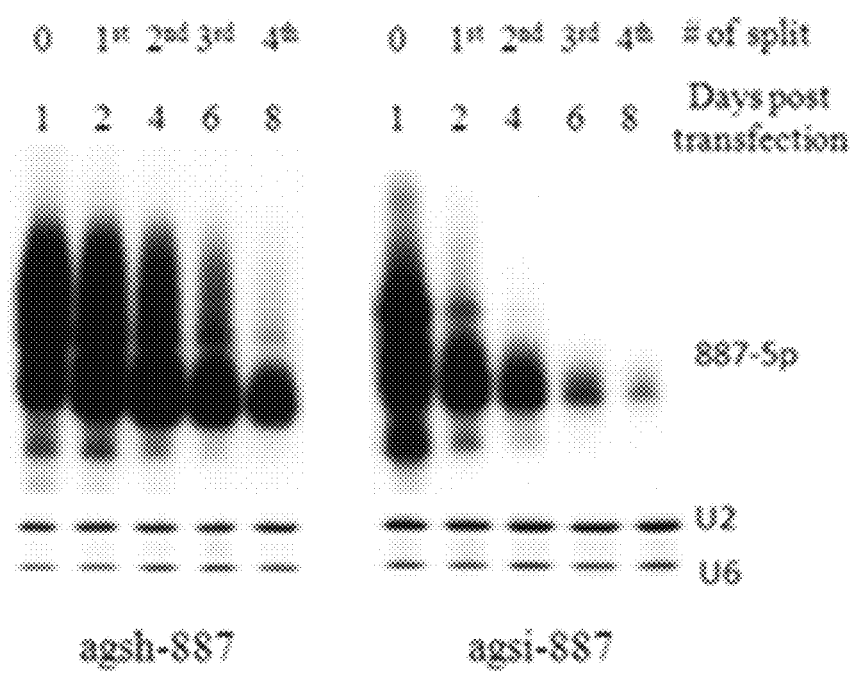
FIG. 22 shows a northern blot analysis to detect products processed from sli-siRNA-887 in HEK-293 cells. Transfected cells were split at days 1, 2, 4, and 6 post-transfection, and total RNA was isolated on days 1, 2, 4, 6, and 8 post-transfection. Blots were probed with 887-5p. U2 and U6 snoRNAs were used as the RNA loading controls.

For the target cleavage activity, a reporter was co-transfected that carried one copy of the perfectly matched target sequence of miR-451 with hmiR-451, mmiR-451, dmiR-451, or siRNA-451 (si-451: di-siRNA containing L21 of the miR-451 sequence). Time course experiments showed that si-451 silenced the reporter in significantly less time than all the miR-451 genes. Knockdown by si-451 peaked at approximately 24 h post-transfection, whereas knockdown by miR-451 peaked at approximately 36 h post-transfection. However, similar silencing levels were obtained using hmiR-451 and si-451 36 h post-transfection (FIG. 20A). These results may indicate that the Ago2 processing step or maturation step slowed down the onset action of sli-siRNA because there are many processing intermediates one day after transfection on Northern blots (FIG. 22).

Figure 20C:
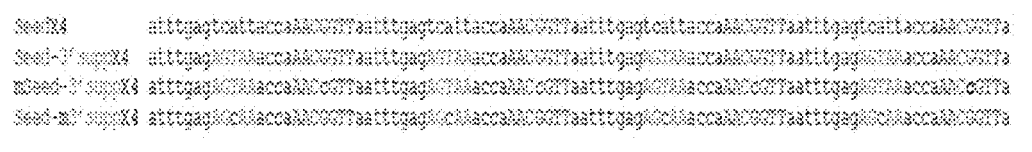

For target repression activity, four reporters were created with miR-451 seed or sequences that base paired with the 3' supp region, or both as partially complementary targets. Each reporter had four copies of the target sequences in tandem in order to see the cooperative binding effect of multiple RISCs (FIG. 20C). It was found that although mismatches in the seed were somewhat tolerated in gene silencing mediated by target cleavage, they were not well tolerated by either sli-RISC or di-RISC for translational repression. However, mismatches in the sequences that base paired with the 3'supp region were well tolerated by both sli-RISC and di-RISC. There was no significant difference between the silencing effect on targets that had only the seed, or the seed plus sequences that base paired with the 3'supp region. There was a significantly higher repression activity for all three reporters that carried the intact seed by si-451 compared to the three miR-451 genes. This difference could be due to the ability of non-slicing Agos to participate in si-451-mediated repression, but not in miR-451-mediated repression, which functions solely through Ago2 (FIGS. 20A and 20B).

Figure 23:
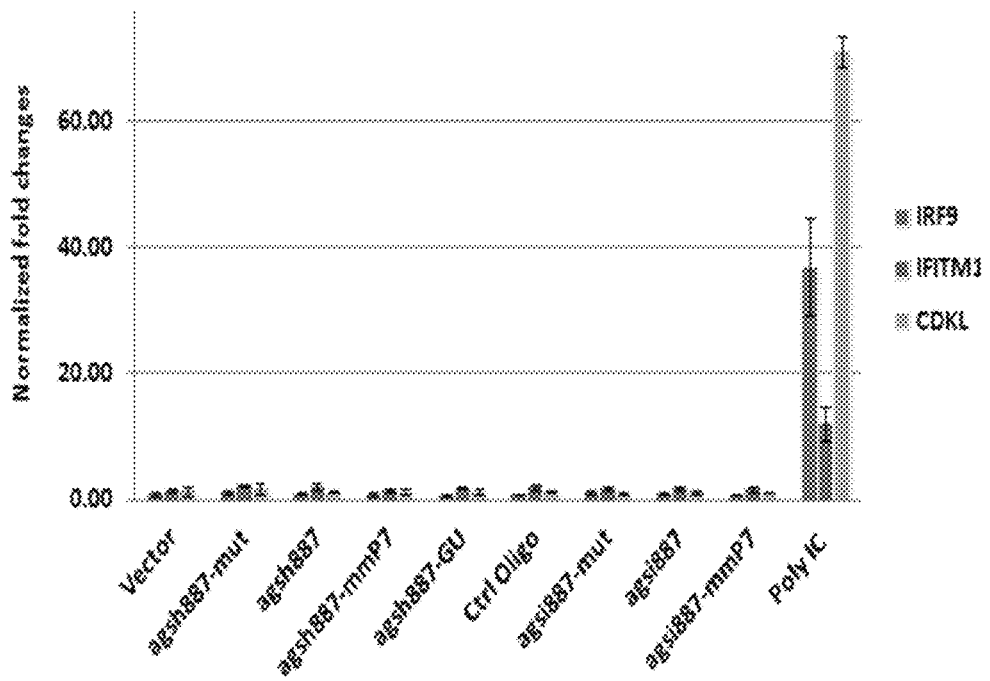
FIG. 23 shows data illustrating the immune response to sli-siRNA-887 in HEK-293 cells. Expression of the innate immune response genes IRF9, IFITM1, and CDKL was analyzed by qPCR in HEK-293 cells transfected with the sli-siRNA-887, -mut, -mmp7, and -GU forms. Polyinosinic:polycytidylic acid (poly I:C), which stimulates innate immune responses, was used as the positive control. Data were normalized to GAPDH and calculated by $\Delta\Delta Ct$ method. Data for the innate immune response genes IRF9, IFITM1, and CDKL are represented by the bars in order from left to right, respectively.
Figure 24A:
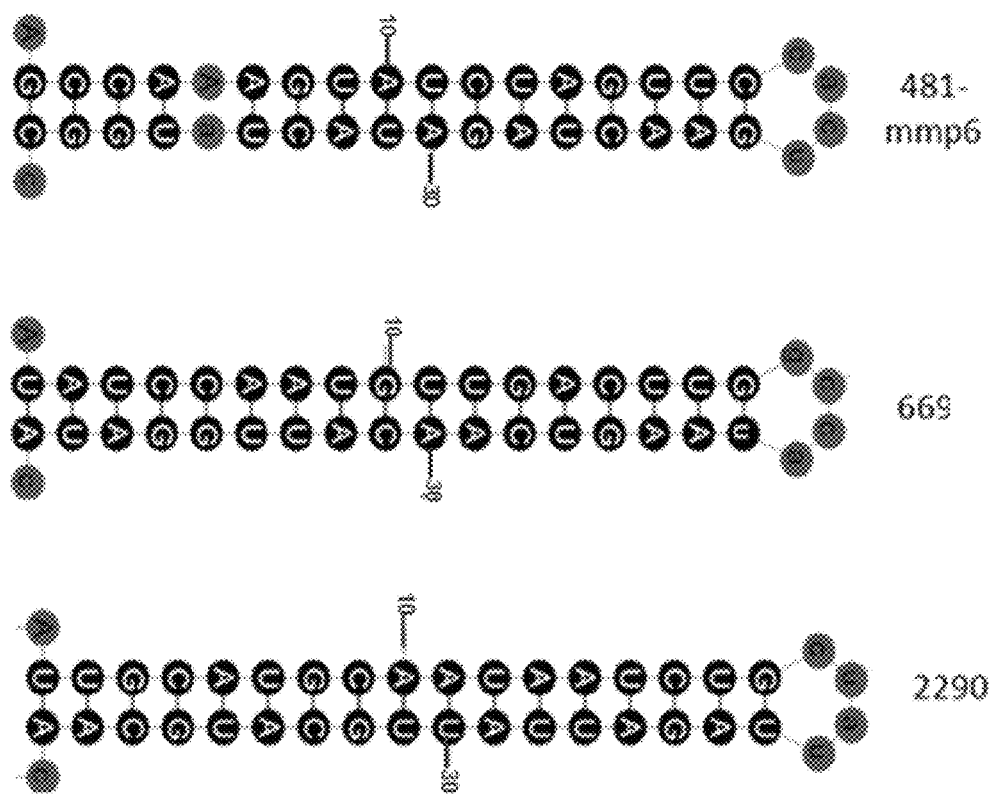
FIGS. 24A, 24B, 24C and 24D show sli-siRNAs targeting R2 partners. Sli-siRNAs were designed to target RR subunit M1 (RRM1 or R1, NM_001033.3) and RR subunit M2B (RRM2B or R2B, also called p53R2, NM_015713), which are the other enzymes in the RR complex.
Figure 24B:
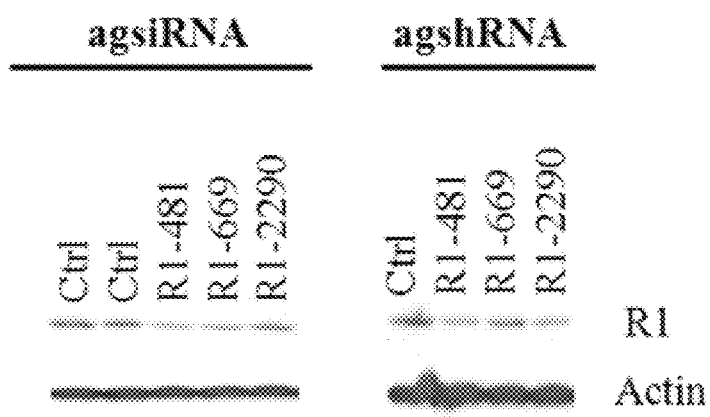
Figure 24C:
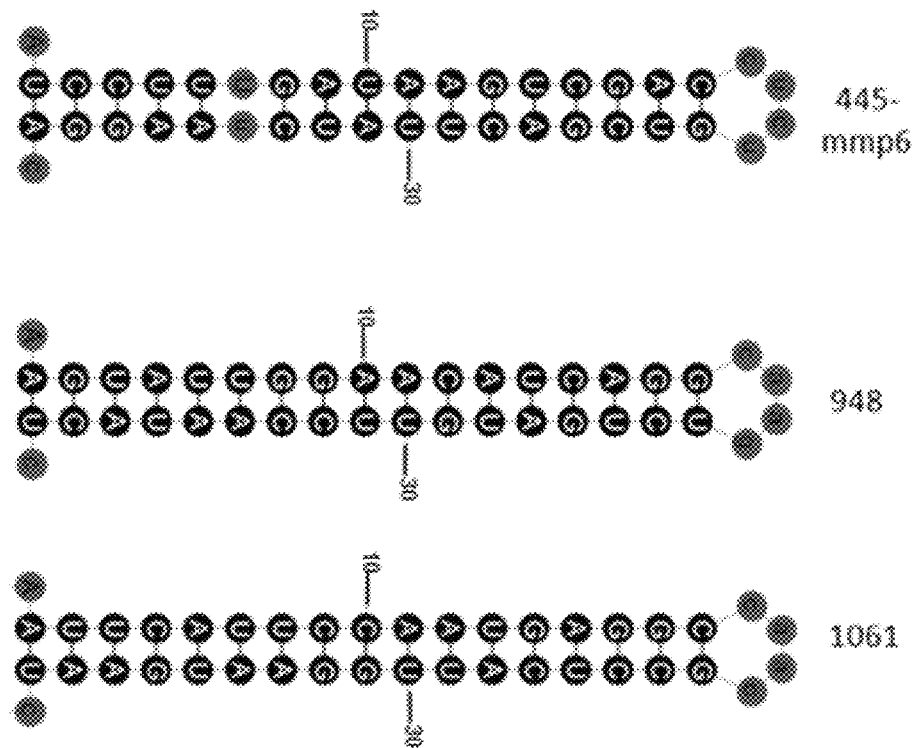
Figure 24D:
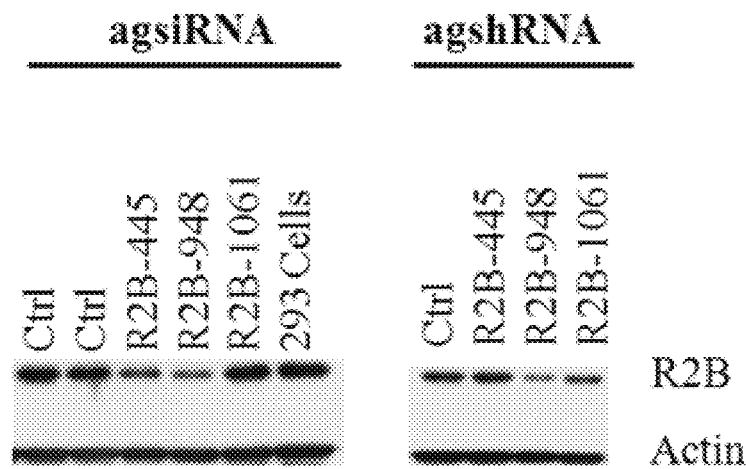

In vivo expression and potential applications of sli-siRNAs. First, the ability of sli-siRNAs to activate the innate immune response was examined. Results indicated that the ability of sli-siRNAs to activate the innate immune response was very low, which agrees with the reported results from sshRNA study (FIG. 23) (Ge 2010). Next, the design parameters were put into practice to generate sli-siRNAs that would target other endogenous genes. The R2 partners R1 and R2B were knocked down by using sli-siRNAs (FIGS. 24A, 24B, 24C and 24D). However, the major concern regarding their usage, especially in vivo, is whether sli-siRNAs would saturate the endogenous miRNA pathways because they require Ago2 for processing and function. This concern is due to the toxicity of traditional shRNAs in that some of them could jeopardize the nuclear export of endogenous miRNAs by Exportin-5 and compete with endogenous miRNAs for Ago proteins (Grimm 2010). Stable, constitutive or inducible agshRNA expression systems were built using lentiviruses (FIG. 6). Sli-sRNA-1148 was chosen for these experiments because it has a 6 nt loop (mmp18) and two GC pair sites that can be converted into two GU wobble sites to better resemble the canonical pre-miRNA structure to compete with endogenous pre-miRNAs (FIGS. 7 and 8A, 8B, 8C and 8D).

Figure 25A:
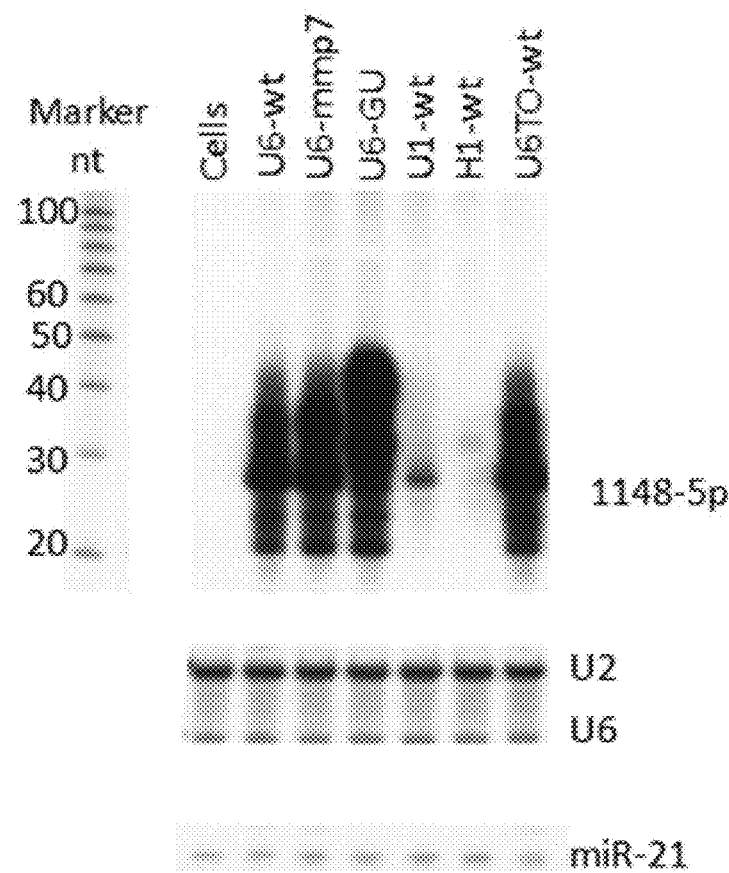
FIGS. 25A, 25B, 25C, 25D and 25E show the results from the application of sli-siRNA-1148 in mammalian cells.

First, these lentiviral constructs were transiently transfected into HEK-293 cells to evaluate their expression and processing. Wt, mmp7, and GU transcribed from U6m, and wt transcribed from U6TO, (a Doxycycline [Dox]-inducible U6m), were strongly expressed and easily detected on Northern blots. Wt and mmp7 had the most mature species, and the GU form had more unprocessed products, probably because of the double G:U bps introduced into the structure. There was no observable difference between mature miR-21 levels in the transfected cells (FIG. 25A). Next, lentiviral vectors were constructed that contain restriction sites engineered for cloning U6 driven agshRNA expression cassettes (vector). AgshRNA was constructed with scrambled sequences as the negative control (ctrl), agshRNA-1148-mutant (mut; nt at p10-12 were swapped with their base pair partners on 3p; it can still be processed by Ago2), -1148 wild-type (wt), -1148-mmp7 (mmp7), and -1148-Gup27p36 (GU; Cs at p27 and p36 both replaced with Us to create wobble bps at these positions) into the lentiviral vectors (FIGS. 7 and 8A, 8B, 8C and 8D).

Figure 25B:
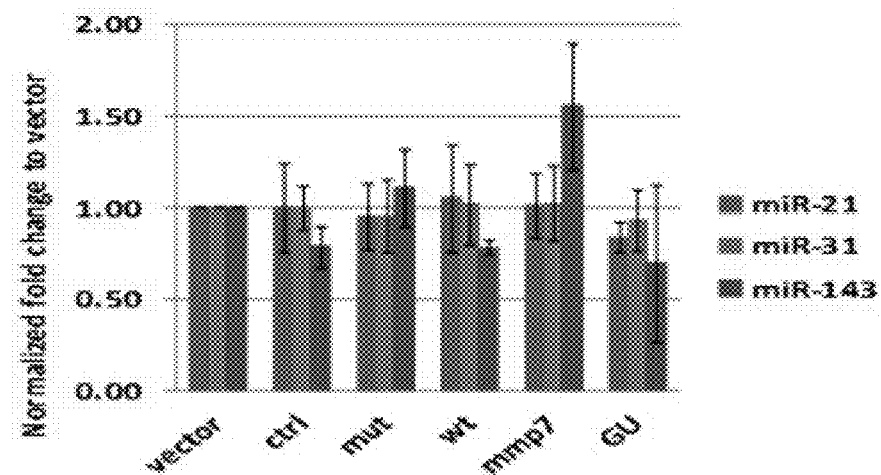
Figure 26A:
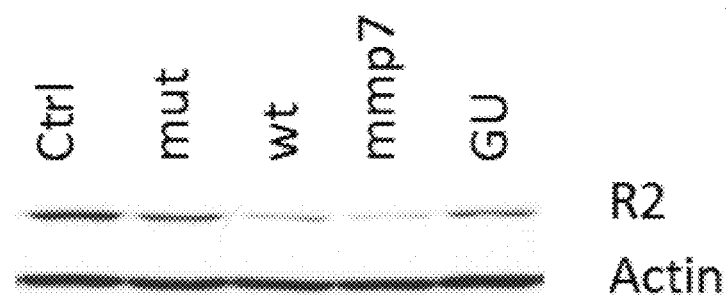
FIGS. 26A, 26B, 26C and 26D show in vivo knock down of R2 in HCT-116 cells by agshRNA-1148.
Figure 26B:
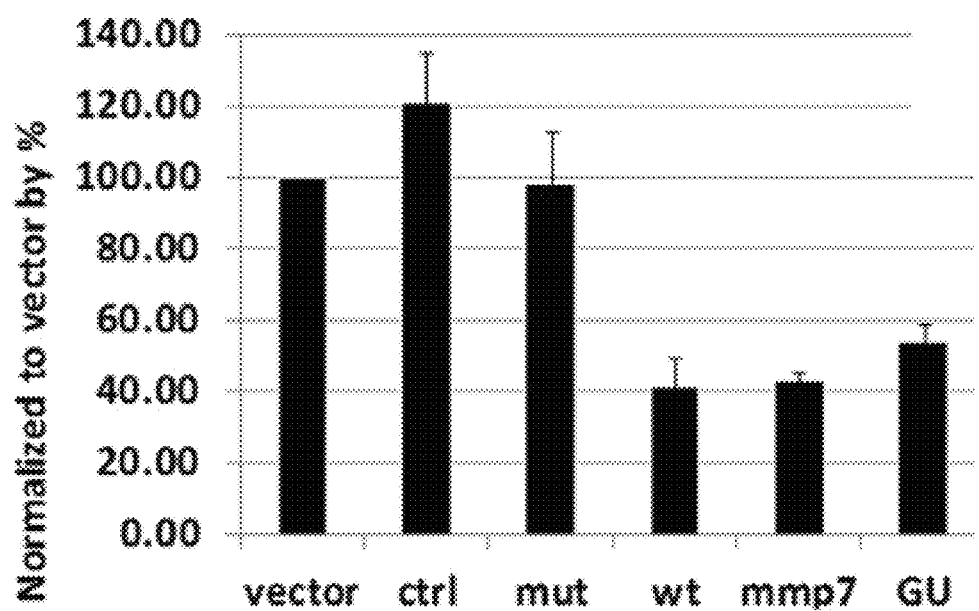
Figure 26C:
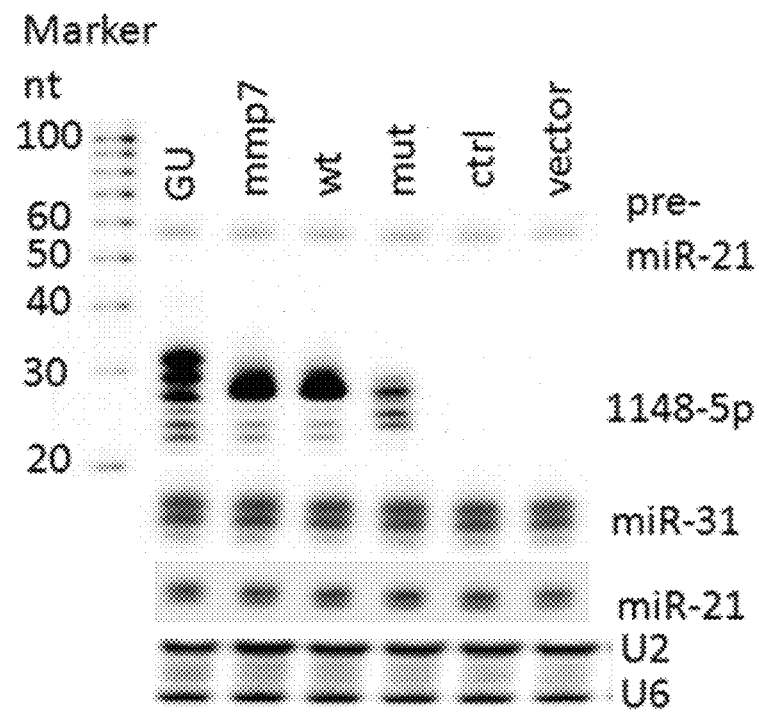
Figure 26D:
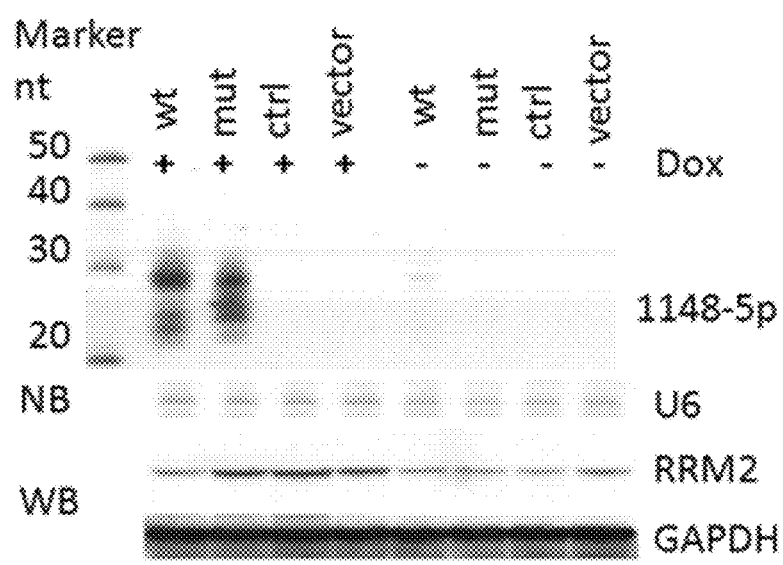

Cell lines were made that stably express wt, mmp7, GU, or mut of agshRNA-1148. Both R2 protein and mRNA were reduced in the cell lines expressing wt, mmp7, or GU (FIGS. 26A and 26B). Northern blot analysis revealed that processed products were present in these cell lines, and there were no observable changes in the levels of either the pre-miRNA-21, or mature miRNAs of miR-21 and miR-31 (FIG. 26C; FIG. 25A). The levels of miR-21 (high expression), miR-31 (medium expression), and miR-143 (low expression) were measured in the stable cell lines by miRNA qPCR. There were no significant changes in miR-21 or miR-31 levels across all samples. There was some variation in miR-143 levels in the mmp7 and GU samples, but this may be due to technical variations that can occur when using qPCR to quantify miRNAs that have very low expression levels (FIG. 25B). The inducible expression of wt and mut agshRNA driven by the Dox inducible U6TO promoter was also evaluated. After adding Dox, products processed from the wt and mut agshRNA-1148 were detected on Northern blots, and R2 levels were reduced in the cells expressing wt agshRNA-1148. Very low amounts of processed product could be detected in wt samples that were not treated with Dox, indicating that the U6TO promoter was slightly leaky. The leakage should not be a concern because it will not produce enough amount of mature agshRNA for effective target knockdown (FIG. 26D).

Figure 25C:
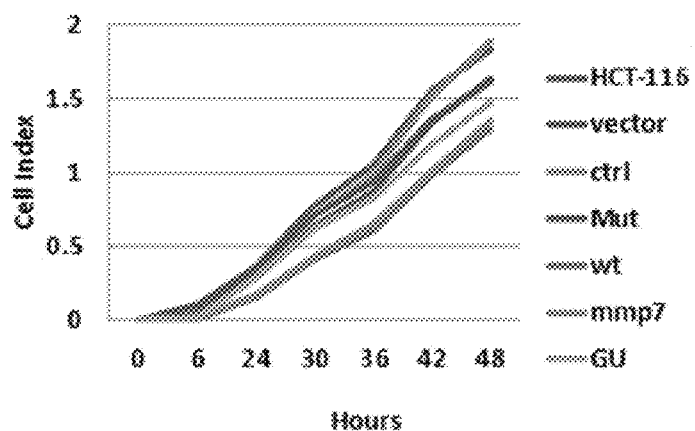
Figure 25D:
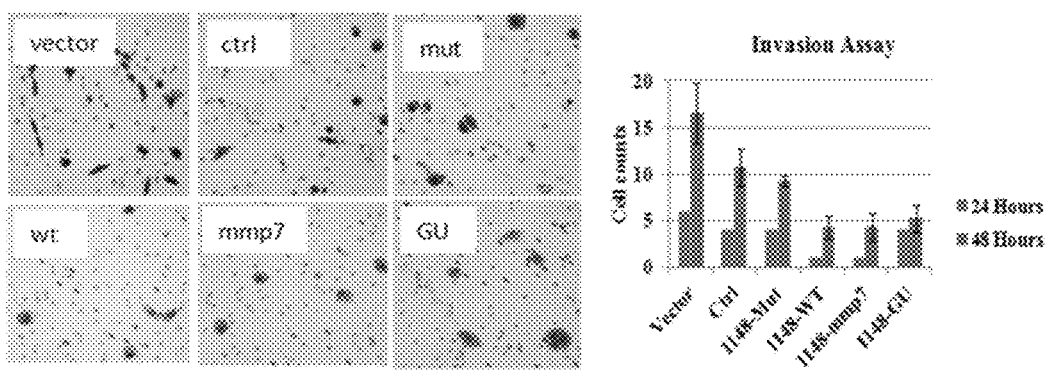
Figure 25E:
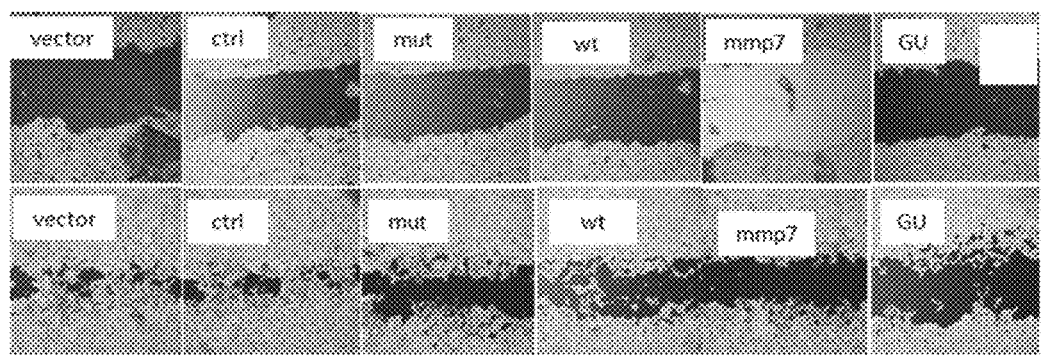

The proliferation rates, invasiveness and wound healing abilities of the above stable cell lines were compared. Real-time cell proliferation experiments showed that wt and mmp7 grew much more slowly than the other variants (FIG. 25C). Matrigel invasion assay showed that cells expressing wt, mmp7, or GU were less invasive than other variants (FIG. 25D). In addition, wound healing assays showed that cells expressing wt, mmp7, or GU did not close the wound gaps as quickly as the other variants (FIG. S25E). Non-transduced cells, cells transduced with vector only, or ctrl RNA had similar proliferation rates, indicating that scrambled agshRNA did not titrate Ago2 protein away to affect cell growth. Therefore, agshRNA have potential for in vivo applications to target genes involved in the pathogenesis of human diseases, such as cancer.

Discussion

Figure 27A:
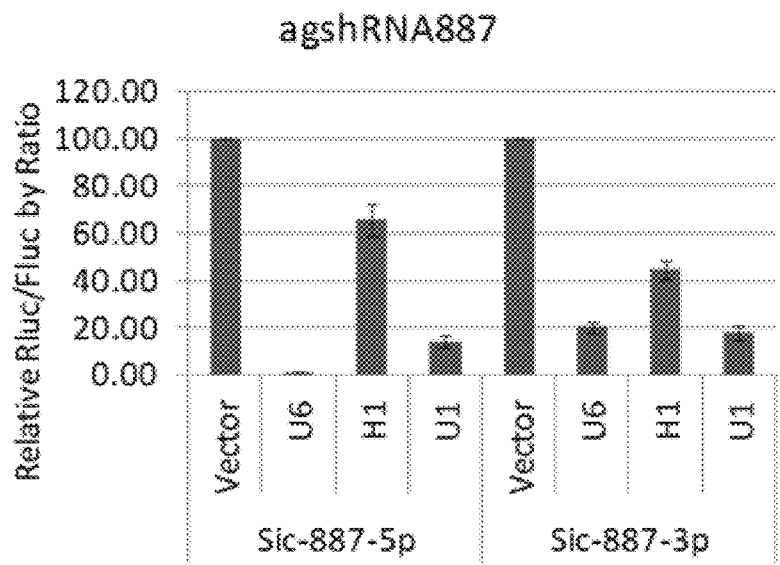
FIGS. 27A, 27B and 27C show comparisons of agshRNA-887, -1148 and -1354 expressed by the U6, U1 and H1 promoters.
Figure 27B:
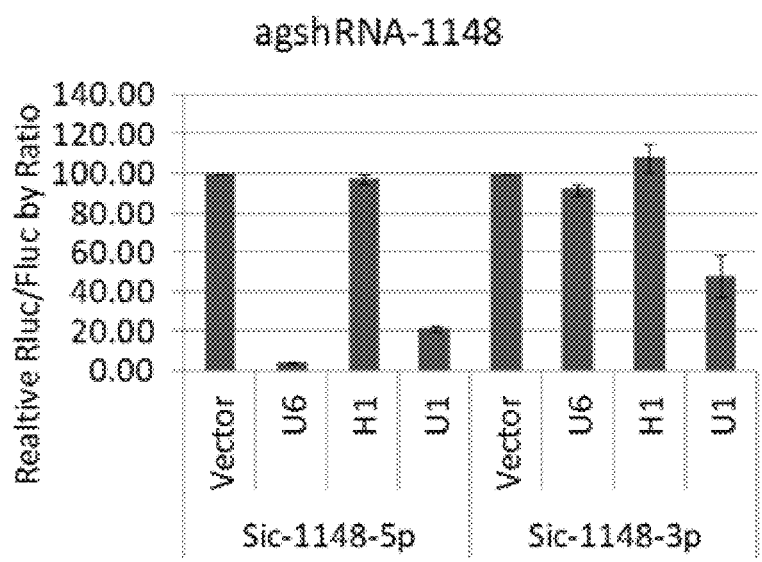
Figure 27C:
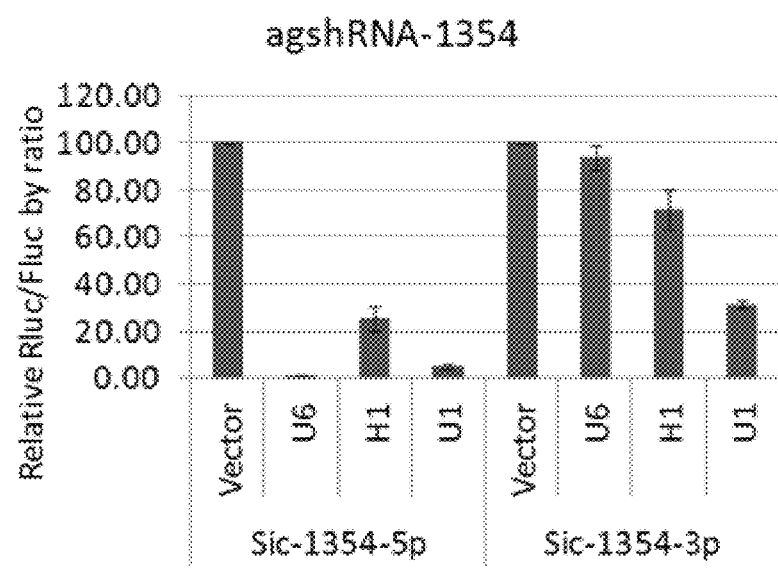

As shown in the example herein, the structural parameters were defined for designing and expressing sli-siRNAs that are as potent as classical di-siRNAs, but have much less sense strand activity, and their potential for physiological use in mammalian cells was demonstrated. Sli-siRNAs can be effectively expressed by a modified U6 promoter to mount a potent target knockdown, but not H1 or U1 promoter with similar modification, presumably due to much weaker transcription by H1 or U1 promoter upon modification (FIG. 19D; FIG. 25A; FIGS. 27A, 27B and 27C). Sli-siRNAs have not only fewer off-target effects by the sense strand, but they are also are easier to design than di-siRNAs because they have 5p as the antisense strand as default and can avoid the concern of end thermodynamics stability in di-siRNA design (Khvorova 2003). Because of similar function mode and molecular structure between sshRNAs and agsiRNAs, the effect of chemical modification on sshRNA should also be applicable to agsiRNA (Ge 2010). The biogenesis mechanism of sli-siRNAs also assumes that incorporation of the sli-siRNAs into non-slicing Ago RISCs will be limited and will avoid the competition for Dicer with endogenous miRNAs (Dueck 2012; Yang 2012; Ma 2014). Therefore, it is possible that sli-siRNAs may also reduce the RNAi off-target effects that are caused by strands being loaded onto non-slicing Agos (Petri 2011). Nevertheless, agsiRNAs clearly have advantages over di-siRNAs, including being single stranded and self-destroying passenger strand during maturation, as well as needing only one synthetic setup procedure, one purification procedure, and fewer nt modifications. Therefore, sli-siRNAs are a viable option for developing novel, potent RNAi triggers.

Although sli-siRNAs and di-siRNAs have similar potency in both target cleavage and repression, there are some differences in their functional mechanisms and may deserve further studies. First, di-siRNAs can use any of the Agos, whereas sli-siRNAs only use Ago2. Second, there is an uridylation and 3' trimming step during sli-siRNA maturation, and it is expected that the rate for this step will be sequence-dependent, e.g., uridylating at U is not necessary and the trimming rate for different nt is not known. It has been shown GC rich sequences in the trimming region will result in poor potency (Yang 2012). The maturation step may cause sli-siRNAs to have a slower silencing rate at the onset. Third, di-siRNAs need go through strand selection, passenger strand displacement, and conformational change for guide strand loaded di-RISC to activate RISCs, whereas sli-siRNAs activates RISCs during its maturation step. The sli-siRNA maturation step may also be able to couple with its silencing function.

In summary, because the sli-siRNA molecule itself enables superb antisense strand selection, it is strongly believed that sli-siRNA will be a viable option as potent RNAi triggers.

Materials and Methods

Antisense sequence selection. The sequences for the L22 forms of sli-siRNAs that targeted the M2 subunit of ribonucleotide reductase (RRM2, or R2) were selected using SiRNA Site Selector (siDuplex), which calculates the theoretical difference in thermodynamic stability of the ends of an siRNA duplex, and the relative accessibility of the target sites for optimal siRNA design (http://infosci.coh.org/HP-CDispatcher/Default.aspx) (Neale 2005). The length of the duplex region was changed to 20 nt and two nt from the native sequence were used as the 3' overhang. The sequences for the L22 forms of the sli-siRNAs that targeted R1 and R2B were selected using the Si-ShRNA Selector set at the default settings, except the length of the duplex was changed to 20 nts. Si-ShRNA Selector uses a different algorithm from siDuplex for selection of antisense strands. It was designed to use the same antisense sequence for both the siRNA and shRNAs, and takes GU pairs and accessibility into consideration (Matveeva 2010).

Cell lines and cell culture. HEK-293 cells, HCT-116 cells, Ago2-knockout MEFs, and Dicer-knockout MEFs were maintained in high glucose (4.5 g/l) DMEM supplemented with 2 mM glutamine, 10% FBS, and 2 mM penicillin/streptomycin. Cells were incubated at 37° C., 5% CO2.

Transfection. For reporter assays, shRNA expression plasmids and reporter constructs were co-transfected into cells by using Lipofectamine 2000 (Invitrogen). For each experiment, at least three independent transfections were performed in duplicate in 24-well plates. Cells were grown to 75 to 85% confluency in 500 μl medium, and were transfected with reporter (50 ng), agshRNA, or differing amount of siRNA or agsiRNA (100 ng of U6-agshRNA vector as stuffer DNA, plus 1 μl of 5 μM, 1 μM, 200 nM, 40 nM, 8 nM, 1.6 nM, or 0.32 nM siRNA or agsiRNA, and 1 μl of Lipofectamine 2000).

For RNA isolation and immunoblots, plasmids (4 μg) or 5 μl of 5 μM siRNA or agsiRNA were transfected into cells in six-well plates, using 10 μl of Lipofectamine 2000 or 5 μl RNAiMAX per well. Prior to transfection, cells were grown to 75 to 85% confluency in 2 ml of culture medium.

Dual-luciferase reporter assays. All reporter assays were performed using psiCheck 2.0-based, dual-luciferase reporters from Promega that express both firefly luciferase (Fluc) and Renilla luciferase (Rluc). Reporters carried complementary target sequences that were constructed by inserting annealed oligonucleotides or digested PCR products into the Xho I/Spe I sites of the 3' UTR of the Rluc gene in psiCheck2.2 vector (Sun 2009). These reporters were used to quantify gene silencing. Forty eight hours after transfection, cells were lysed with 100 μl passive lysis buffer (Promega) and luciferase levels for 20 μl of lysate were determined (Dual-Luciferase reporter assay kit, Promega; Veritas Microplate Luminometer, Turner Biosystems). Changes in expression of Rluc (target) were calculated relative to Fluc (internal control) and normalized to the agshRNA expression vector (U6-agshRNA) or scramble agsiRNA control. The normalized relative ratios of Rluc/Fluc were used to measure the efficiency of silencing. Data were averaged from least three independent transfections and each transfection had at least two replicates. Error bars indicate the standard deviation.

AgshRNA expression vectors. Design of both the constitutive (U6-agshRNA) and inducible (U6TO-agshRNA) expression vectors for agshRNAs was based on a previously reported shRNA expression vector that contains the U6 promoter (Aagaard 2007). Constitutive expression was achieved by transducing cells with lentiviral vectors that expressed U6-agshRNA cassettes (FIGS. 6, 28 and 29A and 29B). To create inducible vectors, part of the 3' end of the U6 promoter sequence was mutated into a TetR binding sequence (U6TO) as previously described (Aagaard 2007) (FIGS. 6, 28, and 29A and 29B). All shRNAs were cloned by ligating annealed oligonucleotides into Bgl II and Xho sites.

Lentiviral vector construction. The lentiviral vector pHIV7-EGFP (Li 2003) was modified by replacing the EGFP expression cassette driven by the CMV promoter with a puromycin (Puro) expression cassette driven by the SSFV promoter to generate SSFVLV-Puro. The lentiviral vector pHIV7-TIG (Tet repressor-IRES-eGFP) (Aagaard 2007)

was modified by replacing the EGFP gene cassette with the Puro gene cassette to generate the CMVLV-TIP (Tet repressor-IRES-Puromycin) vector (FIG. 6). U6-agshRNA was cloned into SSFVLV-Puro for stable, constitutive agshRNA expression, and U6TO-agshRNA was cloned into CMVLV-TIP for stable integration and inducible agshRNA expression.

Lentiviruses production. Lentiviruses were produced as described (Li 2008). Lentiviruses were used to infect HCT-116 cells, and positive clones were screened in media containing 1 ng/ml Puro. Expression of mature processed products was analyzed by northern blot.

RNA isolation and northern blot analysis. RNA isolation, northern blot analysis, and small RNA cloning were carried out as described (Sun 2009). Briefly, RNA was extracted using Trizol, total RNA (20 μg) was separated on 12% SDS-PAGE/8% urea gels, and gels were blotted onto positive charged nylon membranes. A DNA oligonucleotide probe complementary to the target RNA sequence was labeled with γ-32P-ATP. The probe was hybridized to the membranes overnight in PerfectHyb Plus hybridization buffer (Sigma), after which membranes were washed once in 6×SSPE/0.1% SDS for 10-30 min and twice in 6×SSC/0.1° A SDS for 10-30 min each. U2 or U6 snoRNAs were used as RNA loading controls.

Small RNA deep sequencing. Deep sequencing of small RNAs derived from agshRNA was performed using the HiSeq-2000 platform (Illumina). Small RNA library construction and sequence read analyses were conducted as described24. Briefly, 1.0 μg of total RNA was used to construct small RNA libraries for single reads, flow cell cluster generation and 42 cycle (42-nt) sequencing.

Real-time cell proliferation assay. ACEA Biosciences RT-CES was used to monitor cell growth in real time. This system uses microelectronic cell sensor arrays that are integrated at the bottom of microtiter plates to monitor cell growth by measuring changes in electrode resistance. Measurements were taken every 30 min during the 3 day incubation.

Wound healing assay. Cells were grown in 24-well plates to at least 90% confluency, scratched using pipette tips, washed with PBS, and then cultured in complete medium for about two days to allow cells to migrate into the wound areas or until the scratched areas in control cells were filled. Wound areas were photographed before and after the 2 day incubation.

Cell invasion assay. Cell invasion assays were performed with cell invasion chambers (BD Biosciences), according to the manufacturer's instructions. Infiltrated cells were stained with Diff-Quik Stain Kit (Fisher Scientific) 24 or 48 h after plating. Three random areas were chosen for analysis; cells that had infiltrated these areas were counted and averaged.

Bioinformatics analysis. RNA and DNA secondary structures were predicted by mFold (Zuker 2003), the Vienna RNA software package (Hofacker 2003), and RNAstructure (Reuter 2010). CLUSTALW and Jalview (Waterhouse 2009) were used to perform multiple sequence alignments. Three dimensional RNA structures were predicted using the MC-FoldIMC-Sym pipeline (Parisien 2008) and RNAcomposer (Popenda 2012). 3D structures were viewed using PyMOL (The PyMOL Molecular Graphics System, Version 1.5.0.4 Schrödinger, LLC).

Oligonucleotides. All oligonucleotides were synthesized by Integrated DNA Technologies; sequences are listed in FIG. 28.

Immunoblotting. R2, R1, R2B, GAPDH, and beta actin antibodies were purchased from Santa Cruz Biotechnology Inc. Western blot analyses were performed as previously described (Sun 2010). Briefly, cells in six-well plates were washed with cold PBS (2 ml) and lysed in 0.3 ml M-PER mammalian protein extraction reagent (Pierce). Samples were centrifuged at top speed for 10 min, then supernatants were collected. A protease inhibitor cocktail (Roche) was added to the supernatants, and the protein concentration of each sample was quantified by Bradford assay (Bio-Rad, protein assay dye). Twenty micrograms of total protein from each sample was separated by SDS-PAGE at 100 V for 2-3 h, and then electro-blotted at 15 V onto Hybond-P PVDF membranes (GE Healthcare) for 30 min. The membranes were blocked in TBS-T (0.05% Tween 20) plus 5% milk for at least 1 h at 4° C., and then probed with primary antibodies overnight at 4° C. After washing, the membranes were probed with secondary antibodies for 1 h at 4° C. and visualized using standard AP detection chemistry (ECL western blotting substrate, Pierce).

Example 2

Figure 30A:
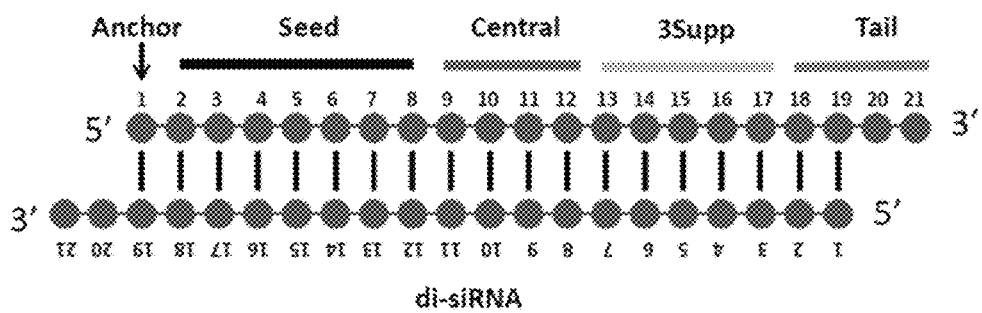
FIGS. 30A, 30B and 30C show schematic illustrations of di-siRNA, sli-siRNA or siRNA targeting.
Figure 30B:
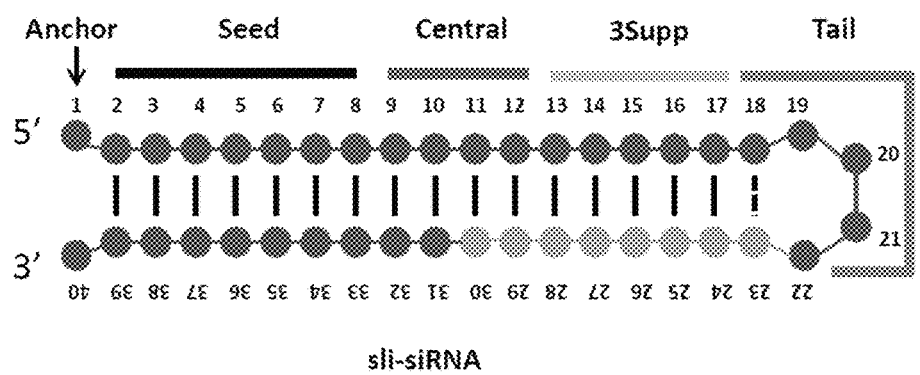

Differences in Silencing Highly Complementary Targets by Sliced Versus Diced RISCs The biogenesis of most miRNAs involves the enzyme Dicer, which processes the precursor-miRNA (pre-miRNA) hairpin in the cytoplasm to create 21 to 23-nt duplex RNAs (5p/3p) with a 3' end overhang. Dicer also chops double stranded RNAs (dsRNAs) into canonical siRNAs (di-siRNAs) as duplexes of guide strand/passenger strand that have a 19 base pair dsRNA stem with an overhang of two nt at the 3' end of each strand (FIG. 30A) (Foulkes et al. 2014). Next, these small RNAs (smRNAs) are loaded onto Agos to form RNA induced silencing complex (RISC) to cleave fully complementary targets or repress partially complementary targets (Ha and Kim 2014). Interestingly, miR-451 and a few other miRNAs use an elegant slicing biogenesis mechanism that involves Ago2, but not necessarily Dicer (Cheloufi et al. 2010; Cifuentes et al. 2010; Yang et al. 2010; Sun et al. 2015). This mechanism was used to design sli-siRNAs that are mainly processed by Ago2 and have significantly reduced sense strand activity (FIG. 30B) (Ge et al. 2010; Dueck et al. 2012; Yang et al. 2012; Liu et al. 2013; Ma et al. 2014; Sun et al. 2015). Despite the fact that sli-smRNAs solely function through Ago2 while di-smRNAs can function through all Agos, both types of RNAi triggers show similar potency in target cleavage and repression (Yang et al. 2012; Sun et al. 2015).

As provided herein in Example 2, it was found that sli-smRNAs are more potent than di-smRNAs for highly complementary targets and this difference is more apparent in targets with mismatched nucleotides that are located in the 3' supplementary base pair region compared to those located in the seed region. This phenomenon may be explained by engagement of both slicing and non-slicing RISCs in di-smRNAs (di-RISC)-mediated silencing, whereas only slicing RISC is used in sli-smRNA (sli-RISC)-mediated silencing, which may result in different dynamics of di-RISC compared to sli-RISC. This observation can be further explained by the different functional mechanisms in slicing RISC activation: Activated di-RISCs are loaded with 21-mer guide RNAs, but sli-RISCs mainly use 23-26 mers as guide RNA. Therefore, based on the length and tertiary structure of smRNAs in activated RISCs, it is proposed herein that sli-smRNAs fit into the fixed-end model, whereas di-smRNAs fit into the two-state putative Ago functional model. The results provided herein suggest that a guide strand from sli-smRNA will cause substantially stronger off-target effects than the same guide strand from di-smRNA and that the duplex RNA generation step by Dicer plays a pivotal role in the specificity of RNAi targeting.

Results

Despite reports of sli-siRNA being as potent as classical di-siRNA for both target cleavage (fully complementary targets) and target repression (partially complementary targets) (Yang et al. 2012; Ma et al. 2014; Sun et al. 2015), it was thought that these two types of RNAi molecules might have different targeting dynamics during silencing because different Ago-mediated RISCs will be involved, and sli-siRNAs also need to be uridylated and trimmed at bases p30 to p23 during maturation (FIG. 30B) (Cheloufi et al. 2010; Cifuentes et al. 2010; Yang et al. 2010; Yoda et al. 2013). It was hypothesized that highly complementary targets will put RISC into mixed action mode of cleavage (fast) and repression (slow), and the tolerance of mismatches in targets may reveal differences in silencing between these two types of RNAi triggers. Mutations were introduced in targets to create reporters carrying mismatches between the target and the RNAi molecules: two mutations were created for each position and mutations at one position are different from another by two bases. Wild type (wt: fully complementary) and mutants (mut: one or two nucleotides ("nts") mismatch) reporters for previously categorized sli-siRNA-887 that target RRM2 (Sun et al. 2015), sli-siRNA-ARX1 that target ARX gene, and mouse version pre-miR-451 (mmiR-451) converted sli-siRNA-451 were created for this experiment (FIG. 31).

Figure 30C:
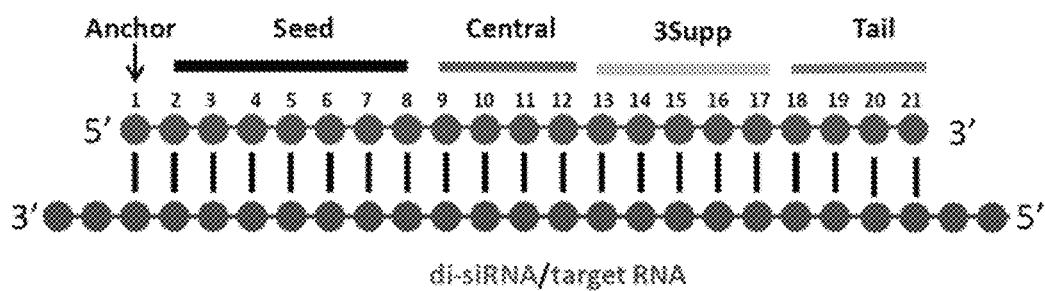

Sli-smRNAs have much stronger tolerance for mutated targets, especially mutations at the 3' supplementary regions of targets. In smRNA targeting, the sequence of smRNA or its base pair region on a target can be divided into three regions: the seed, central, and 3' supplementary (3supp) regions (FIGS. 30A-30C) (Wee et al. 2012). Many lines of evidence have shown that siRNAs/miRNAs use the 'seed' to nucleate their binding to targets and the 3supp region stabilizes RISC for action (Lewis et al. 2003; Brennecke et al. 2005; Lewis et al. 2005; Wee et al. 2012; Schirle et al. 2014).

Figure 33:
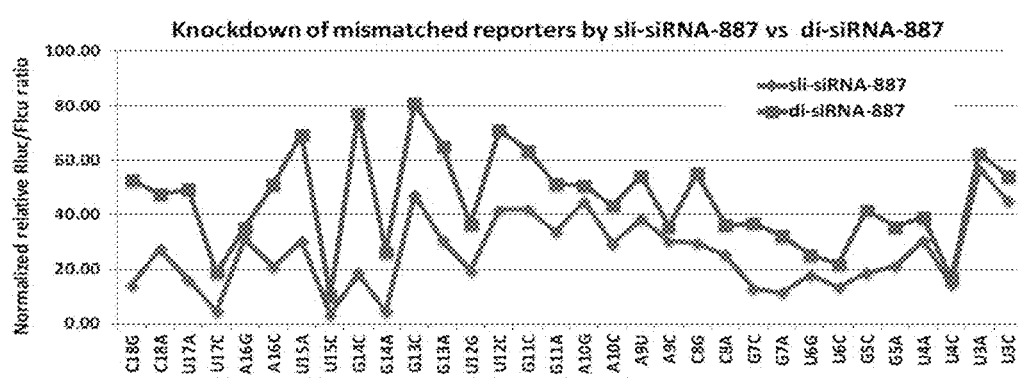
FIG. 33 shows highly complementary target knockdown by sli-siRNA-887 and di-siRNA-887 (about 200 fmol). Normalized Rluc/Fluc ratios are plotted according to the mutation and corresponding position number of the bases in the sli-siRNA or di-siRNA. Error bars represent standard deviation.
Figure 34:
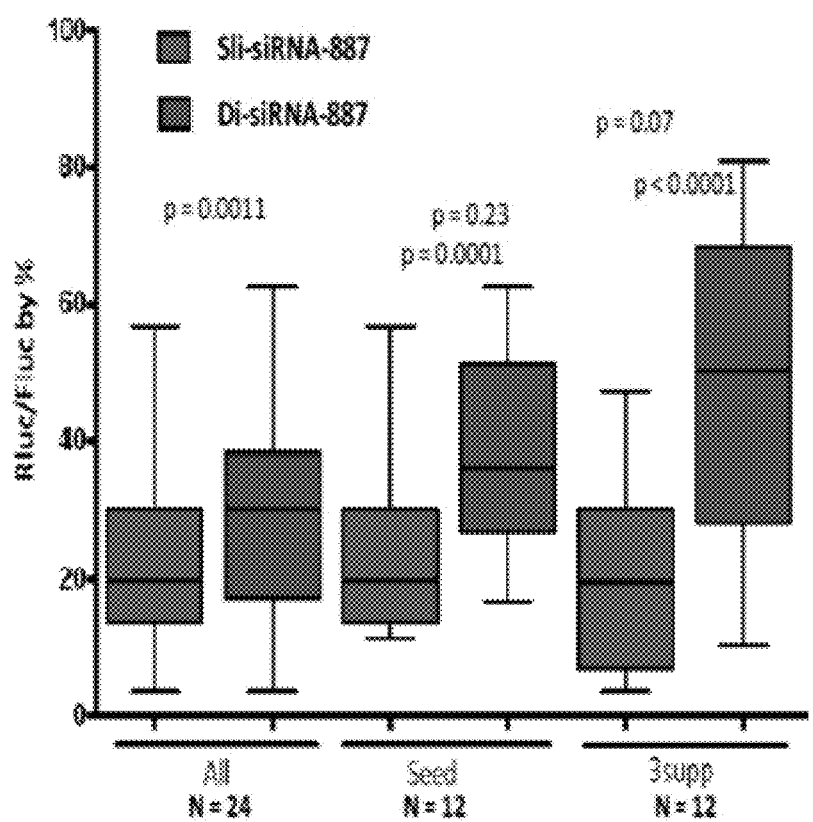
FIG. 34 shows box plots and statistical analysis of data shown in FIG. 33. Data are plotted and grouped by all targets (All), targets with mutations in the seed region (seed), and mutations in the 3supp region (3supp). Paired student's T-test was used to calculate the P values as two-tailed 95% confidence intervals.
Figure 35:
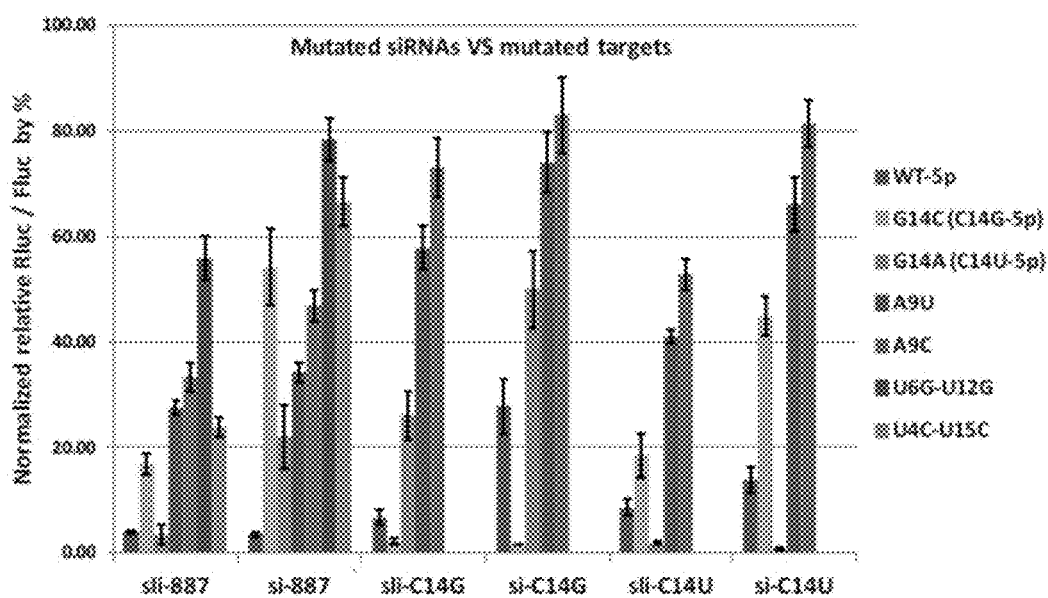
FIG. 35 shows knockdown of highly complementary targets by sli-siRNA-887 and di-siRNA-887 mutants (400 fmol): G14C perfectly complements sli-siRNA-887-C14G and di-siRNA-887-C14G (p14 C was mutated to a G). G14A perfectly complements sli-siRNA-887-C14U and di-siRNA-887-C14U (p14 C was mutated to a U). A9U and A9C are mutated reporters for all three of the sli-siRNAs and di-siRNAs. Error bars represent standard deviation.

The dosage of sli-887 or di-887 that can knockdown the fully complementary reporter by about 95% was first optimized, then the sli-887 and di-887 knockdown efficiency for a set of highly complementary reporters under the same condition was compared (FIG. 32). Despite the expected context-dependent influences of some mutated sequences, sli-887 tolerated mismatches in the target much better than di-887 (FIG. 33). The difference was more obvious for targets with mutations in the 3supp region (FIG. 34). For some mismatched reporters, sli-887 even had a several-fold higher knockdown efficiency than di-887 (FIG. 33). Next, the C at position 14 (p14C) in sli-887 was mutated to a G or U, creating the mutant sli-887-C14U and -C14G (their perfectly matched 5p targets will be mismatch reporters G14A and G14C of sli-887-5p, respectively, FIG. 32). Sli-887-wt, -C14U, and -C14G, and the corresponding di-887-wt, -C14U, and -C14G, had similar silencing potencies for perfectly matched targets, but sli-siRNAs were more potent for mismatched targets than di-siRNAs (FIG. 35). Sli-887 was also more potent than di-887 for silencing reporters that carried two mismatches (U6G-U12G and U4C-U15C; FIG. 35). The two G:U wobble pair reporters (A10G and A16G) showed similar knockdown effect, which is also an indication that sli-siRNAs have higher tolerances for mismatch targets (FIG. 33).

The above observations were further tested using a set of reporters for sli-siRNA-ARX1 (sli-ARX1) (FIG. 36). This time the dosage of sli-siRNA or di-siRNA was titrated to knockdown the fully complementary reporter by about 80%. The data clearly showed that sli-ARX1 tolerated mismatches in the target much better than di-siRNA-ARX1 (di-ARX1), and the former is much more potent than the latter when the mismatches are located in the 3supp region versus in the seed region. When the mismatches are located in the seed region, the sli-siRNA and di-siRNA have similar knockdown efficiency, whereas the knockdown rate by sli-ARX1 is about two-fold of that by di-ARX1 for most mismatch reporters with mismatches located in the 3supp region (FIG. 37).

Figure 37:
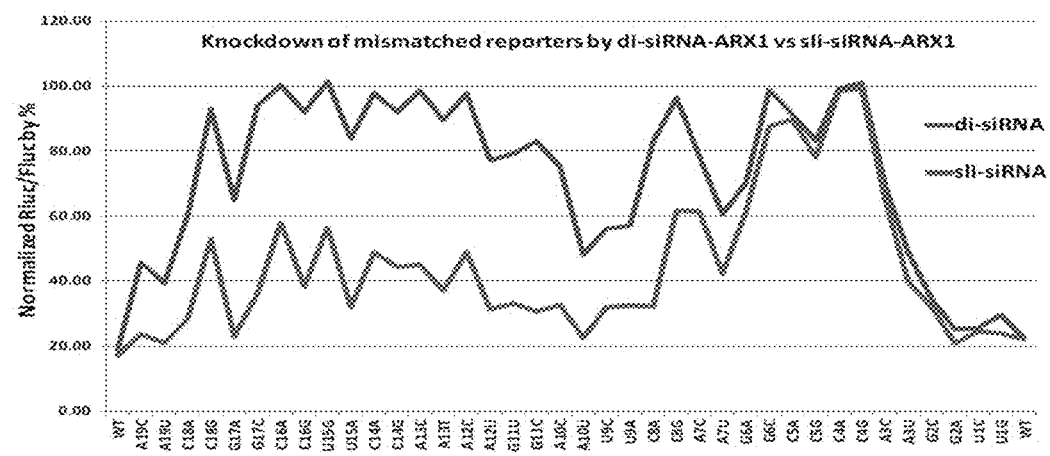
FIG. 37 shows highly complementary target knockdown by sli-siRNA-ARX1 vs di-siRNA-ARX1. About 12.5 fmol was used for each transfection to knockdown the fully complementary target at about 80%. Normalized Rluc/Fluc ratios are plotted according to the mutation and corresponding position number of the bases in the sli-siRNA or disiRNA. Error bars represent standard deviation. di-siRNA data is represented by the top line and sli-siRNA is represented by the bottom line in the graph.
Figure 39:
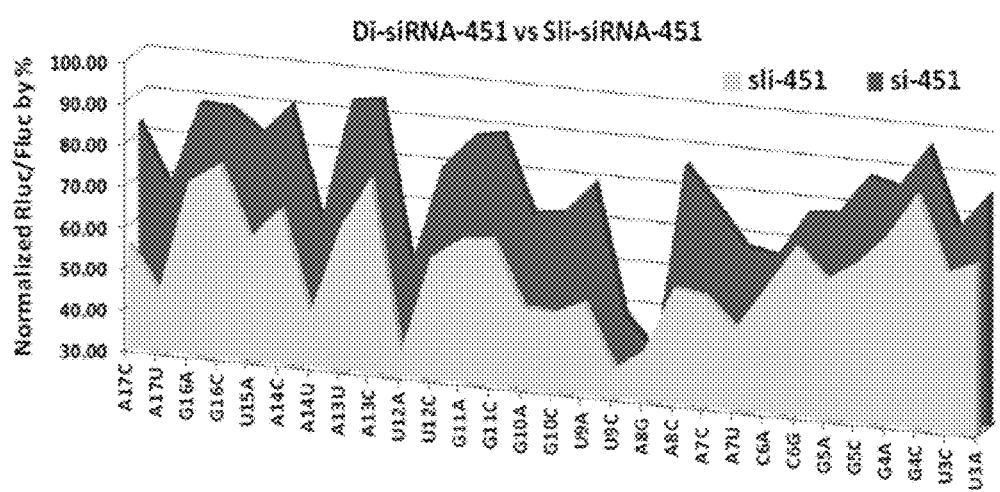
FIG. 39 shows knockdown of highly complementary reporters by mmiR-451 (sli-451) and siRNA-451 (si-451). About 6.5 fmol was used for each transfection to knockdown the fully complementary target at about 80%. Data are 3-D area plotted according to the mutations and corresponding position number of the bases in the siRNA. Normalized Rluc/Fluc ratios were used.
Figure 40:
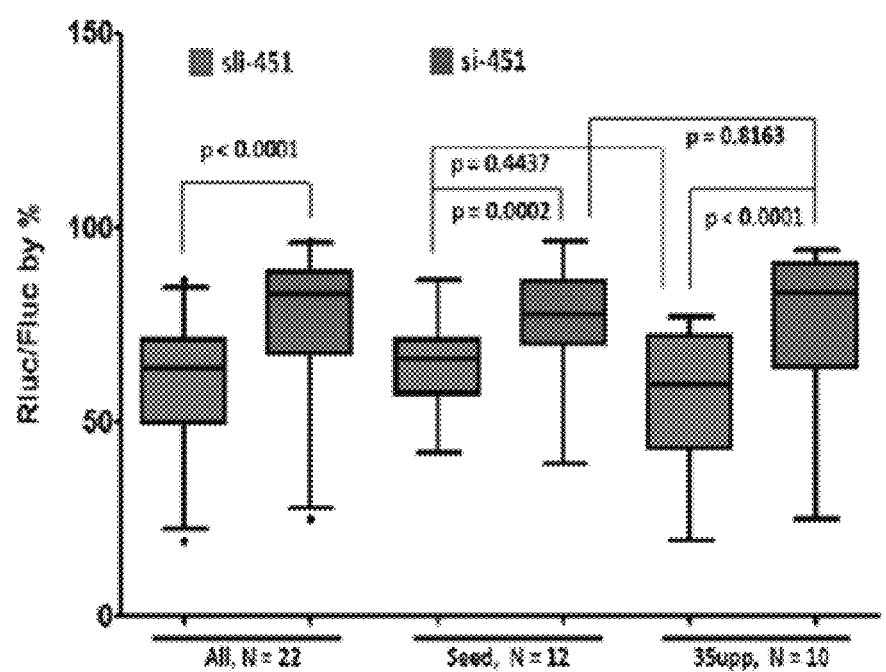
FIG. 40 shows box plots and statistical analysis of data shown in FIG. 39. Data are plotted and grouped by all targets (All), targets with mutations in the seed region (Seed), and targets with mutations in the 3'supp region (3Supp). Paired student's t-test was used to calculate the P values as two-tailed 95% confidence intervals.

The above siRNAs that target RRM2 and ARX are artificially designed sequences that showed similar knockdown effect but also exhibited sequence context dependent differences in silencing (FIGS. 33, 37). Whether the miR-451 sequence which has been selected during evolution shows similar properties remains unknown. We performed a similar assay for miR-451 using highly complementary reporters (FIG. 38). Our results showed that the ability of the mmiR-451 converted sli-siRNA-451 (sli-451) to tolerate mismatches was significantly higher than that of siRNA mimics of mature miR-451 (di-451), and the differences were more significant for targets that had mismatches in the 3supp of targets. These results also indicate that the miR-451 sequence exhibited the difference across all target regions (FIGS. 39, 40).

Figures 41A, 41B:
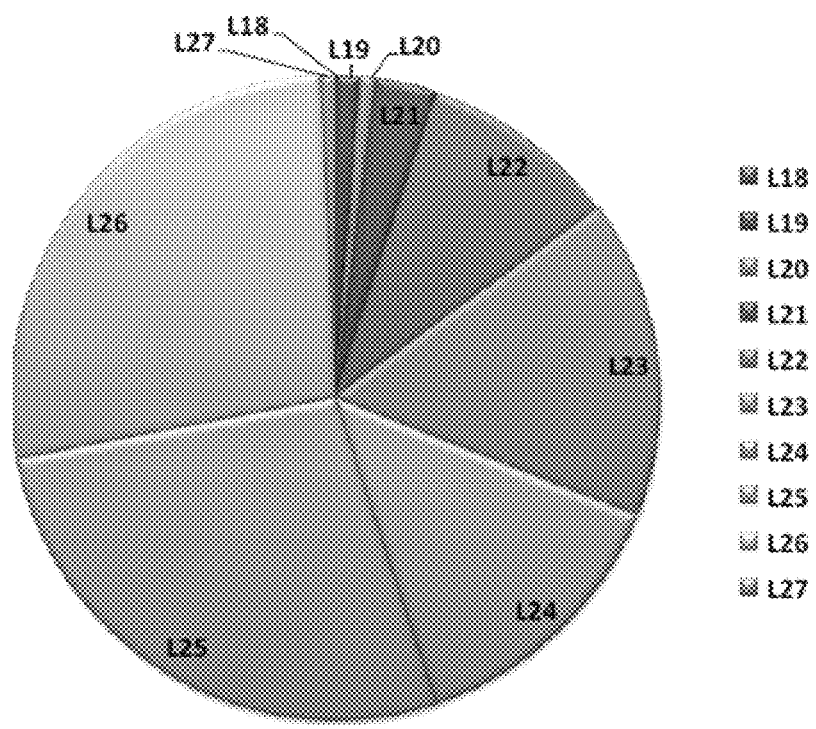
FIGS. 41A and 41B show iso-miRs of mmu-miR-451 and functional model of sli-smRNA.

Sli-RISC uses 23 to 26-mer smRNAs for function. Published Northern blot data and in vitro processing data of pre-miR-451 mimics indicated that the sli-siRNA mainly present as 23 to 26 nt processed products (Yang et al. 2012; Yoda et al. 2013; Sun et al. 2015). While poly(A)-specific ribonuclease was identified as the enzyme responsible for 3'-5' trimming of Ago2 resected pre-miR-451 mimics, the trimming step per se is dispensable for miR-451 mimics silencing function in vivo, supporting the idea that sli-RISCs can use longer intermediate guide RNAs for target silencing (Yoda et al. 2013). Deep sequence reads of both human and mouse miR-451 isoforms documented in miRBase were analyzed. It was found that the L23 to L26 forms cover almost 70% of isomiR-451 (FIGS. 41A, 41B). Therefore, it is possible that sli-RISC and di-RISC use different length of guide smRNAs and the tertiary structure of these functional smRNAs may lead them to adapt a different mechanism of function.

Figure 42A:
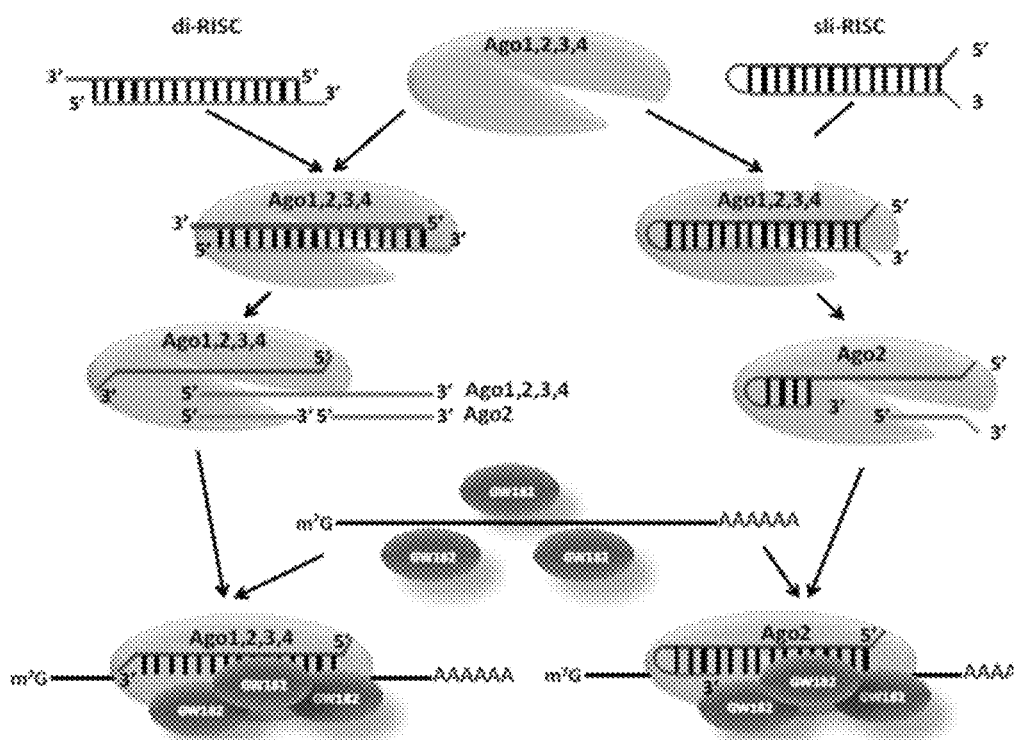
FIGS. 42A and 42B show schematic representations.

The hairpin structure of sli-smRNA and the duplex structure of di-smRNA may initiate RISC differently (FIG. 42A). Studies on the properties of sli-siRNA also support this hypothesis. In contrast to the tolerance of mutation in the 3supp of a target, mismatches in the 3supp of sli-smRNA molecules exhibited a much stronger effect on both sli-smRNA processing and silencing potency than mismatches in the seed region (Sun et al. 2015). It appears that base pairs at the 3supp of a sli-smRNA are important to maintain sli-RISC in a catalytically competent conformation, but base pairs at 3supp between sli-smRNA and targets are less important for silencing effects. This result suggests that the groove formed by the PIWI, PAZ, N domains, and L1 linker in Ago2 (PPNL1 groove, FIG. 42B), where the 3supp region of sli-siRNAs resides, is important for positioning Ago2 into its catalytically competent conformations. These observations are consistent with the finding that the domains at the N terminus (N-L1-PAZ) of Ago2 are critical for correctly aligning the target RNA with the Ago2 catalytic center for slicing (Faehnle et al. 2013; Hauptmann et al. 2013; Hauptmann et al. 2014). The groove formed by the PAZ, PIWI, Mid domains, and L2 linker (PPML2 groove, FIG. 42B), where the seed region resides, has more flexibility for mismatches and wobble base pairs. This may facilitate the subsequent release of short fragments and mediate target binding, but the PPNL1 groove will be important for maintaining sli-RISC in the catalytically competent conformation.

Discussion

The discovery of miR-451 biogenesis and functional mechanism has raised an intriguing question: why did nature not select Ago2 as the sole RNAi factor and eliminate Dicer and non-slicing Agos during evolution? Instead, most miRNAs use Dicer generated intermediates that can be loaded onto all Agos for function. Only a few miRNAs use the seemingly simpler Ago2 processed pathway (Cheloufi et al. 2010; Cifuentes et al. 2010; Yang et al. 2010), despite smRNAs generated from both pathways having similar silencing potencies toward target cleavage and repression (Yang et al. 2012; Ma et al. 2014; Sun et al. 2015). The results from the experiments in Example 2 herein showed that sli-RISC and di-RISC exhibit different potency in silencing highly complementary targets.

One simple explanation for this observation is that displaced passenger strand or cleaved passenger strand fragments could act as target decoys and compete with targets for activated RISCs. Sli-RISCs will generate a 10-nt short resected passenger strand and di-RISCs can generate two short (10 nt and 11 nt) passenger strand fragments through passenger strand cleavage and a full length passenger strand through passenger ejection. In the case of di-RISC, the full length passenger strand could compete much better with mismatched target for active RISC than fragments of passenger strands, and the cleaved passenger strand fragments from di-RISCs can bind to both seed and 3supp regions. On the other hand, in the case of sli-RISC, only resected passenger strand can affect target binding and only can affect the seed region. Since the reporter system used in the experiments in Example 2 herein was saturated with targets and limited by RNAi triggers and the passenger strand or the cleaved passenger strand usually gets degraded (Liu et al. 2009; Kawamata and Tomari 2010; Ye et al. 2011), the sponge effect from the passenger strand will be limited.

Figure 42B:
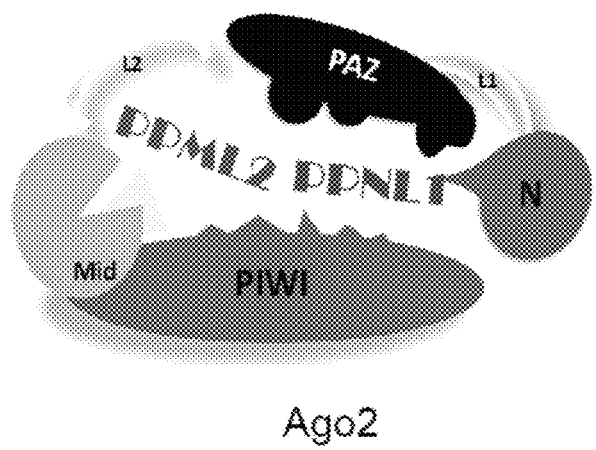
Figure 43:
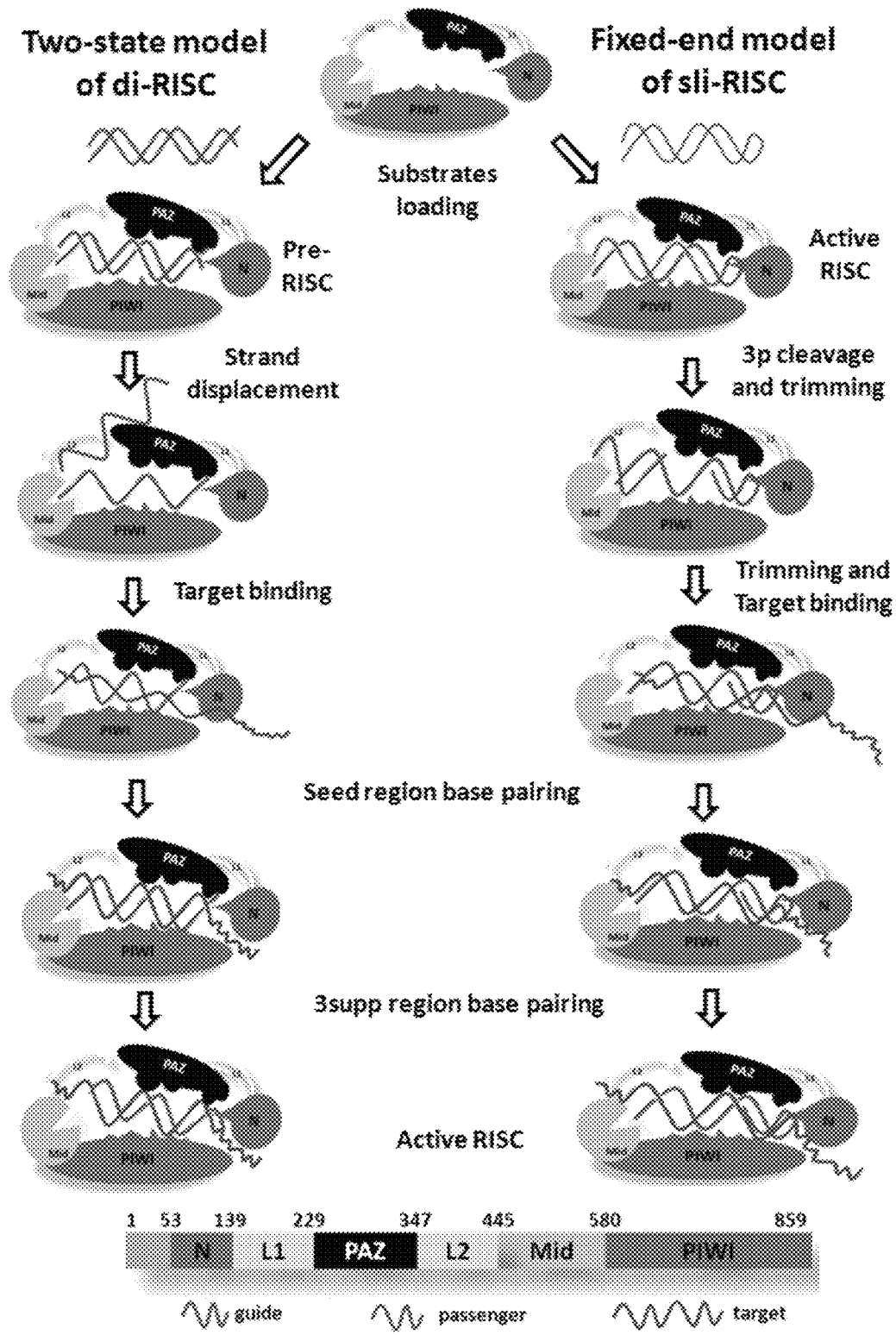
FIG. 43 shows a schematic representation of the proposed working models for sli-RISC versus di-RISC.

An alternative explanation is proposed for the observation shown in Example 2: the difference may result from the participation of non-slicing Agos in di-RISCs and the two types of slicing RISCs loaded with different lengths of guide smRNAs. The tertiary structure of these functional RISCs with different lengths of guide smRNAs may allow them to adapt to different RISC function mechanisms. Although non-slicing Agos can be loaded with pre-miR-451 mimics to form sli-pre-RISCs, only the Ago2 loaded form can be further processed to mature sli-RISCs (Dueck et al. 2012). Most likely non-slicing Agos loaded sli-smRNAs were released and reloaded onto Ago2 for maturation and this may have led to the previous observation that the silencing action from di-RISC peaked about 12 hours earlier than that from sli-RISC (Sun et al. 2015). The results that sli-siRNAs cannot use the L30 and 3L10 reconstituted slicing intermediates for function, suggest that the slicing passenger strand is necessary for activation of sli-RISC and sli-siRNA maturation may be coupled with its silencing activities; target silencing could be occurring while the 3' end is still being trimmed or the trimming is not necessary (Yoda et al. 2013; Sun et al. 2015). The L23 to L26 forms, which resemble a δ-shaped guide smRNA inside the RISC, the small loop may be confined inside the niche formed by PAZ, N, and PIWI domains and maintain RISCs in their slicing-competent conformation (FIGS. 42A, 42B, 43). This fits well with the proposed fixed-end working model of RISCs (Jinek and Doudna 2009). Conversely, di-siRNAs can use segmented passenger strand and non-slicing Agos for function, indicating that it is not necessary to nick the passenger strand for Ago2-di-RISCs activation and it is impossible for non-slicing Agos-di-RISCs to cleavage the passenger strand to be activated (Bramsen et al. 2007; Park and Shin 2015). Instead, it is a two-step process for di-RISCs: duplex smRNA loading based on the ends thermal dynamic properties and anchoring of the 5' phosphate group in the MID domain of Agos; guide strand selection which includes duplex wedging by N domain and passenger strand ejection (Kawamata and Tomari 2010). Once a mature di-RISC is formed, the seed of the guide strand nucleates its binding to the target, which also promotes the 3supp binding to the target and initiates the silencing function of di-RISCs (Kawamata and Tomari 2010; Park and Shin 2015). This activated di-RISC carries a guide RNA that resembles a horizontal ζ-shaped RNA inside Ago's RNA binding grooves: the 5' end of the strand is anchored to the Mid domain, and the 3' end of the strand is tethered to the PAZ domain (FIGS. 42A, 42B, and 43). The di-RISC model fits well with the proposed two-state RISC working model that requires 3supp to bind to both the PAZ and N domains to induce the Ago2 conformational change for RISC activation (Jinek and Doudna 2009).

The results provided herein in Example 2 suggest that guide strands from sli-smRNAs could cause more off-target effects than guide strands from di-smRNAs. These results may have revealed a previously unknown pivotal role in targeting specificity played by Dicer together with non-slicing Agos. This indicates that the Dicer processing step in smRNA biogenesis plays multiple pivotal roles: producing smRNA duplexes, enabling the loading of smRNAs to non-slicing Agos, and enhancing smRNA targeting specificity by affecting the dynamics of RISC function. Because target repression is the dominant gene silencing method adapted in animals, it is conceivable that this kind of natural adaption is driven by selection pressure of target specificity. It seems that the short length of the seed will broaden the target spectrum at the cost of reduced potency, but this could be overcome by using multiple seed sites to enhance on-target effects and achieve synergy in both silencing efficacy and specificity.

The experiments in Example 2 were carried out in a reporter system for highly complementary targets when targets are saturated and the amount of siRNAs is limited. However, for both research and clinical applications, it is usually necessary to use siRNAs at a high dosage to achieve an ideal silencing effect. Therefore, siRNAs are often used at saturating conditions and the amounts of targets are usually limited by their biological expression levels. A carefully designed siRNA should avoid targeting highly complementary targets and the number of this kind of target is often very low. It is the seed targeted genes that usually exist in hundreds or thousands are really needed to be considered for off-target effects in RNAi applications (Saxena et al. 2003; Jackson et al. 2006; Grimson et al. 2007). To this end, off-target effects are not avoidable for both sli-smRNAs and di-smRNAs, but the passenger strand activities from sli-smRNAs are usually reduced by 100 to 1000 fold when compared to the di-smRNA molecule (Cheloufi et al. 2010; Cifuentes et al. 2010; Yang et al. 2010; Sun et al. 2015), therefore, sli-smRNAs will have much less off-target effects caused by passenger strand than di-smRNAs.

Materials and Methods

Cell lines and cell culture. HEK-293 cells were maintained in high glucose (4.5 g/l) DMEM supplemented with 2 mM glutamine, 10% FBS, and 2 mM penicillin/streptomycin. Cells were incubated at 37° C., 5% CO2.

Transfection. For reporter assays, RNAi triggers and reporter constructs were co-transfected into cells by using Lipofectamine 2000 (Invitrogen) as previously reported (Sun et al. 2015). For each experiment, at least three independent transfections were performed in duplicate in 24-well plates. Cell were grown to 75 to 85% confluency in 500 µl medium, and were transfected with luciferase reporter (50 ng), and different amounts of di-siRNA or sli-siRNA (100 ng of stuffer DNA, plus 1 µl of siRNA, and 1 µl of Lipofectamine 2000).

Dual-luciferase reporter assays. All reporter assays were performed using psiCheck 2.0-based, dual-luciferase reporters from Promega that express both firefly luciferase (Fluc) and Renilla luciferase (Rluc). Reporters carried complementary target sequences that were constructed by inserting annealed oligonucleotides into the Xho I/Spe I sites of the 3' UTR of the Rluc gene in psiCheck2.2 vector (Sun et al. 2015). These reporters were used to quantify gene silencing. Forty eight hours after transfection, cells were lysed with 100 µl passive lysis buffer (Promega) and luciferase levels for 20 µl of lysate were determined (Dual-Luciferase reporter assay kit and GloMax 96 Microplate Luminometer, Promega). Changes in expression of Rluc (target) were normalized to Fluc (internal control) and then calculated relative to the scramble sli-siRNA control. The relative ratios of Rluc/Fluc were used to measure the efficiency of silencing. Data were averaged from least three independent transfections and each transfection had at least two replicates. Error bars indicate the standard deviation.

Oligonucleotides. All oligonucleotides were synthesized by Integrated DNA Technologies; sequences are listed in the table shown in FIG. 31.

REFERENCES

The references, patents and published patent applications listed below, and all references cited in the specification above are hereby incorporated by reference in their entirety, as if fully set forth herein.

1. Elbashir, S. M., Harborth, J., Lendeckel, W., Yalcin, A., Weber, K. & Tuschl, T. (2001). Duplexes of 21-nucleotide RNAs mediate RNA interference in cultured mammalian cells. *Nature* 411: 494-498.
2. Doench, J. G., Petersen, C. P. & Sharp, P. A. (2003). siRNAs can function as miRNAs. *Genes Dev* 17: 438-442.
3. Zeng, Y., Yi, R. & Cullen, B. R. (2003). MicroRNAs and small interfering RNAs can inhibit mRNA expression by similar mechanisms. *Proc Natl Acad Sci USA* 100: 9779-9784.
4. McManus, M. T., Petersen, C. P., Haines, B. B., Chen, J. & Sharp, P. A. (2002). Gene silencing using micro-RNA designed hairpins. *RNA* 8: 842-850.
5. Brummelkamp, T. R., Bernards, R. & Agami, R. (2002). A system for stable expression of short interfering RNAs in mammalian cells. *Science* 296: 550-553.
6. Gu, S., Jin, L., Zhang, Y., Huang, Y., Zhang, F., Valdmanis, P. N. et al. (2012). The loop position of shRNAs and pre-miRNAs is critical for the accuracy of dicer processing in vivo. *Cell* 151: 900-911.
7. Herrera-Carrillo, E., Harwig, A., Liu, Y. P. & Berkhout, B. (2014). Probing the shRNA characteristics that hinder Dicer recognition and consequently allow Ago-mediated processing and AgoshRNA activity. *RNA*.
8. McIntyre, G. J., Yu, Y. H., Lomas, M. & Fanning, G. C. (2011). The effects of stem length and core placement on shRNA activity. *BMC Mol Biol* 12: 34.
9. Siolas, D., Lerner, C., Burchard, J., Ge, W., Linsley, P. S., Paddison, P. J. et al. (2005). Synthetic shRNAs as potent RNAi triggers. *Nat Biotechnol* 23: 227-231.
10. Ge, Q., lives, H., Dallas, A., Kumar, P., Shorenstein, J., Kazakov, S. A. et al. (2010). Minimal-length short hairpin RNAs: the relationship of structure and RNAi activity. *RNA* 16: 106-117.
11. Dallas, A., lives, H., Ge, Q., Kumar, P., Shorenstein, J., Kazakov, S. A. et al. (2012). Right- and left-loop short shRNAs have distinct and unusual mechanisms of gene silencing. *Nucleic Acids Res*.
12. Jackson, A. L., Bartz, S. R., Schelter, J., Kobayashi, S. V., Burchard, J., Mao, M. et al. (2003). Expression profiling reveals off-target gene regulation by RNAi. *Nat Biotechnol* 21: 635-637.
13. Jackson, A. L. & Linsley, P. S. (2010). Recognizing and avoiding siRNA off-target effects for target identification and therapeutic application. *Nat Rev Drug Discov* 9: 57-67.
14. Petri, S. & Meister, G. (2013). siRNA design principles and off-target effects. *Methods Mol Biol* 986: 59-71.
15. Cheloufi, S., Dos Santos, C. O., Chong, M. M. & Hannon, G. J. (2010). A dicer-independent miRNA biogenesis pathway that requires Ago catalysis. *Nature* 465: 584-589.
16. Cifuentes, D., Xue, H., Taylor, D. W., Patnode, H., Mishima, Y., Cheloufi, S. et al. (2010). A novel miRNA processing pathway independent of Dicer requires Argonaute2 catalytic activity. *Science* 328: 1694-1698.
17. Yang, J. S., Maurin, T., Robine, N., Rasmussen, K. D., Jeffrey, K. L., Chandwani, R. et al. (2010). Conserved vertebrate mir-451 provides a platform for Dicer-independent, Ago2-mediated microRNA biogenesis. *Proc Natl Acad Sci USA* 107: 15163-15168.
18. Dueck, A., Ziegler, C., Eichner, A., Berezikov, E. & Meister, G. (2012). microRNAs associated with the different human Argonaute proteins. *Nucleic Acids Res* 40: 9850-9862.
19. Yang, J. S., Maurin, T. & Lai, E. C. (2012). Functional parameters of Dicer-independent microRNA biogenesis. *RNA* 18: 945-957.
20. Liu, Y. P., Schopman, N. C. & Berkhout, B. (2013). Dicer-independent processing of short hairpin RNAs. *Nucleic Acids Res* 41: 3723-3733.
21. Ma, H., Zhang, J. & Wu, H. (2014). Designing Ago2-specific siRNA/shRNA to Avoid Competition with Endogenous miRNAs. *Mol Ther Nucleic Acids* 3: e176.
22. Frank, F., Sonenberg, N. & Nagar, B. (2010). Structural basis for 5'-nucleotide base-specific recognition of guide RNA by human AGO2. *Nature* 465: 818-822.
23. Elkayam, E., Kuhn, C. D., Tocilj, A., Haase, A. D., Greene, E. M., Hannon, G. J. et al. (2012). The structure of human argonaute-2 in complex with miR-20a. *Cell* 150: 100-110.
24. Sun, G., Wu, X., Wang, J., Li, H., Li, X., Gao, H. et al. (2011). A bias-reducing strategy in profiling small RNAs using Solexa. *RNA* 17: 2256-2262.
25. Martinez, J., Patkaniowska, A., Urlaub, H., Luhrmann, R. & Tuschl, T. (2002). Single-stranded antisense siRNAs guide target RNA cleavage in RNAi. *Cell* 110: 563-574.

26. Schwarz, D. S., Hutvagner, G., Du, T., Xu, Z., Aronin, N. & Zamore, P. D. (2003). Asymmetry in the assembly of the RNAi enzyme complex. *Cell* 115: 199-208.
27. Ma, J. B., Yuan, Y. R., Meister, G., Pei, Y., Tuschl, T. & Patel, D. J. (2005). Structural basis for 5'-end-specific recognition of guide RNA by the *A. fulgidus* Piwi protein. *Nature* 434: 666-670.
28. Ramirez, A., Shuman, S. & Schwer, B. (2008). Human RNA 5'-kinase (hClp1) can function as a tRNA splicing enzyme in vivo. *RNA* 14: 1737-1745.
29. Chi, S. W., Hannon, G. J. & Darnell, R. B. (2012). An alternative mode of microRNA target recognition. *Nat Struct Mol Biol* 19: 321-327.
30. Sun, X., Rogoff, H. A. & Li, C. J. (2008). Asymmetric RNA duplexes mediate RNA interference in mammalian cells. *Nat Biotechnol* 26: 1379-1382.
31. Chang, C. I., Yoo, J. W., Hong, S. W., Lee, S. E., Kang, H. S., Sun, X. et al. (2009). Asymmetric shorter-duplex siRNA structures trigger efficient gene silencing with reduced nonspecific effects. *Mol Ther* 17: 725-732.
32. Chu, C. Y. & Rana, T. M. (2008). Potent RNAi by short RNA triggers. *RNA* 14: 1714-1719.
33. Bramsen, J. B., Laursen, M. B., Damgaard, C. K., Lena, S. W., Babu, B. R., Wengel, J. et al. (2007). Improved silencing properties using small internally segmented interfering RNAs. *Nucleic Acids Res* 35: 5886-5897.
34. Ge, Q., Dallas, A., Ilves, H., Shorenstein, J., Behlke, M. A. & Johnston, B. H. (2010). Effects of chemical modification on the potency, serum stability, and immunostimulatory properties of short shRNAs. *RNA* 16: 118-130.
35. Grimm, D., Wang, L., Lee, J. S., Schurmann, N., Gu, S., Borner, K. et al. (2010). Argonaute proteins are key determinants of RNAi efficacy, toxicity, and persistence in the adult mouse liver. *J Clin Invest* 120: 3106-3119.
36. Khvorova, A., Reynolds, A. & Jayasena, S. D. (2003). Functional siRNAs and miRNAs exhibit strand bias. *Cell* 115: 209-216.
37. Petri, S., Dueck, A., Lehmann, G., Putz, N., Rudel, S., Kremmer, E. et al. (2011). Increased siRNA duplex stability correlates with reduced off-target and elevated on-target effects. *RNA* 17: 737-749.
38. Neale, B. S., Soifer, H. S., Bowers, C. & Rossi, J. J. (2005). siRNA target site secondary structure predictions using local stable substructures. *Nucleic Acids Res* 33: e30.
39. Matveeva, O. V., Kang, Y. B., Spiridonov, A. N., Saetrom, P., Nemtsov, V. A., Ogurtsov, A. Y. et al. (2010). Optimization of Duplex Stability and Terminal Asymmetry for shRNA Design. *PLoS ONE* 5.
40. Sun, G. & Rossi, J. J. (2009). Problems associated with reporter assays in RNAi studies. *RNA Biol* 6: 406-411.
41. Aagaard, L., Amarzguioui, M., Sun, G., Santos, L. C., Ehsani, A., Prydz, H. et al. (2007). A facile lentiviral vector system for expression of doxycycline-inducible shRNAs: knockdown of the pre-miRNA processing enzyme Drosha. *Mol Ther* 15: 938-945.
42. Li, M. J., Bauer, G., Michienzi, A., Yee, J. K., Lee, N. S., Kim, J. et al. (2003). Inhibition of HIV-1 infection by lentiviral vectors expressing Pol III-promoted anti-HIV RNAs. *Mol Ther* 8: 196-206.
43. Li, M. & Rossi, J. J. (2008). Lentiviral vector delivery of siRNA and shRNA encoding genes into cultured and primary hematopoietic cells. *Methods Mol Biol* 433: 287-299.
44. Sun, G., Yan, J., Noltner, K., Feng, J., Li, H., Sarkis, D. A. et al. (2009). SNPs in human miRNA genes affect biogenesis and function. *RNA* 15: 1640-1651.
45. Zuker, M. (2003). Mfold web server for nucleic acid folding and hybridization prediction. *Nucleic Acids Res* 31: 3406-3415.
46. Hofacker, I. L. (2003). Vienna RNA secondary structure server. *Nucleic Acids Res* 31: 3429-3431.
47. Reuter, J. S. & Mathews, D. H. (2010). RNAstructure: software for RNA secondary structure prediction and analysis. *BMC Bioinformatics* 11: 129.
48. Waterhouse, A. M., Procter, J. B., Martin, D. M., Clamp, M. & Barton, G. J. (2009). Jalview Version 2—a multiple sequence alignment editor and analysis workbench. *Bioinformatics* 25: 1189-1191.
49. Parisien, M. & Major, F. (2008). The MC-Fold and MC-Sym pipeline infers RNA structure from sequence data. *Nature* 452: 51-55.
50. Popenda, M., Szachniuk, M., Antczak, M., Purzycka, K. J., Lukasiak, P., Bartol, N. et al. (2012). Automated 3D structure composition for large RNAs. *Nucleic Acids Res* 40: e112.
51. Sun, G., Li, H. & Rossi, J. J. (2010). Sequence context outside the target region influences the effectiveness of miR-223 target sites in the RhoB 3'UTR. *Nucleic Acids Res* 38: 239-252.
52. Brennecke J, Stark A, Russell R B, Cohen S M. 2005. Principles of microRNA-target recognition. *PLoS Biol* 3: e85.
53. Faehnle C R, Elkayam E, Haase A D, Hannon G J, Joshua-Tor L. 2013. The making of a slicer: activation of human Argonaute-1. *Cell Rep* 3: 1901-1909.
54. Foulkes W D, Priest J R, Duchaine T F. 2014. DICER1: mutations, microRNAs and mechanisms. *Nat Rev Cancer* 14: 662-672.
55. Grimson A, Farh K K, Johnston W K, Garrett-Engele P, Lim L P, Bartel D P. 2007. MicroRNA targeting specificity in mammals: determinants beyond seed pairing. *Mol Cell* 27: 91-105.
56. Ha M, Kim V N. 2014. Regulation of microRNA biogenesis. *Nat Rev Mol Cell Biol* 15: 509-524.
57. Hauptmann J, Dueck A, Harlander S, Pfaff J, Merkl R, Meister G. 2013. Turning catalytically inactive human Argonaute proteins into active slicer enzymes. *Nat Struct Mol Biol*.
58. Hauptmann J, Kater L, Loffler P, Merkl R, Meister G. 2014. Generation of catalytic human Ago4 identifies structural elements important for RNA cleavage. *RNA* 20: 1532-1538.
59. Jackson A L, Burchard J, Schelter J, Chau B N, Cleary M, Lim L, Linsley P S. 2006. Widespread siRNA "off-target" transcript silencing mediated by seed region sequence complementarity. *RNA* 12: 1179-1187.
60. Jinek M, Doudna J A. 2009. A three-dimensional view of the molecular machinery of RNA interference. *Nature* 457: 405-412.
Kawamata T, Tomari Y. 2010. Making RISC. *Trends Biochem Sci* 35: 368-376.
61. Lewis B P, Burge C B, Bartel D P. 2005. Conserved seed pairing, often flanked by adenosines, indicates that thousands of human genes are microRNA targets. *Cell* 120: 15-20.
62. Lewis B P, Shih I H, Jones-Rhoades M W, Bartel D P, Burge C B. 2003. Prediction of mammalian microRNA targets. *Cell* 115: 787-798.
63. Liu Y, Ye X, Jiang F, Liang C, Chen D, Peng J, Kinch L N, Grishin N V, Liu Q. 2009. C3PO, an endoribonuclease that promotes RNAi by facilitating RISC activation. *Science* 325: 750-753.

64. Ma H, Zhang J, Wu H. 2014. Designing Ago2-specific siRNA/shRNA to Avoid Competition with Endogenous miRNAs. *Mol Ther Nucleic Acids* 3: e176.
65. Park J H, Shin C. 2015. Slicer-independent mechanism drives small-RNA strand separation during human RISC assembly. *Nucleic Acids Res*.
66. Saxena S, Jonsson Z O, Dutta A. 2003. Small RNAs with imperfect match to endogenous mRNA repress translation. Implications for off-target activity of small inhibitory RNA in mammalian cells. *J Biol Chem* 278: 44312-44319.
67. Schirle N T, Sheu-Gruttadauria J, MacRae I J. 2014. Gene regulation. Structural basis for microRNA targeting. *Science* 346: 608-613.
68. Sun G, Yeh S Y, Yuan C W, Chiu M J, Yung B S, Yen Y. 2015. Molecular Properties, Functional Mechanisms, and Applications of Sliced siRNA. *Mol Ther Nucleic Acids* 4: e221.
69. Wee L M, Flores-Jasso C F, Salomon W E, Zamore P D. 2012. Argonaute divides its RNA guide into domains with distinct functions and RNA-binding properties. *Cell* 151: 1055-1067.
70. Ye X, Huang N, Liu Y, Paroo Z, Huerta C, Li P, Chen S, Liu Q, Zhang H. 2011. Structure of C3PO and mechanism of human RISC activation. *Nat Struct Mol Biol* 18: 650-657.
71. Yoda M, Cifuentes D, Izumi N, Sakaguchi Y, Suzuki T, Giraldez A J, Tomari Y. 2013. Poly(A)-specific ribonuclease mediates 3'-end trimming of Argonaute2-cleaved precursor microRNAs. *Cell Rep* 5: 715-726.

What is claimed is:

1. A non-naturally occurring short hairpin RNA (shRNA) molecule designed to repress expression of a target gene, the non-naturally occurring shRNA molecule comprising a nucleotide sequence selected from the group consisting of SEQ ID NOs 32-40, 42-69, 79-83, 88-91, 95, 99, and 105.

2. The shRNA molecule of claim 1, wherein the target gene is ribonucleotide reductase.

3. The shRNA molecule of claim 1, further comprising a phosphate at a 5' end of the shRNA molecule.

4. The shRNA molecule of claim 1, further comprising a dideoxy C (ddC) at a 3' end of the shRNA molecule.

5. A vector comprising a nucleotide sequence encoding one or more short hairpin RNA (shRNA) molecules designed to repress expression of a target gene, wherein the nucleotide sequence is selected from the group consisting of SEQ ID NOs 9-10, 14-28, 75-77, 85-86, 98, and 104.

6. The vector of claim 5, wherein the vector comprises nucleotide sequences encoding one, two, three, four, five, six, seven, eight, nine, or ten shRNA molecules.

7. The vector of claim 5, wherein the vector is a lentivirus vector, adenovirus vector, adeno-associated virus, or retroviral vector.

8. The vector of claim 5, wherein the vector further comprises a nucleotide sequence encoding a promoter.

9. The vector of claim 8, wherein the promotor is a U6 promoter.

10. The vector of claim 9, wherein the U6 promoter comprises SEQ ID NO: 143 (U6+MCS) or SEQ ID NO: 144 (U6TO+MCS).

11. The vector of claim 8, wherein the promotor is an inducible promoter, a conditional promoter, or a constitutive promoter.

12. The vector of claim 5, wherein the target gene is ribonucleotide reductase.

13. A vector comprising a nucleotide sequence expressing one or more short hairpin RNA (shRNA) molecules designed to repress expression of a target gene, wherein the shRNA sequence comprises a nucleotide sequence selected from the group consisting of SEQ ID NOs 32-40, 42-69, 79-83, 88-91, 95, 99, and 105.

14. The vector of claim 13, wherein the vector comprises nucleotide sequences expressing one, two, three, four, five, six, seven, eight, nine, or ten shRNA molecules.

15. The vector of claim 13, wherein the vector is a lentivirus vector, adenovirus vector, adeno-associated virus, or retroviral vector.

16. The vector of claim 13, wherein the vector further comprises a nucleotide sequence encoding a promoter.

17. The vector of claim 16, wherein the promotor is a U6 promoter.

18. The vector of claim 17, wherein the U6 promoter comprises SEQ ID NO: 143 (U6+MCS) or SEQ ID NO: 144 (U6TO+MCS).

19. The vector of claim 16, wherein the promotor is an inducible promoter, a conditional promoter, or a constitutive promoter.

20. The vector of claim 13, wherein the target gene is ribonucleotide reductase.

* * * * *